United States Patent
Lipford et al.

(10) Patent No.: US 12,280,056 B2
(45) Date of Patent: Apr. 22, 2025

(54) COMBINATION THERAPY INCLUDING A KRAS$^{G12C}$ INHIBITOR AND ONE OR MORE ADDITIONAL PHARMACEUTICALLY ACTIVE AGENTS FOR THE TREATMENT OF CANCERS

(71) Applicant: Amgen Inc., Thousand Oaks, CA (US)

(72) Inventors: James Russell Lipford, Thousand Oaks, CA (US); Jude Robert Canon, Newbury Park, CA (US); Anne Y. Saiki, Moorpark, CA (US); Karen Louise Rex, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 18/545,932

(22) Filed: Dec. 19, 2023

(65) Prior Publication Data
US 2024/0245686 A1    Jul. 25, 2024

Related U.S. Application Data

(63) Continuation of application No. 17/870,573, filed on Jul. 21, 2022, now Pat. No. 11,918,584, which is a continuation of application No. 16/687,563, filed on Nov. 18, 2019, now Pat. No. 11,439,645.

(60) Provisional application No. 62/865,819, filed on Jun. 24, 2019, provisional application No. 62/821,376, filed on Mar. 20, 2019, provisional application No. 62/769,355, filed on Nov. 19, 2018.

(51) Int. Cl.
| | |
|---|---|
| A61P 35/00 | (2006.01) |
| A61K 31/506 | (2006.01) |
| A61K 31/519 | (2006.01) |
| A61K 31/555 | (2006.01) |
| C07K 16/28 | (2006.01) |

(52) U.S. Cl.
CPC ............ *A61K 31/519* (2013.01); *A61P 35/00* (2018.01); *A61K 31/555* (2013.01); *C07K 16/2818* (2013.01)

(58) Field of Classification Search
CPC ....... A61P 35/00; A61K 45/06; A61K 31/519; A61K 31/506; A61K 31/555; A61K 39/3955; A61K 2300/00; C07K 16/2818
See application file for complete search history.

(56) References Cited

U.S. PATENT DOCUMENTS

| | | | |
|---|---|---|---|
| 4,232,027 A | 11/1980 | Turk et al. | |
| 5,100,883 A | 3/1992 | Schiehser | |
| 5,118,677 A | 6/1992 | Caufield | |
| 5,118,678 A | 6/1992 | Kao et al. | |
| 5,120,842 A | 6/1992 | Failli et al. | |
| 5,151,413 A | 9/1992 | Caufield et al. | |
| 5,256,790 A | 10/1993 | Nelson | |
| 5,258,389 A | 11/1993 | Goulet et al. | |
| 5,521,184 A | 5/1996 | Zimmerman | |
| 5,650,415 A | 7/1997 | Tang et al. | |
| 5,656,643 A | 8/1997 | Spada et al. | |
| 5,712,291 A | 1/1998 | D'Amato | |
| 5,728,813 A | 3/1998 | Lyman et al. | |
| 5,747,498 A | 5/1998 | Schnur et al. | |
| 5,770,599 A | 6/1998 | Gibson | |
| 5,789,427 A | 8/1998 | Chen et al. | |

(Continued)

FOREIGN PATENT DOCUMENTS

| | | |
|---|---|---|
| DE | 19629652 A1 | 1/1998 |
| EP | 0090505 A2 | 10/1983 |

(Continued)

OTHER PUBLICATIONS

Rex, et al., Proceedings of the American Association for Cancer Research Annual Meeting 2019; Mar. 29-Apr. 3, 2019; Atlanta, GA, USA, AACR, Cancer Res 79(13 Suppl): Abstract nr 3090 (2019).*
"A Phase 1, Study Evaluating the Safety, Tolerability, PK, and Efficacy of AMG 510 in Subjects With Solid Tumors With a S Mutation." NCT03600883, comparison of version submitted Oct. 29, 2018 and Oct. 9, 2019 (update posted Oct. 10, 2019), for full history of changes see https://clinicaltrials.gov/ct2/history/NCT03600883 (last accessed Nov. 11, 2020), pp. 1-22.

(Continued)

*Primary Examiner* — Sun Jae Yoo
(74) *Attorney, Agent, or Firm* — Markus Bergauer

(57) ABSTRACT

The present invention provides combination therapy that includes an KRAS$^{G12C}$ inhibitor, such as

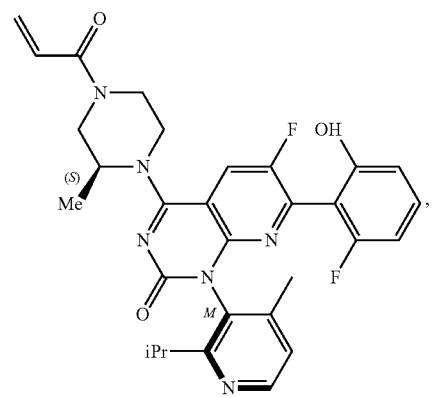

or a pharmaceutically acceptable salt thereof, and one or more additional pharmaceutically active agents, particularly for the treatment of cancers. The invention also relates to pharmaceutical compositions that contain an KRAS$^{G12C}$ inhibitor and one or more additional pharmaceutically active agents for the treatment of cancers.

37 Claims, 91 Drawing Sheets
Specification includes a Sequence Listing.

(56) References Cited

U.S. PATENT DOCUMENTS

| | | |
|---|---|---|
| 5,792,783 A | 8/1998 | Tang et al. |
| 5,861,510 A | 1/1999 | Piscopio et al. |
| 5,863,949 A | 1/1999 | Robinson et al. |
| 5,892,112 A | 4/1999 | Levy et al. |
| 5,969,110 A | 10/1999 | Beckmann et al. |
| 5,981,245 A | 11/1999 | Fox et al. |
| 5,990,141 A | 11/1999 | Hirth et al. |
| 6,057,124 A | 5/2000 | Bartley et al. |
| 6,111,090 A | 8/2000 | Gorman et al. |
| 6,232,447 B1 | 5/2001 | Cerretti |
| 6,235,764 B1 | 5/2001 | Larson et al. |
| 6,258,812 B1 | 7/2001 | Bold et al. |
| 6,413,932 B1 | 7/2002 | Cerretti et al. |
| 6,515,004 B1 | 2/2003 | Misra et al. |
| 6,596,852 B2 | 7/2003 | Cerretti et al. |
| 6,630,500 B2 | 10/2003 | Gingrich et al. |
| 6,656,963 B2 | 12/2003 | Firestone et al. |
| 6,713,485 B2 | 3/2004 | Carter et al. |
| 6,727,225 B2 | 4/2004 | Wiley |
| 7,025,962 B1 | 4/2006 | Gorman et al. |
| 7,354,944 B2 | 4/2008 | Zeng et al. |
| 7,361,760 B2 | 4/2008 | Sircar et al. |
| 7,514,566 B2 | 4/2009 | Zeng et al. |
| 7,618,632 B2 | 11/2009 | Collins et al. |
| 7,700,636 B2 | 4/2010 | Monenschein et al. |
| 7,812,135 B2 | 10/2010 | Smith et al. |
| 7,897,619 B2 | 3/2011 | Zeng et al. |
| 7,919,504 B2 | 4/2011 | Zeng et al. |
| 7,919,514 B2 | 4/2011 | Monenschein et al. |
| 8,388,967 B2 | 3/2013 | Smith et al. |
| 8,586,023 B2 | 11/2013 | Shiku et al. |
| 8,591,886 B2 | 11/2013 | Ponath et al. |
| 10,519,146 B2 | 12/2019 | Lanman et al. |
| 10,532,042 B2 | 1/2020 | Lanman et al. |
| 10,640,504 B2 | 5/2020 | Lanman et al. |
| 10,988,485 B2 | 4/2021 | Minatti et al. |
| 11,045,484 B2 | 6/2021 | Wurz et al. |
| 11,053,226 B2 | 7/2021 | Shin et al. |
| 11,090,304 B2 | 8/2021 | Allen et al. |
| 11,096,939 B2 | 8/2021 | Booker et al. |
| 11,236,091 B2 | 2/2022 | Chaves et al. |
| 11,285,135 B2 | 3/2022 | Lanman et al. |
| 11,285,156 B2 | 3/2022 | Allen et al. |
| 11,299,491 B2 | 4/2022 | Parsons et al. |
| 11,306,087 B2 | 4/2022 | Lanman et al. |
| 11,426,404 B2 | 8/2022 | Henary et al. |
| 11,439,645 B2 | 9/2022 | Lipford et al. |
| 11,766,436 B2 | 9/2023 | Allen et al. |
| 11,827,635 B2 | 11/2023 | Chaves et al. |
| 11,905,281 B2 | 2/2024 | Lanman et al. |
| 11,918,584 B2 | 3/2024 | Lipford et al. |
| 11,993,597 B2 | 5/2024 | Lanman et al. |
| 12,083,121 B2 | 9/2024 | Allen et al. |
| 2002/0042368 A1 | 4/2002 | Fanslow, III et al. |
| 2003/0105091 A1 | 6/2003 | Riedl et al. |
| 2003/0162712 A1 | 8/2003 | Cerretti et al. |
| 2009/0012085 A1 | 1/2009 | Baum et al. |
| 2009/0023761 A1 | 1/2009 | Chen et al. |
| 2009/0030002 A1 | 1/2009 | Chen et al. |
| 2009/0054405 A1 | 2/2009 | Booker et al. |
| 2009/0137581 A1 | 5/2009 | Chen et al. |
| 2009/0163489 A1 | 6/2009 | Booker et al. |
| 2009/0270445 A1 | 10/2009 | Zeng et al. |
| 2010/0273764 A1 | 10/2010 | Andrews et al. |
| 2010/0331293 A1 | 12/2010 | Chushing et al. |
| 2010/0331306 A1 | 12/2010 | Bui et al. |
| 2011/0092504 A1 | 4/2011 | Bo et al. |
| 2011/0097305 A1 | 4/2011 | Connors et al. |
| 2014/0288045 A1 | 9/2014 | Ren et al. |
| 2015/0239900 A1 | 8/2015 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2018/0015087 A1 | 1/2018 | Liu et al. |
| 2018/0072723 A1 | 3/2018 | Blake et al. |
| 2019/0336514 A1 | 11/2019 | Wurz et al. |
| 2019/0343838 A1 | 11/2019 | Allen et al. |
| 2019/0345169 A1 | 11/2019 | Minatti et al. |
| 2019/0374542 A1 | 12/2019 | Allen et al. |
| 2019/0375749 A1 | 12/2019 | Chen et al. |
| 2020/0030324 A1 | 1/2020 | Booker et al. |
| 2020/0055845 A1 | 2/2020 | Lanman et al. |
| 2020/0069657 A1 | 5/2020 | Lanman et al. |
| 2020/0165231 A1 | 5/2020 | Shin et al. |
| 2020/0207766 A1 | 7/2020 | Lanman et al. |
| 2020/0216446 A1 | 7/2020 | Parsons et al. |
| 2020/0360374 A1 | 11/2020 | Henary et al. |
| 2020/0369662 A1 | 11/2020 | Chaves et al. |
| 2021/0009577 A1 | 1/2021 | Lanman et al. |
| 2022/0002298 A1 | 1/2022 | Chen et al. |
| 2022/0106313 A1 | 4/2022 | Chaves et al. |
| 2022/0168280 A1 | 6/2022 | Lanman et al. |
| 2022/0175782 A1 | 6/2022 | Allen et al. |
| 2022/0213101 A1 | 7/2022 | Lanman et al. |
| 2022/0220112 A1 | 7/2022 | Parsons et al. |
| 2022/0235045 A1 | 7/2022 | Chaves et al. |
| 2022/0378787 A1 | 12/2022 | Henary et al. |
| 2022/0395504 A1 | 12/2022 | Allen et al. |
| 2023/0028414 A1 | 1/2023 | Henary et al. |
| 2023/0121955 A1 | 4/2023 | Lipford et al. |
| 2023/0248729 A1 | 8/2023 | Henary et al. |
| 2024/0050430 A1 | 2/2024 | Allen et al. |
| 2024/0067647 A1 | 2/2024 | Chaves et al. |
| 2024/0082251 A1 | 3/2024 | Henary et al. |
| 2024/0173328 A1 | 5/2024 | Lipford et al. |
| 2024/0174660 A1 | 5/2024 | Lanman et al. |
| 2024/0190862 A1 | 6/2024 | Wang et al. |
| 2024/0287068 A1 | 8/2024 | Lanman et al. |
| 2024/0408089 A1 | 12/2024 | Henary et al. |

FOREIGN PATENT DOCUMENTS

| | | |
|---|---|---|
| EP | 404355 A1 | 12/1990 |
| EP | 511792 A2 | 11/1992 |
| EP | 0520722 A1 | 12/1992 |
| EP | 0566226 A1 | 10/1993 |
| EP | 0606046 A1 | 7/1994 |
| EP | 0682027 A1 | 11/1995 |
| EP | 0407122 A1 | 10/1996 |
| EP | 0770622 A2 | 5/1997 |
| EP | 0780386 A1 | 6/1997 |
| EP | 0787772 A2 | 8/1997 |
| EP | 0818442 A2 | 1/1998 |
| EP | 0837063 A1 | 4/1998 |
| EP | 0931788 A2 | 7/1999 |
| EP | 0970070 B1 | 1/2000 |
| EP | 1004578 A2 | 5/2000 |
| EP | 1181017 B1 | 2/2002 |
| EP | 1786785 B9 | 5/2007 |
| EP | 1866339 B1 | 12/2007 |
| EP | 1947183 A1 | 7/2008 |
| EP | 3401314 A1 | 11/2019 |
| EP | 3055290 B1 | 12/2019 |
| JP | 02233610 A | 9/1990 |
| JP | 2019031476 A | 2/2019 |
| WO | 1990005719 A1 | 5/1990 |
| WO | 1992005179 A1 | 4/1992 |
| WO | 1992020642 A1 | 11/1992 |
| WO | 1993011130 A1 | 6/1993 |
| WO | 1994002136 A1 | 2/1994 |
| WO | 1994002485 A1 | 2/1994 |
| WO | 1994009010 A1 | 4/1994 |
| WO | 1995009847 A1 | 4/1995 |
| WO | 1995014023 A1 | 5/1995 |
| WO | 1995016691 A1 | 6/1995 |
| WO | 1995019774 A1 | 7/1995 |
| WO | 1995019970 A1 | 7/1995 |
| WO | 1996027583 A1 | 9/1996 |
| WO | 1996030347 A1 | 10/1996 |
| WO | 1996031510 A1 | 10/1996 |
| WO | 1996033172 A1 | 10/1996 |
| WO | 1996033980 A1 | 10/1996 |
| WO | 1996041807 A1 | 12/1996 |
| WO | 1997002266 A1 | 1/1997 |

(56) References Cited

FOREIGN PATENT DOCUMENTS

| | | |
|---|---|---|
| WO | 1997013771 A1 | 4/1997 |
| WO | 1997019065 A1 | 5/1997 |
| WO | 1997027199 A1 | 7/1997 |
| WO | 1997030034 A1 | 8/1997 |
| WO | 1997030044 A1 | 8/1997 |
| WO | 1997032880 A1 | 9/1997 |
| WO | 1997032881 A1 | 9/1997 |
| WO | 1997034895 A1 | 9/1997 |
| WO | 1997038983 A1 | 10/1997 |
| WO | 1997038994 A1 | 10/1997 |
| WO | 1997049688 A1 | 12/1997 |
| WO | 1998002434 A1 | 1/1998 |
| WO | 1998002437 A1 | 1/1998 |
| WO | 1998002438 A1 | 1/1998 |
| WO | 1998002441 A2 | 1/1998 |
| WO | 1998003516 A1 | 1/1998 |
| WO | 1998007697 A1 | 2/1998 |
| WO | 1998007726 A1 | 2/1998 |
| WO | 1998014449 A1 | 4/1998 |
| WO | 1998014450 A1 | 4/1998 |
| WO | 1998014451 A1 | 4/1998 |
| WO | 1998017662 A1 | 4/1998 |
| WO | 1998030566 A1 | 7/1998 |
| WO | 1998033768 A1 | 8/1998 |
| WO | 1998033798 A2 | 8/1998 |
| WO | 1998034915 A1 | 8/1998 |
| WO | 1998034918 A1 | 8/1998 |
| WO | 1999007675 A1 | 2/1999 |
| WO | 1999007701 A1 | 2/1999 |
| WO | 1999020758 A1 | 4/1999 |
| WO | 1999029667 A1 | 6/1999 |
| WO | 1999035132 A1 | 7/1999 |
| WO | 1999035146 A1 | 7/1999 |
| WO | 1999040196 A1 | 8/1999 |
| WO | 1999045009 A1 | 9/1999 |
| WO | 1999052889 A1 | 10/1999 |
| WO | 1999052910 A1 | 10/1999 |
| WO | 1999061422 A1 | 12/1999 |
| WO | 2000002871 A1 | 1/2000 |
| WO | 2000012089 A1 | 3/2000 |
| WO | 2000059509 A1 | 10/2000 |
| WO | 2001003720 A2 | 1/2001 |
| WO | 2001014387 A1 | 3/2001 |
| WO | 2001032651 A1 | 5/2001 |
| WO | 2001037820 A2 | 5/2001 |
| WO | 2002055501 A2 | 7/2002 |
| WO | 2002059110 A1 | 8/2002 |
| WO | 2002066470 A1 | 8/2002 |
| WO | 2002068406 A2 | 9/2002 |
| WO | 2004005279 A2 | 1/2004 |
| WO | 2004007458 A1 | 1/2004 |
| WO | 2004007481 A2 | 1/2004 |
| WO | 2004009784 A2 | 1/2004 |
| WO | 2004063195 A1 | 7/2004 |
| WO | 2005005434 A1 | 1/2005 |
| WO | 2005007190 A1 | 1/2005 |
| WO | 2005011700 A1 | 2/2005 |
| WO | 2005016252 A2 | 2/2005 |
| WO | 2005021546 A1 | 3/2005 |
| WO | 2005055808 A2 | 6/2005 |
| WO | 2005115451 A2 | 12/2005 |
| WO | 2006044453 A1 | 4/2006 |
| WO | 2006083289 A2 | 8/2006 |
| WO | 2006121168 A1 | 11/2006 |
| WO | 2006122806 A2 | 11/2006 |
| WO | 2007133822 A1 | 11/2007 |
| WO | 2008070740 A1 | 6/2008 |
| WO | 2008118454 A2 | 10/2008 |
| WO | 2008118455 A1 | 10/2008 |
| WO | 2008118468 A1 | 10/2008 |
| WO | 2008153947 A2 | 12/2008 |
| WO | 2009036082 A2 | 3/2009 |
| WO | 2009055730 A1 | 4/2009 |
| WO | 2009085185 A1 | 7/2009 |
| WO | 2010003118 A1 | 1/2010 |
| WO | 2010083246 A1 | 7/2010 |
| WO | 2010096314 A1 | 8/2010 |
| WO | 2010108074 A2 | 9/2010 |
| WO | 2010126895 A1 | 11/2010 |
| WO | 2010132598 A1 | 11/2010 |
| WO | 2010149786 A1 | 12/2010 |
| WO | 2010151735 A2 | 12/2010 |
| WO | 2010151737 A2 | 12/2010 |
| WO | 2010151740 A2 | 12/2010 |
| WO | 2010151791 A1 | 12/2010 |
| WO | 2011028683 A1 | 3/2011 |
| WO | 2011031842 A1 | 3/2011 |
| WO | 2011051726 A2 | 5/2011 |
| WO | 2011090754 A1 | 7/2011 |
| WO | 2012142498 A2 | 10/2012 |
| WO | 2013039954 A1 | 3/2013 |
| WO | 2013155223 A1 | 10/2013 |
| WO | 2014023385 A1 | 2/2014 |
| WO | 2014143659 A1 | 9/2014 |
| WO | 2014152588 A1 | 9/2014 |
| WO | 2015001076 A1 | 1/2015 |
| WO | 2015054572 A1 | 4/2015 |
| WO | 2015075483 A1 | 5/2015 |
| WO | 2015109285 A1 | 7/2015 |
| WO | 2016035008 A1 | 3/2016 |
| WO | 2016044772 A1 | 3/2016 |
| WO | 2016049524 A1 | 3/2016 |
| WO | 2016049565 A1 | 3/2016 |
| WO | 2016049568 A1 | 3/2016 |
| WO | 2016164675 A1 | 10/2016 |
| WO | 2016168540 A1 | 10/2016 |
| WO | 2017015562 A1 | 1/2017 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017087528 A1 | 5/2017 |
| WO | 2017100546 A1 | 6/2017 |
| WO | 2017172979 A1 | 10/2017 |
| WO | 2017201161 A1 | 11/2017 |
| WO | 2018064510 A1 | 4/2018 |
| WO | 2018068017 A1 | 4/2018 |
| WO | 2018119183 A2 | 6/2018 |
| WO | 2018119183 A3 | 6/2018 |
| WO | 2018140598 A1 | 8/2018 |
| WO | 2018217651 A1 | 11/2018 |
| WO | 2018218069 A1 | 11/2018 |
| WO | 2019051291 A1 | 3/2019 |
| WO | 2019213516 A1 | 11/2019 |
| WO | 2019213526 A1 | 11/2019 |
| WO | 2019217691 A1 | 11/2019 |
| WO | 2019232419 A1 | 12/2019 |
| WO | 2019241157 A1 | 12/2019 |
| WO | 2019243533 A1 | 12/2019 |
| WO | 2019243535 A1 | 12/2019 |
| WO | 2020050890 A2 | 3/2020 |
| WO | 2020102730 A1 | 5/2020 |
| WO | 2020106640 A1 | 5/2020 |
| WO | 2020232130 A1 | 11/2020 |
| WO | 2020236947 A1 | 11/2020 |
| WO | 2020236948 A1 | 11/2020 |
| WO | 2021081212 A1 | 4/2021 |
| WO | 2021097207 A1 | 5/2021 |
| WO | 2021097212 A1 | 5/2021 |
| WO | 2021126816 A1 | 6/2021 |
| WO | 2021236920 A1 | 11/2021 |
| WO | 2002006213 A2 | 1/2022 |

OTHER PUBLICATIONS

"Acute Leukemia," *The Merck Manual* (Online Edition), pp. 1-6 (2013).
"KRASG12C Inhibitor," Mirati Therapeutics, retrieved on Nov. 27, 2018, from https://www.mirati.com/mrtx849/, 5 pages.
4-methyl-2-(1-methylethyl)-3-pyridinamine, STN Registry, CAS RN 1698293-93-4, STN entry date May 5, 2015 (May 5, 2015).

(56) References Cited

OTHER PUBLICATIONS

Ahmadian, et al., "Guanosine triphosphatase stimulation of oncogenic Ras mutants," *PNAS*, 96: 7065-7070, 1999.

Airoldi, et al., "Glucose-Derived Ras Pathway Inhibitors: Evidence of Ras-Ligand Binding and Ras-GEF (Cdc25) Interaction Inhibition," *ChemBioChem*, 8: 1376-1379 (2007).

AMG-510; CS-0081316; Source: AbaChemScene (CS-0081316); Deposit Date: May 13, 2019 Available Date: May 13, 2019; SID: 384060804[CID: 137278711] (available at https://pubchem.ncbi.nlm.nih.gov/substance/384060804/).

AMG-510; HY-114277; Source: MedChemexpress Mce (HY-114277); Deposit Date: May 13, 2019 Available Date: May 13, 2019; SID: 384060569[CID: 137278711] (available at https://pubchem.ncbi.nlm.nih.gov/substance/384060569).

Amgen Press Release, "Amgen Announces New Clinical Data Evaluating Novel Investigational KRAS(G12C) Inhibitor in Larger Patient Group at WCLC 2019," dated Sep. 8, 2019 (last accessed Apr. 13, 2021).

ATTC "Organism: *Mus musculus* (B cell); *Mus musculus* (myeloma), mouse (B cell); mouse (myeloma)," Accession No. HB-8508, retrieved from https://www.atcc.org/~/media/0DF7351153724BD6A3E7D78D5BA2F933.ashx, on Nov. 29, 2018.

Barnett, et al., "Identification and characterization of pleckstrin-holomogy-domain-dependent and isoenzyme specific Akt inhibitors," *Biochem. J.*, 385 (2): 399-408 (2005).

Bhatia, et al., "A Review on Bioisosterism: A Rational Approach for Drug Design and Molecular Modification," *Pharmacologyonline*, 1:272-299 (2011).

Brauswetter et al., "Molecular subtype specific efficacy of MEK inhibitors in pancreatic cancers", *Plos One*, 12(9): e0185687 (pp. 1-8) (2017).

Bull, et al., "Isoquino[2,1-c][1,3,2] Benzodiazaphosphorine Derivatives: New Potential Agents for Cancer Chemotherapy," *Phosphorus, Sulfur, and Silicon*, 162:231-243 (2000).

Campillo, et al., "Novel Bronchodilators: Synthesis, Transamination Reactions, and Pharmacology of a Series of Pyrazino[2,3-c][1,2,6]thiadiazine 2,2-Dioxides," *J. Med. Chem.*, 43: 4219-4227 (2000).

Canon, et al., "The clinical KRAS(G12C) inhibitor AMG 510 drives anti-tumour immunity," *Nature*, 575(7781): 217-223 (2019).

Canon, et al., "The clinical KRAS(G12C) inhibitor AMG 510 drives anti-tumour immunity," *Nature*, 575(7781): 217-223 (2019) (Supplementary Material, pp. 1-55).

Cee, et al., "Discovery of AMG 510, a first-in-humancovalent inhibitor of KRAS$^{G12C}$ for the treatment of solid tumors," Abstract and Presentation, ACS Spring Meeting, Orlando, FL, USA, Mar. 31-Apr. 4, 2019.

Cohen, "The development and therapeutic potential of protein kinase inhibitors," *Current Opinion in Chemical Biology*, 3:459-465 (1999).

Communication Pursuant to Rule 114(2) EPC, Third Party Observation, European Patent Application No. 21183032.8, Apr. 3, 2023, 6 pages.

Cowen Slide deck—Warp Drive Bio, slides 1-32, "Corporate Overview Exploiting the Molecules and Mechanisms of Nature to Create Transformative Medicines" http://www.warpdrivebio.com/news/cowen%202016.pdf (last visited Apr. 2016).

Dasmahapatra, et al., "In vitro Combination Treatment with Perifosine and UCN-01 Demonstrates Synergism Against Prostate (PC-3) and Lung (A549) Epithelial Adenocarcinoma Cell Lines," *Clin. Cancer Res.* 10(15): 5242-5252 (2004).

Database Registry [Online], Chemical Abstracts Service, Columbus, Ohio, US; Jul. 31, 2017 (Jul. 31, 2017), XP002801805, retrieved from STN Database accession No. 2105944-09-8.

Dermer, et al., "Another Anniversary for the War on Cancer," *Bio/Technology*, 12: 320 (1994).

Dimartino et al., "Preparation and Physical Characterization of Forms II and III of Paracetamol," *Journal of Thermal Analysis*, 48:447-458 (1997).

Douelle, et al., "Highly Diastereoselective Synthesis of vicinal Quaternary and Tertiary Stereocenters Using the Iodo-aldol Cyclization," *Org. Lett.*, 9 (10): 1931-1934 (2007).

Erkkilä, et al., "Mild Organocatalytic α-Methylenation of Aldehydes," *J. Org. Chem.*, 71 (6), 2538-2541 (2006).

Examiner-Initiated Interview Summary, mailed Dec. 9, 2021, for U.S. Appl. No. 16/817,109, 1 page.

Extended European Search Report for European Patent Application No. 19208193.2, dated Jun. 3, 2020, pp. 1-8.

Fakih, et al., "Phase 1 study evaluating the safety, tolerability, pharmacokinetics (PK), and efficacy of AMG 510, a novel small molecule KRASG12C inhibitor, in advanced solid tumors," *Journal of Clinical Oncology*, 37(15 suppl) (May 20, 2019) 3003, published online May 26, 2019.

Fakih, et al., "Phase 1 study evaluating the safety, tolerability, pharmacokinetics (PK), and efficacy of AMG 510, a novel small molecule KRASG12C inhibitor, in advanced solid tumors," Presentation, ASCO, Chicago, IL, USA, May 31-Jun. 4, 2019.

Final Office Action for U.S. Appl. No. 15/984,855, mailed Mar. 28, 2019, 7 pages.

Final Office Action for U.S. Appl. No. 16/436,647, mailed Mar. 24, 2021, 7 pages.

Final Office Action for U.S. Appl. No. 16/661,907, mailed Mar. 27, 2020, 29 pages.

Freshney, et al., Culture of Animal Cells, *A Manual of Basic Technique*, Alan R. Liss, Inc, New York, p. 4 (1983).

Gentile, et al., "Discovery and Structural Investigation of Novel Binders to the Ras Switch II Pocket," NCI Initiative Symposium Poster (2015).

Gills and Dennis, "The development of phosphatidylinositol ether lipid analogues as inhibitors of the serine/threonine kinase, Akt," *Expert. Opin. Investig. Drugs*, 13: 787-797 (2004).

Goldberg, et al., "Role of PD-1 and its ligand, B7-H1, in early fate decisions of CD8 T cells," *Blood*, 110(1): 186-192 (2007).

Goldstein, et al., "Biological efficacy of a chimeric antibody to the epidermal growth factor receptor in a human tumor xenograft model," *Clin. Cancer Res.*, 1: 1311-1318 (1995).

Golub, et al., "Molecular Classification of Cancer: Class Discovery and Class Prediction by Gene Expression Monitoring," *Science*, 286: 531-537(1999).

Govindan et al., "OA01.06 Safety, Efficacy, and Pharmacokinetics of AMG 510, a Novel KRAS$^{G12C}$ Inhibitor, in Patients with Non-Small Cell Lung Cancer," *J. Thorac. Oncol.*, 14(11, Supplement 1):S1125-1126 (Nov. 2019).

Govindan, et al., "Safety, Efficacy, and Pharmacokinetics of AMG 510, a Novel KRASG12C Inhibitor, in Patients with Non-Small Cell Lung Cancer," Abstract and Presentation, North American Conference on Lung Cancer (NACLC), Chicago, IL, USA, Oct. 10-12, 2019.

Govindan, et al., "Phase 1 Study of AMG 510, a Novel KRAS G12C Inhibitor, in Advanced Solid Tumors with KRAS p.G12C Mutation," Abstract, ESMO Congress, Barcelona, Spain, Sep. 27-Oct. 1, 2019.

Govindan, et al., "Phase 1 Study of AMG 510, a Novel Kras G12C Inhibitor, in Advanced Solid Tumors with KRAS p.G12C Mutation," Poster, ESMO Congress, Barcelona, Spain, Sep. 27, 2019-Oct. 1, 2019.

Govindan, et al., "Phase 1 Study of Safety, Tolerability, Pharmacokinetics, and Efficacy of AMG 510, a Novel KRAS$^{G12C}$ Inhibitor, in Non-Small Cell Lung Cancer," Abstract and Presentation, World Conference on Lung Cancer (WCLC), Barcelona, Spain, Sep. 7-10, 2019.

Gura, "Cancer Models: Systems for Identifying New Drugs Are Often Faulty," *Science*, 278(5340):1041-1042 (1997).

Halford, "Amgen unveils its Kras covalent inhibitor AMG 510," *Chemical & Engineering News* 97(14):4 (2019).

Hallin, et al., "The KRAS$^{G12C}$ Inhibitor MRTX849 Provides Insight toward Therapeutic Susceptibility of KRAS-Mutant Cancers in Mouse Models and Patients," *Cancer Discov.*, 10: 54-71 (2020).

Hansen, et al., "Abstract 686: Drugging an undruggable pocket: the biochemical mechanism of covalent KRAS$^{G12C}$ inhibitors," Proceedings of the American Association for Cancer Research Annual

(56) References Cited

OTHER PUBLICATIONS

Meeting 2018; Apr. 14-18, 2018; Chicago, IL; AACR; *Cancer Res.*, 78(13 Suppl): Abstract 686 (2018).
Hichri, et al., "A Convenient Synthesis of 1,3,2-Benzodiazaphophorine-2-Oxide," *Phosphorus, Sulfur, and Silicon*, 190: 29-35 (2015).
Hichri, et al., CAPLUS Abstract, 162:245378 (2015).
Hirayama, "Handbook for Making Crystal of Organic Compound,—Principles and Know-how—", Maruzen Co., Ltd., Jul. 25, 2008, pp. 57-84 (incl. English translation).
Hocker, et al., "Andrographolide derivatives inhibit guanine nucleotide exchange and abrogate oncogenic Ras function," *PNAS*, 110(25): 10201-10206 (2013).
Hong, et al., "KRAS$^{G12C}$ Inhibition with Sotorasib in Advanced Solid Tumors," *N. Engl. Med.*, 383:1207-1217 (2020).
Huang, et al., "Epidermal Growth Factor Receptor Blockade with C225 Modulates Proliferation, Apoptosis, and Radiosensitivity in Squamous Cell Carcinomas of the Head and Neck," *Cancer Res.*, 59(8): 1935-1940 (1999).
International Search Report for PCT/US2017/067801, mailed Jul. 25, 2018, 6 pages.
International Search Report for PCT/US2018/033714, mailed Jul. 17, 2018, 3 pages.
International Search Report for PCT/US2018/050044, mailed Oct. 30, 2018, 7 pages.
International Search Report for PCT/US2019/030593, mailed Aug. 6, 2019, 4 pages.
International Search Report for PCT/US2019/030606, mailed Jul. 23, 2019, 5 pages.
International Search Report for PCT/US2019/031535, mailed Jul. 25, 2019, 7 pages.
International Search Report for PCT/US2019/034974, mailed Aug. 9, 2019, 5 pages.
International Search Report for PCT/US2019/036397, mailed Aug. 26, 2019, 5 pages.
International Search Report for PCT/US2019/036626, mailed Jun. 2, 2020, 5 pages.
International Search Report for PCT/US2019/061815, mailed Mar. 5, 2020, 6 pages.
International Search Report for PCT/US2019/062051, mailed Mar. 2, 2020, 3 pages.
International Search Report for PCT/US2019/62064, mailed Oct. 29, 2020, 9 pages.
International Search Report for PCT/US2020/032686, mailed Aug. 14, 2020, 4 pages.
International Search Report for PCT/US2020/033831, mailed Jul. 9, 2020, 6 pages.
International Search Report for PCT/US2020/033832, mailed Jul. 8, 2020, 4 pages.
International Search Report for PCT/US2020/056874, mailed Feb. 12, 2021, 7 pages.
International Search Report for PCT/US2020/060415, mailed Feb. 3, 2021, 7 pages.
International Search Report for PCT/US2020/060421, mailed Feb. 18, 2021, 4 pages.
International Search Report for PCT/US2020/065050, mailed Mar. 29, 2021, 7 pages.
Janes, et al., "Targeting KRAS Mutant Cancers with a Covalent G12C-Specific Inhibitor," *Cell*, 172: 578-589 (2018).
Jarvis, "Notorious KRAS: Taking down cancer researchers' biggest foe," *Chemical & Engineering News*, 97(37), 9 pages (2019).
Jin, et al., "Inhibition of AKT survival pathway by a small molecule inhibitor in human endometrial cancer cells," *Br. J. Cancer*, 91: 1808-1812 (2004).
Johnson et al., "Relationships between drug activity in NCI preclinical in vitro and in vivo models and early clinical trials," *British Journal of Cancer*, 84(10): 1424-1431 (2001).
Knapman, "Polymorphic Predictions: Understanding the nature of crystalline compounds can be critical in drug development and manufacture", *Modern Drug Discovery*, 53-57 (2000).
Kojima, "Aiming to Improve the Efficiency of Crystallization Selection in Drug Development", Pharmaceutics, Sep. 1, 2008, vol. 68, No. 5, pp. 344-349 (incl. English translation).
Lanman, et al., "Abstract 4455: Discovery of AMG 510, a first-in-human covalent inhibitor of KRAS$^{G12C}$ for the treatment of solid tumors," Presentation, American Association for Cancer Research (AACR) Annual Meeting, Atlanta, GA, USA, Mar. 29-Apr. 3, 2019.
Lanman, et al., "Abstract 4455: Discovery of AMG 510, a first-in-human covalent inhibitor of KRAS$^{G12C}$ for the treatment of solid tumors," Proceedings of the American Association for Cancer Research Annual Meeting 2019; Mar. 29-Apr. 3, 2019; Atlanta, GA, USA, AACR, Cancer Res. 79(13 Suppl): Abstract nr 4455 (2019).
Lanman, et al., "Discovery of a Covalent Inhibitor of KRAS$^{G12C}$ (AMG 510) for the Treatment of Solid Tumors," *J. Med. Chem.*, 63: 52-65 (2020).
Li, et al., "Targeting Protein-Protein Interaction with Covalent Small-Molecule Inhibitors," *Current Topics in Medicinal Chemistry*, 19(21): 1872-1876 (2019).
Lim, et al., "Therapeutic Targeting of Oncogenic K-Ras by a Covalent Catalytic Site Inhibitor," *Angew. Chem. Int. Ed*, 53: 199-204 (2014).
Lipford, et al., "Pre-Clinical Development of AMG 510: The First Inhibitor of KRAS$^{G12C}$ in Clinical Testing," Presentation, American Association for Cancer Research (AACR) Annual Meeting, Atlanta, GA, USA, Mar. 29-Apr. 3, 2019.
Liu, Y., "Session SY28—Transformative Small Molecule Therapies—Targeting KRAS mutant cancers with a covalent G12C—specific inhibitor," Presentation on Apr. 4, 2017, AACR Annual Meeting Presentation, Apr. 1-5, 2017, Washington, D.C. (2017).
Lopez, et al., "Optimization of quinazolinone-based covalent inhibitors of KRAS$^{G12C}$ in the discovery of AMG 510," Abstract and Poster, ACS Fall Meeting, San Diego, CA, USA, Aug. 25-29, 2019.
Lu, et al., "KRAS G12C Drug Development: Discrimination between Switch II Pocket Configurations Using Hydrogen/Deuterium-Exchange Mass Spectrometry," *Structure*, 25: 1-7 (2017).
Maurer, et al., "Small-molecule ligands bind to a distinct pocket in Rad and inhibit SOS-mediated nucleotide exchange activity," *PNAS*, 109(14): 5299-5304 (2012).
Mcgregor, et al., "Expanding the Scope of Electrophiles Capable of Targeting K-Ras Oncogenes," *ACS Bio. Chem.*, 56: 3179-3183 (2017).
Meanwell, "Synopsis of Some Recent Tactical Application of Bioisosteres in Drug Design," *J. Med. Chem*. 54:2529-2591 (2011).
Mirati Therapeutics, "Corporate Presentation Nov. 2017," Slides 1-41 (2017).
Modjtahedi, et al., "The human EGF receptor as a target for cancer therapy: six new rat mAbs AGainst the receptor on the breast carcinoma MDA-MB 468," *Br. J. Cancer*, 67(2): 247-253 (1993).
Morrissey et al., "Immunotherapy and Novel Combinations in Oncology: Current Landscape, Challenges, and Opportunities," *Clin. Transl. Sci.*, 9(2):89-104 (2016).
National Cancer Institute identifier: NSC 154020, retrieved on Nov. 29, 2018, from https://cactus.nci.nih.gov/ncidb2.2/.
NCBI Reference Sequence, "GTPase KRas isoform a [Homo sapiens]," GenBank Accession No. NM 203524.1, Retrieved on Nov. 29, 2018 from https://www.ncbi.nlm.nih.gov/protein/15718763?sat-4&satkey-234448549, 4 pages.
Non-Final Office Action (Corrected) for U.S. Appl. No. 16/125,359, mailed Apr. 8, 2019, 13 pages.
Non-Final Office Action for U.S. Appl. No. 15/849,905, mailed Mar. 20, 2019, 18 pages.
Non-Final Office Action for U.S. Appl. No. 15/930,606, mailed Jan. 13, 2022, 4 pages.
Non-Final Office Action for U.S. Appl. No. 15/984,855, mailed Sep. 27, 2018, 25 pages.
Non-Final Office Action for U.S. Appl. No. 16/125,359, mailed Apr. 5, 2019, 13 pages.
Non-Final Office Action for U.S. Appl. No. 16/402,538, mailed Oct. 30, 2019, 12 pages.
Non-Final Office Action for U.S. Appl. No. 16/402,589, mailed Mar. 6, 2020, 17 pages.
Non-Final Office Action for U.S. Appl. No. 16/407,889, mailed Jul. 1, 2020, 6 pages.

(56) References Cited

OTHER PUBLICATIONS

Non-Final Office Action for U.S. Application No. 16/428, 163, mailed Sep. 15, 2020, 6 pages.
Non-Final Office Action for U.S. Appl. No. 16/436,647, mailed Aug. 7, 2020, 19 pages.
Non-Final Office Action for U.S. Appl. No. 16/438,349, mailed Dec. 13, 2019, 15 pages.
Non-Final Office Action for U.S. Appl. No. 16/661,907, mailed Nov. 18, 2019, 20 pages.
Non-Final Office Action for U.S. Appl. No. 16/675,121, mailed Feb. 2, 2021, 10 pages.
Non-Final Office Action for U.S. Appl. No. 16/817,109, mailed Mar. 3, 2021, 12 pages.
Non-Final Office Action for U.S. Appl. No. 17/031,607, mailed Mar. 31, 2023, 7 pages.
Non-Final Office Action for U.S. Appl. No. 17/553,598, mailed Apr. 26, 2023, 4 pages.
Non-Final Office Action for U.S. Appl. No. 17/692,026, mailed May 11, 2023, 17 pages.
Noriyuki, "API Form Screening and Selection at the Drug Discovery Stage", Pharm Stage, vol. 6, No. 10, Jan. 15, 2007, pp. 20-25 (incl. English translation).
Notice of Allowance, mailed Mar. 29, 2023, for U.S. Appl. No. 17/363,878, 8 pages.
Office Communication (Ex Parte Quayle) for U.S. Appl. No. 16/687,563, mailed Jan. 14, 2022, 5 pages.
Ostrem, et al., "Development of mutant-specific small molecule inhibitors of K-Ras," Poster, AACR 104th Annual Meeting 2013; Apr. 6-10, 2013; Washington, D.C. (2013).
Ostrem, et al., "K-Ras(G12C) inhibitors allosterically control GTP affinity and effector interactions," *Nature*, 503: 548-551 (2013).
Paez, et al., "EGFR Mutations in Lung Cancer Correlation with Clinical Response to Gefitinib Therapy," *Science*, 304(5676): 1497-500 (2004).
Saiki, et al., "Abstract 4484: Discovery and in vitro characterization of AMG 510—a potent and selective covalent small-molecule inhibitor of KRAS$^{G12C}$," Presentation, American Association for Cancer Research (AACR) Annual Meeting, Atlanta, GA, USA, Mar. 29-Apr. 3, 2019.
Saiki, et al., "Abstract 4484: Discovery and in vitro characterization of AMG 510—a potent and selective covalent small-molecule inhibitor of KRAS$^{G12C}$," Proceedings of the American Association for Cancer Research Annual Meeting 2019; Mar. 29-Apr. 3, 2019; Atlanta, GA, USA, AACR, Cancer Res. 79(13 Suppl): Abstract nr 4484 (2019).
Sarkar, et al., "Indole-3-Carbinol and Prostate Cancer[1,2]," *J. Nutr.*, 134(12 Suppl): 3493S-3498S (2004).
Shibata et al., "A Convenient Synthesis of 3-Cyano-2-methylpyridines under Ultrasonic Irradiation," *Bull. Chem. Soc. Jpn.*, 61:2199-2200 (1988).
Shima, et al., "In silico discovery of small-molecule Ras inhibitors that display antitumor activity by blocking the Ras-effector interaction," *PNAS*, 110(20): 8182-8187 (2013).
Simone, "Part XIV Oncology: Introduction," *Cecil Textbook of Medicine*, 20th Edition, 1:1004-1010 (1996).
Singh, et al., "Improving Prospects for Targeting RAS," *J. Clinc. Oncl*, 33(31): 3650-3660 (2015).
Smith et al., "SHP2 inhibition as the backbone of targeted therapy combinations for the treatment of cancers driven by oncogenic mutations in the RAS pathway," American Association for Cancer Research Annual Meeting 2020, Virtual Meeting II, Jun. 22-24, 2020, Poster 1943.
Stanetty et al., "Synthesis of Aza Analogs of the Herbicide Sindone B," *Monatshefte Fuer Chemie*, 130:441-450 (1999).
Statsyuk, "Let K-Ras activate its own inhibitor," *Nature Structural & Molecular Biology*, 25:435-439 (2018).
Sun, et al., "Discovery of Small Molecules that Bind to K-Ras and Inhibit Sos-Mediated Activation," *Angew. Chem. Int. Ed.*, 51: 6140-6143 (2012).

Taveras, et al., "Ras Oncoprotein Inhibitors: The Discovery of Potent, Ras Nucleotide Exchange Inhibitors and the Structural Determination of a Drug-Protein Complex," *Biorg. Med. Chem. Lett.*, 5(1): 125-133 (1997).
Teramoto, et al., 1996, Cancer 77 (4):639-645.
The ASCO Post Staff, "AACR-NCI-EORTC: Investigational KRAS G12C Inhibitor for KRAS-Mutant Solid Tumors," The ASCO Post (2019).
Third Party Observation filed for PCT/US2020/033831, submitted Jan. 15, 2021, 2 pages.
Thompson, et al., "PD-1 is Expressed by Tumor-Infiltrating Immune Cells and is Associated with Poor Outcome for Patients with Renal Cell Carcinoma," *Clin. Cancer Res.*, 13(6): 1757-1761 (2007).
Traxler, "Tyrosine kinase inhibitors in cancer treatment (Part II)," *Exp. Opin. Ther. Patents*, 8(12): 1599-1625 (1998).
U.S. Appl. No. 60/528,340, filed Dec. 9, 2003.
Wang, et al., "Ras inhibition via direct Ras binding—is there a path forward?," *Bioorg. Med. Chem. Lett.*, 22: 5766-5776 (2012).
Written Opinion for PCT/US2017/067801, mailed Jul. 25, 2018, 10 pages.
Written Opinion for PCT/US2018/033714, mailed Jul. 17, 2018, 5 pages.
Written Opinion for PCT/US2018/050044, mailed Oct. 30, 2018, 7 pages.
Written Opinion for PCT/US2019/030593, mailed Aug. 6, 2019, 5 pages.
Written Opinion for PCT/US2019/030606, mailed Jul. 23, 2019, 6 pages.
Written Opinion for PCT/US2019/031535, mailed Jul. 25, 2019, 7 pages.
Written Opinion for PCT/US2019/034974, mailed Aug. 9, 2019, 5 pages.
Written Opinion for PCT/US2019/036397, mailed Aug. 26, 2019, 5 pages.
Written Opinion for PCT/US2019/036626, mailed Jun. 2, 2020, 12 pages.
Written Opinion for PCT/US2019/061815, mailed Mar. 5, 2020, 4 pages.
Written Opinion for PCT/US2019/062051, mailed Mar. 2, 2020, 5 pages.
Written Opinion for PCT/US2019/62064, mailed Oct. 29, 2020, 14 pages.
Written Opinion for PCT/US2020/032686, mailed Aug. 14, 2020, 6 pages.
Written Opinion for PCT/US2020/033831, mailed Jul. 9, 2020, 7 pages.
Written Opinion for PCT/US2020/033832, mailed Jul. 8, 2020, 6 pages.
Written Opinion for PCT/US2020/056874, mailed Feb. 12, 2021, 10 pages.
Written Opinion for PCT/US2020/060415, mailed Feb. 3, 2021, 9 pages.
Written Opinion for PCT/US2020/060421, mailed Feb. 18, 2021, 5 pages.
Written Opinion for PCT/US2020/065050, mailed Mar. 29, 2021, 8 pages.
Xiong, et al., "Covalent Guanosine Mimetic Inhibitors of G12C KRAS," *ACS Med. Chem. Lett.*, 8: 61-66 (2017).
Yan, et al., "Pharmacogenetics and pharmacogenomics in oncology therapeutic antibody development," *BioTechniques*, 29(4): 565-568 (2005).
Yang et al., "Docetaxel and Cisplatin regimen for non-small-cell lung cancer," *Hosp. Pharm.* 48(7):550-557 (2013).
Yang et al., "Effect of dose adjustment on the safety and efficacy of afatinib for EGFR mutation-positive lung adenocarcinoma: post hoc analyses of the randomized LUX-Lung 3 and 6 trials," *Ann. Oncol.* 27(11):2103-2110 (2016).
Yang, et al., "Akt/Protein Kinase B Signaling Inhibitor-2, a Selective Small Molecule Inhibitor of Akt Signaling with Antitumor Activity in Cancer Cells Overexpressing Akt," *Cancer Res.*, 64, 4394-4399 (2004).

(56) References Cited

OTHER PUBLICATIONS

Yang, et al., "Eradication of Established Tumors by a Fully Human Monoclonal Antibody to the Epidermal Growth Factor Receptor without Concomitant Chemotherapy," *Cancer Res.*, 59: 1236-1243 (1999).
Zeng, et al., "Potent and Selective Covalent Quinazoline Inhibitors of KRAS G12C," *Cell Chemical Biology*, 24: 1-12 (2017).
Zimmerman, et al., "Small molecule inhibition of the KRAS-PDEδ interaction impairs oncogenic KRAS signaling," *Nature*, 1-5 (2017).
Lee, "A practical guide to pharmaceutical polymorph screening & selection." *Asian Journal of Pharmaceutical Sciences* 9(4): 163-175 (2014).
Non-Final Office Action for U.S. Appl. No. 17/579,359, mailed Dec. 14, 2023, 13 pages.
Non-Final Office Action for U.S. Appl. No. 17/871,178, mailed Aug. 14, 2023, 9 pages.
Notice of Allowance, mailed Oct. 20, 2023, for U.S. Appl. No. 17/870,573, 7 pages.
Notice of Allowance, mailed Oct. 3, 2023, for U.S. Appl. No. 17/031,607, 7 pages.
Rex et al., "Combination of the KRASG12C inhibitor sotorasib with targeted agents improves anti-tumor efficacy in KRAS p.G12C cancer models" (Abstract and Poster), American Association for Cancer Research (AACR) Annual Meeting 2021; Philadelphia (PA, USA).
Communication Pursuant to Rule 114(2) EPC, Third Party Observation, European Patent Application No. 21183032.8, Dec. 19, 2023, 11 pages.
Communication Pursuant to Rule 114(2) EPC, Third Party Observation, European Patent Application No. 21183032.8, Aug. 16, 2024, 7 pages.
Mainardi et al., "SHP2 is required for growth of KRAS-mutant non-small-cell lung cancer in vivo," Nature Medicine 24(7):961-967 (2018).
Non-Final Office Action for U.S. Appl. No. 18/213,464, mailed Jul. 25, 2024, 18 pages.
Non-Final Office Action for U.S. Appl. No. 18/422,704, mailed Oct. 10, 2024, 8 pages.
Notice of Allowance, mailed Jan. 22, 2024, for U.S. Appl. No. 17/692,026, 9 pages.
Pubchem, http://www.ncbi.nlm.nih.gov/#query=sotorasib, National Library of Medicine, Sotorasib; pp. 1-3 (Jan. 26, 2019).
Fessas et al., "A molecular and preclinical comparison of the PD-1-targeted T-cell checkpoint inhibitors nivolumab and pembrolizumab," Semin. Oncol. 44(2):136-140 (2017).
Nichols et al., "RAS nucleotide cycling underlies the SHP2 phosphatase dependence of mutant Braf-, NF1- and RAS-driven cancers," Nat. Cell. Biol. 20(9):1064-1073 (2018).
Ruess et al., "Mutant KRAS-driven cancers depend on PTPN11/SHP2 phosphatase," Nat. Med. 24(7):954-960 (2018).
Non-Final Office Action for U.S. Appl. No. 18/213,464, mailed Nov. 13, 2024, 13 pages.
Non-Final Office Action for U.S. Appl. No. 18/382,927, mailed Dec. 9, 2024, 7 pages.
Panitumumab, a second anti-EGFR monoclonal antibody formulation, Nikkei Medical, Jun. 10, 2010 (available at https://medical.nikkeibp.co.jp/leaf/all/series/drug/update/201006/515542.html?pr=1) (including Microsoft Machine Translation), pp. 1-4.
CARBOPLATIN Intravenous Infusion 50 mg [SW]; Carboplatin Intravenous Infusion 150 mg [SW]; Carboplatin Intravenous Infusion 450 mg [SW], Antineoplastic, Poisonous drug/Prescription drug, Japanese pharmacopeia, Carboplatin Injection Solution, Jan. 2018 (including Microsoft Machine Translation), pp. 1-8.

* cited by examiner

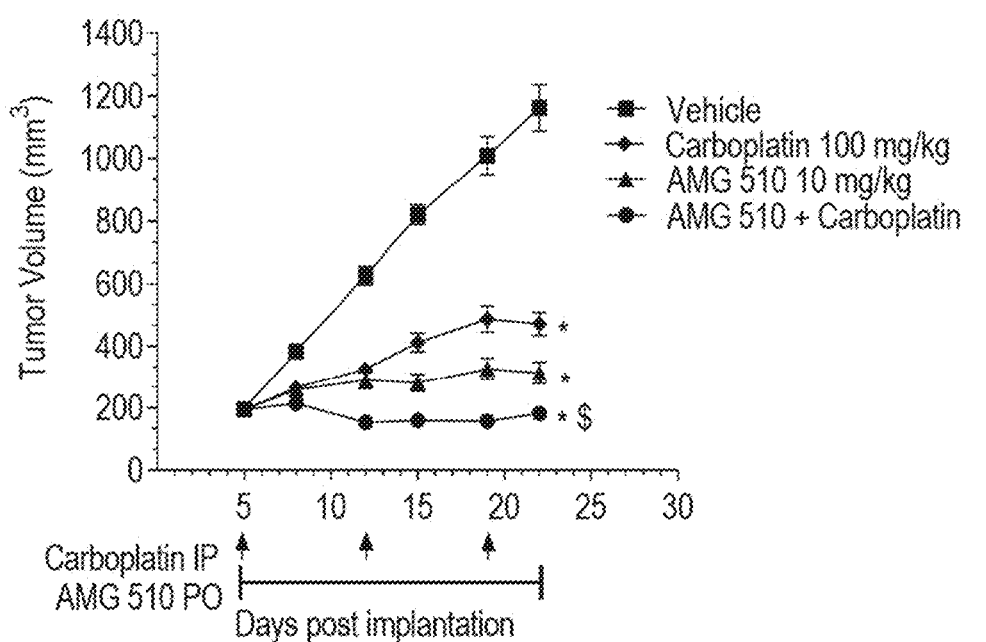

AMG 510 and PD-325901 doses PO, QD
TGI: tumor growth inhibition

* p<0.0001 by Dunnett's post hoc compared to Vehicle
# p<0.0001 regression by Paired T-test
$ p<0.0005 combo compared to either single agent Percent Change in Body Weight

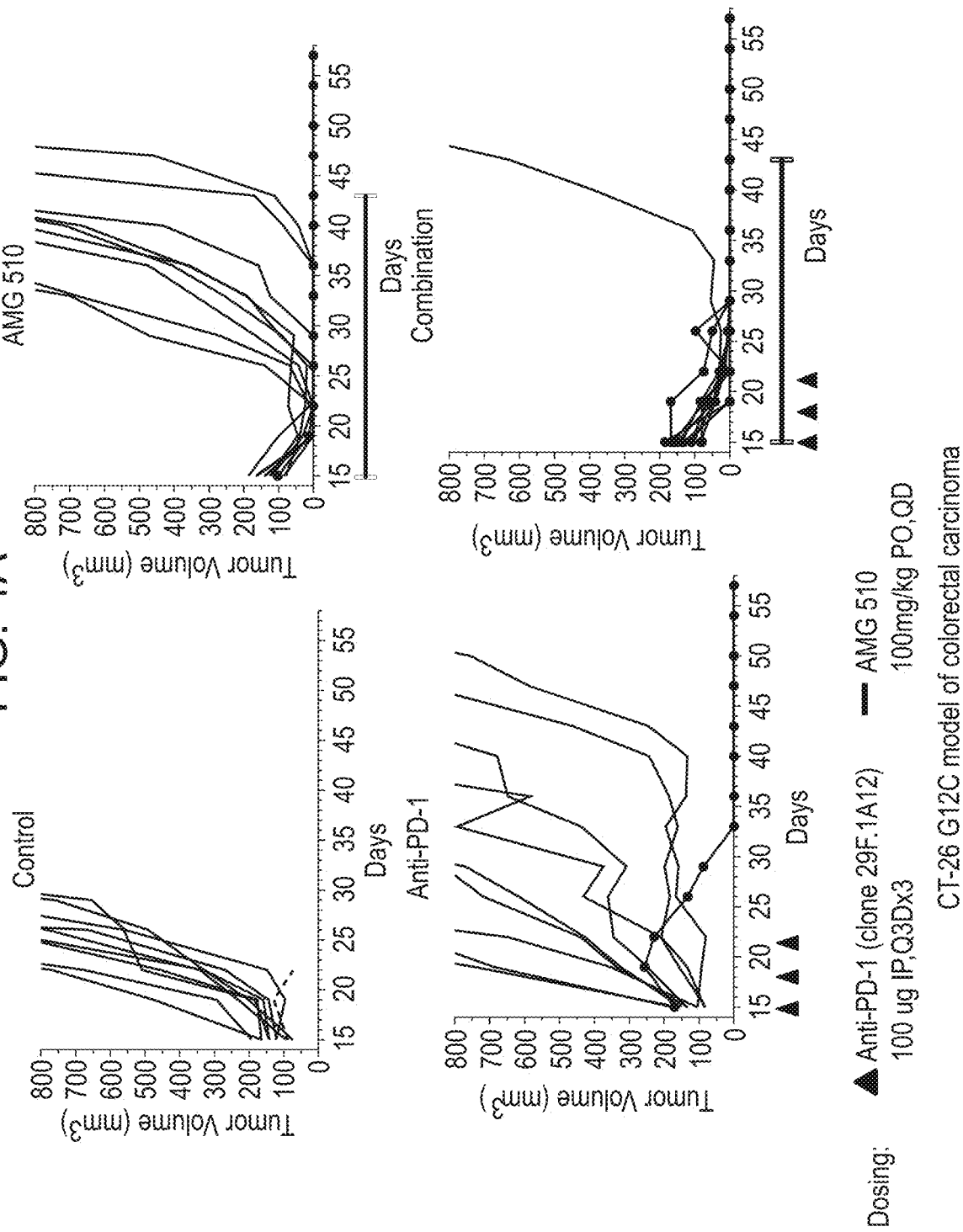

* p= <0.001 compared to control
$ p= <0.005 Combo vs AMG 510 or anti-PD-1

Survival is a surrogate endpoint defined as time to reach tumor size of >800mm$^3$ AMG 510 TREATMENT LEADS TO INCREASE IN CD8+ AND CD4+ T-CELL INFILTRATION IN CT-26 G12C-H10 TUMORS (ABSOLUTE NUMBERS)

\* p= <0.05 compared to vehicle group by Two-way ANOVA followed by Tukey's post hoc
$ p= <0.05 AMG 510 vs anti-PD-1 by paired t-test
# p= <0.05 AMG 510 vs PD-325901 by paired t-test \* = p<0.0005 compared to vehicle control by Two-way ANOVA followed by Tukey's post hoc
$ p<0.05 AMG 510 vs anti-PD-1
# p<0.05 AMG 510 vs PD-325901

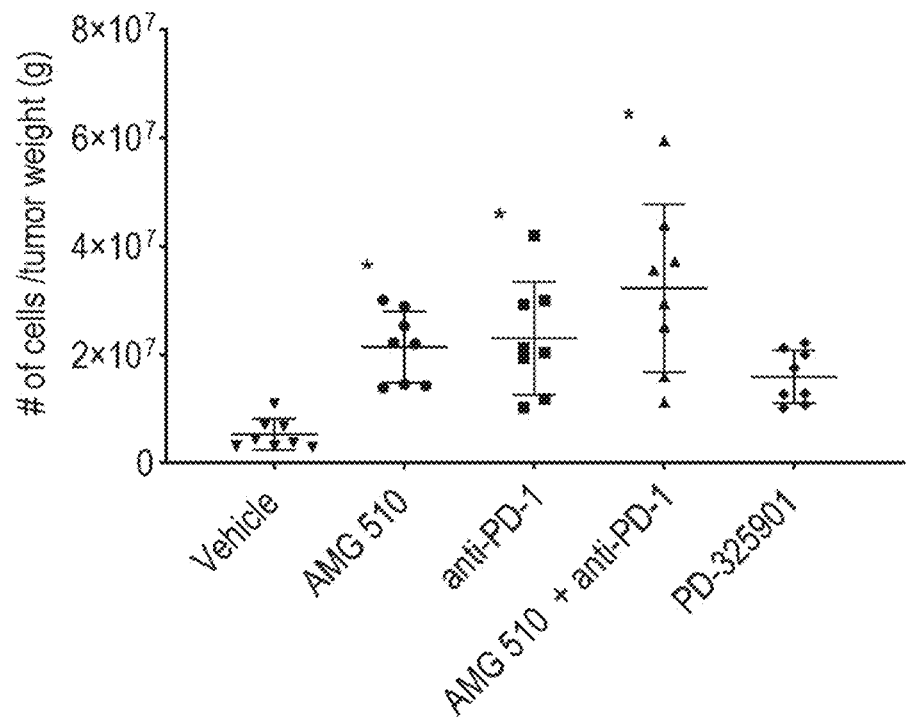

CT26-G12C-H10 Tumor Immune Cell Infiltration
% PD-L1+

CT26-G12C-H10 Tumor Immune Cell Infiltration
PD-L1 MFI

AMG 510 (30mg/kg) or vehicle control was administered for 2 or 7 days, and tumors were harvested for immunophenotyping
*$p<0.01$ by paired t test

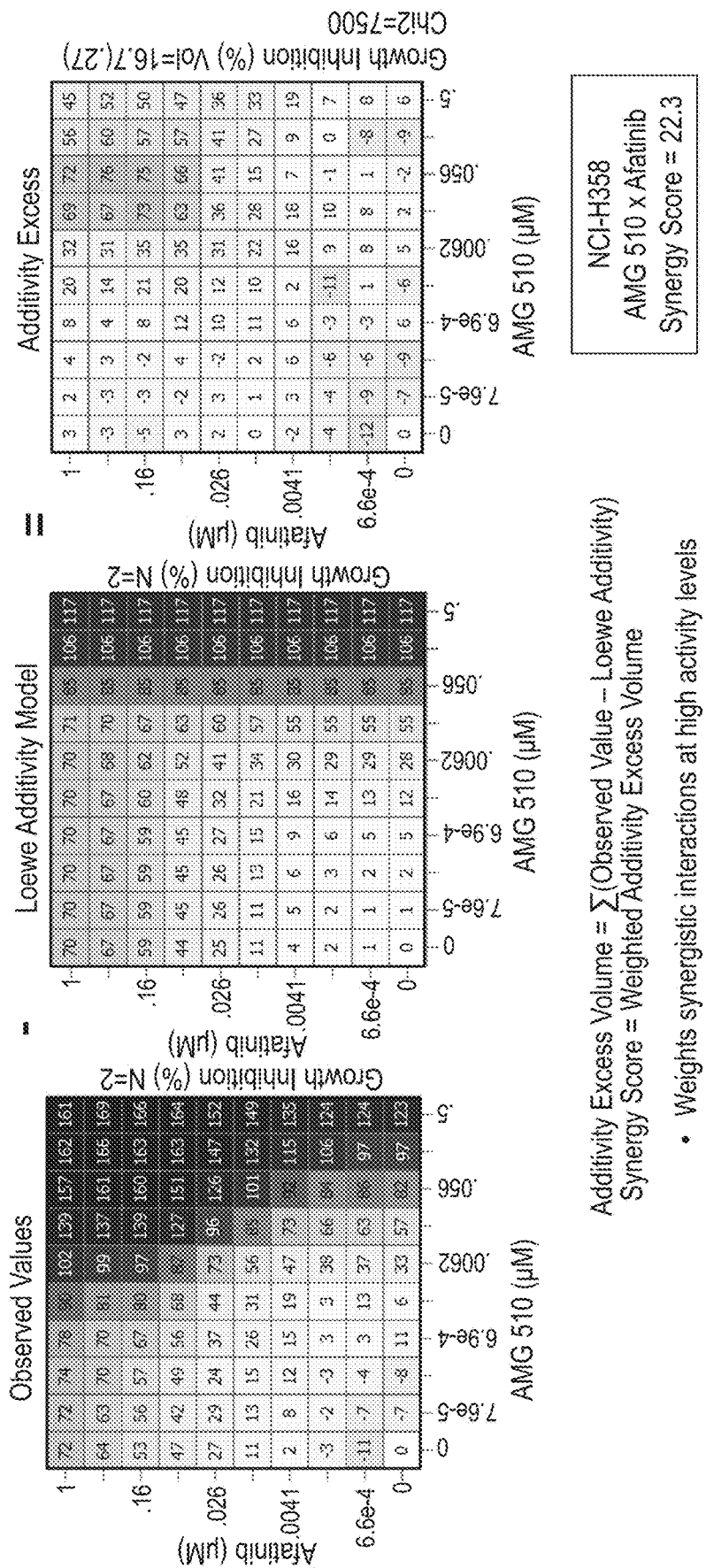

FIG. 8
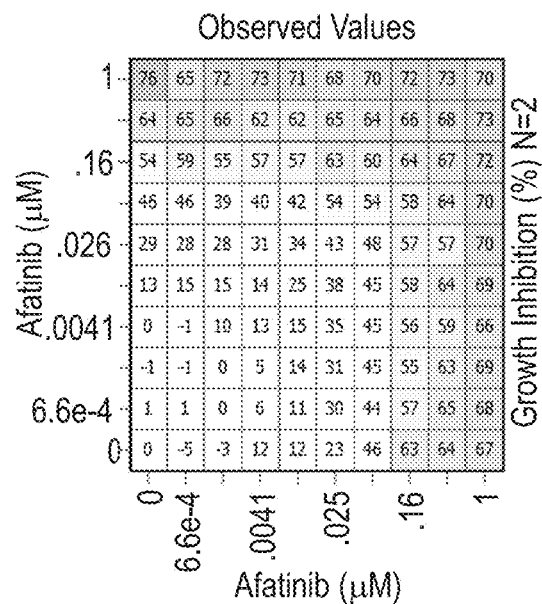
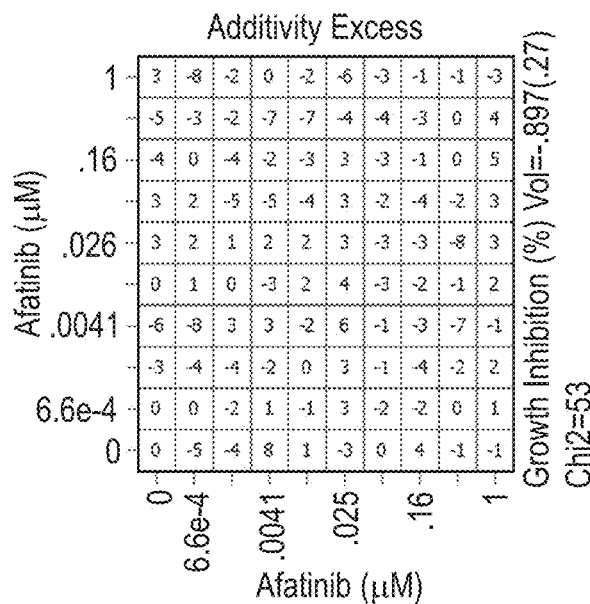
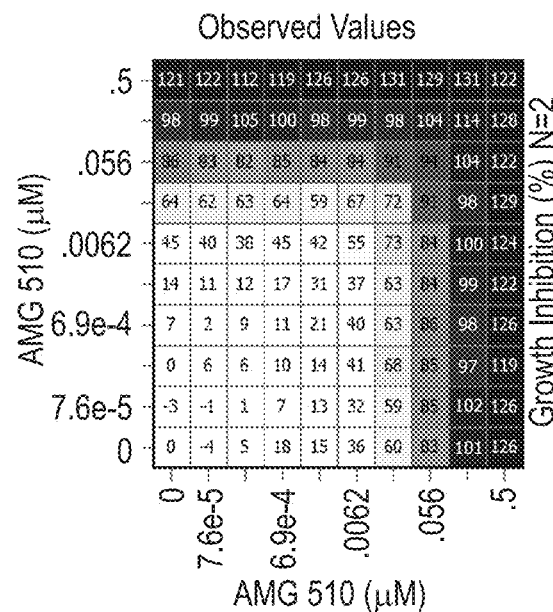
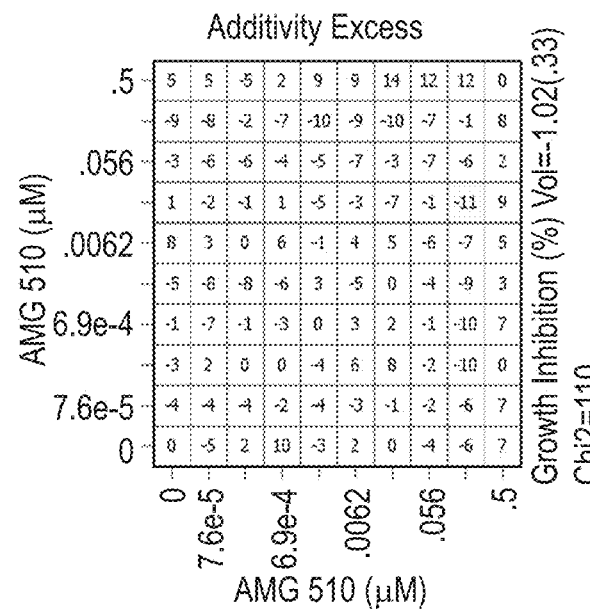
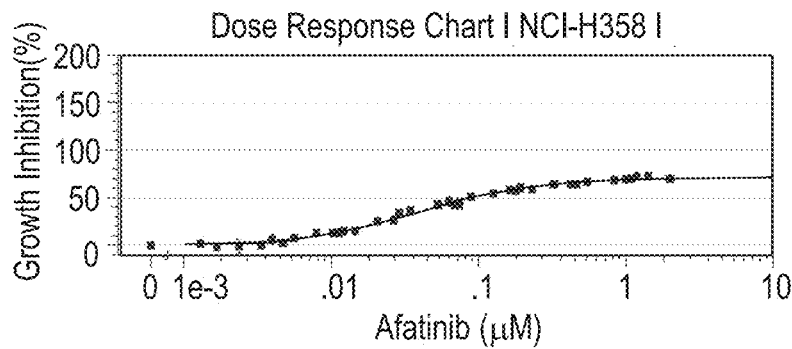

Monolayer (2D)

MIA PaCa-2 (2D) Synergy Score
AMG 510 x Trametinib = 3.06

Spheroid (3D)

MIA PaCa-2 (3D) Synergy Score
AMG 510 x Trametinib = 7.46

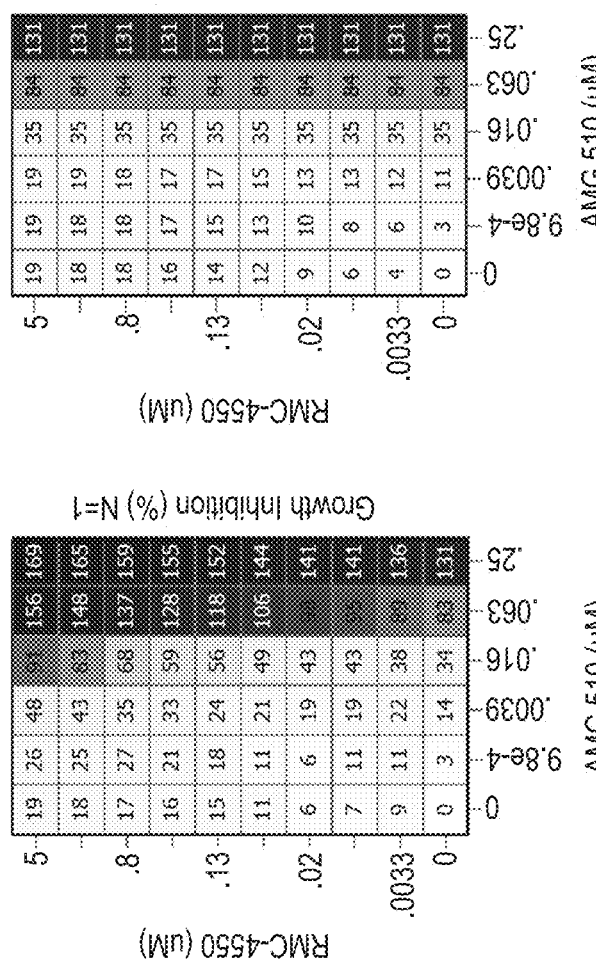
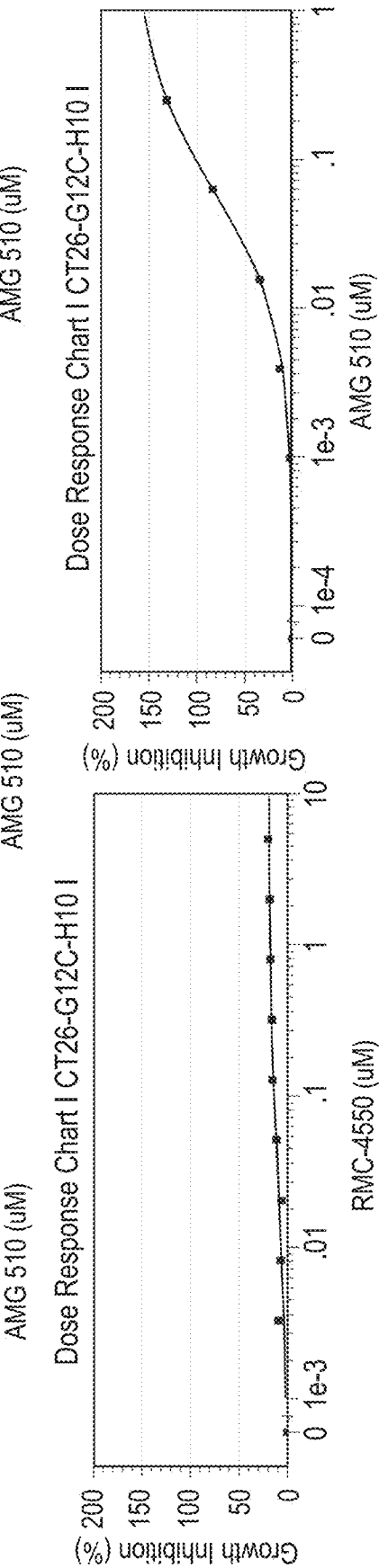
FIG. 31

FIG. 40A
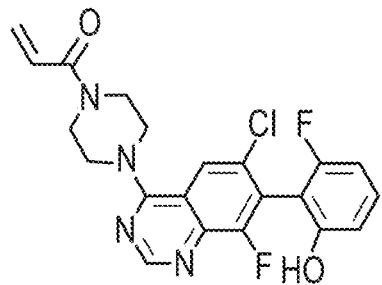
ARS-1620
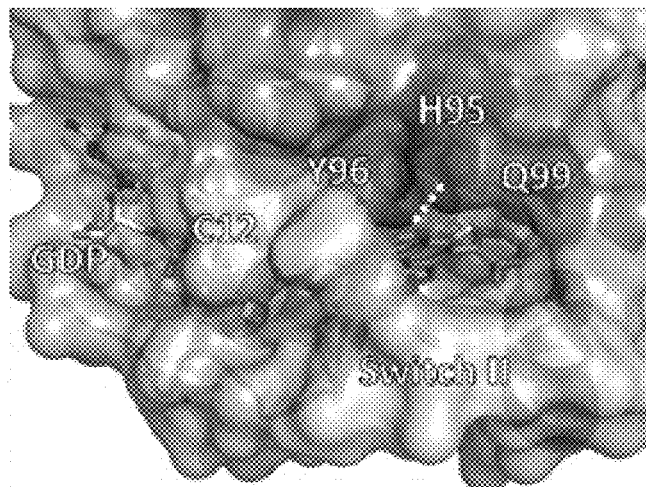
FIG. 40B
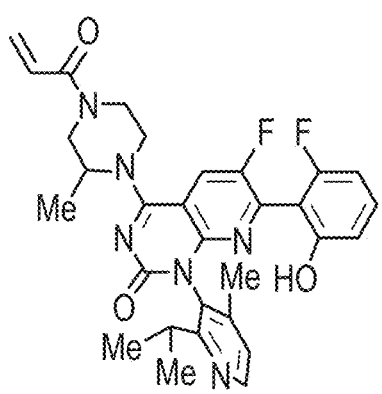
ARS-1620
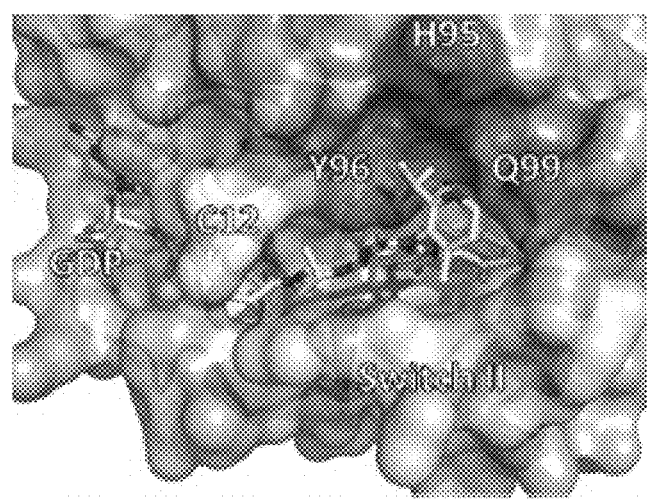

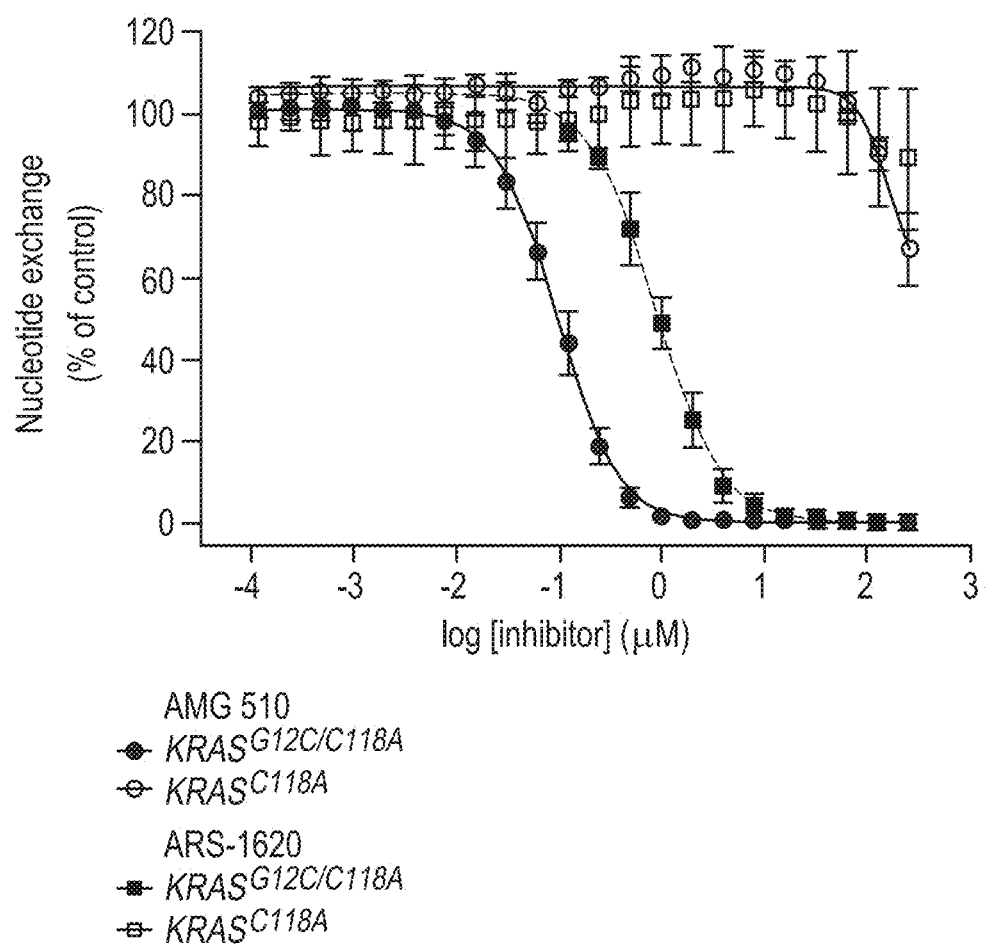

FIG. 46A
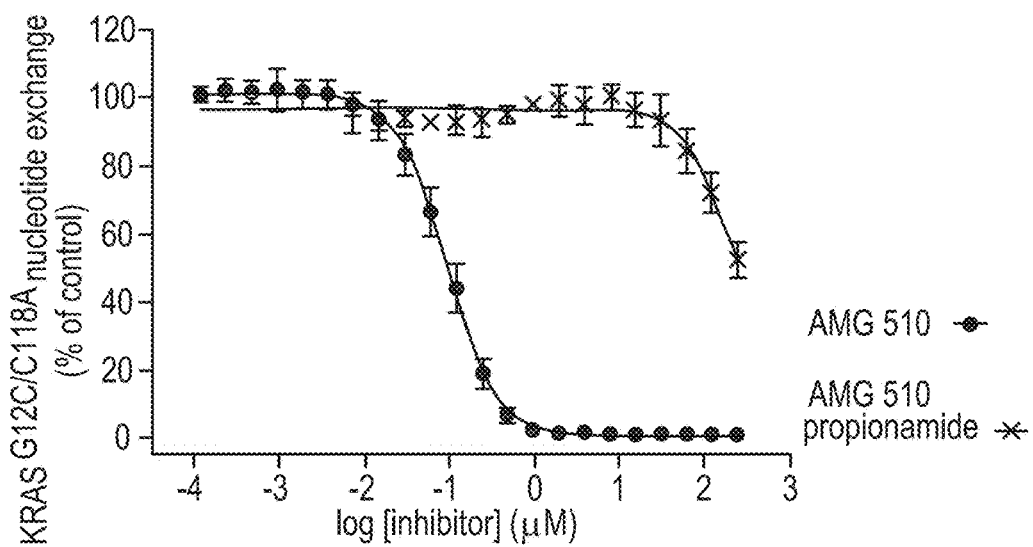
FIG. 46B
| | | Max $k_{inact}$ or $k_{obs}$ (s$^{-1}$) | $K_I$ or $[I]_{50}$ (M) | Max $k_{inact}$/ or $K_I$ or Max $k_{obs}$ /$[I]_{50}$ (M$^{-1}$s$^{-1}$) |
|---|---|---|---|---|
| Mass Spectrometry | AMG 510 | 8.5E-01 ± 7.8E-02 | 8.6E-05 ± 1.4E-05 | 9.8E+03 ± 1.8E+03 |
| | ARS-1620 | 7.3E-02 ± 3.0E-03 | 3.1E-05 ± 3.1E-06 | 2.4E+03 |
| MIA PaCa-2 | AMG 510 | 7.3E-04 ± 3.6E-05 | 2.5E-07 ± 6.2E-09 | 3.0E+03 ± 7.1E+01 |
| | ARS-1620 | 3.1E-04 ± 2.2E-05 | 2.4E-06 ± 6.6E-07 | 1.3E+02 ± 2.7E+01 |
| NCI-H358 | AMG 510 | 8.9E-04 ± 7.4E-05 | 1.3E-07 ± 1.5E-08 | 7.1E+03 ± 1.4E+03 |
| | ARS-1620 | 4.6E-04 ± 3.7E-05 | 1.1E-06 ± 4.9E-07 | 4.8E+02 ± 2.5E+02 |
FIG. 46C
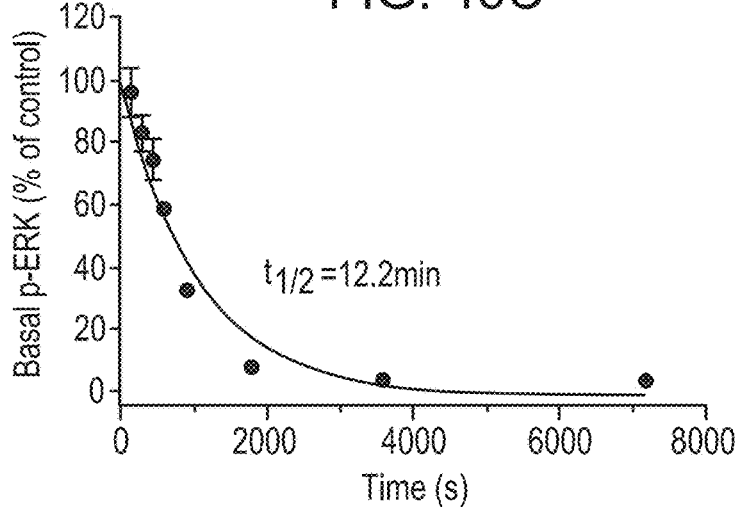

| Cell | Assay duration (h) | Cell doubling time (h) | Without $k_{dil}$ correction | | With $k_{dil}$ correction | | |
|---|---|---|---|---|---|---|---|
| | | | $k_{dec}$ (h$^{-1}$) | $KRAS^{G12C}$ half-life (h) | $k_{dil}$ (h$^{-1}$) | $k_{dec}$ (h$^{-1}$) | $KRAS^{G12C}$ half-life (h) |
| MIA PaCa-2 | 72 | 24 | 0.042 | 17 | 0.006 | 0.035 | 20 |
| NCI-H358 | 96 | 36 | 0.037 | 19 | 0.010 | 0.029 | 24 |

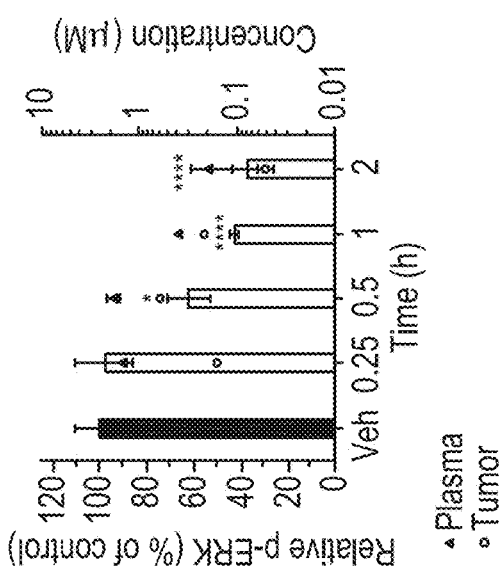
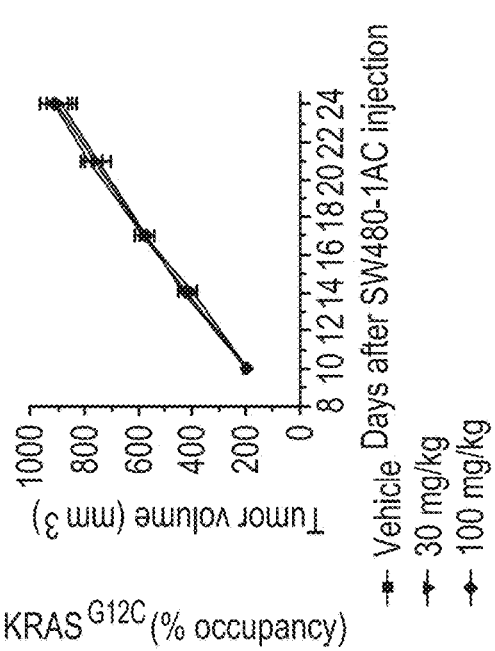
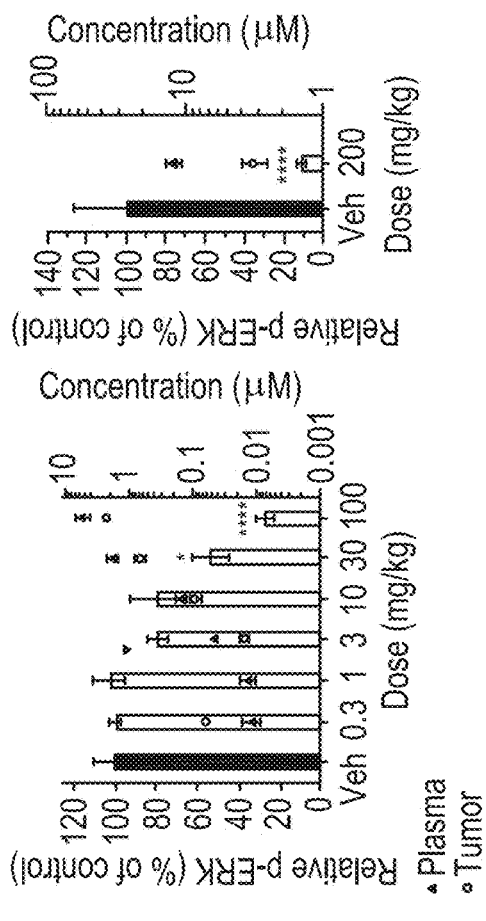
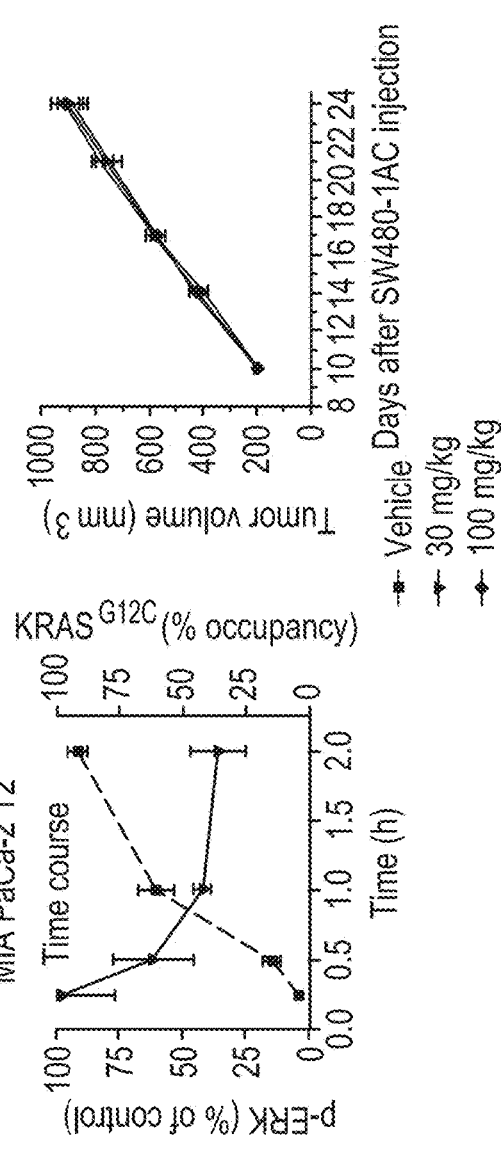
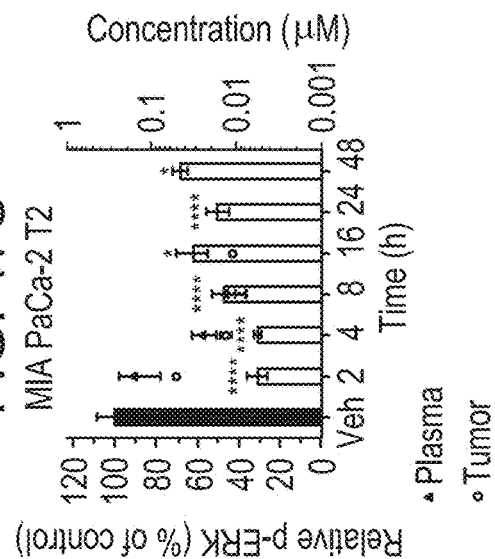

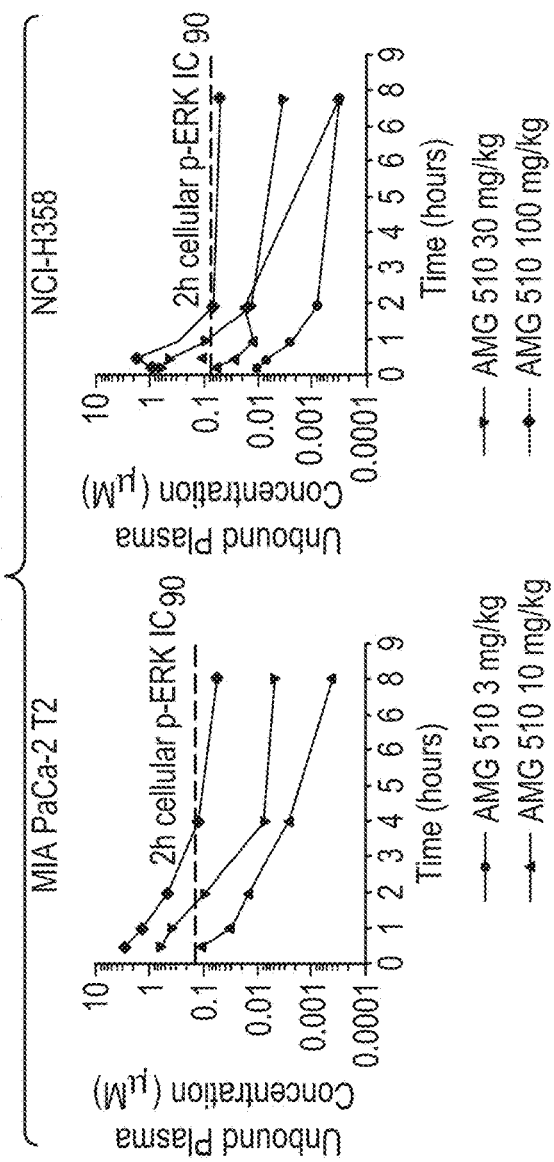
FIG. 47F
FIG. 47G
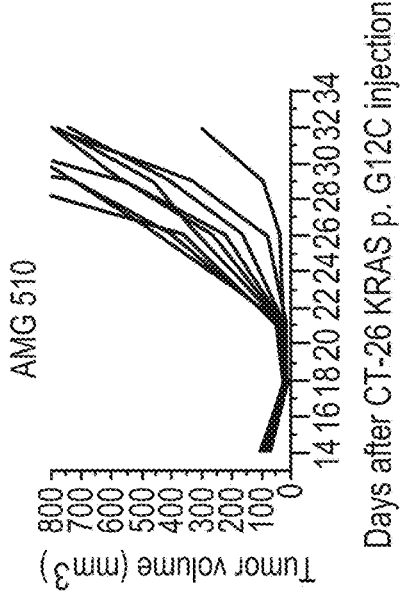
FIG. 47H
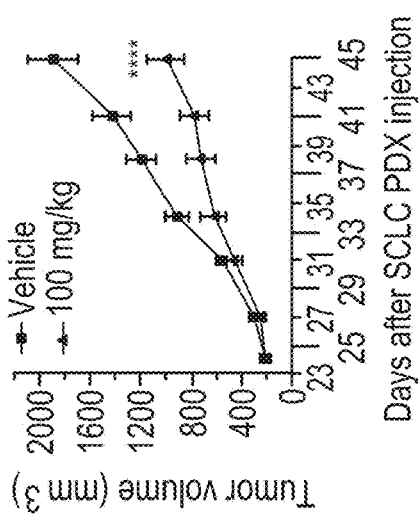
FIG. 47I
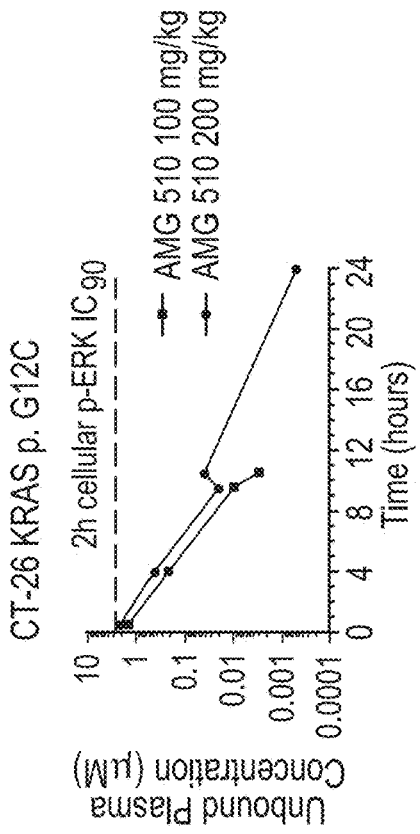

| | Synergy Score Combination Self-crosses | | Max [Inhibitor] (μM) |
|---|---|---|---|
| RMC-4550 vs AMG 510 | 2.15 | | |
| | 0.107 | RMC-4550 | 10 (1:3) |
| | 0.140 | AMG 510 | 10 (1:3) |
| Trametinib vs AMG 510 | 0.817 | | |
| | 0.141 | Trametinib | 0.5 (1:2) |
| | 0.140 | AMG 510 | 10 (1:3) |
| AMG 511 vs AMG 510 | 3.87 | | |
| | 0.782 | AMG 511 | 3 (1:3) |
| | 0.140 | AMG 510 | 10 (1:3) |
| AMG 511 vs Trametinib | 3.02 | | |
| | 0.782 | AMG 511 | 3 (1:3) |
| | 0.141 | Trametinib | 0.5 (1:2) |

CT-26 KRAS p.G12C - Spheroid

| | Growth Inhibition (%) | Loewe Excess | Synergy Score Combination Self-crosses | | Max [Inhibitor] (µM) |
|---|---|---|---|---|---|
| Afatinib | (heatmap) | (heatmap) | 10.8 | | |
| | | | 1.37 | Afatinib | 5 (1:2.5) |
| | | | 1.47 | AMG 510 | 0.25 (1:4) |
| RMC-4550 | (heatmap) | (heatmap) | 11.7 | | |
| | | | 4.14 | RMC-4550 | 5 (1:2.5) |
| | | | 1.47 | AMG 510 | 0.25 (1:4) |
| Trametinib | (heatmap) | (heatmap) | 2.63 | | |
| | | | 2.21 | Trametinib | 0.01 (1:2.5) |
| | | | 1.47 | AMG 510 | 0.25 (1:4) |
| AMG 511 | (heatmap) | (heatmap) | 10.8 | | |
| | | | 2.24 | AMG 511 | 0.5 (1:2.5) |
| | | | 1.47 | AMG 510 | 0.25 (1:4) |

AMG 510      AMG 510

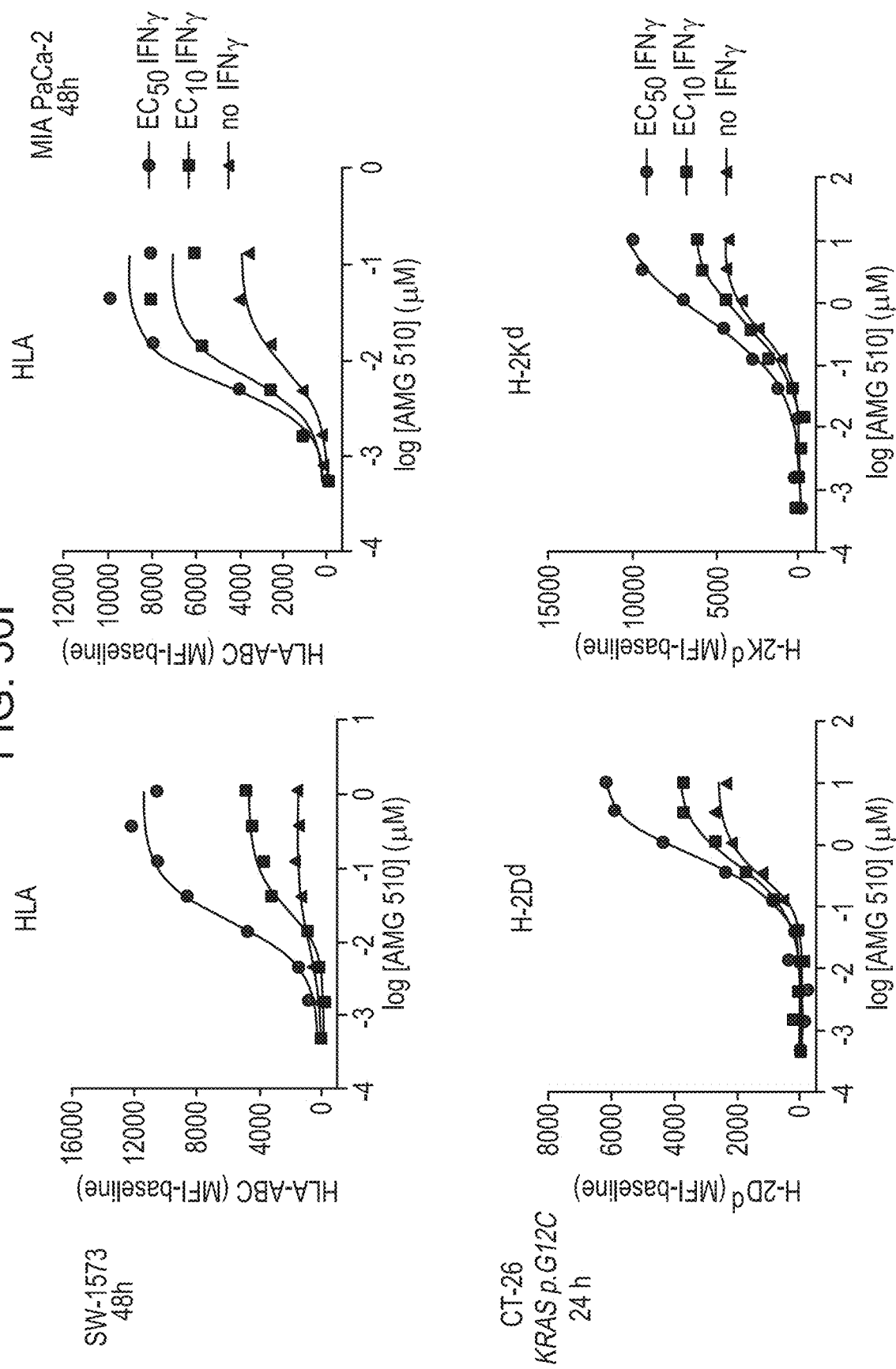

SEQUENCE LISTING

```
Sequence total quantity: 21
SEQ ID NO: 1                moltype = AA  length = 5
FEATURE                     Location/Qualifiers
REGION                      1..5
                            note = Synthetic peptide
source                      1..5
                            mol_type = protein
                            organism = synthetic construct
SEQUENCE: 1
SYDMS                                                                   5

SEQ ID NO: 2                moltype = AA  length = 16
FEATURE                     Location/Qualifiers
REGION                      1..16
                            note = Synthetic peptide
source                      1..16
                            mol_type = protein
                            organism = synthetic construct
SEQUENCE: 2
LISGGGSQTY YAESVK                                                      16

SEQ ID NO: 3                moltype = AA  length = 11
FEATURE                     Location/Qualifiers
REGION                      1..11
                            note = Synthetic peptide
source                      1..11
                            mol_type = protein
                            organism = synthetic construct
SEQUENCE: 3
PSGHYFYAMD V                                                           11

SEQ ID NO: 4                moltype = AA  length = 11
FEATURE                     Location/Qualifiers
REGION                      1..11
                            note = Synthetic peptide
source                      1..11
                            mol_type = protein
                            organism = synthetic construct
SEQUENCE: 4
RASQGISNWL A                                                           11

SEQ ID NO: 5                moltype = AA  length = 7
FEATURE                     Location/Qualifiers
REGION                      1..7
                            note = Synthetic peptide
source                      1..7
                            mol_type = protein
                            organism = synthetic construct
SEQUENCE: 5
AASSLQS                                                                 7
```

```
SEQ ID NO: 6              moltype = AA   length = 9
FEATURE                   Location/Qualifiers
REGION                    1..9
                          note = Synthetic peptide
source                    1..9
                          mol_type = protein
                          organism = synthetic construct
SEQUENCE: 6
QQAESFPHT                                                                    9

SEQ ID NO: 7              moltype = AA   length = 120
FEATURE                   Location/Qualifiers
REGION                    1..120
                          note = Synthetic peptide
source                    1..120
                          mol_type = protein
                          organism = synthetic construct
SEQUENCE: 7
EVQLLESGGG LVQPGGSLRL SCAASGFTFS SYDMSWVRQA PGKGLEWVSL ISGGGSQTYY    60
AESVKGRFTI SRDNSKNTLY LQMNSLRAED TAVYFCASPS GHYFYAMDVW GQGTTVTVSS   120

SEQ ID NO: 8              moltype = AA   length = 107
FEATURE                   Location/Qualifiers
REGION                    1..107
                          note = Synthetic peptide
source                    1..107
                          mol_type = protein
                          organism = synthetic construct
SEQUENCE: 8
DIQMTQSPSS VSASVGDRVT ITCRASQGIS NWLAWYQQKP GKAPKLLIFA ASSLQSGVPS    60
RFSGSGSGTD FTLTISSLQP EDFATYYCQQ AESFPHTFGG GTKVEIK                 107

SEQ ID NO: 9              moltype = AA   length = 472
FEATURE                   Location/Qualifiers
REGION                    1..472
                          note = Synthetic peptide
source                    1..472
                          mol_type = protein
                          organism = synthetic construct
SEQUENCE: 9
MDMRVPAQLL GLLLLWLRGA RCEVQLLESG GGLVQPGGSL RLSCAASGFT FSSYDMSWVR    60
QAPGKGLEWV SLISGGGSQT YYAESVKGRF TISRDNSKNT LYLQMNSLRA EDTAVYFCAS   120
PSGHYFYAMD VWGQGTTVTV SSASTKGPSV FPLAPSSKST SGGTAALGCL VKDYFPEPVT   180
VSWNSGALTS GVHTFPAVLQ SSGLYSLSSV VTVPSSSLGT QTYICNVNHK PSNTKVDKKV   240
EPKSCDKTHT CPPCPAPELL GGPSVFLFPP KPKDTLMISR TPEVTCVVVD VSHEDPEVKF   300
NWYVDGVEVH NAKTKPCEEQ YGSTYRCVSV LTVLHQDWLN GKEYKCKVSN KALPAPIEKT   360
ISKAKGQPRE PQVYTLPPSR EEMTKNQVSL TCLVKGFYPS DIAVEWESNG QPENNYKTTP   420
PVLDSDGSFF LYSKLTVDKS RWQQGNVFSC SVMHEALHNH YTQKSLSLSP GK           472

SEQ ID NO: 10             moltype = AA   length = 236
FEATURE                   Location/Qualifiers
REGION                    1..236
                          note = Synthetic peptide
source                    1..236
                          mol_type = protein
                          organism = synthetic construct
SEQUENCE: 10
MDMRVPAQLL GLLLLWLRGA RCDIQMTQSP SSVSASVGDR VTITCRASQG ISNWLAWYQQ    60
KPGKAPKLLI FAASSLQSGV PSRFSGSGSG TDFTLTISSL QPEDFATYYC QQAESFPHTF   120
GGGTKVEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC       236

SEQ ID NO: 11             moltype = DNA   length = 15
FEATURE                   Location/Qualifiers
misc_feature              1..15
                          note = Synthetic polynucleotide
source                    1..15
                          mol_type = other DNA
                          organism = synthetic construct
SEQUENCE: 11
agctatgaca tgagc                                                             15

SEQ ID NO: 12             moltype = DNA   length = 51
FEATURE                   Location/Qualifiers
misc_feature              1..51
                          note = Synthetic polynucleotide
source                    1..51
                          mol_type = other DNA
```

```
                        organism = synthetic construct
SEQUENCE: 12
cttattagtg gtggtggtag tcaaacatac tacgcagaat ccgtgaaggg c          51

SEQ ID NO: 13           moltype = DNA   length = 33
FEATURE                 Location/Qualifiers
misc_feature            1..33
                        note = Synthetic polynucleotide
source                  1..33
                        mol_type = other DNA
                        organism = synthetic construct
SEQUENCE: 13
cccagtggcc actacttcta cgctatggac gtc                              33

SEQ ID NO: 14           moltype = DNA   length = 33
FEATURE                 Location/Qualifiers
misc_feature            1..33
                        note = Synthetic polynucleotide
source                  1..33
                        mol_type = other DNA
                        organism = synthetic construct
SEQUENCE: 14
cgggcgagtc aggtattag caactggtta gcc                               33

SEQ ID NO: 15           moltype = DNA   length = 21
FEATURE                 Location/Qualifiers
misc_feature            1..21
                        note = Synthetic polynucleotide
source                  1..21
                        mol_type = other DNA
                        organism = synthetic construct
SEQUENCE: 15
gctgcatcca gtttgcaaag t                                           21

SEQ ID NO: 16           moltype = DNA   length = 27
FEATURE                 Location/Qualifiers
misc_feature            1..27
                        note = Synthetic polynucleotide
source                  1..27
                        mol_type = other DNA
                        organism = synthetic construct
SEQUENCE: 16
caacaggctg aaagtttccc tcacact                                     27

SEQ ID NO: 17           moltype = DNA   length = 360
FEATURE                 Location/Qualifiers
misc_feature            1..360
                        note = Synthetic polynucleotide
source                  1..360
                        mol_type = other DNA
                        organism = synthetic construct
SEQUENCE: 17
gaggtgcagc tgttggagtc tgggggaggc ttggtacagc ctgggggtc cctgagactc  60
tcctgtgcag cctctggatt caccttagc agctatgaca tgagctgggt ccgcaggct   120
ccagggaagg ggctggaatg ggtctcactt attagtggtg gtggtagtca aacatactac 180
gcagaatccg tgaagggccg gttcaccatc tccagagaca attccaagaa cacgctgtat 240
ctgcaaatga acagcctgag agccgaggac acggccgtat atttctgtgc gtcccccagt 300
ggccactact tctacgctat ggacgtctgg ggccaaggga ccacggtcac cgtctcctca 360

SEQ ID NO: 18           moltype = DNA   length = 321
FEATURE                 Location/Qualifiers
misc_feature            1..321
                        note = Synthetic polynucleotide
source                  1..321
                        mol_type = other DNA
                        organism = synthetic construct
SEQUENCE: 18
gacatccaga tgacccagtc tccatcttcc gtgtctgcat ctgttggaga cagagtcacc 60
atcacttgtc gggcgagtca gggtattagc aactggttag cctggtatca gcagaaacca 120
gggaaagccc ctaagctcct gatctttgct gcatccagtt tgcaaagtgg gtcccatca  180
aggttcagcg gcagtggatc tgggacagat ttcaccctca ccatcagcag cctgcagcct 240
gaagatttg caacttacta ttgtcaacag gctgaaagtt tccctcacac tttcggcgga 300
gggaccaagg tggagatcaa a                                           321

SEQ ID NO: 19           moltype = DNA   length = 1416
FEATURE                 Location/Qualifiers
misc_feature            1..1416
                        note = Synthetic polynucleotide
source                  1..1416
```

```
                        mol_type = other DNA
                        organism = synthetic construct
SEQUENCE: 19
atggacatga gggtgcccgc tcagctcctg gggctcctgc tgctgtggct gagaggtgcg    60
cgctgtgagg tgcagctgtt ggagtctggg ggaggcttgg tacagcctgg ggggtccctg   120
agactctcct gtgcagcctc tggattcacc tttagcagct atgacatgag ctgggtccgc   180
caggctccag ggaaggggct ggaatgggtc tcacttatta gtggtggtgg tagtcaaaca   240
tactacgcag aatccgtgaa gggccggttc accatctcca gagacaattc caagaacacg   300
ctgtatctgc aaatgaacag cctgagagcc gaggacacgg cctatatttt ctgtgcgtcc   360
cccagtggcc actacttcta cgctatggac gtctggggcc aagggaccac ggtcaccgtc   420
tcctcagcct ccaccaaggg cccatcggtc ttccccctgg cacccctcct caagagcacc   480
tctgggggca cagcggccct gggctgcctg gtcaaggact acttcccga accggtgacg   540
gtgtcgtgga actcaggcgc cctgaccagc ggcgtgcaca ccttcccggc tgtcctacag   600
tcctcaggac tctactccct cagcagcgtg gtgaccgtgc cctccagcag cttgggcacc   660
cagacctaca tctgcaacgt gaatcacaag cccagcaaca ccaaggtgga caagaaagtt   720
gagcccaaat cttgtgacaa aactcacaca tgcccaccgt gcccagcacc tgaactcctg   780
gggggaccgt cagtcttcct cttccccca aaacccaagg acaccctcat gatctcccgg   840
acccctgagg tcacatgcgt ggtggtggac gtgagccacg aagacctga ggtcaagttc   900
aactggtacg tggacggcgt ggaggtgcat aatgccaaga caaagccgtg cgaggagcag   960
tacggcagca cgtaccgttg cgtcagcgtc ctcaccgtcc tgcaccagga ctggctgaat  1020
ggcaaggagt acaagtgcaa ggtgtccaac aaagcccctcc cagcccccat cgagaaaacc  1080
atctccaaag ccaaagggca gccccgagaa ccacaggtgt acaccctgcc cccatcccgg  1140
gaggagatga ccaagaacca ggtcagcctg acctgcctgg tcaaaggctt ctatcccagc  1200
gacatcgccg tggagtggga gagcaatggg cagccggaga acaactacaa gaccacgcct  1260
cccgtgctga ctccgacgg ctccttcttc ctctatagca agctcaccgt ggacaagagc  1320
aggtggcagc aggggaacgt cttctcatgc tccgtgatgc atgaggctct gcacaaccac  1380
tacacgcaga agagcctctc cctgtctccg ggtaaa                            1416

SEQ ID NO: 20           moltype = DNA  length = 708
FEATURE                 Location/Qualifiers
misc_feature            1..708
                        note = Synthetic polynucleotide
source                  1..708
                        mol_type = other DNA
                        organism = synthetic construct
SEQUENCE: 20
atggacatga gggtgcccgc tcagctcctg gggctcctgc tgctgtggct gagaggtgcg    60
cgctgtgaca tccagatgac ccagtctcca tcttccgtgt ctgcatctgt tggagacaga   120
gtcaccatca cttgtcgggc gagtcagggt attagcaact ggttagcctg gtatcagcag   180
aaaccaggga aagcccctaa gctcctgatc tttgctgcat ccagtttgca aagtggggtc   240
ccatcaaggt tcagcggcag tggatctggg acagatttca ccctcaccat cagcagcctg   300
cagcctgaag attttgcaac ttactattgt caacaggcta aagtttccc tcacactttc   360
ggcggaggga ccaaggtgga gatcaaacga acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt                708

SEQ ID NO: 21           moltype = AA  length = 20
FEATURE                 Location/Qualifiers
REGION                  1..20
                        note = CRISPR Molecule
source                  1..20
                        mol_type = protein
                        organism = synthetic construct
SEQUENCE: 21
CTTGTGATGG TTGGAGCTGA                                                 20
```

COMBINATION THERAPY INCLUDING A KRAS$^{G12C}$ INHIBITOR AND ONE OR MORE ADDITIONAL PHARMACEUTICALLY ACTIVE AGENTS FOR THE TREATMENT OF CANCERS

CROSS-REFERENCE TO RELATED APPLICATIONS

The present application is a continuation of U.S. patent application Ser. No. 17/870,573, filed Jul. 21, 2022, which is a continuation of U.S. patent application Ser. No. 16/687,563, filed on Nov. 18, 2019, now U.S. Pat. No. 11,439,645, which claims the benefit of U.S. Provisional Application No. 62/865,819, filed Jun. 24, 2019, U.S. Provisional Application No. 62/821,376, filed Mar. 20, 2019, and U.S. Provisional Application No. 62/769,355, filed Nov. 19, 2018, all of which are incorporated herein by reference in their entireties for all purposes.

SEQUENCE LISTINGS

The present application is being filed along with a sequence listing in electronic format. The sequence listing is provided as a file entitled A-2326-US06-CNT_SeqList_ST26.xml, created Dec. 19, 2023, which is 30.5 kb in size. The information in the electronic format of the sequence listing is incorporated herein by reference in its entirety.

FIELD OF THE INVENTION

The present invention provides combination therapy that includes a KRAS$^{G12C}$ inhibitor and one or more additional pharmaceutically active agents, particularly for the treatment of cancers. The invention also relates to pharmaceutical compositions that contain a KRAS$^{G12C}$ inhibitor and one or more additional pharmaceutically active agents for the treatment of cancers.

BACKGROUND OF THE INVENTION

KRAS gene mutations are common in pancreatic cancer, lung adenocarcinoma, colorectal cancer, gall bladder cancer, thyroid cancer, and bile duct cancer. KRAS mutations are also observed in about 25% of patients with NSCLC, and some studies have indicated that KRAS mutations are a negative prognostic factor in patients with NSCLC. Recently, V-Ki-ras2 Kirsten rat sarcoma viral oncogene homolog (KRAS) mutations have been found to confer resistance to epidermal growth factor receptor (EGFR) targeted therapies in colorectal cancer; accordingly, the mutational status of KRAS can provide important information prior to the prescription of TKI therapy. Taken together, there is a need for new medical treatments for patients with pancreatic cancer, lung adenocarcinoma, or colorectal cancer, especially those who have been diagnosed to have such cancers characterized by a KRAS mutation and including those who have progressed after chemotherapy. Oncogenic KRAS mutations at residues G12, G13, and Q61 represent the most common RAS mutations found in solid malignancies. Recently it has been demonstrated that KRAS$^{G12C}$ can be targeted with covalent small molecule inhibitors which react with the mutant cysteine adjacent to the switch II pocket (SIIP), locking KRAS in its inactive GDP-bound state.

KRAS is the most frequently mutated oncogene in human cancer and encodes a key signaling protein in tumors. The KRAS$^{G12C}$ mutant harbors a cysteine that has been exploited to design covalent inhibitors with promising preclinical activity. We optimized a series of inhibitors with novel binding interactions and markedly enhanced potency and selectivity. These efforts led to the discovery of AMG 510, the first KRAS$^{G12C}$ inhibitor in clinical development. Preclinically AMG 510 treatment regressed KRAS p.G12C tumors and significantly improved the anti-tumor efficacy of chemotherapy and targeted agents. In immune-competent mice. AMG 510 treatment resulted in a pro-inflammatory tumor microenvironment and produced durable cures in combination with immune checkpoint inhibition. Cured mice rejected the growth of isogenic KRAS p.G12D tumors, suggesting adaptive immunity against shared antigens. AMG 510 demonstrated preliminary evidence of clinical anti-tumor activity in the first dosing cohort and represents a potentially transformative therapy for patients lacking effective treatments.

The KRAS oncoprotein is a GTPase that is an essential mediator of intracellular signaling pathways involved in tumor cell growth and survival. In normal cells. KRAS functions as a molecular switch, alternating between inactive GDP-bound and active GTP-bound states. Transition between these states is facilitated by guanine nucleotide exchange factors (GEFs) which load GTP and activate KRAS, and GTP hydrolysis, which is catalyzed by GTPase-activating proteins (GAPs) to inactivate KRAS. GTP-binding to KRAS promotes binding of effectors to trigger signal transduction pathways including RAF-MEK-ERK (MAPK). Somatic, activating mutations in KRAS are a hallmark of cancer and prevent the association of GAPs, thereby stabilizing effector-binding and enhancing KRAS signaling. Patients with KRAS mutant tumors have significantly poorer outcomes and worse prognosis. While there are clinically-approved inhibitors of several MAPK pathway proteins (e.g. MEK. BRAF. EGFR) for a subset of tumor types, to date there have been no clinical molecules that are selective for KRAS mutant tumors. Moreover, several MAPK-pathway targeted therapies are contra-indicated for treatment of KRAS mutant tumors due to lack of clinical efficacy. Additionally, non-tumor or non-mutant selective therapies can introduce on-target toxicities due to inhibition of MAPK signaling in normal cells. This might limit the utility for combining such agents with standard-of-care or immunotherapy. Thus, there exists a significant unmet need for the development of tumor-selective therapies that do not introduce liabilities for normal cells.

KRAS p.G12C is present in approximately 13% of lung adenocarcinoma, 3% of colorectal cancer, and 2% of other solid tumors. The mutant cysteine of KRAS$^{G12C}$ resides adjacent to a pocket (P2) present in the inactive GDP-bound form of KRAS. The proximity of P2 and a mutant cysteine led to a broad search for covalent inhibitors. The first reported electrophile screen of KRAS$^{G12C}$ led to the eventual identification of ARS-1620, which demonstrates in vivo efficacy in preclinical KRAS p.G12C models. While Araxes Pharma's ARS-1620 was a milestone for proof-of-concept, mutant-selective KRAS inhibition, it was positioned as a tool compound for preclinical studies. The scientists at Amgen, Inc. identified a series of novel acrylamide-based molecules that utilize a previously unexploited surface groove in KRAS$^{G12C}$ to substantially enhance potency and selectivity. Intensive electrophile-screening and structure-based design culminated in the discovery of AMG 510, the first KRAS$^{G12C}$ inhibitor to reach clinical testing in humans (See www.clinicaltrials.gov NCT03600883). The present invention comprises the compelling preclinical activity of AMG 510, its ability to enhance tumor-cell killing as monotherapy or when combined with other therapies, and the dramatic impact on immune cell infiltration which renders the tumor microenvironment exquisitely sensitive to immunotherapy. Preliminary evidence for clinical efficacy is also presented herein.

SUMMARY OF THE INVENTION

The present invention comprises a pharmaceutical composition comprising

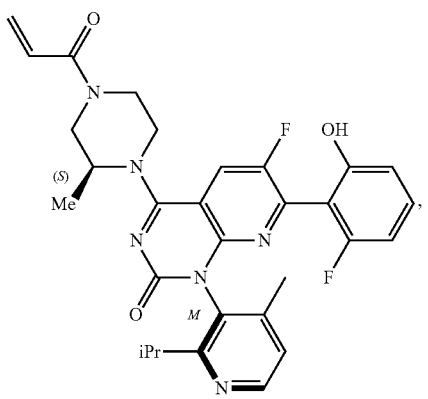

AMG 510 or a pharmaceutically acceptable salt thereof; and one or more therapeutic or pharmaceutically active agents; and a pharmaceutically acceptable excipient.

The present invention further comprises a method of treating cancers, such as solid tumors, including but not limited to lung, colon and pancreatic cancer with a combination of AMG 510, or a pharmaceutically acceptable salt, and at least one therapeutic agent, wherein the therapeutic agent is selected from an anti-PD-1 antibody, a chemotherapeutic agent, a MEK inhibitor, an EGFR inhibitor, a TOR inhibitor, a SHP2 inhibitor, PI3K inhibitor, and an AKT inhibitor.

The present invention further comprises an isolated cell line comprising two $KRAS^{G12C}$ alleles, wherein the cell line is CT-26 KRAS p.G12C.

The present invention further comprises a method of generating a cell line comprising two $KRAS^{G12C}$ alleles, the method comprising:
a) incubating a cell line comprising two $KRAS^{G12D}$ alleles with a CRISPR construct that induces the replacement of a nucleotide on both the two KRAS alleles such that two $KRAS^{G12C}$ alleles are formed; and
b) isolating the cell line comprising the two $KRAS^{G12C}$ alleles.

First Set of Embodiments

1. In one embodiment of the present invention, the present invention comprises a method of treating pancreatic cancer, the method comprising administering to a patient in need thereof a therapeutically effective amount of an $KRAS^{G12C}$ inhibitor and at least one chemotherapeutic agent.

2. In another embodiment of the present invention, the present invention comprises a method of treating colon cancer, the method comprising administering to a patient in need thereof a therapeutically effective amount of an $KRAS^{G12C}$ inhibitor and at least one chemotherapeutic agent.

3. In another embodiment of the present invention, the present invention comprises the method of embodiment 2 wherein the colon cancer has a KRAS p.G12C mutation.

4. In another embodiment of the present invention, the present invention comprises a method of treating lung cancer, the method comprising administering to a patient in need thereof a therapeutically effective amount of an $KRAS^{G12C}$ inhibitor and a chemotherapeutic agent.

In some such embodiments, the lung cancer is non-small cell lung carcinoma.

5. In another embodiment of the present invention, the present invention comprises the method of embodiment 1, wherein the pancreatic cancer has a KRAS p.G12C mutation.

6. In another embodiment of the present invention, the present invention comprises the method of any one of embodiments 1-5, wherein the chemotherapeutic agent is carboplatin.

7. In another embodiment of the present invention, the present invention comprises a method of treating pancreatic cancer, the method comprising administering to a patient in need thereof a therapeutically effective amount of an $KRAS^{G12C}$ inhibitor and a MEK inhibitor.

8. In another embodiment of the present invention, the present invention comprises a method of treating colon cancer, the method comprising administering to a patient in need thereof a therapeutically effective amount of an $KRAS^{G12C}$ inhibitor and a MEK inhibitor.

9. In another embodiment of the present invention, the present invention comprises a method of treating lung cancer, the method comprising administering to a patient in need thereof a therapeutically effective amount of an $KRAS^{G12C}$ inhibitor and a MEK inhibitor.

10. In another embodiment of the present invention, the present invention comprises the method of embodiment 9 wherein the lung cancer has a p.KRAS G12C mutation.

11. In another embodiment of the present invention, the present invention comprises the method of any one of embodiments 7-10 wherein the MEK inhibitor is trametinib.

12. In another embodiment of the present invention, the present invention comprises the method of any one of embodiments 7-10 wherein the MEK inhibitor is pimasertib, PD-325901, MEK162, TAK-733, GDC-0973 or AZD8330.

13. In another embodiment of the present invention, the present invention comprises a method of treating pancreatic cancer, the method comprising administering to a patient in need thereof a therapeutically effective amount of an $KRAS^{G12C}$ inhibitor and an EGFR inhibitor.

14. In another embodiment of the present invention, the present invention comprises a method of treating colon cancer, the method comprising administering to a patient in need thereof a therapeutically effective amount of an $KRAS^{G12C}$ inhibitor and a EGFR inhibitor.

15. In another embodiment of the present invention, the present invention comprises a method of treating lung cancer, the method comprising administering to a patient in need thereof a therapeutically effective amount of an $KRAS^{G12C}$ inhibitor and a EGFR inhibitor.

16. In another embodiment of the present invention, the present invention comprises the method of any one of embodiments 13-15 wherein the EGFR inhibitor is afatinib.

17. In another embodiment of the present invention, the present invention comprises the method of any one of embodiments 13 and 15 wherein the EGFR inhibitor is erlotinib.

18. In another embodiment of the present invention, the present invention comprises the method of embodiment 15 wherein the EGFR inhibitor is lapatinib.

19. In another embodiment of the present invention, the present invention comprises a method of treating pancreatic cancer, the method comprising administering to a patient in need thereof a therapeutically effective amount of an KRAS$^{G12C}$ inhibitor and a SHP2 inhibitor.

20. In another embodiment of the present invention, the present invention comprises a method of treating colon cancer, the method comprising administering to a patient in need thereof a therapeutically effective amount of an KRAS$^{G12C}$ inhibitor and a SHP2 inhibitor.

21. In another embodiment of the present invention, the present invention comprises a method of treating lung cancer, the method comprising administering to a patient in need thereof a therapeutically effective amount of an KRAS$^{G12C}$ inhibitor and a SHP2 inhibitor.

22. In another embodiment of the present invention, the present invention comprises the method of any one of embodiments 19-21 wherein the SHP2 inhibitor is selected from is RMC-4550

23. In another embodiment of the present invention, the present invention comprises the method of embodiment 22 wherein the SHP2 inhibitor is RMC 4550.

24. In another embodiment of the present invention, the present invention comprises a method of treating pancreatic cancer, the method comprising administering to a patient in need thereof a therapeutically effective amount of an KRAS$^{G12C}$ inhibitor and a PI3K inhibitor.

25. In another embodiment of the present invention, the present invention comprises a method of treating colon cancer, the method comprising administering to a patient in need thereof a therapeutically effective amount of an KRAS$^{G12C}$ inhibitor and a PI3K inhibitor.

26. In another embodiment of the present invention, the present invention comprises a method of treating lung cancer, the method comprising administering to a patient in need thereof a therapeutically effective amount of an KRAS$^{G12C}$ inhibitor and a PI3K inhibitor.

27. In another embodiment of the present invention, the present invention comprises the method of any one of embodiments 24-26 wherein the PI3K inhibitor is AMG 511.

28. In another embodiment of the present invention, the present invention comprises the method of embodiment 26 wherein the PI3K inhibitor is buparlisib.

29. In another embodiment of the present invention, the present invention comprises a method of treating pancreatic cancer, the method comprising administering to a patient in need thereof a therapeutically effective amount of an KRAS$^{G12C}$ inhibitor and an AKT inhibitor.

30. In another embodiment of the present invention, the present invention comprises a method of treating lung cancer, the method comprising administering to a patient in need thereof a therapeutically effective amount of an KRAS$^{G12C}$ inhibitor and a AKT inhibitor.

31. In another embodiment of the present invention, the present invention comprises the method of any one of embodiments 29-30 wherein the AKT inhibitor is AZD5363.

32. In another embodiment of the present invention, the present invention comprises a method of treating colon cancer, the method comprising administering to a patient in need thereof a therapeutically effective amount of an KRAS$^{G12C}$ inhibitor and a EGFR antibody.

33. In another embodiment of the present invention, the present invention comprises the method of embodiment 32 wherein the EGFR antibody is cetuximab.

32. In another embodiment of the present invention, the present invention comprises a method of treating colon cancer, the method comprising administering to a patient in need thereof a therapeutically effective amount of an KRAS$^{G12C}$ inhibitor and an anti-PD-1 antibody.

33. In another embodiment of the present invention, the present invention comprises the method of embodiment 32 wherein the anti-PD-1 antibody is selected from AMG 404, pembrolizumab and nivolumab.

34. In another embodiment of the present invention, the present invention comprises the method of embodiment 33 wherein the anti-PD-1 antibody is pembrolizumab.

35. In another embodiment of the present invention, the present invention comprises the method of embodiment 33 wherein the anti-PD-1 antibody is AMG 404.

36. In another embodiment of the present invention, the present invention comprises the method of embodiment 33 wherein the anti-PD-1 antibody is nivolumab.

37. In another embodiment of the present invention, the present invention comprises a pharmaceutical composition comprising

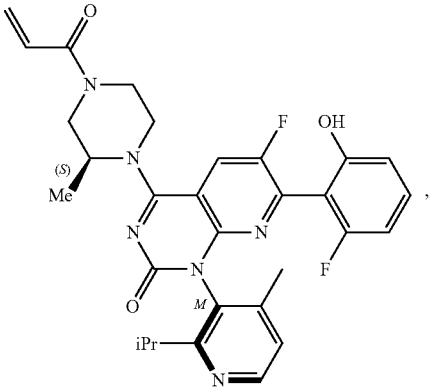

or a pharmaceutically acceptable salt thereof; carboplatin; and a pharmaceutically acceptable excipient.

38. In another embodiment of the present invention, the present invention comprises a pharmaceutical composition comprising

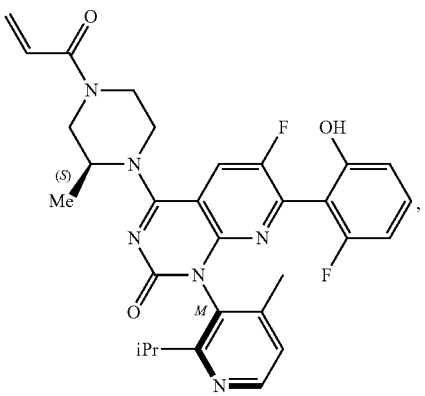

or a pharmaceutically acceptable salt thereof; trametinib; and a pharmaceutically acceptable excipient.

39. In another embodiment of the present invention, the present invention comprises a pharmaceutical composition comprising:

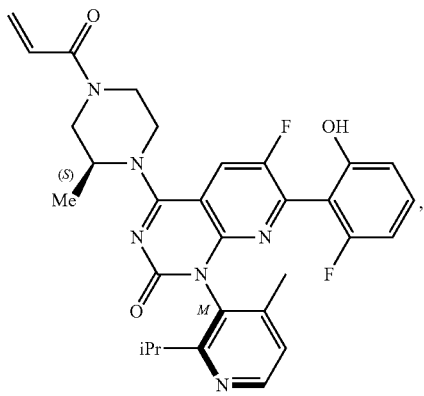

or a pharmaceutically acceptable salt thereof; afatinib; and a pharmaceutically acceptable excipient.

40. In another embodiment of the present invention, the present invention comprises a pharmaceutical composition comprising

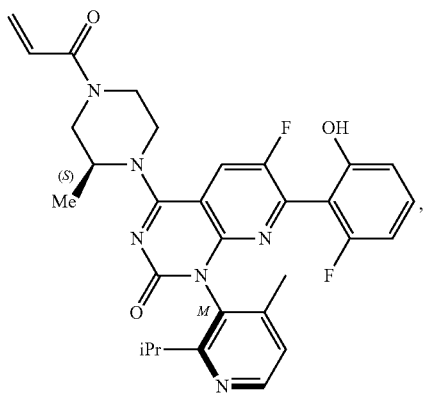

or a pharmaceutically acceptable salt thereof; erlotinib; and a pharmaceutically acceptable excipient.

41. In another embodiment of the present invention, the present invention comprises a pharmaceutical composition comprising

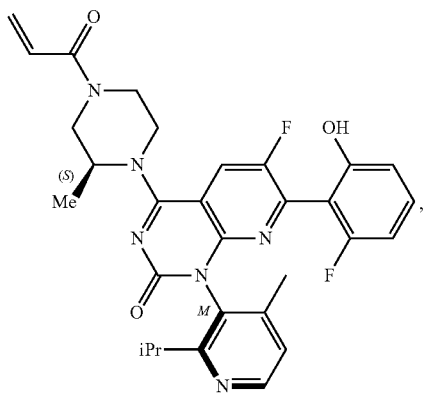

or a pharmaceutically acceptable salt thereof; lapatinib; and a pharmaceutically acceptable excipient.

42. In another embodiment of the present invention, the present invention comprises a pharmaceutical composition comprising

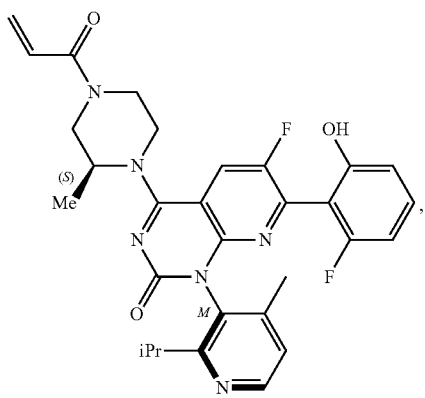

or a pharmaceutically acceptable salt thereof; RMC-4550; and a pharmaceutically acceptable excipient.

43. In another embodiment of the present invention, the present invention comprises a pharmaceutical composition comprising

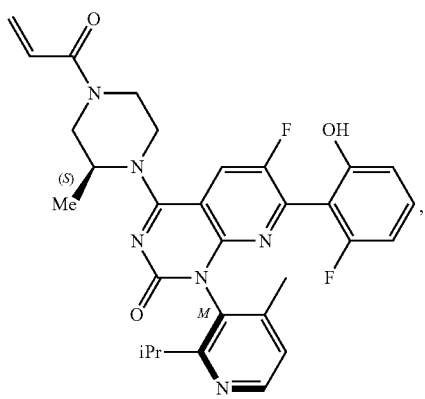

or a pharmaceutically acceptable salt thereof; AMG 511; and a pharmaceutically acceptable excipient.

44. In another embodiment of the present invention, the present invention comprises a pharmaceutical composition comprising

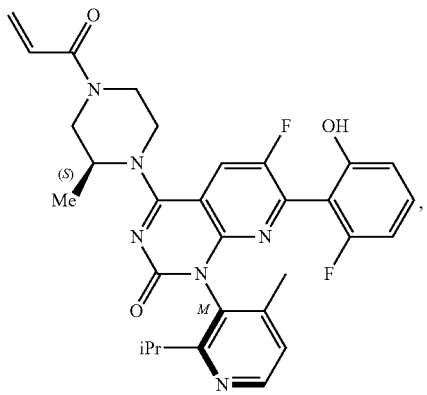

or a pharmaceutically acceptable salt thereof; buparlisib; and a pharmaceutically acceptable excipient.

45. In another embodiment of the present invention, the present invention comprises pharmaceutical composition comprising

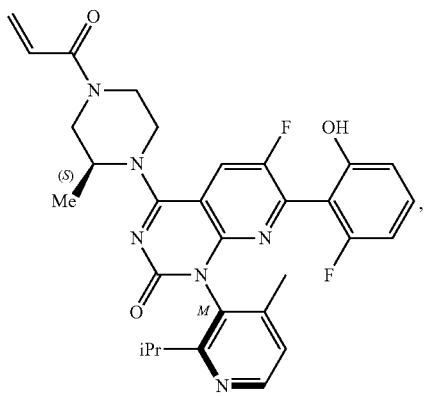

or a pharmaceutically acceptable salt thereof; AZD5363; and a pharmaceutically acceptable excipient.

46. In another embodiment of the present invention, the present invention comprises a pharmaceutical composition comprising

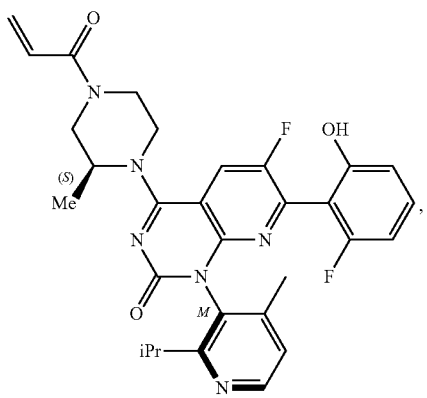

or a pharmaceutically acceptable salt thereof; cetuximab; and a pharmaceutically acceptable excipient.

47. In another embodiment of the present invention, the present invention comprises a pharmaceutical composition comprising

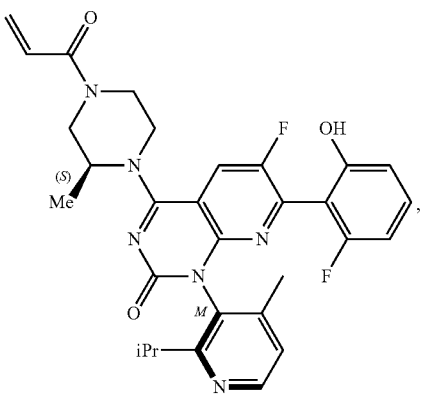

or a pharmaceutically acceptable salt thereof; an anti PD-1 antibody; and a pharmaceutically acceptable excipient.

48. In another embodiment of the present invention, the present invention comprises a pharmaceutical composition comprising

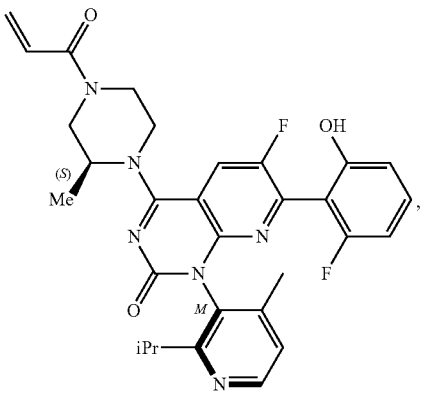

or a pharmaceutically acceptable salt thereof; AMG 404; and a pharmaceutically acceptable excipient.

49. In another embodiment of the present invention, the present invention comprises a pharmaceutical composition comprising

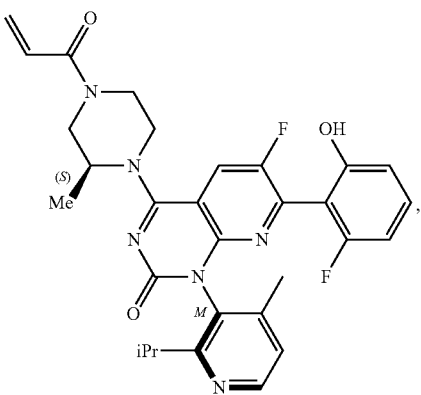

or a pharmaceutically acceptable salt thereof; pembrolizumab; and a pharmaceutically acceptable excipient.

50. In another embodiment of the present invention, the present invention comprises a pharmaceutical composition comprising

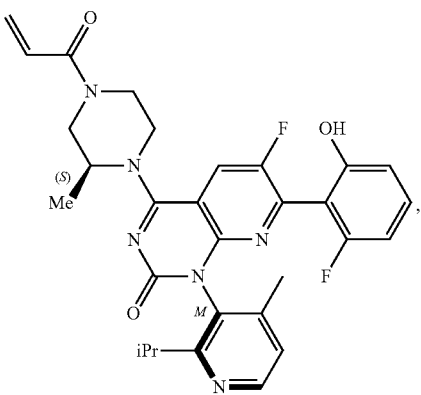

or a pharmaceutically acceptable salt thereof; nivolumab; and a pharmaceutically acceptable excipient.

51. In another embodiment of the present invention, the present invention comprises the method of any one of embodiments 1-4, or 7-36 wherein the KRAS$^{G12C}$ inhibitor is

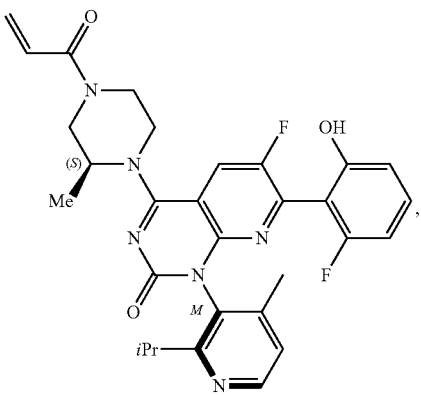

or a pharmaceutically acceptable salt thereof.

52. In another embodiment of the present invention, the present invention comprises a combination of an KRAS$^{G12C}$ inhibitor medicament and a MEK inhibitor medicament for treating a solid tumor.

53. In another embodiment of the present invention, the present invention comprises a combination of an KRAS$^{G12C}$ inhibitor medicament and a MEK inhibitor medicament for treating lung cancer.

54. In another embodiment of the present invention, the present invention comprises a combination of an KRAS$^{G12C}$ inhibitor medicament and a MEK inhibitor medicament for treating colon cancer.

55. In another embodiment of the present invention, the present invention comprises a combination of an KRAS$^{G12C}$ inhibitor medicament and a MEK inhibitor medicament for treating pancreatic cancer.

56. In another embodiment of the present invention, the present invention comprises a combination of an KRAS$^{G12C}$ inhibitor medicament and a chemotherapeutic agent medicament for treating a solid tumor.

57. In another embodiment of the present invention, the present invention comprises a combination of an KRAS$^{G12C}$ inhibitor medicament and a chemotherapeutic agent medicament for treating lung cancer. 58. In another embodiment of the present invention, the present invention comprises a combination of an KRAS$^{G12C}$ inhibitor medicament and a chemotherapeutic agent medicament for treating colon cancer. 59. In another embodiment of the present invention, the present invention comprises a combination of an KRAS$^{G12C}$ inhibitor medicament and a chemotherapeutic agent medicament for treating pancreatic cancer.

60. In another embodiment of the present invention, the present invention comprises a combination of an KRAS$^{G12C}$ inhibitor medicament and an EGFR inhibitor medicament for treating a solid tumor.

61. In another embodiment of the present invention, the present invention comprises a combination of an KRAS$^{G12C}$ inhibitor medicament and an EGFR inhibitor medicament for treating lung cancer.

62. In another embodiment of the present invention, the present invention comprises a combination of an KRAS$^{G12C}$ inhibitor medicament and an EGFR inhibitor medicament for treating colon cancer.

63. In another embodiment of the present invention, the present invention comprises a combination of an KRAS$^{G12C}$ inhibitor medicament and an EGFR inhibitor medicament for treating pancreatic cancer.

64. In another embodiment of the present invention, the present invention comprises a combination of an KRAS$^{G12C}$ inhibitor medicament and an anti-PD-1 antibody medicament for treating a solid tumor.

65. In another embodiment of the present invention, the present invention comprises a combination of an KRAS$^{G12C}$ inhibitor medicament and an anti-PD-1 antibody medicament for treating lung cancer.

66. In another embodiment of the present invention, the present invention comprises a combination of an KRAS$^{G12C}$ inhibitor medicament and an anti-PD-1 antibody medicament for treating colon cancer.

67. In another embodiment of the present invention, the present invention comprises a combination of an KRAS$^{G12C}$ inhibitor medicament and an anti-PD-1 antibody medicament for treating pancreatic cancer.

68. In another embodiment of the present invention, the present invention comprises a use of an KRAS$^{G12C}$ inhibitor in combination with a chemotherapeutic agent for manufacture of a medicament for the management or treatment of pancreatic cancer, lung cancer, or colon cancer in a subject.

69. In another embodiment of the present invention, the present invention comprises a use of an KRAS$^{G12C}$ inhibitor in combination with a MEK inhibitor for manufacture of a medicament for the management or treatment of pancreatic cancer, lung cancer, or colon cancer in a subject.

70. In another embodiment of the present invention, the present invention comprises a use of an KRAS$^{G12C}$ inhibitor in combination with a EGFR inhibitor for manufacture of a medicament for the management or treatment of pancreatic cancer, lung cancer, or colon cancer in a subject.

71. In another embodiment of the present invention, the present invention comprises a use of an KRAS$^{G12C}$ inhibitor in combination with an anti-PD-1 antibody for manufacture of a medicament for the management or treatment of pancreatic cancer, lung cancer, or colon cancer in a subject.

72. In another embodiment of the present invention, the present invention comprises an isolated cell line comprising two KRAS$^{G12C}$ alleles.

73. In another embodiment of the present invention, the present invention comprises the cell line of embodiment 68, wherein the cell line is CT-26 KRAS p.G12C.

74. In another embodiment of the present invention, the present invention comprises a method of generating a cell line comprising two KRAS$^{G12C}$ alleles, the method comprising:
a) incubating a cell line comprising two KRAS G12D alleles with a CRISPR construct that induces the replacement of a nucleotide on both the two KRAS alleles such that two KRAS$^{G12C}$ alleles are formed; and
b) isolating the cell line comprising the two KRAS$^{G12C}$ alleles.

75. In another embodiment of the present invention, the present invention comprises the method of embodiment 70, wherein the CRISPR construct comprises a sequence CTTGTGATGGTTGGAGCTGA (SEQ ID NO.: 21).

76. In another embodiment of the present invention, the present invention comprises a method of treating cancer, the method comprising administering to a patient in need thereof a therapeutically effective amount of an KRAS$^{G12C}$ inhibitor and at least one additional chemotherapeutic agent.

77. In another embodiment of the present invention, the present invention comprises a combination of an KRAS$^{G12C}$ inhibitor medicament and an anti-PD-1 antibody medicament for treating a solid tumor.

78. In another embodiment of the present invention, the present invention comprises a use of an KRAS$^{G12C}$ inhibitor in combination with at least one additional chemotherapeutic agent for the manufacture of a medicament for the management or treatment of pancreatic cancer, lung cancer, or colon cancer in a subject.

79. In another embodiment of the present invention, the present invention comprises the method of embodiment 76, wherein the KRAS$^{G12C}$ inhibitor is

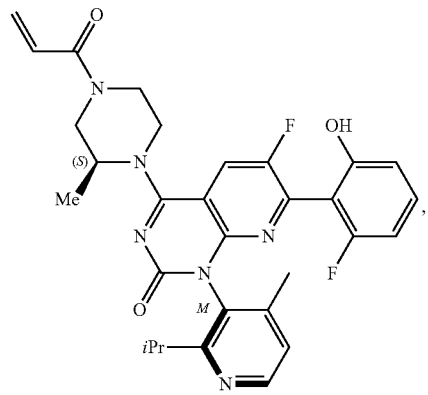

or a pharmaceutically acceptable salt thereof.

80. In another embodiment of the present invention, the present invention comprises the combination of embodiment 77, wherein the KRAS$^{G12C}$ inhibitor is

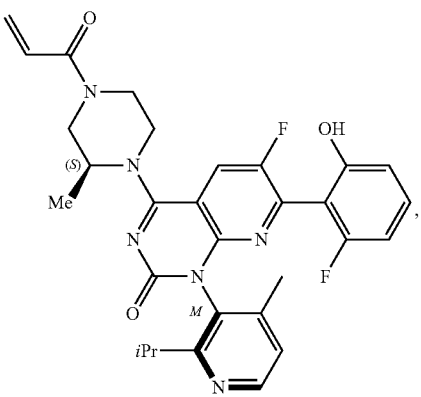

or a pharmaceutically acceptable salt thereof.

81. In another embodiment of the present invention, the present invention comprises the use of embodiment 78, wherein the KRAS$^{G12C}$ inhibitor is

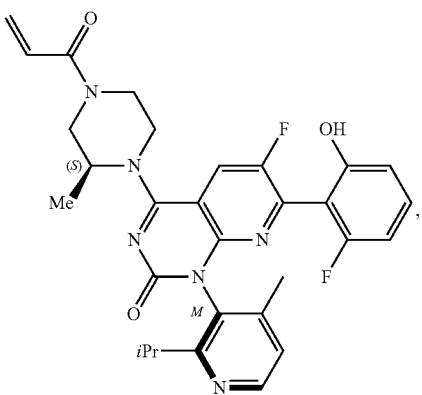

or a pharmaceutically acceptable salt thereof.

82. In another embodiment of the present invention, the present invention comprises the use of embodiment 78, wherein the lung cancer is a non-small cell lung carcinoma (NSCLC).

Second Set of Embodiments

1. In another embodiment of the present invention, the present invention relates to a method of treating cancer, the method comprising administering to a patient in need thereof a therapeutically effective amount of an KRAS$^{G12C}$ inhibitor and at least one additional pharmaceutically active agent.

2. In a further embodiment, the method of embodiment 1, wherein the KRAS$^{G12C}$ inhibitor is

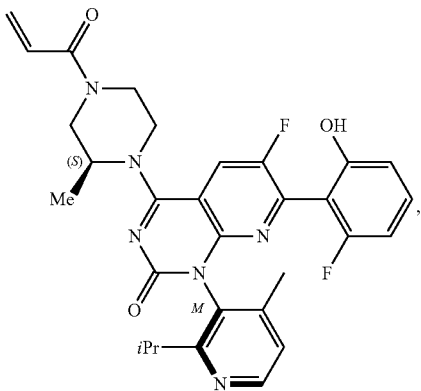

or a pharmaceutically acceptable salt thereof.

3. In a further embodiment, the method of embodiment 1, wherein the cancer a KRAS p.G12C mutation.

4. In a further embodiment, the method of embodiment 1, wherein the cancer is pancreatic, colorectal, lung, appendix, endometrial, or small intestine cancer.

5. In a further embodiment, the method of embodiment 4, wherein the cancer is pancreatic cancer.

6. In a further embodiment, the method of embodiment 4, wherein the cancer is colorectal cancer.

7. In a further embodiment, the method of embodiment 4, wherein the cancer is lung cancer.

8. In a further embodiment, the method of embodiment 7, wherein the lung cancer is non-small cell lung cancer (NSCLC).

9. In a further embodiment, the method of embodiment 4, wherein the cancer is appendix cancer.

10. In a further embodiment, the method of embodiment 4, wherein the cancer is endometrial cancer.

11. In a further embodiment, the method of embodiment 4, wherein the cancer is small intestine cancer.

12. In a further embodiment, the method of embodiment 1, wherein the at least one additional pharmaceutically active agent is carboplatin, an anti-PD-1 inhibitor, a MEK inhibitor, an EGFR inhibitor, TOR inhibitor, SHP2 inhibitor, a PI3K inhibitor or an AKT inhibitor.

13. In a further embodiment, the method of embodiment 12, wherein the at least one additional pharmaceutically active agent is carboplatin.

14. In a further embodiment, the method of embodiment 12, wherein the at least one additional pharmaceutically active agent is an anti-PD-1 inhibitor.

15. In a further embodiment, the method of embodiment 14, wherein the anti-PD-1 inhibitor is selected from AMG 404, pembrolizumab, and nivolumab.

16. In a further embodiment, the method of embodiment 15 wherein the anti-PD-1 inhibitor is pembrolizumab.

17. In a further embodiment, the method of embodiment 15 wherein the anti-PD-1 inhibitor is AMG 404.

18. In a further embodiment, the method of embodiment 15 wherein the anti-PD-1 inhibitor is nivolumab.

19. In a further embodiment, the method of embodiment 12, wherein the at least one additional pharmaceutically active agent is a MEK inhibitor.

20. In a further embodiment, the method of embodiment 19, wherein the MEK inhibitor is trametinib, pimasertib, PD-325901, MEK162, TAK-733, GDC-0973 or AZD8330.

21. In a further embodiment, the method of embodiment 20, wherein the MEK inhibitor is trametinib.

22. In a further embodiment, the method of embodiment 12, wherein the at least one additional pharmaceutically active agent is an EGFR inhibitor.

23. In a further embodiment, the method of embodiment 22, wherein the EGFR inhibitor is afatinib, erlotinib, lapatinib, or cetuximab.

24. In a further embodiment, the method of embodiment 23, wherein the EGFR inhibitor is afatinib.

25. In a further embodiment, the method of embodiment 23, wherein the EGFR inhibitor is cetuximab.

26. In a further embodiment, the method of embodiment 12, wherein the at least one additional pharmaceutically active agent is a SHP2 inhibitor.

27. In a further embodiment, the method of embodiment 26, wherein the SHP2 inhibitor is RMC 4550.

28. In a further embodiment, the method of embodiment 26, wherein the SHP2 inhibitor is RMC 4630.

29. In a further embodiment, the method of embodiment 12, wherein the at least one additional pharmaceutically active agent is a PI3K inhibitor.

30. In a further embodiment, the method of embodiment 29, wherein the PI3K inhibitor is AMG 511 or buparlisib.

31. In a further embodiment, the method of embodiment 30, wherein the PI3K inhibitor is AMG 511.

32. In a further embodiment, the method of embodiment 30, wherein the PI3K inhibitor is buparlisib.

33. In a further embodiment, the method of embodiment 12, wherein the at least one additional pharmaceutically active agent is an AKT inhibitor.

34. In a further embodiment, the method of embodiment 33, wherein the AKT inhibitor is AZD5363.

35. In a further embodiment, a pharmaceutical composition comprising

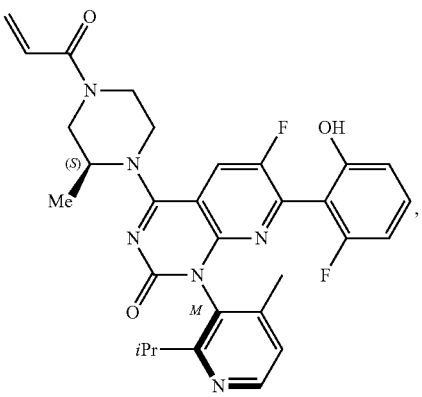

or a pharmaceutically acceptable salt thereof; at least one additional pharmaceutically active agent; and a pharmaceutically acceptable excipient.

36. In a further embodiment, the composition of embodiment 35, wherein at least one additional pharmaceutically active agent is carboplatin, an anti-PD-1 inhibitor, a MEK inhibitor, an EGFR inhibitor, a TOR inhibitor, a SHP2 inhibitor, a PI3K inhibitor or an AKT inhibitor.

37. In a further embodiment, the composition of embodiment 36, wherein at least one additional pharmaceutically active agent is carboplatin.

38. In a further embodiment, the composition of embodiment 36, wherein the at least one additional pharmaceutically active agent is an anti-PD-1 inhibitor.

39. In a further embodiment, the composition of embodiment 38, wherein the anti-PD-1 inhibitor is selected from AMG 404, pembrolizumab, and nivolumab.

40. In a further embodiment, the composition of embodiment 39 wherein the anti-PD-1 inhibitor is pembrolizumab.

41. In a further embodiment, the composition of embodiment 39 wherein the anti-PD-1 inhibitor is AMG 404.

42. In a further embodiment, the composition of embodiment 39 wherein the anti-PD-1 inhibitor is nivolumab.

43. In a further embodiment, the composition of embodiment 36, wherein the at least one additional pharmaceutically active agent is a MEK inhibitor.

44. In a further embodiment, the composition of embodiment 43, wherein the MEK inhibitor is trametinib, pimasertib, PD-325901, MEK162, TAK-733, GDC-0973 or AZD8330.

45. In a further embodiment, the composition of embodiment 44, wherein the MEK inhibitor is trametinib.

46. In a further embodiment, the composition of embodiment 36, wherein the at least one additional pharmaceutically active agent is an EGFR inhibitor.

47. In a further embodiment, the composition of embodiment 46, wherein the EGFR inhibitor is afatinib, erlotinib, lapatinib, or cetuximab.

48. In a further embodiment, the composition of embodiment 47, wherein the EGFR inhibitor is afatinib.

49. In a further embodiment, the composition of embodiment 47, wherein the EGFR inhibitor is cetuximab.

50. In a further embodiment, the composition of embodiment 36, wherein the at least one additional pharmaceutically active agent is a SHP2 inhibitor.

51. In a further embodiment, the composition of embodiment 50, wherein the SHP2 inhibitor is RMC 4550.

52. In a further embodiment, the composition of embodiment 50, wherein the SHP2 inhibitor is RMC 4630.

53. In a further embodiment, the composition of embodiment 36, wherein the at least one additional pharmaceutically active agent is a PI3K inhibitor.

54. In a further embodiment, the composition of embodiment 53, wherein the PI3K inhibitor is AMG 511 or buparlisib.

55. In a further embodiment, the composition of embodiment 54, wherein the PI3K inhibitor is AMG 511.

56. In a further embodiment, the composition of embodiment 54, wherein the PI3K inhibitor is buparlisib.

57. In a further embodiment, the composition of embodiment 36, wherein the at least one additional pharmaceutically active agent is an AKT inhibitor.

58. In a further embodiment, the composition of embodiment 57, wherein the AKT inhibitor is AZD5363.

59. In a further embodiment, a kit, the kit comprising: a $KRAS^{G12C}$ inhibitor, or a pharmaceutically acceptable salt thereof; and at least one additional pharmaceutically active agent.

60. In a further embodiment, the kit of embodiment 59, wherein the $KRAS^{G12C}$ inhibitor is

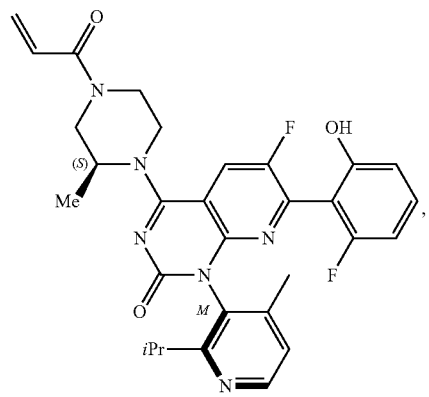

or the pharmaceutically acceptable salt thereof.

61. In a further embodiment, the kit of embodiment 59, wherein at least one additional pharmaceutically active agent is carboplatin, an anti-PD-1 inhibitor, a MEK inhibitor, an EGFR inhibitor, a TOR inhibitor, a SHP2 inhibitor, a PI3K inhibitor or an AKT inhibitor.

62. In a further embodiment, the kit of embodiment 59, wherein at least one additional pharmaceutically active agent is carboplatin.

63. In a further embodiment, the kit of embodiment 59, wherein the at least one additional pharmaceutically active agent is an anti-PD-1 inhibitor.

64. In a further embodiment, the kit of embodiment 63, wherein the anti-PD-1 inhibitor is selected from AMG 404, pembrolizumab, and nivolumab.

65. In a further embodiment, the kit of embodiment 64 wherein the anti-PD-1 inhibitor is pembrolizumab.

66. In a further embodiment, the kit of embodiment 64 wherein the anti-PD-1 inhibitor is AMG 404.

67. In a further embodiment, the kit of embodiment 64 wherein the anti-PD-1 inhibitor is nivolumab.

68. In a further embodiment, the kit of embodiment 61, wherein the at least one additional pharmaceutically active agent is a MEK inhibitor.

69. In a further embodiment, the kit of embodiment 68, wherein the MEK inhibitor is trametinib, pimasertib, PD-325901, MEK162, TAK-733, GDC-0973 or AZD8330.

70. In a further embodiment, the kit of embodiment 69, wherein the MEK inhibitor is trametinib.

71. In a further embodiment, the kit of embodiment 61, wherein the at least one additional pharmaceutically active agent is an EGFR inhibitor.

72. In a further embodiment, the kit of embodiment 61, wherein the EGFR inhibitor is afatinib, erlotinib, lapatinib, or cetuximab.

73. In a further embodiment, the kit of embodiment 62, wherein the EGFR inhibitor is afatinib.

74. In a further embodiment, the kit of embodiment 62, wherein the EGFR inhibitor is cetuximab.

75. In a further embodiment, the kit of embodiment 61, wherein the at least one additional pharmaceutically active agent is a SHP2 inhibitor.

76. In a further embodiment, the kit of embodiment 75, wherein the SHP2 inhibitor is RMC 4550.

77. In a further embodiment, the kit of embodiment 75, wherein the SHP2 inhibitor is RMC 4630.

78. In a further embodiment, the kit of embodiment 61, wherein the at least one additional pharmaceutically active agent is a PI3K inhibitor.

79. In a further embodiment, the kit of embodiment 78, wherein the PI3K inhibitor is AMG 511 or buparlisib.

80. In a further embodiment, the kit of embodiment 79, wherein the PI3K inhibitor is AMG 511.

81. In a further embodiment, the kit of embodiment 79, wherein the PI3K inhibitor is buparlisib.

82. In a further embodiment, the kit of embodiment 61, wherein the at least one additional pharmaceutically active agent is an AKT inhibitor.

83. In a further embodiment, the kit of embodiment 82, wherein the AKT inhibitor is AZD5363.

84. In a further embodiment, the kit of embodiment 59, wherein the kit is for treating cancer.

85. In a further embodiment, the kit of embodiment 84, wherein the cancer a KRAS p.G12C mutation.

86. In a further embodiment, the kit of embodiment 84, wherein the cancer is pancreatic, colorectal, lung, appendix, endometrial, or small intestine cancer.

87. In a further embodiment, the kit of embodiment 86, wherein the cancer is pancreatic cancer.

88. In a further embodiment, the kit of embodiment 86, wherein the cancer is colorectal cancer.

89. In a further embodiment, the kit of embodiment 86, wherein the cancer is lung cancer.

90. In a further embodiment, the kit of embodiment 89, wherein the lung cancer is non-small cell lung cancer (NSCLC).

91. In a further embodiment, the kit of embodiment 86, wherein the cancer is appendix cancer.

92. In a further embodiment, the kit of embodiment 86, wherein the cancer is endometrial cancer.

93. In a further embodiment, the kit of embodiment 86, wherein the cancer is small intestine cancer.

94. In a further embodiment, a use of an $KRAS^{G12C}$ inhibitor in combination with at least one additional chemotherapeutic agent for the manufacture of a medicament for the management or treatment of cancer in a subject.

95. In a further embodiment, the use of embodiment 94, wherein the $KRAS^{G12C}$ inhibitor is

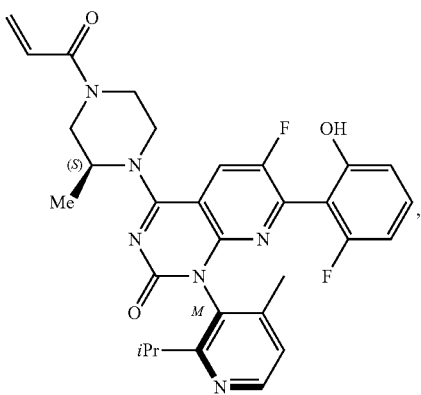

or a pharmaceutically acceptable salt thereof.

96. In a further embodiment, a compound which is a $KRAS^{G12C}$ inhibitor for use in treating cancer with at least one additional pharmaceutically active agent.

97. In a further embodiment, the compound of embodiment 96, wherein the $KRAS^{G12C}$ inhibitor is

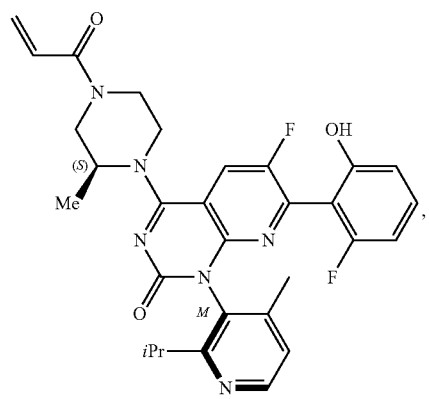

or a pharmaceutically acceptable salt thereof.

98. In a further embodiment, the compound of embodiment 96, wherein the cancer a KRAS p.G12C mutation.

99. In a further embodiment, the compound of embodiment 96, wherein the cancer is pancreatic, colorectal, lung, appendix, endometrial, or small intestine cancer.

100. In a further embodiment, the compound of embodiment 99, wherein the cancer is pancreatic cancer.

101. In a further embodiment, the compound of embodiment 99, wherein the cancer is colorectal cancer.

102. In a further embodiment, the compound of embodiment 99, wherein the cancer is lung cancer.

103. In a further embodiment, the compound of embodiment 102, wherein the lung cancer is non-small cell lung cancer (NSCLC).

104. In a further embodiment, the compound of embodiment 99, wherein the cancer is appendix cancer.

105. In a further embodiment, the compound of embodiment 99, wherein the cancer is endometrial cancer.

106. In a further embodiment, the compound of embodiment 99, wherein the cancer is small intestine cancer.

107. In a further embodiment, the compound of embodiment 96, wherein the at least one additional pharmaceutically active agent is carboplatin, an anti-PD-1 inhibitor, a MEK inhibitor, an EGFR inhibitor, a TOR inhibitor, a SHP2 inhibitor, a PI3K inhibitor or an AKT inhibitor.

108. In a further embodiment, the compound of embodiment 107, wherein the at least one additional pharmaceutically active agent is carboplatin.

109. In a further embodiment, the compound of embodiment 107, wherein the at least one additional pharmaceutically active agent is an anti-PD-1 inhibitor.

110. In a further embodiment, the compound of embodiment 109, wherein the anti-PD-1 inhibitor is selected from AMG 404, pembrolizumab, and nivolumab.

111. In a further embodiment, the compound of embodiment 110 wherein the anti-PD-1 inhibitor is pembrolizumab.

112. In a further embodiment, the compound of embodiment 110 wherein the anti-PD-1 inhibitor is AMG 404.

113. In a further embodiment, the compound of embodiment 110 wherein the anti-PD-1 inhibitor is nivolumab.

114. In a further embodiment, the compound of embodiment 107, wherein the at least one additional pharmaceutically active agent is a MEK inhibitor.

115. In a further embodiment, the compound of embodiment 114, wherein the MEK inhibitor is trametinib, pimasertib, PD-325901, MEK162, TAK-733, GDC-0973 or AZD8330.

116. In a further embodiment, the compound of embodiment 115, wherein the MEK inhibitor is trametinib.

117. In a further embodiment, the compound of embodiment 107, wherein the at least one additional pharmaceutically active agent is an EGFR inhibitor.

118. In a further embodiment, the compound of embodiment 117, wherein the EGFR inhibitor is afatinib, erlotinib, lapatinib, or cetuximab.

119. In a further embodiment, the compound of embodiment 118, wherein the EGFR inhibitor is afatinib.

120. In a further embodiment, the compound of embodiment 118, wherein the EGFR inhibitor is cetuximab.

121. In a further embodiment, the compound of embodiment 107, wherein the at least one additional pharmaceutically active agent is a SHP2 inhibitor.

122. In a further embodiment, the compound of embodiment 121, wherein the SHP2 inhibitor is RMC 4550.

123. In a further embodiment, the compound of embodiment 121, wherein the SHP2 inhibitor is RMC 4630.

124. In a further embodiment, the compound of embodiment 107, wherein the at least one additional pharmaceutically active agent is a PI3K inhibitor.

125. In a further embodiment, the compound of embodiment 124, wherein the PI3K inhibitor is AMG 511 or buparlisib.

126. In a further embodiment, the compound of embodiment 125, wherein the PI3K inhibitor is AMG 511.

127. In a further embodiment, the compound of embodiment 125, wherein the PI3K inhibitor is buparlisib.

128. In a further embodiment, the compound of embodiment 107, wherein the at least one additional pharmaceutically active agent is an AKT inhibitor.

129. In a further embodiment, the compound of embodiment 128, wherein the AKT inhibitor is AZD5363.

130. In a further embodiment, the method of embodiment 1, wherein the $KRAS^{G12C}$ inhibitor and the at least one additional pharmaceutically active agent are administered simultaneously.

131. In a further embodiment, the method of embodiment 1, wherein the $KRAS^{G12C}$ inhibitor and the at least one additional pharmaceutically active agent are administered separately.

A further embodiment of the invention includes the use of a combination comprising an $KRAS^{G12C}$ inhibitor with another therapeutic agent selected from a chemotherapeutic agent, a PD-1 inhibitor, a MEK inhibitor, a Pi3K a selective inhibitor, an EGFR inhibitor, a TOR inhibitor, a SHP2 inhibitor, or an AKT inhibitor. A further embodiment of the invention includes the use of a combination for treatment of cancer, the combination comprising an $KRAS^{G12C}$ inhibitor with another therapeutic agent selected from a chemotherapeutic agent, a PD-1 inhibitor, a MEK inhibitor, a Pi3K a selective inhibitor, an EGFR inhibitor, a TOR inhibitor, a SHP2 inhibitor, or an AKT inhibitor. A further embodiment of the invention includes a method of using a combination comprising an $KRAS^{G12C}$ inhibitor with another therapeutic agent selected from a chemotherapeutic agent, a PD-1 inhibitor, a MEK inhibitor, a Pi3K a selective inhibitor, an EGFR inhibitor, a TOR inhibitor, a SHP2 inhibitor, or an AKT inhibitor, for the treatment of cancer. A further embodiment of the invention includes the use of a combination for treatment of cancer, the combination comprising a $KRAS^{G12C}$ inhibitor with another therapeutic agent selected from a chemotherapeutic agent, a PD-1 inhibitor, a MEK inhibitor, a Pi3K a selective inhibitor, an EGFR inhibitor, a TOR inhibitor, a SHP2 inhibitor, or an AKT inhibitor, wherein the use comprises self-administering the combination.

A further embodiment of the invention includes a method of treating cancer comprising prescribing a combination further comprising an $KRAS^{G12C}$ inhibitor with another therapeutic agent selected from a chemotherapeutic agent, a PD-1 inhibitor, a MEK inhibitor, a Pi3K a selective inhibitor, an EGFR inhibitor, a TOR inhibitor, a SHP2 inhibitor, or an AKT inhibitor. A further embodiment of the invention includes a method of treating cancer comprising prescribing to a subject in need thereof, a combination further comprising an $KRAS^{G12C}$ inhibitor with another therapeutic agent selected from a chemotherapeutic agent, a PD-1 inhibitor, a MEK inhibitor, a Pi3K a selective inhibitor, an EGFR inhibitor, a TOR inhibitor, a SHP2 inhibitor, or an AKT inhibitor.

A further embodiment of the invention includes a method of treating cancer using a combination comprising a $KRAS^{G12C}$ inhibitor with another therapeutic agent selected from a chemotherapeutic agent, a PD-1 inhibitor, a MEK inhibitor, a Pi3K a selective inhibitor, an EGFR inhibitor, a TOR inhibitor, a SHP2 inhibitor, or an AKT inhibitor, wherein such method further comprises listing said combination in a formulary and directing a patient in need of such cancer A further embodiment of the invention includes a method of using a combination comprising a $KRAS^{G12C}$ inhibitor with another therapeutic agent selected from a chemotherapeutic agent, a PD-1 inhibitor, a MEK inhibitor, a Pi3K a selective inhibitor, an EGFR inhibitor, a TOR inhibitor, a SHP2 inhibitor, or an AKT inhibitor, for the treatment of cancer, wherein such method comprises purchasing said combination for self-administration by a patient in need of such cancer treatment.

A further embodiment of the invention includes a method of treating cancer comprising instructing a subject in need of such treatment to administer a combination comprising an $KRAS^{G12C}$ inhibitor with another therapeutic agent selected from a chemotherapeutic agent, an anti-PD-1 inhibitor, a MEK inhibitor, a Pi3K a selective inhibitor, an EGFR inhibitor, a TOR inhibitor, a SHP2 inhibitor, or an AKT inhibitor.

A further embodiment of the invention includes a process of treating cancer comprising
   A]prescribing
   B]selling or advertising to sell,
   C]purchasing,
   D]instructing to self-administer, or
   E]administering
of a combination described herein, wherein the combination has been approved by a regulatory agency for the treatment of cancer, to a subject in need of cancer treatment.

A further embodiment of the invention includes a method of supplying a combination comprising an $KRAS^{G12C}$ inhibitor with another therapeutic agent selected from a chemotherapeutic agent, a PD-1 inhibitor, a MEK inhibitor, a PI3K a selective inhibitor, an EGFR inhibitor, a TOR inhibitor, a SHP2 inhibitor, or an AKT inhibitor for treating cancer, said method comprises reimbursing a physician, a formulary, a patient or an insurance company for the sale of said combination.

For clarity, the term "instructing" is meant to include information on a label approved by a regulatory agency, in addition to its commonly understood definition.

BRIEF DESCRIPTION OF THE DRAWINGS

FIGS. 1A, 1B and 1C show AMG 510 in combination with carboplatin enhances the suppression of NCI-H358 NSCLC tumor growth.

FIGS. 4A and 4B show AMG 510 combined with an anti-PD-1 antibody results in increased survival and durable cures in a mouse model of KRAS p.G12C mutant cancer.

FIGS. 5A, 5B and 5C show AMG 510 treatment leads to increase in CD8+ and CD4+ T-cell infiltration in CT-26 G12C-H10 tumors.

7 shows the additivity excess matrix identifies regions of synergistic interaction.

FIG. 8 shows the self-cross matrices model additivity experimentally.

Figure 9A:
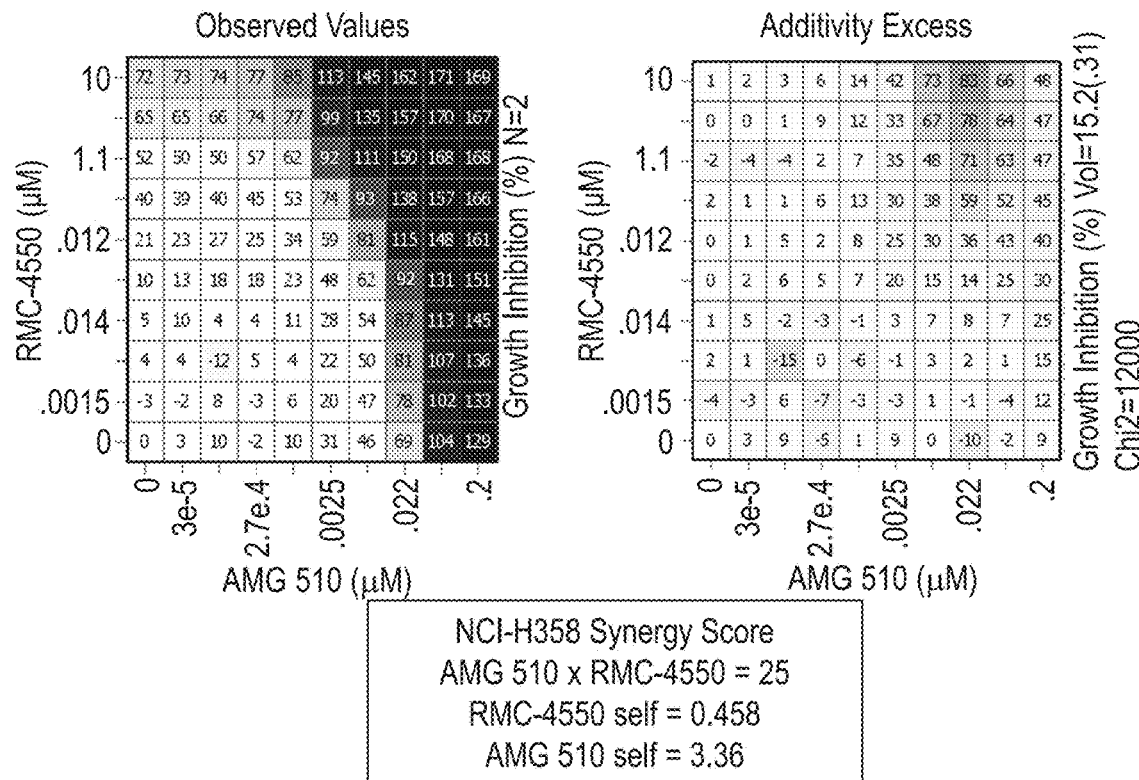
Figure 9B:
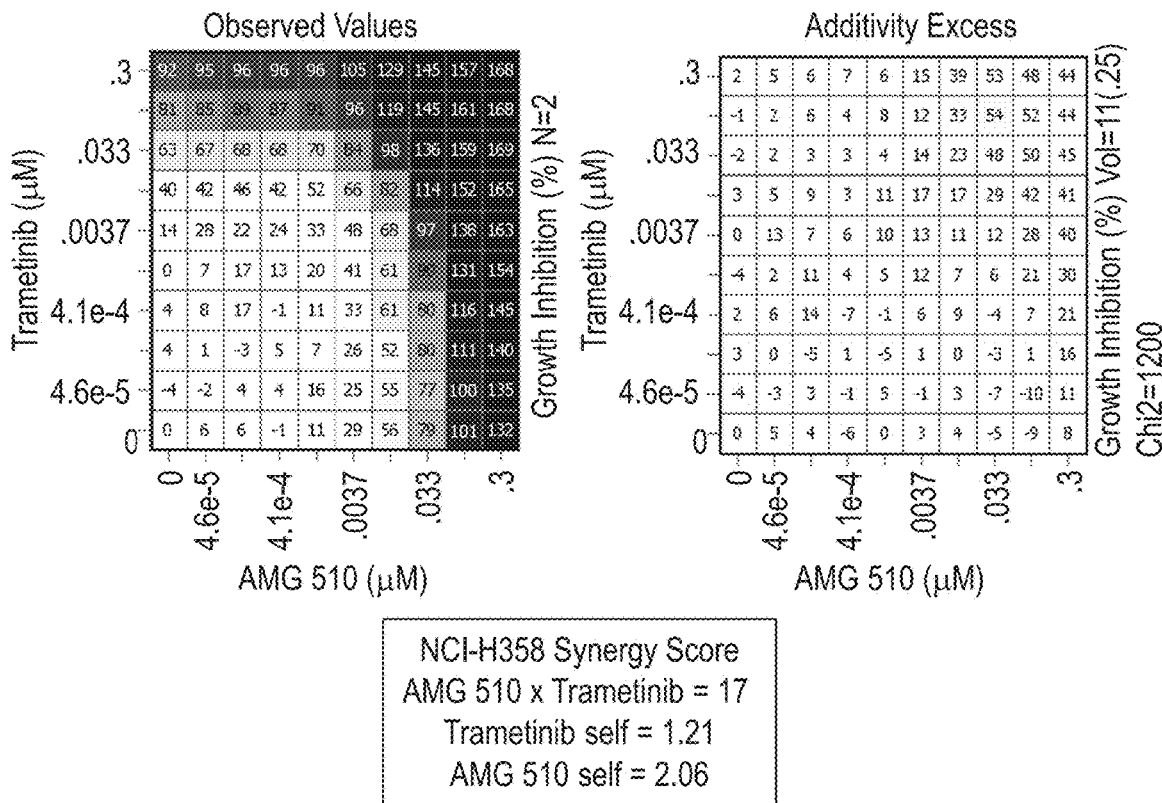

FIGS. 9A and 9B show AMG 510 synergizes with both RMC-4550 (SHP2i) and trametinib (MEKi) to achieve cell killing in NCI-H358 cell line.

Figure 10A:
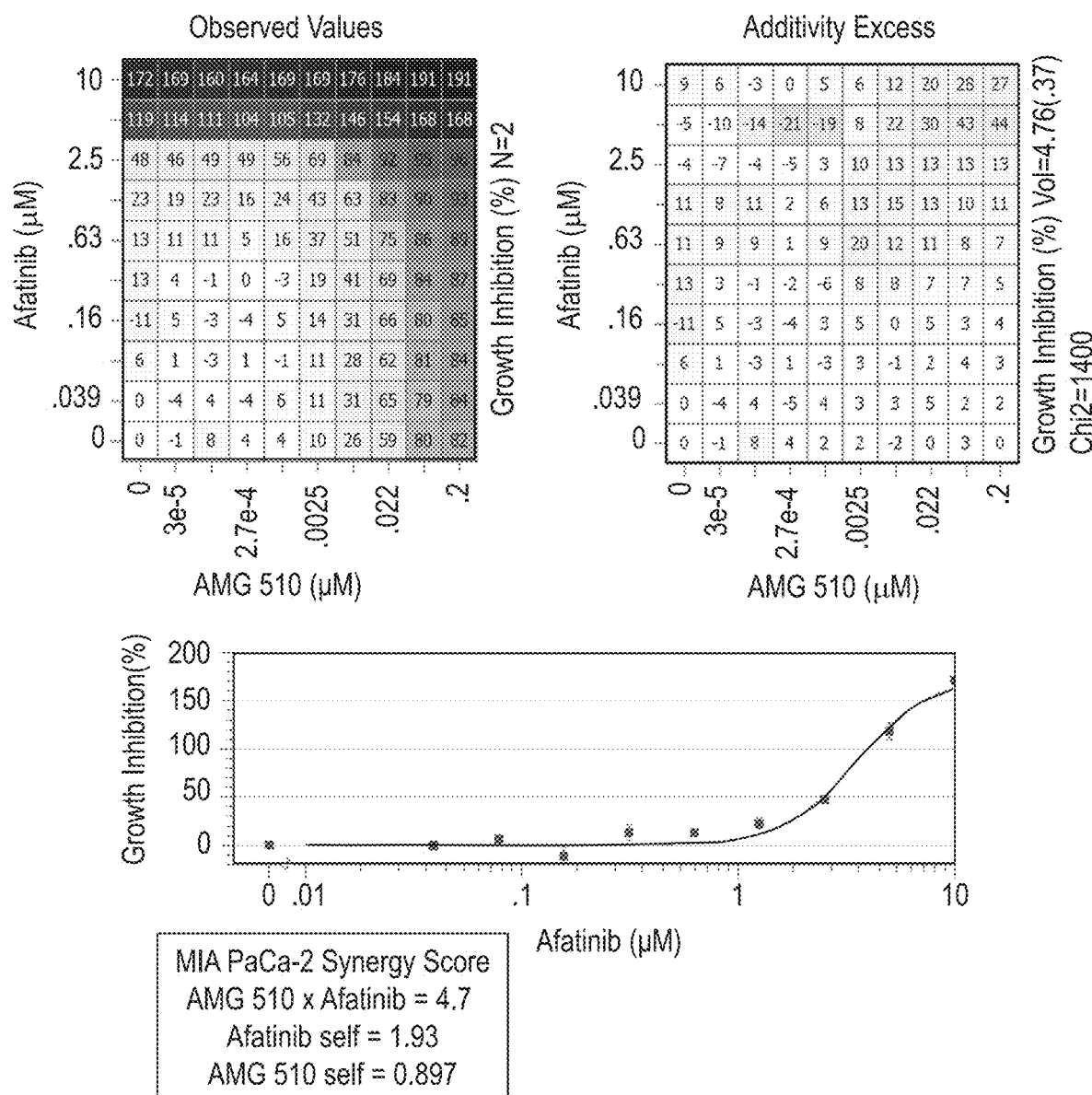
Figure 10B:
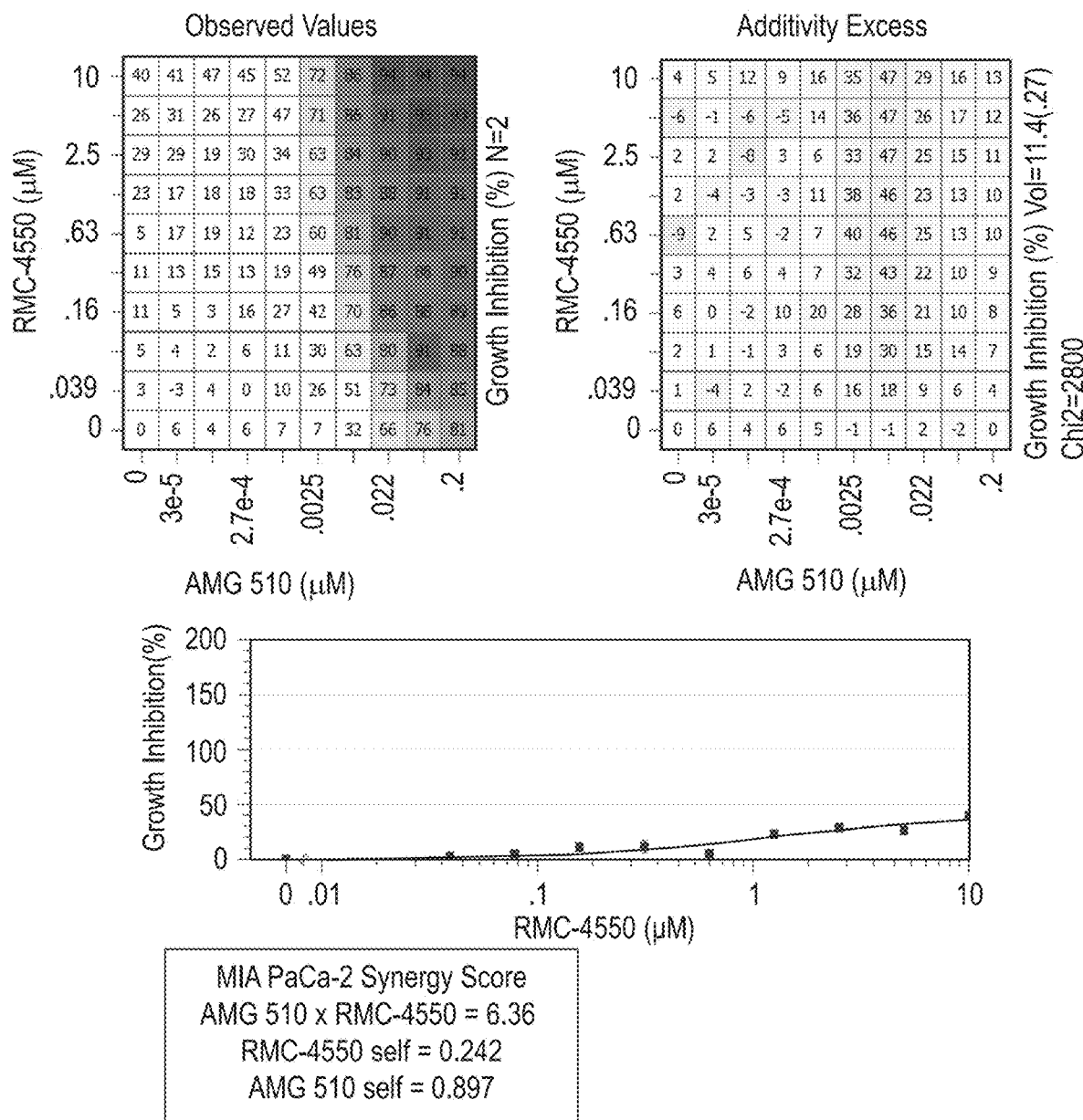

FIGS. 10A and 10B show the lack of single agent activity with afatinib or RMC-4550 may contribute to weaker synergy in MIA PaCA-2 cell line.

Figure 11A:
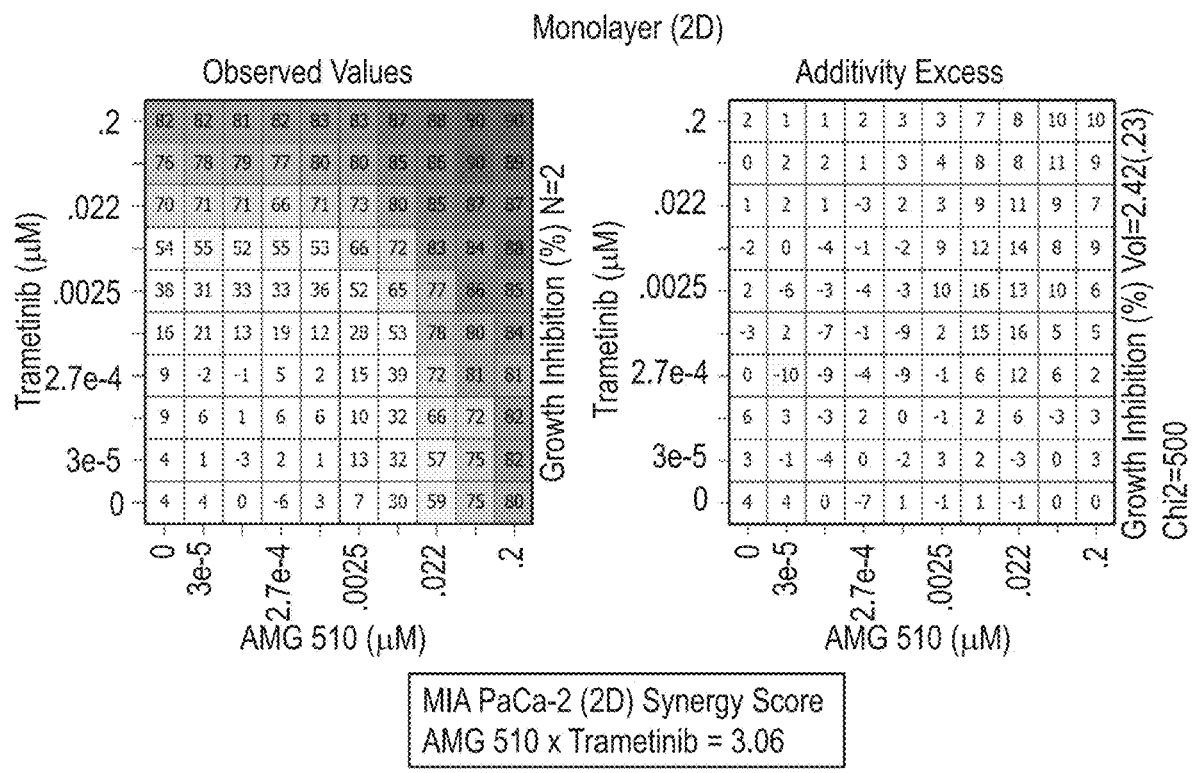
Figure 11B:
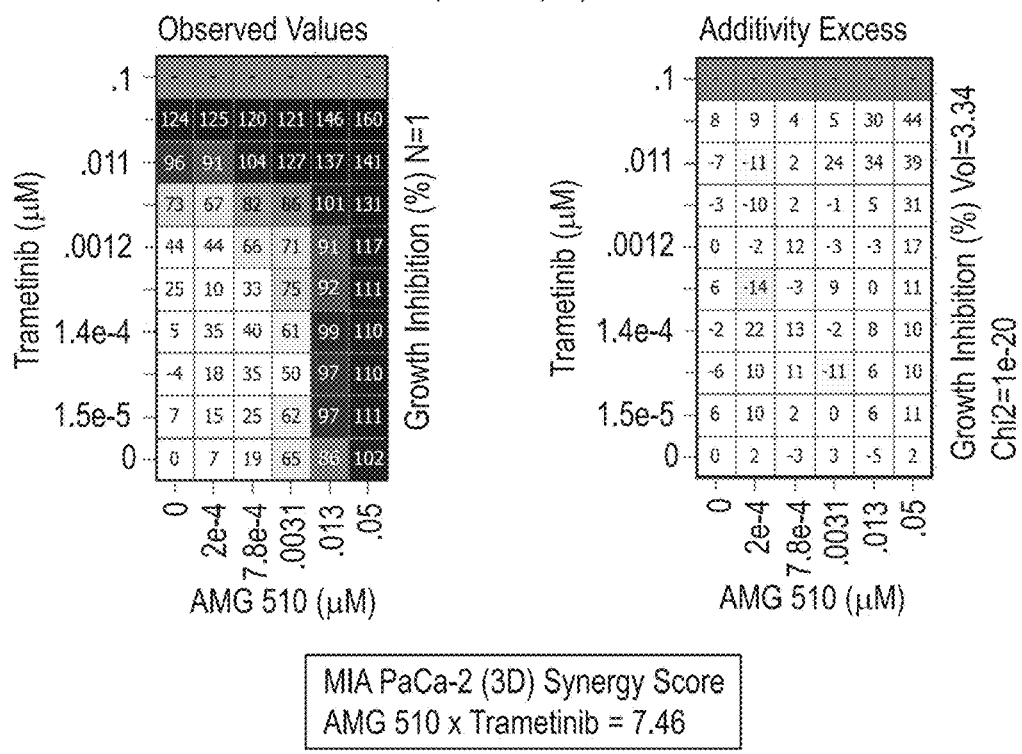

FIGS. 11A and 11B show combinations in 3D culture may reveal increased synergy.

Figure 12:
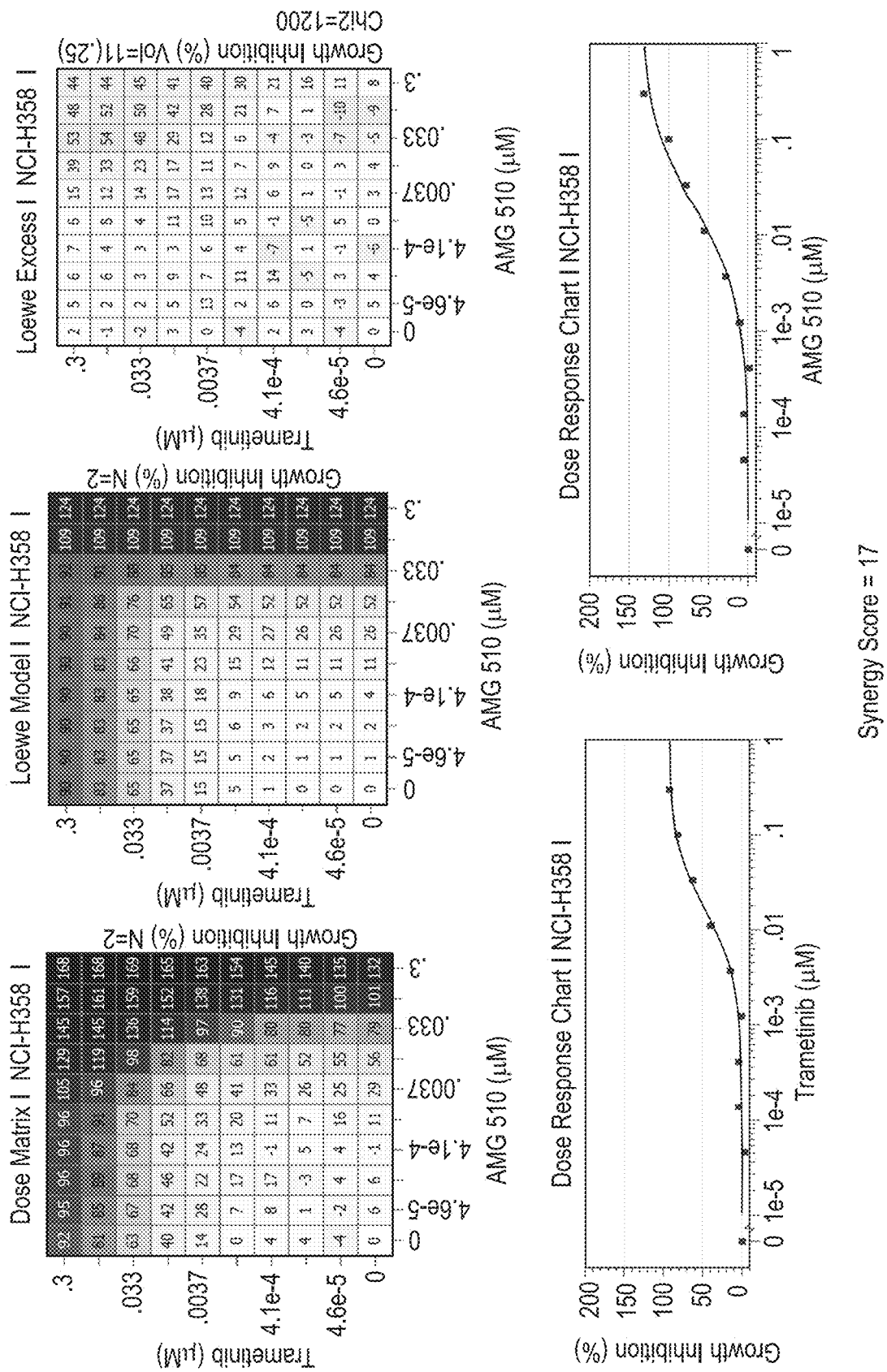

FIG. 12 shows AMG 510 X trametinib is synergistic in NCI-H358.

Figure 13:
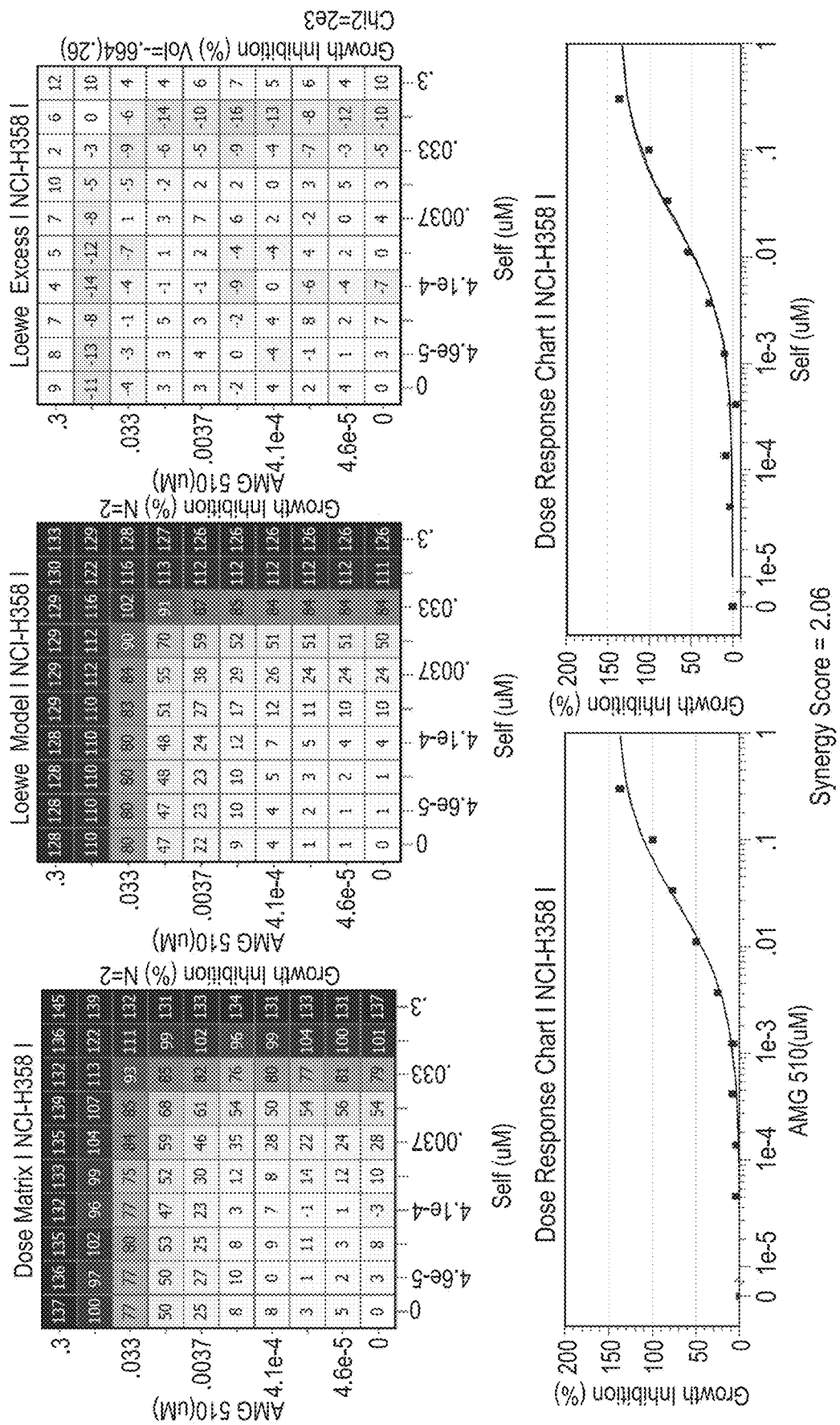

FIG. 13 shows AMG self-cross in NCI-H358 cell line.

Figure 14:
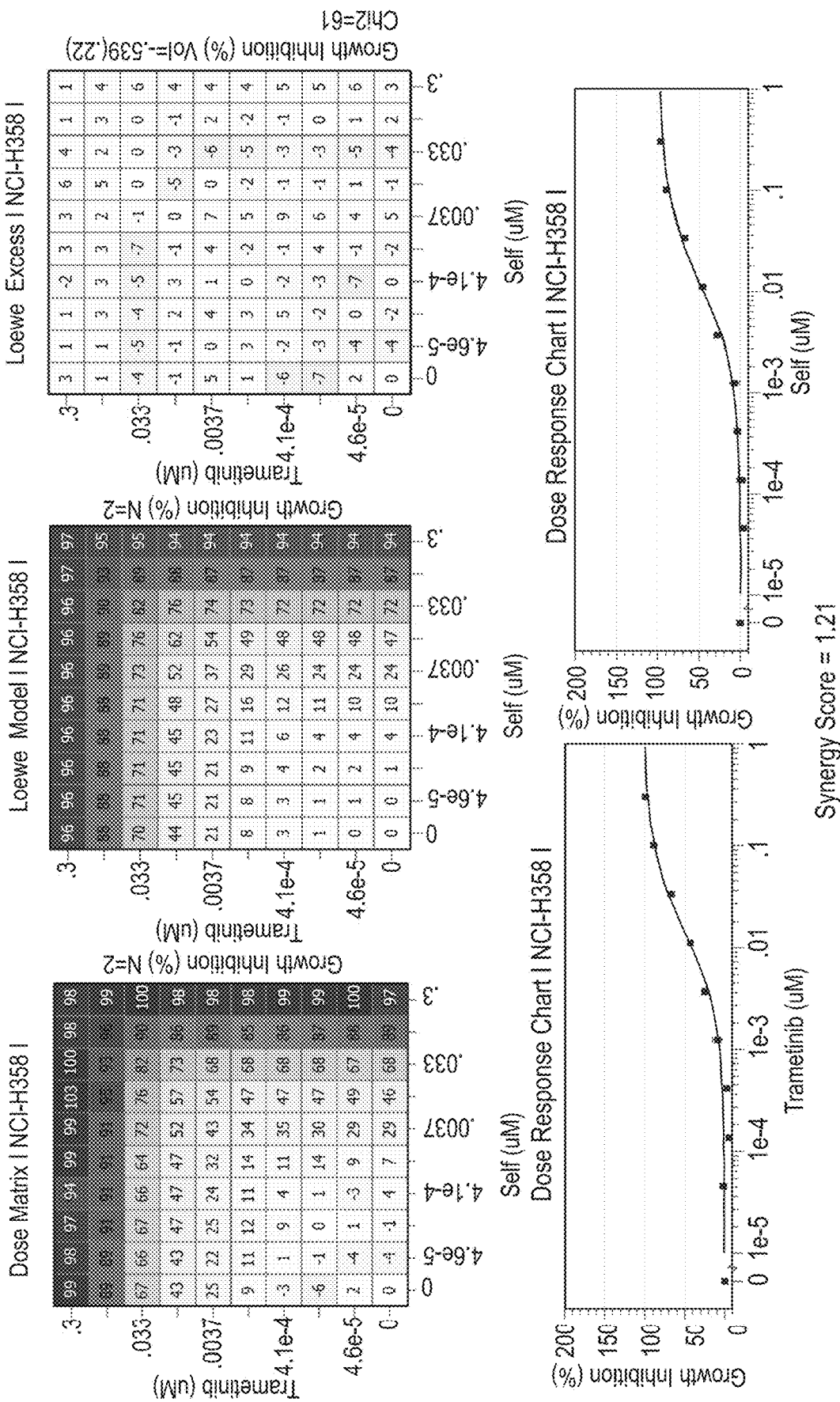

FIG. 14 shows trametinib self-cross in NCI-H358 cell line.

Figure 15:
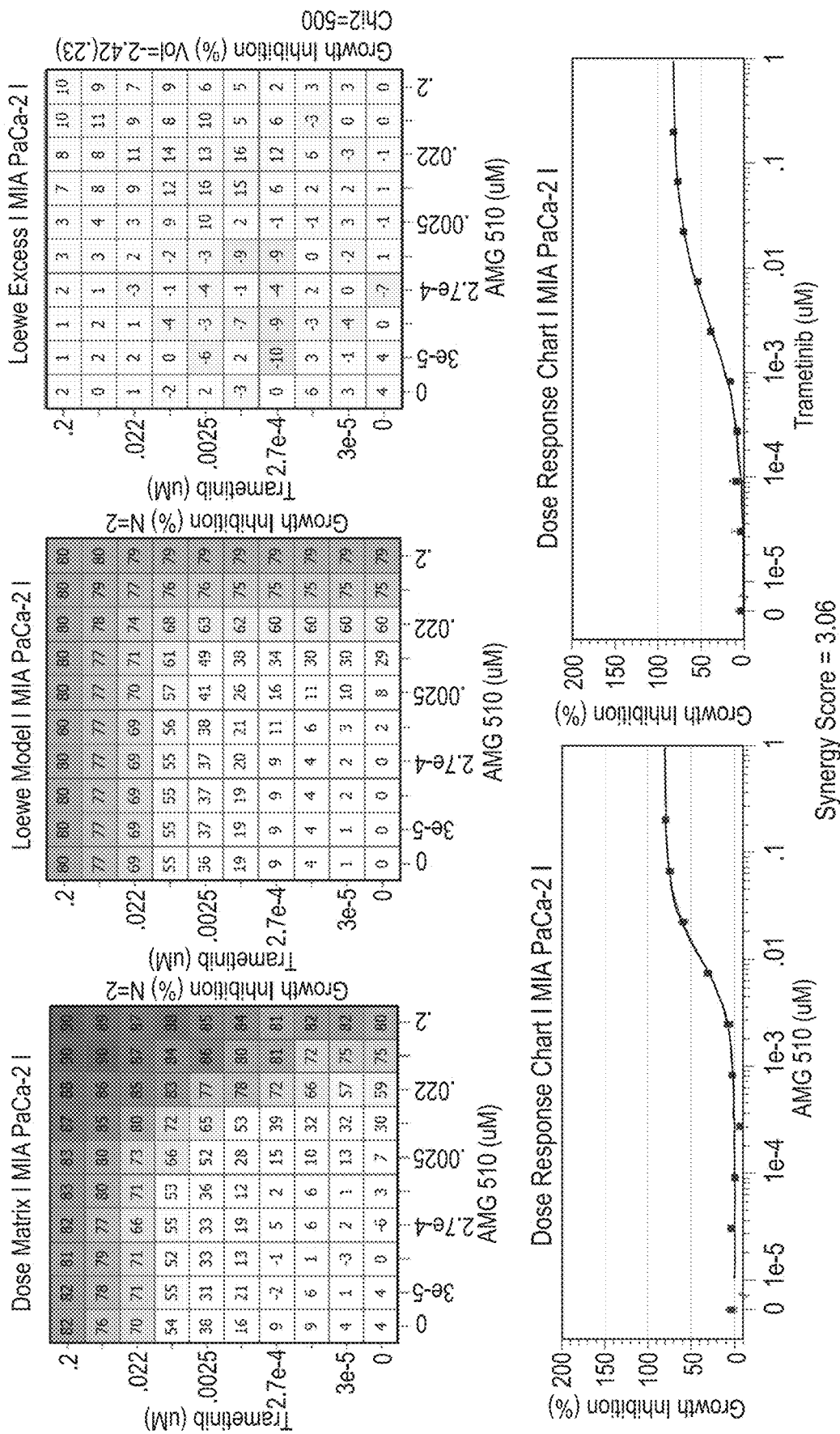

FIG. 15 shows AMG 510 X trametinib exhibits weak synergy in MIA PaCa-2 cell line.

Figure 16:
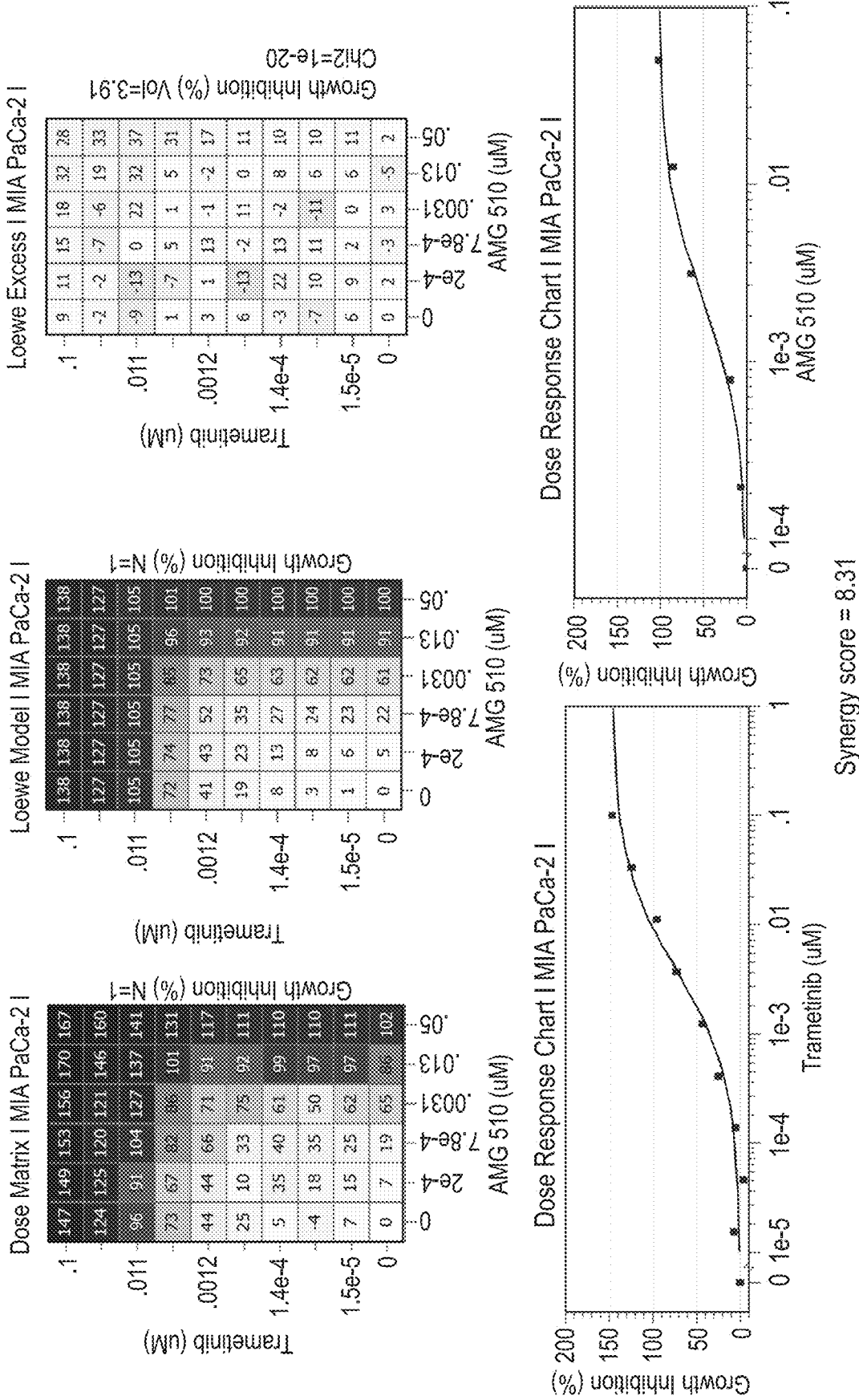

FIG. 16 shows 3D culture improves synergy of AMG 510 X trametinib in MIA PaCa-2.

Figure 17:
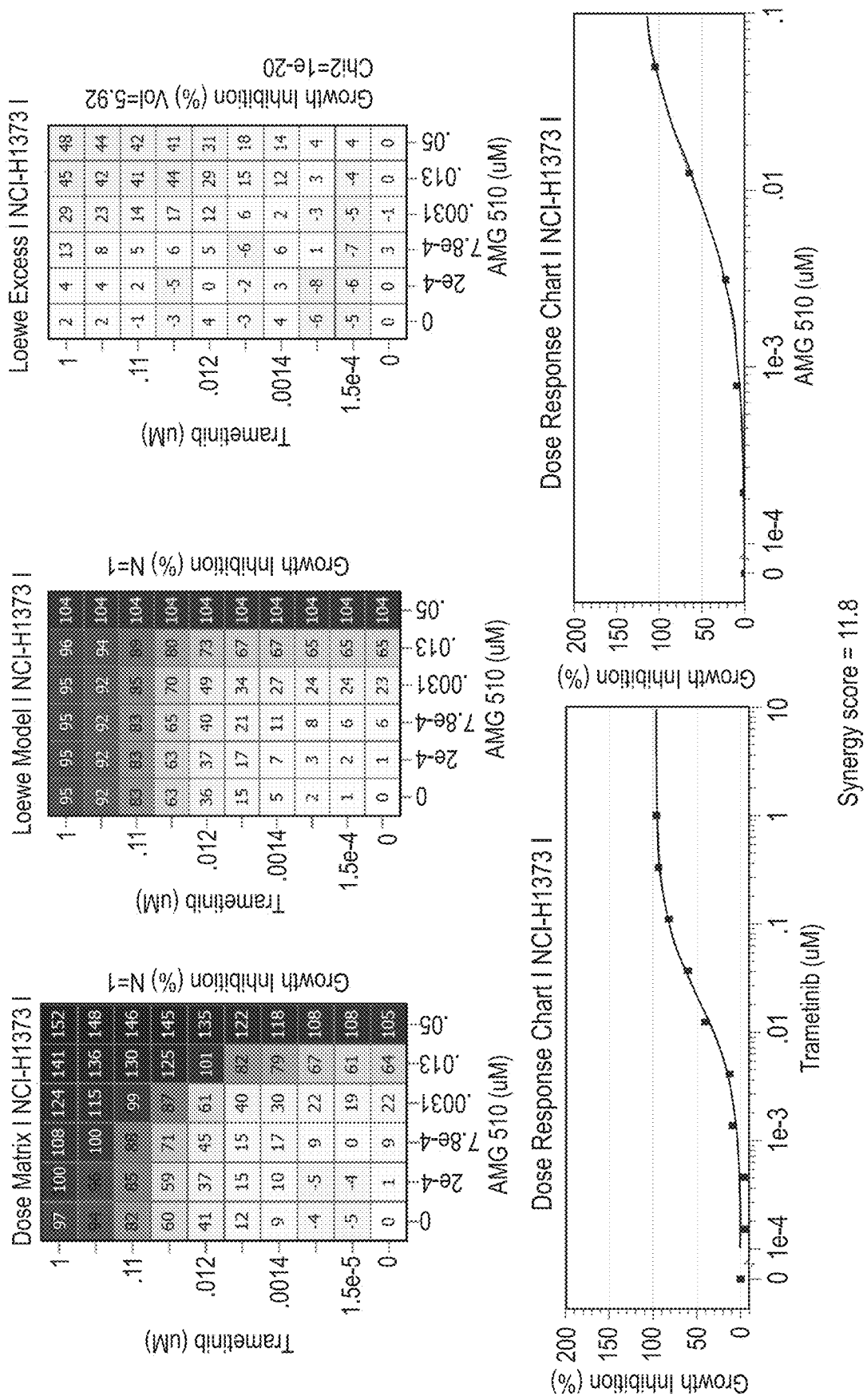

FIG. 17 shows AMG 510 X trametinib (3D) in NCI-H1373 cell line.

Figure 18:
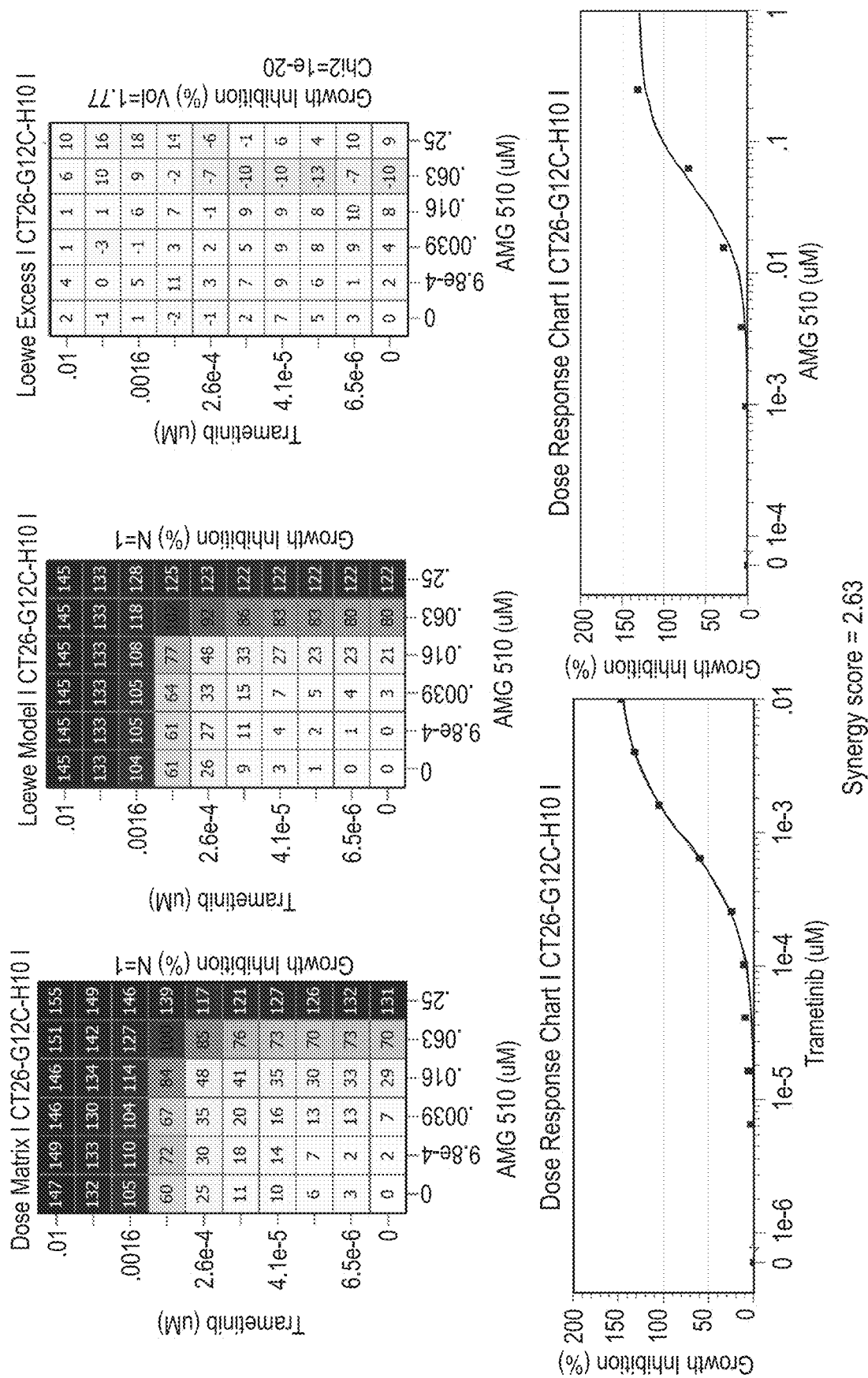

FIG. 18 shows AMG 510 X trametinib exhibits weak synergy due to high potency of each single agent in CT-26 KRAS p.G12C.

Figure 19:
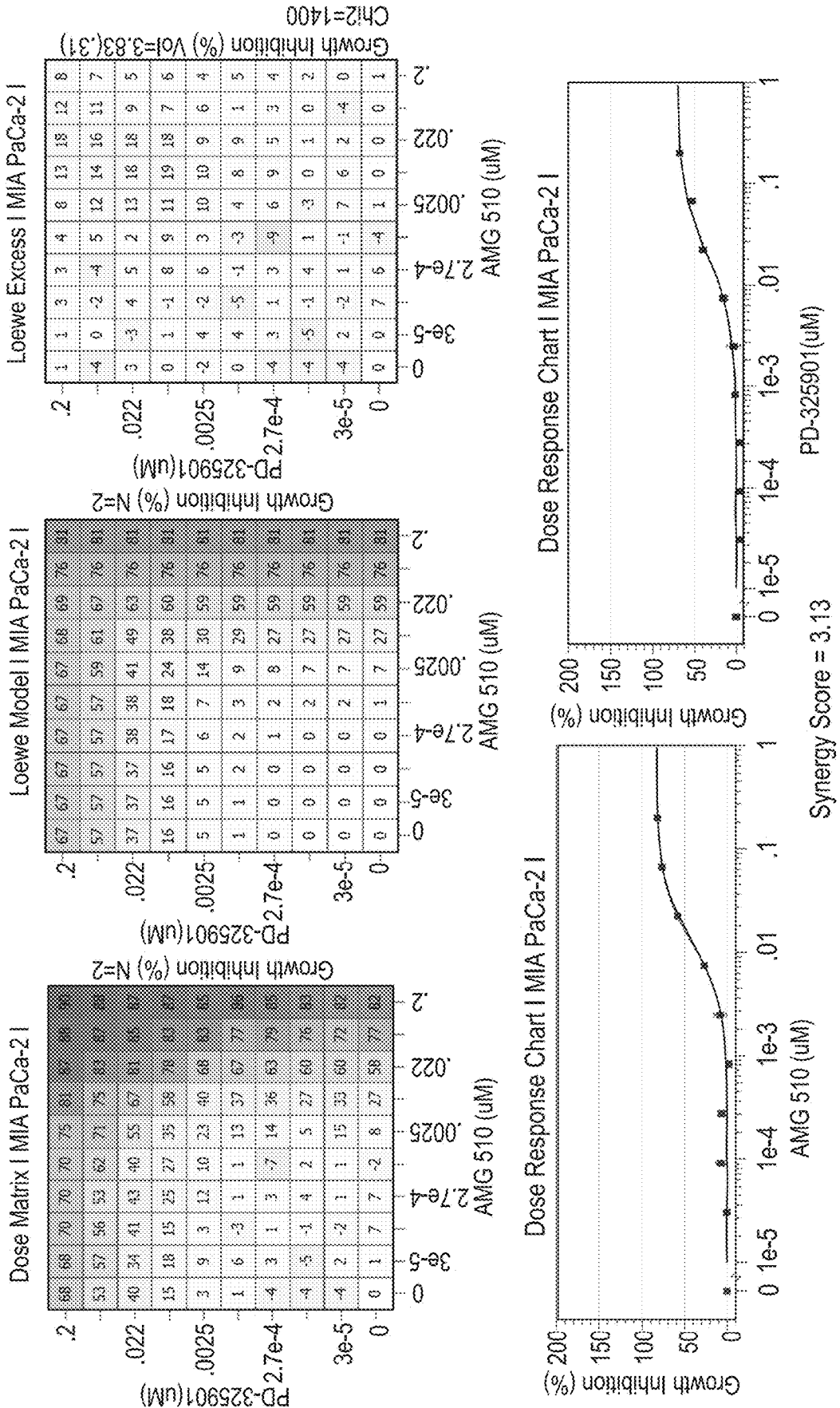

FIG. 19 shows AMG 510 X PD-325901 exhibits weak synergy in MIA PaCa-2.

Figure 20:
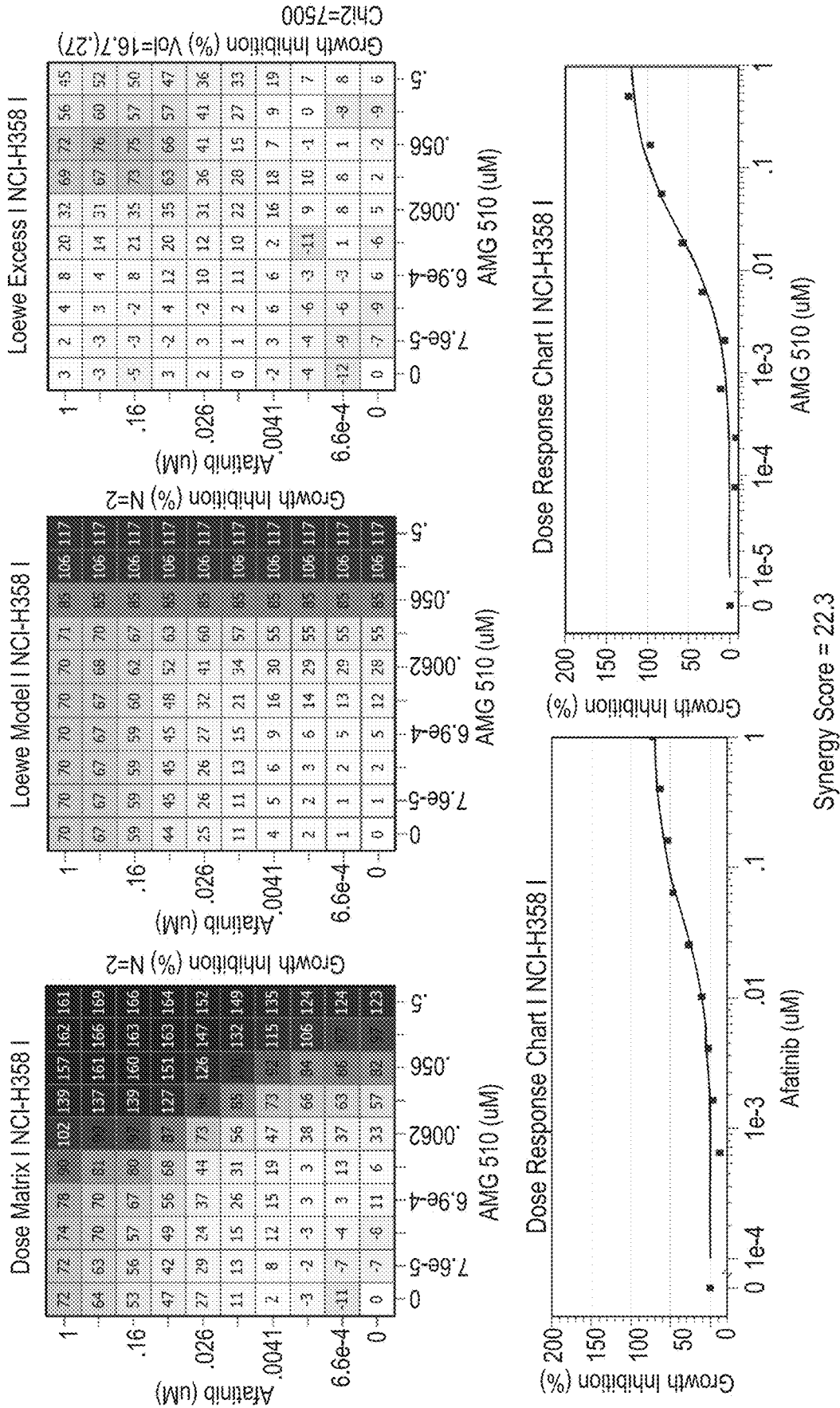

FIG. 20 shows AMG 510 X afatinib is synergistic in NCI-H358 cell line.

Figure 21:
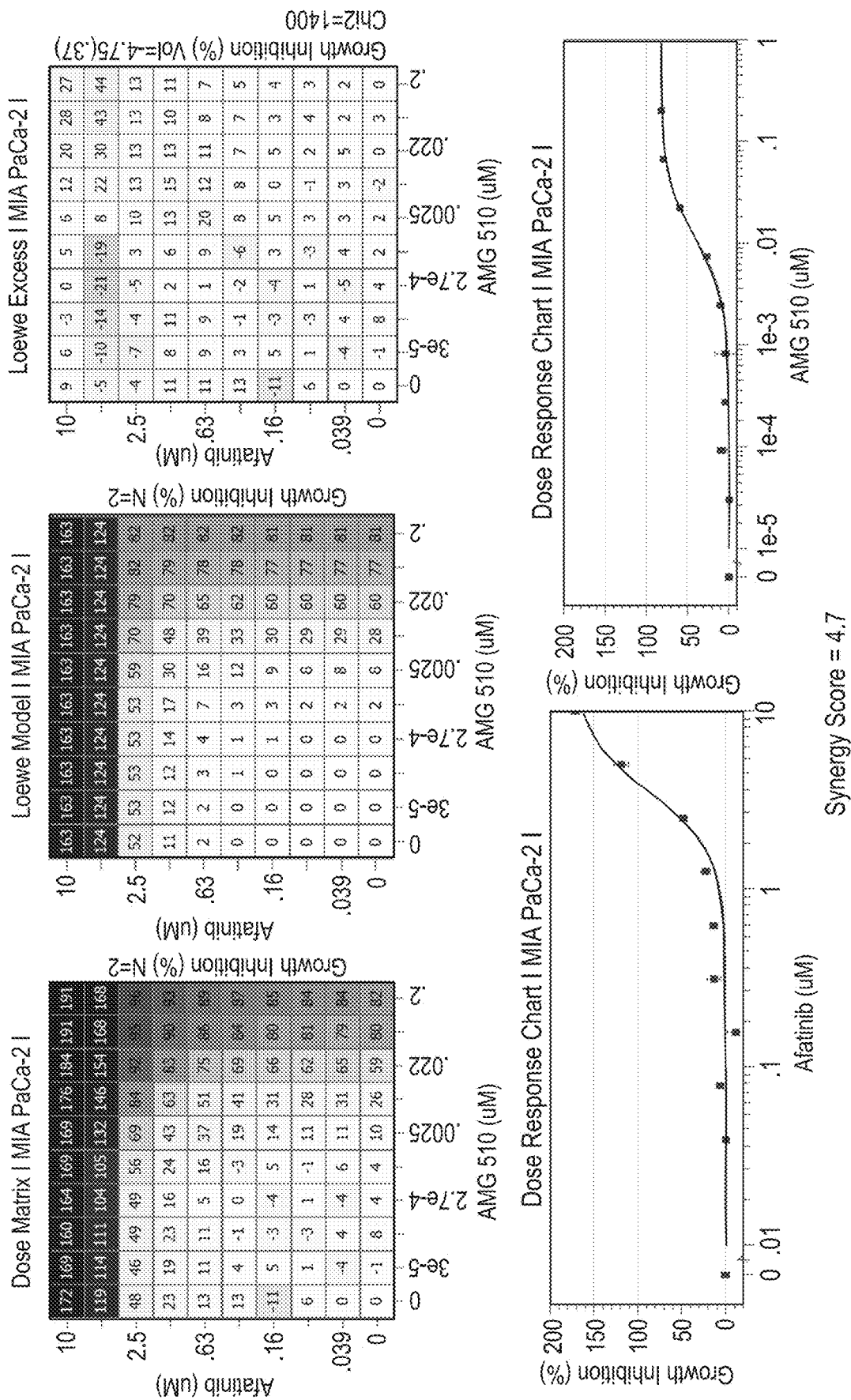

FIG. 21 shows AMG 510 X afatinib is weakly synergistic in MIA PaCa-2 cell line.

Figure 22:
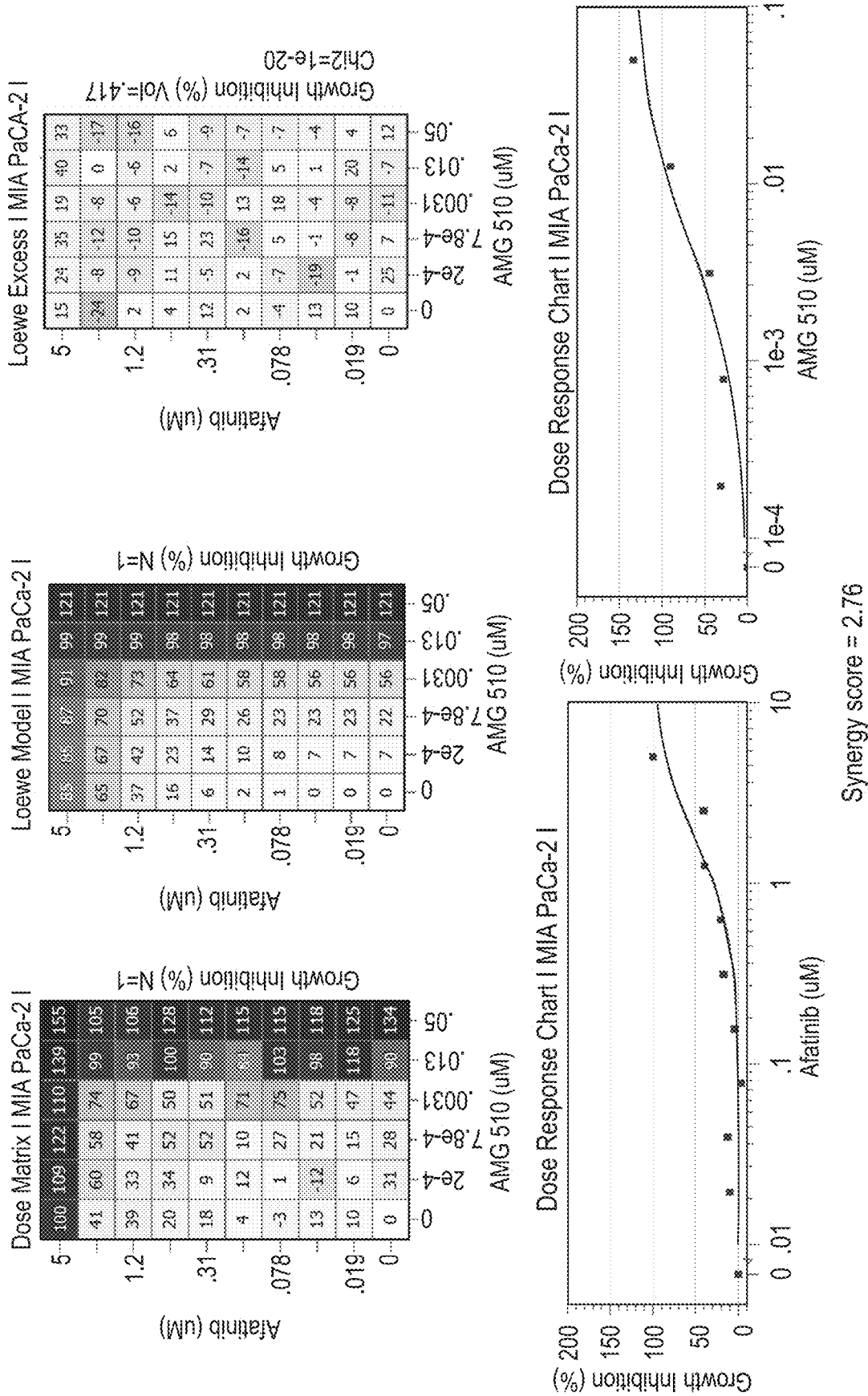

FIG. 22 shows 3D culture does not improve synergy of AMG 510 X afatinib in MIA PaCa-2 cell line.

Figure 23:
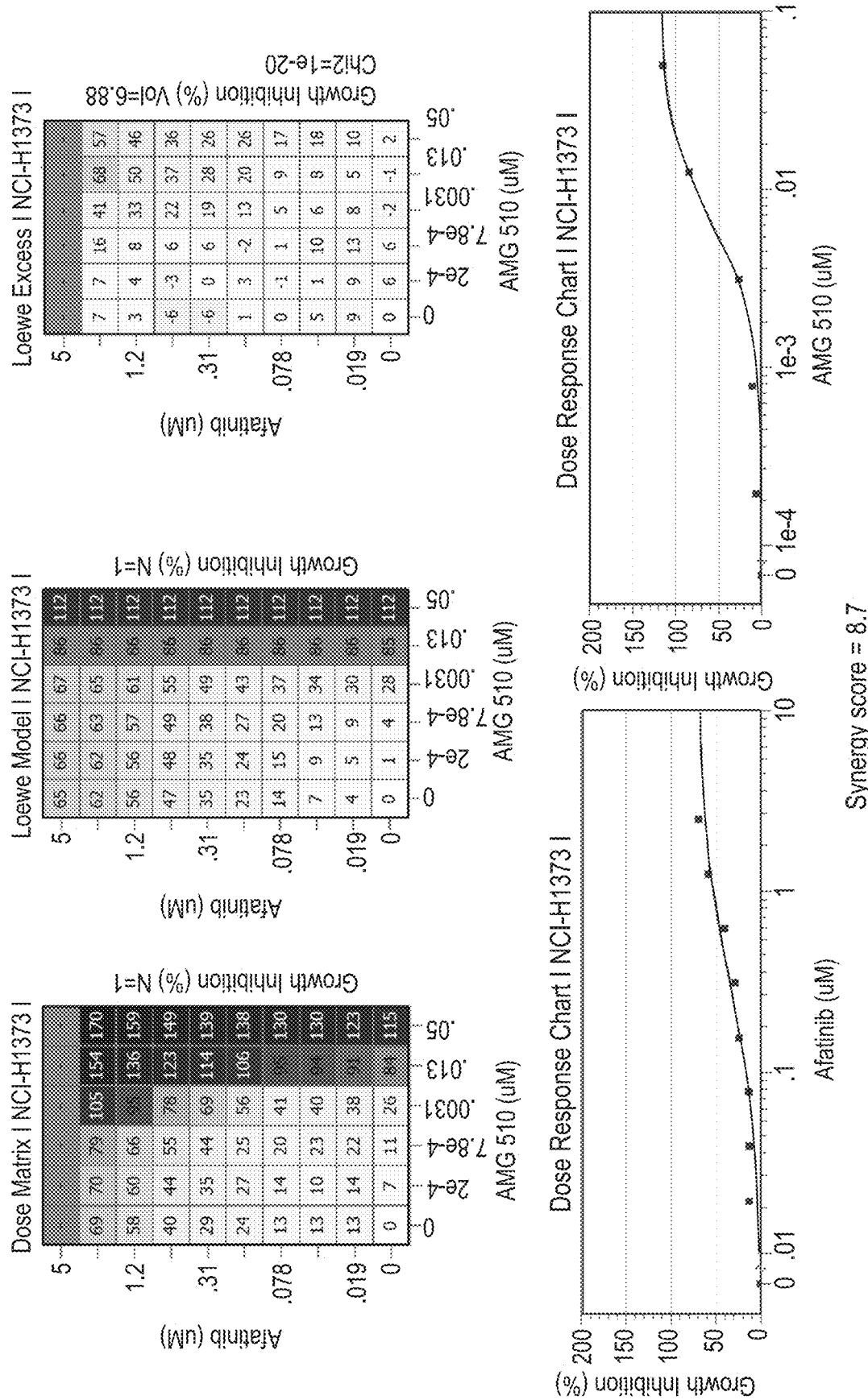

FIG. 23 shows AMG 510 X afatinib (3D) in NCI-H1373 cell line.

Figure 24:
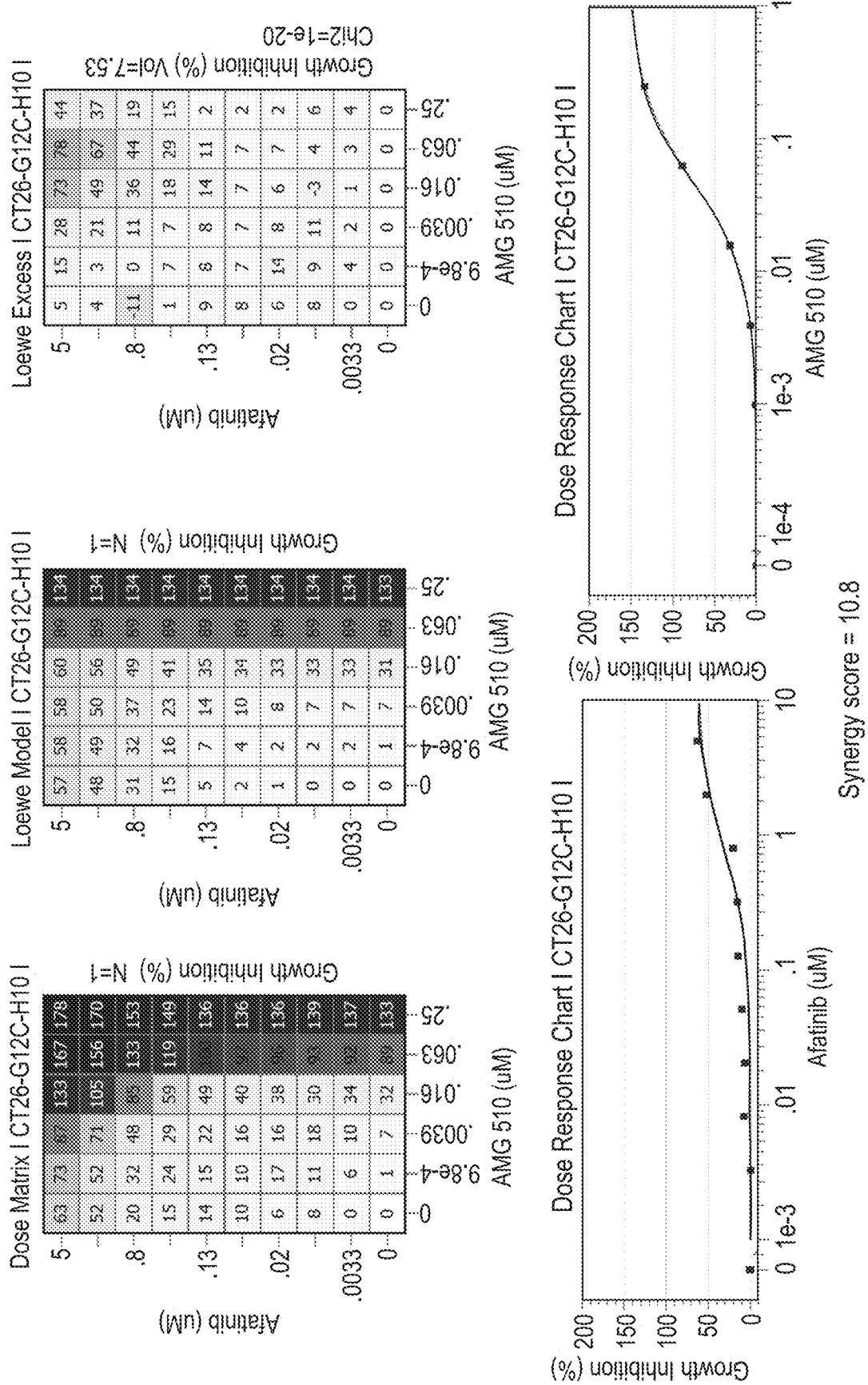

FIG. 24 shows AMG 510 X afatinib is moderately synergistic in CT-26 KRAS p.G12C.

Figure 25:
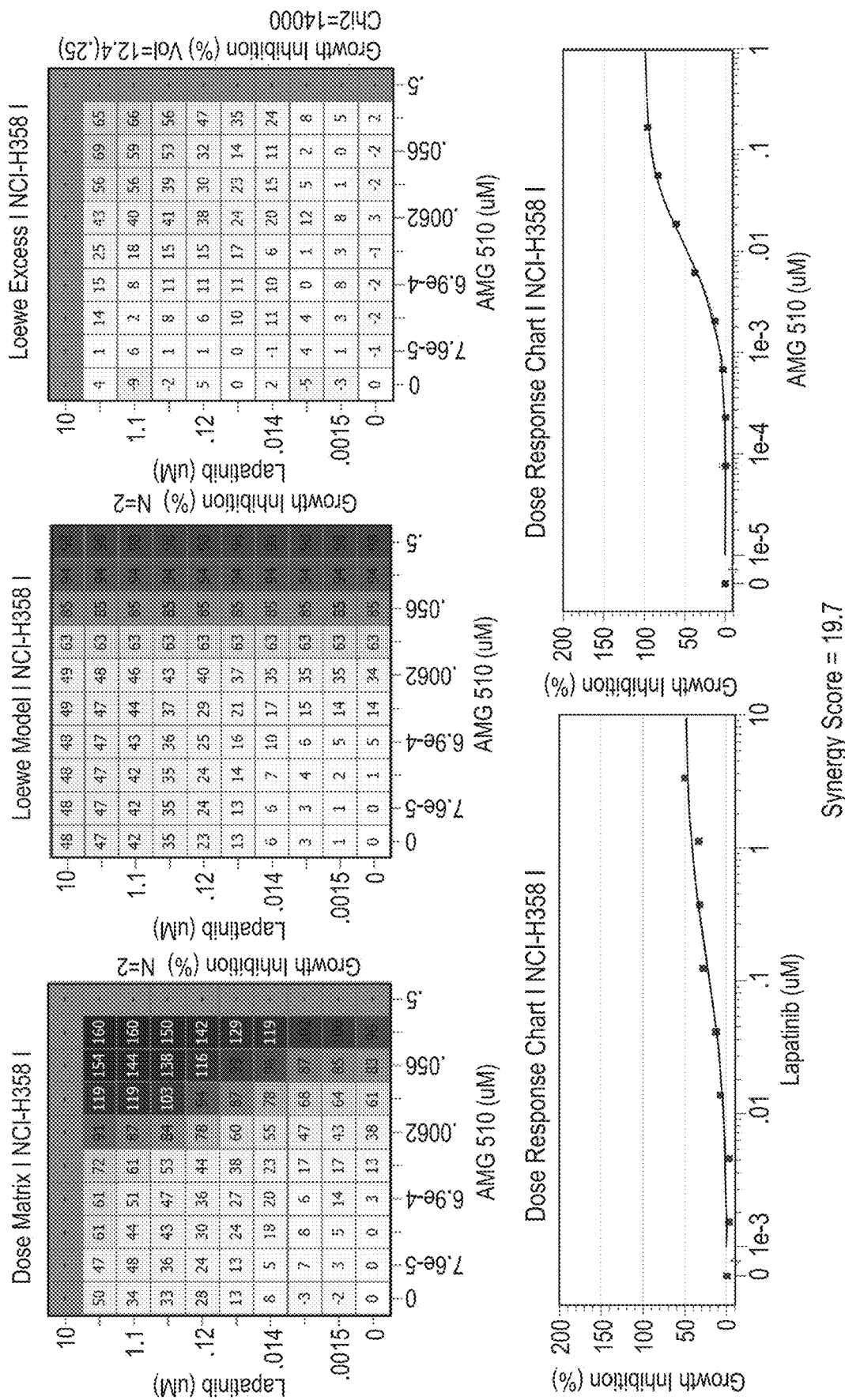

FIG. 25 shows AMG 510 X lapatinib is synergistic in NCI-H358 cell line.

Figure 26:
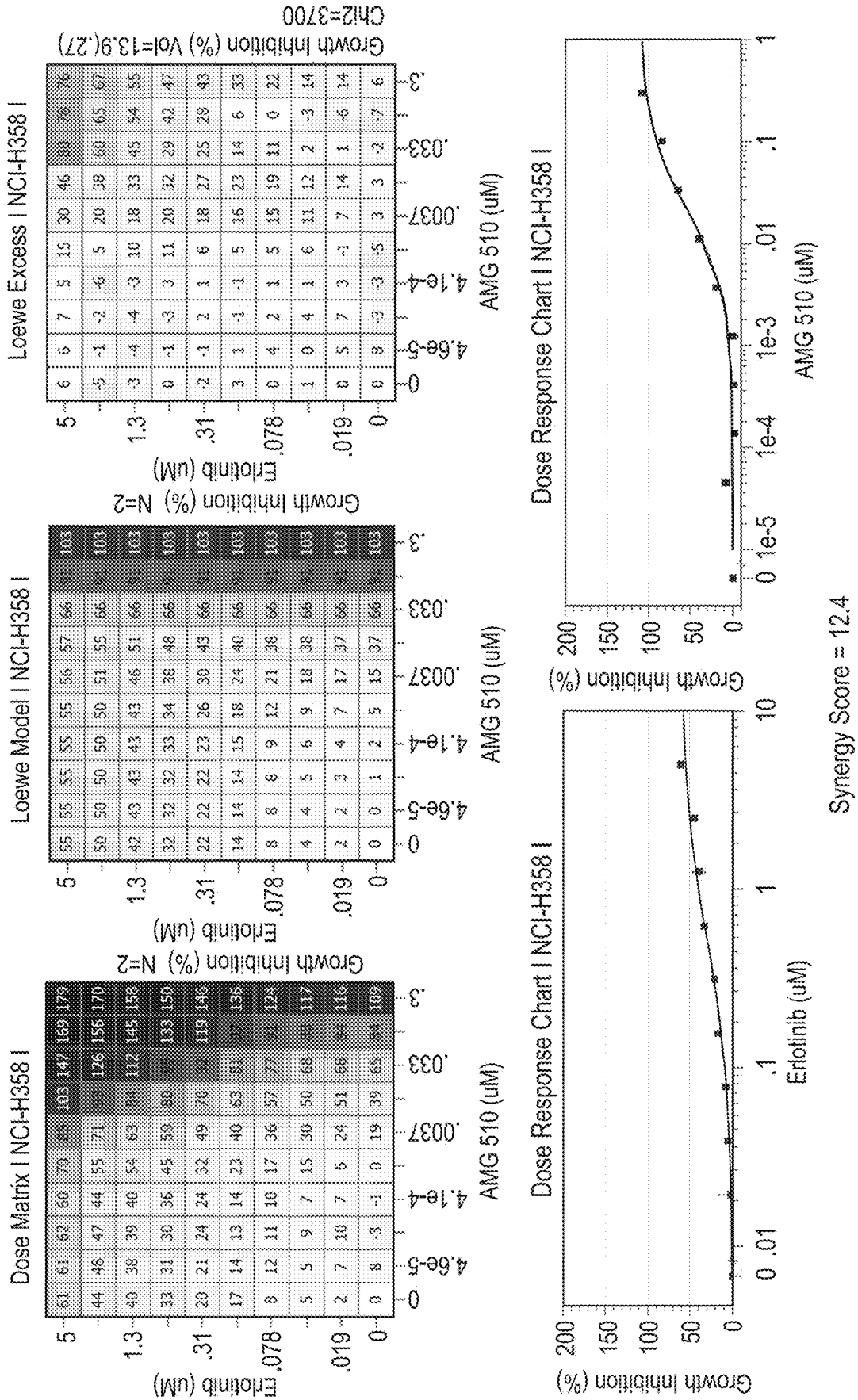

FIG. 26 shows AMG X erlotinib is moderately synergistic in NCI-H358 cell line.

Figure 27:
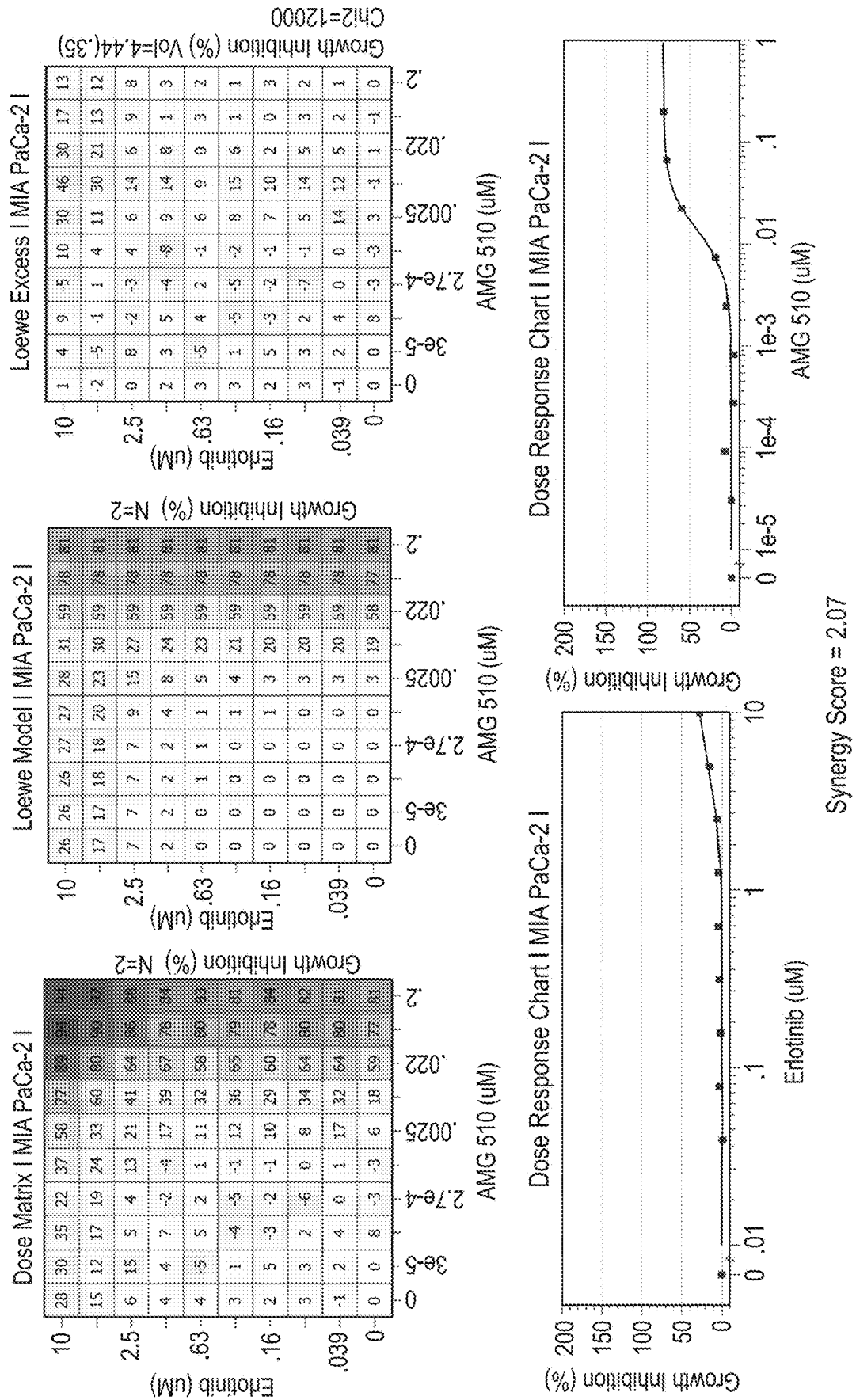

FIG. 27 shows no synergy observed with AMG 510 X erlotinib in MIA PaCa-2 cell line due to lack of erlotinib activity.

Figure 28:
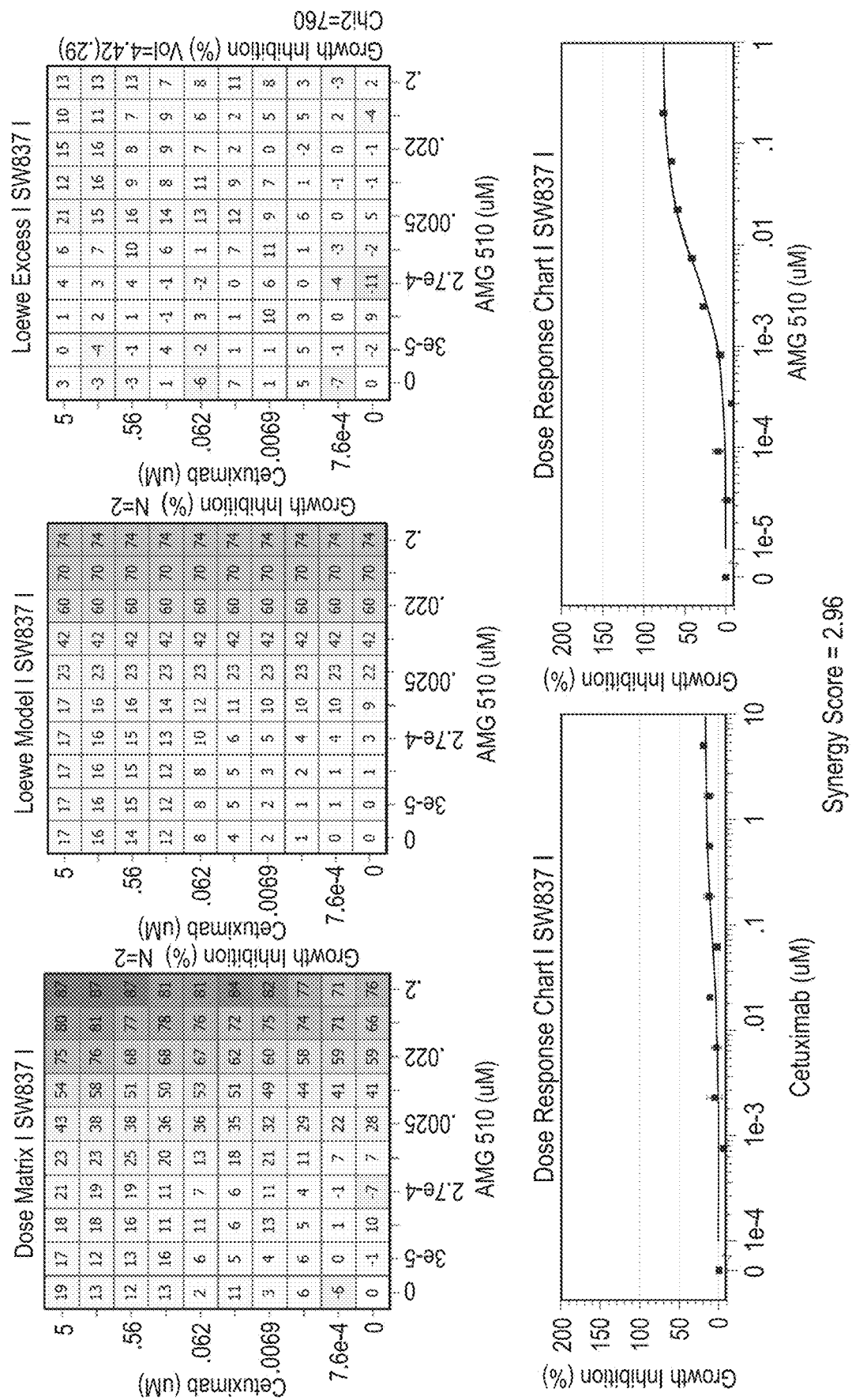

FIG. 28 shows no synergy observed with AMG 510 X cetuximab in SW837 due to lack of cetuximab activity in vivo.

Figure 29:
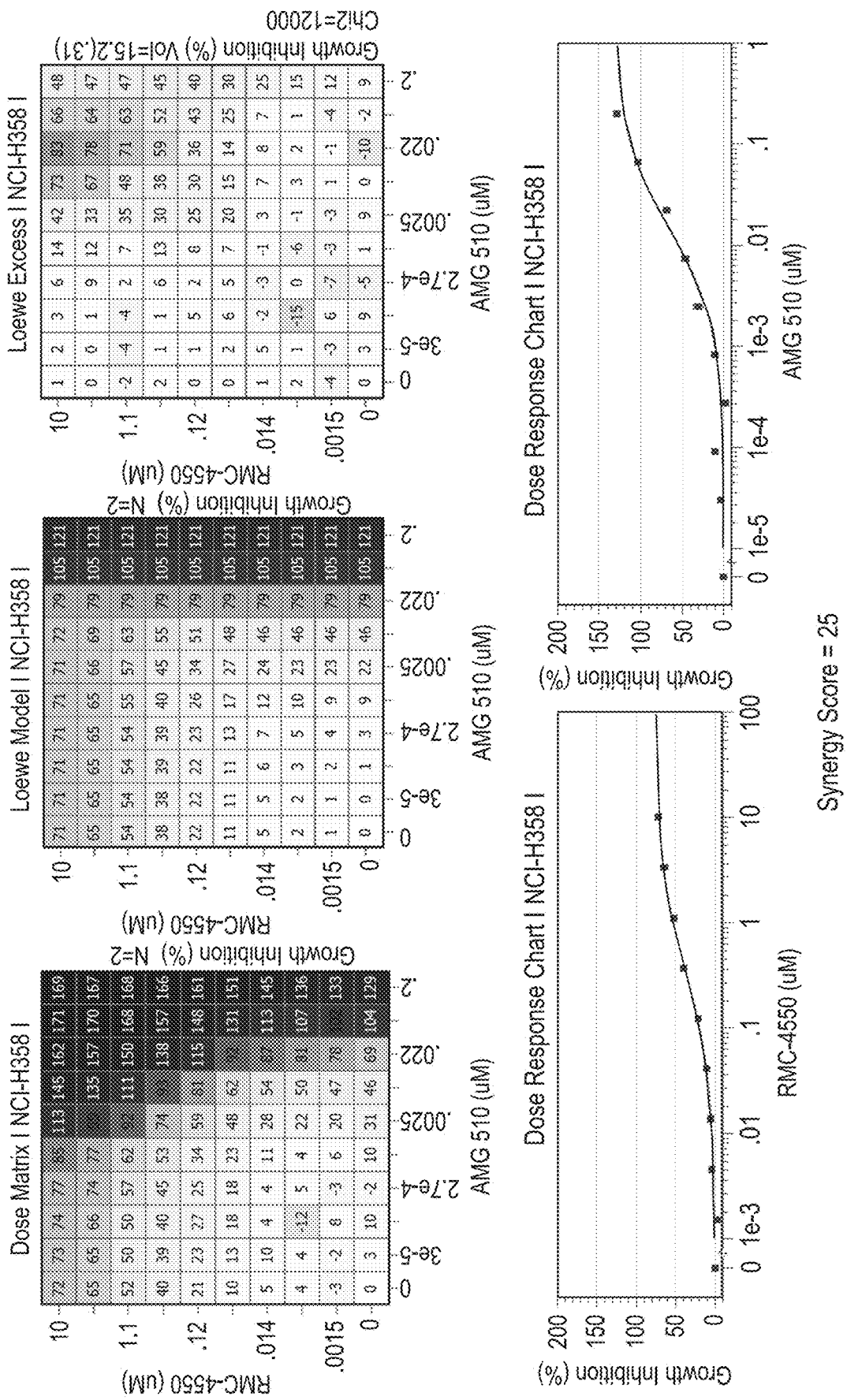

FIG. 29 shows AMG 510 X RMC-4550 is synergistic in NCI-H358 cell line.

Figure 30:
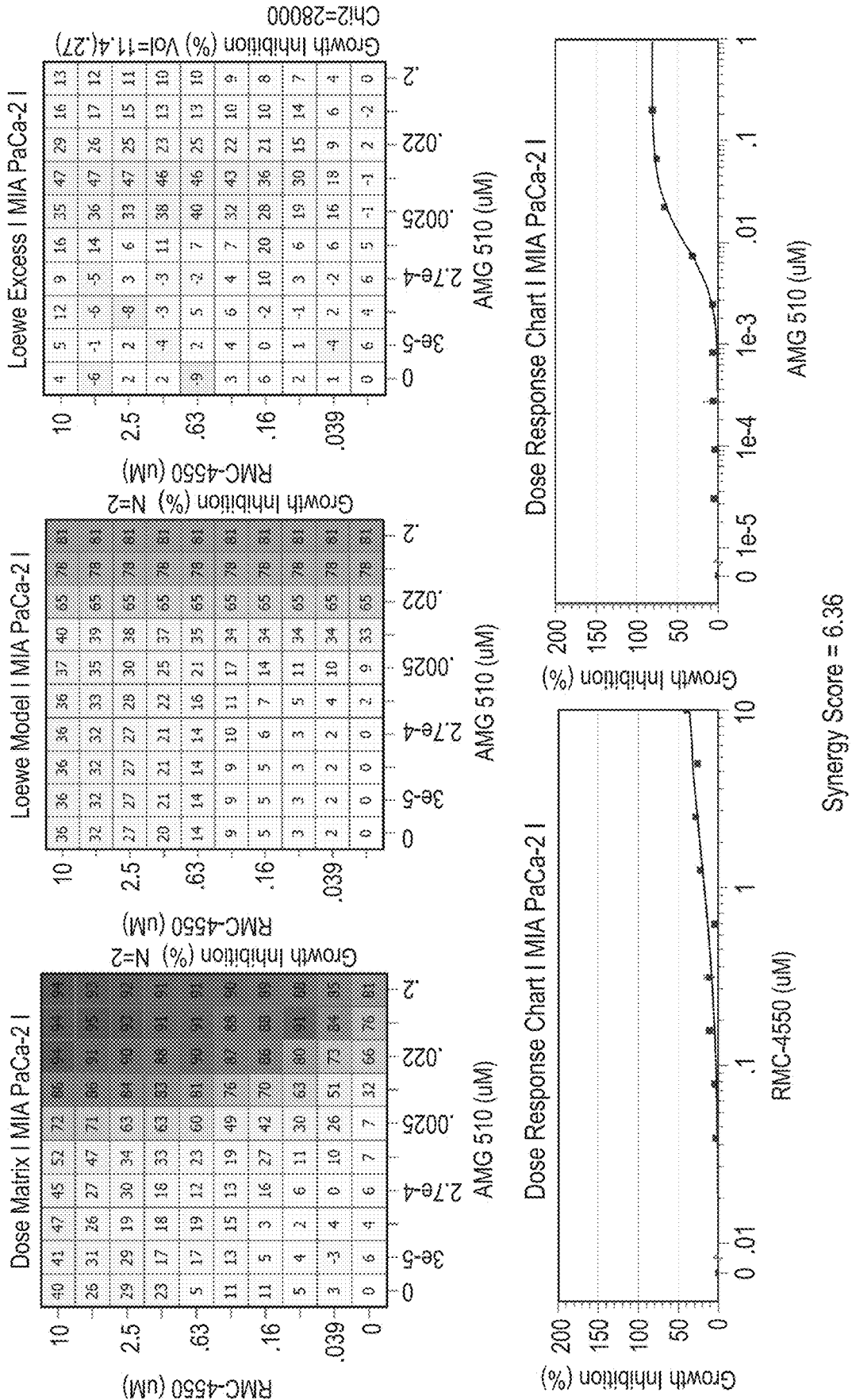

FIG. 30 shows AMG 510 X RMC-4550 is weakly synergistic in MIA PaCa-2 cell line.

FIG. 31 shows AMG 510 X RMC-4550 is moderately synergistic in CT-26 KRAS p.G12C.

Figure 32:
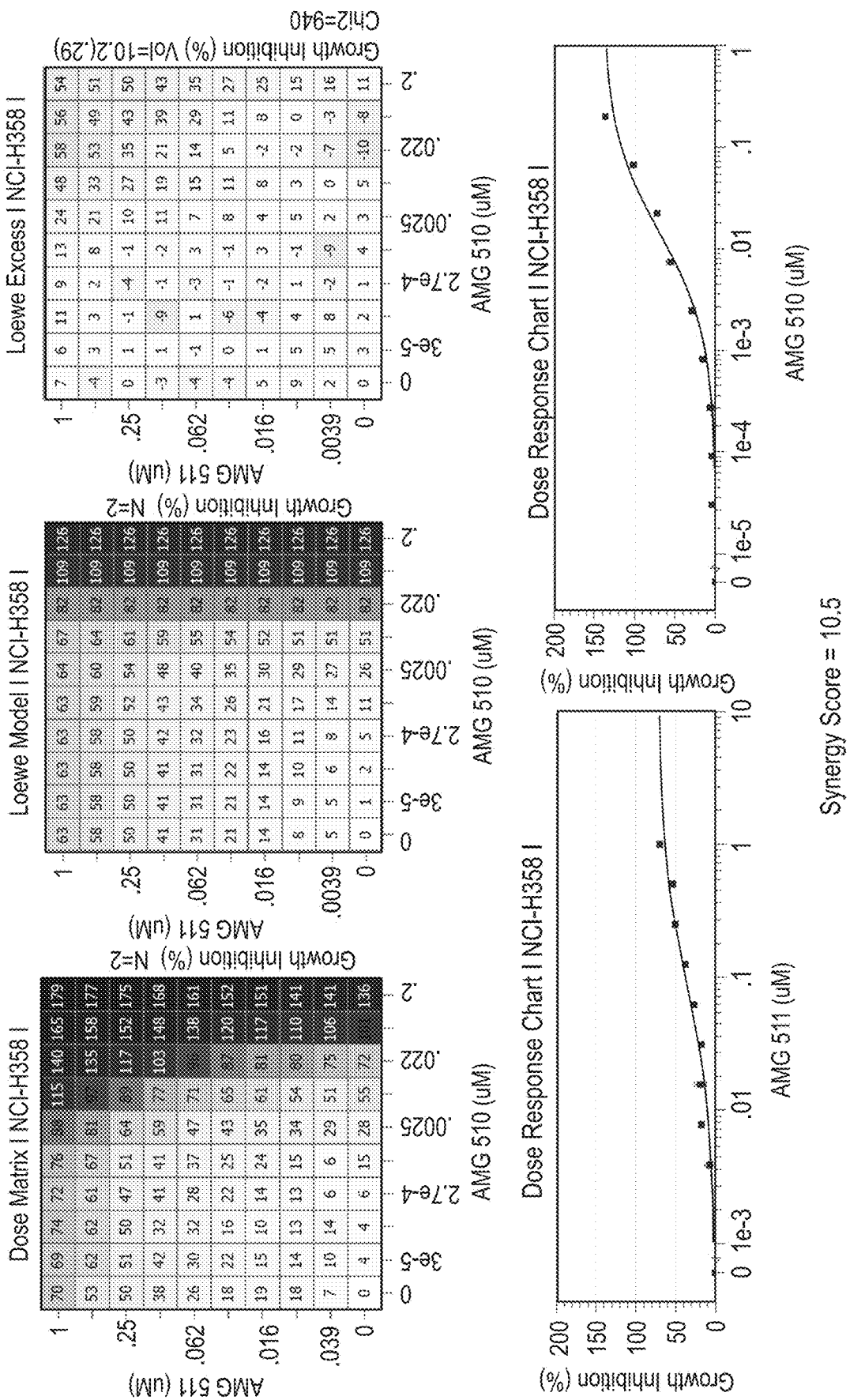

FIG. 32 shows AMG 510 X AMG 511 is moderately synergistic in NCI-H358 cell line.

Figure 33:
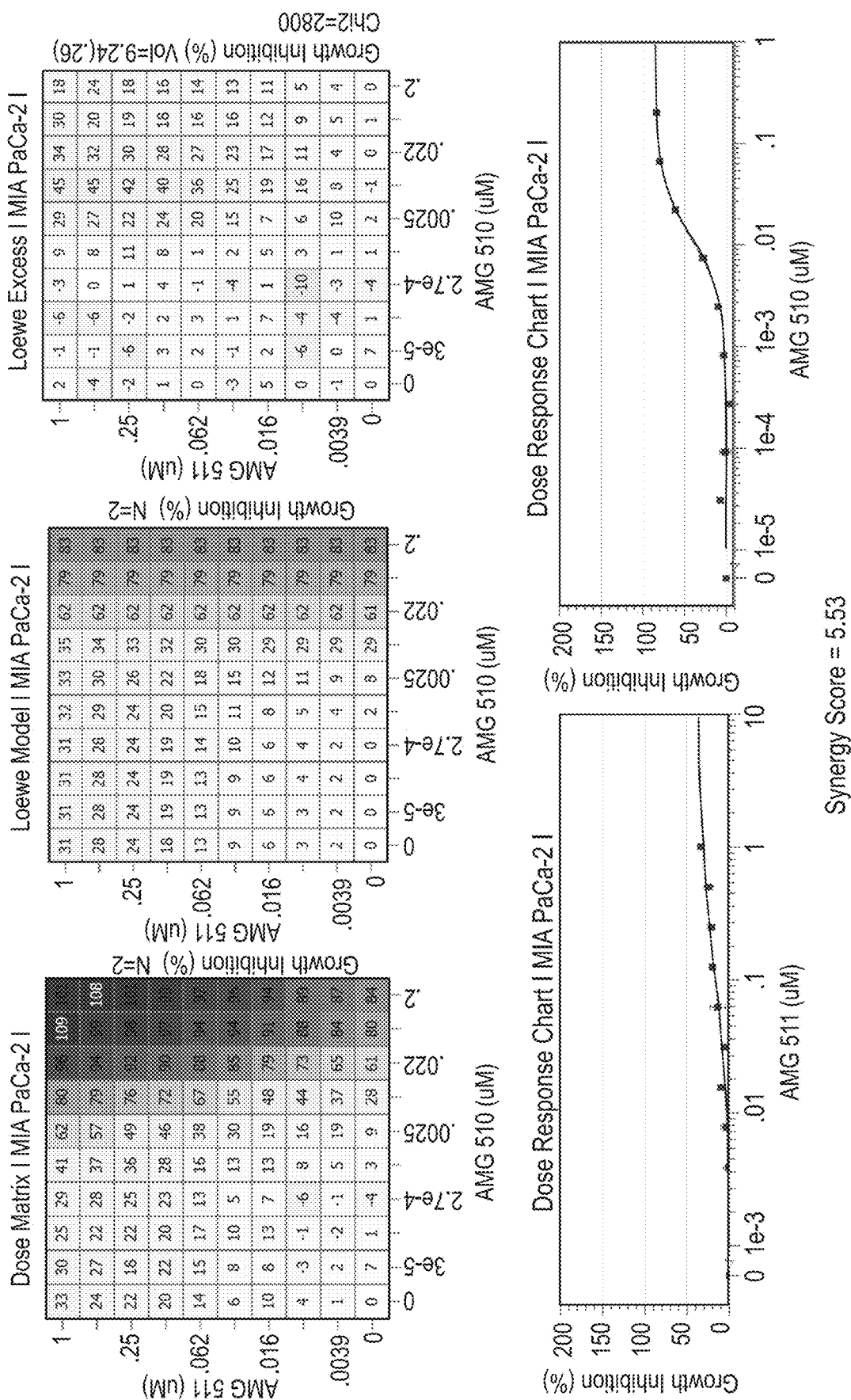

FIG. 33 shows AMG 510 X AMG 511 is weakly synergistic in MIA PaCa-2 cell line.

Figure 34:
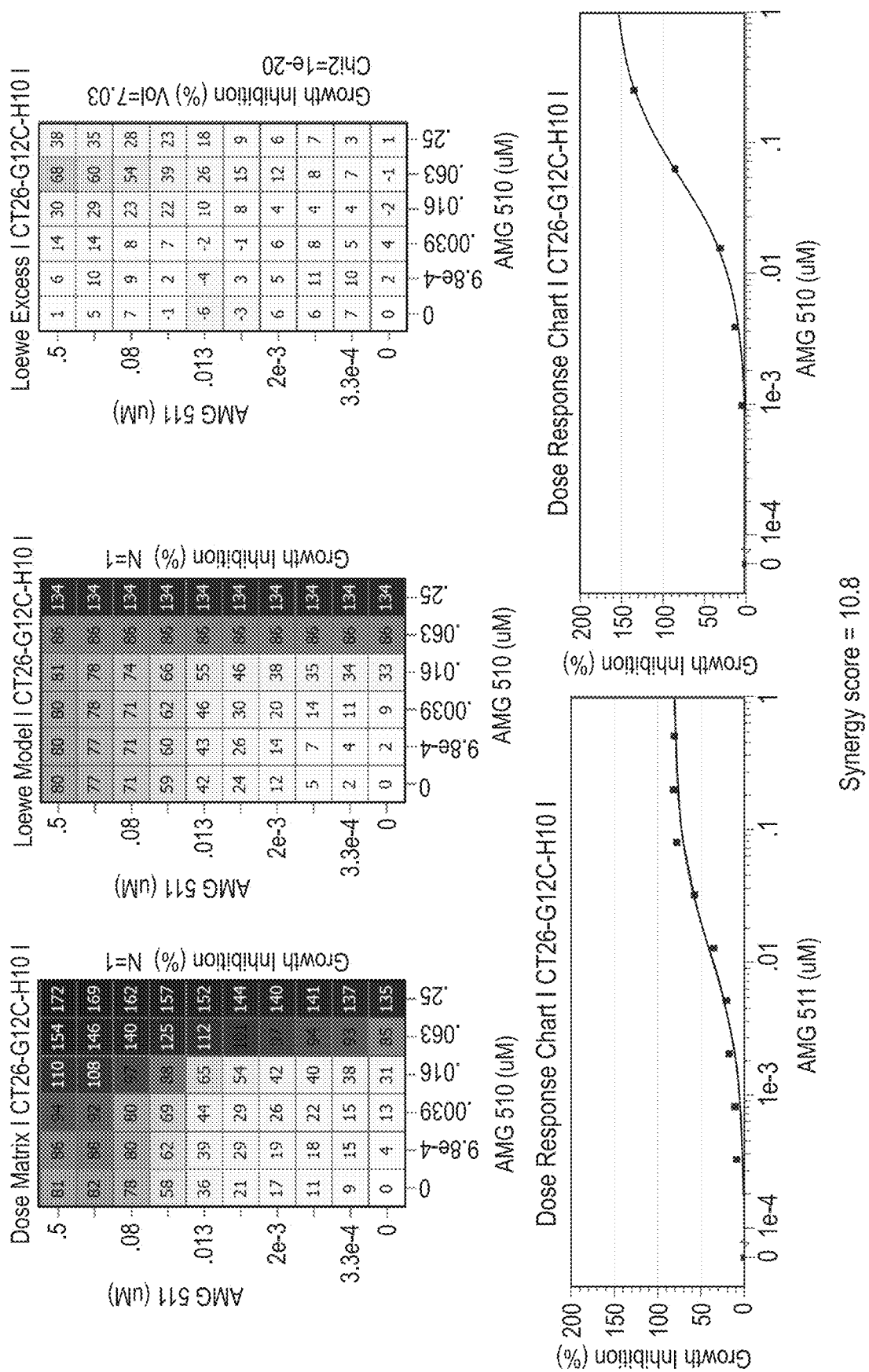

FIG. 34 shows AMG 510 X AMG 511 is moderately synergistic in CT-26 KRAS p.G12C.

Figure 35:
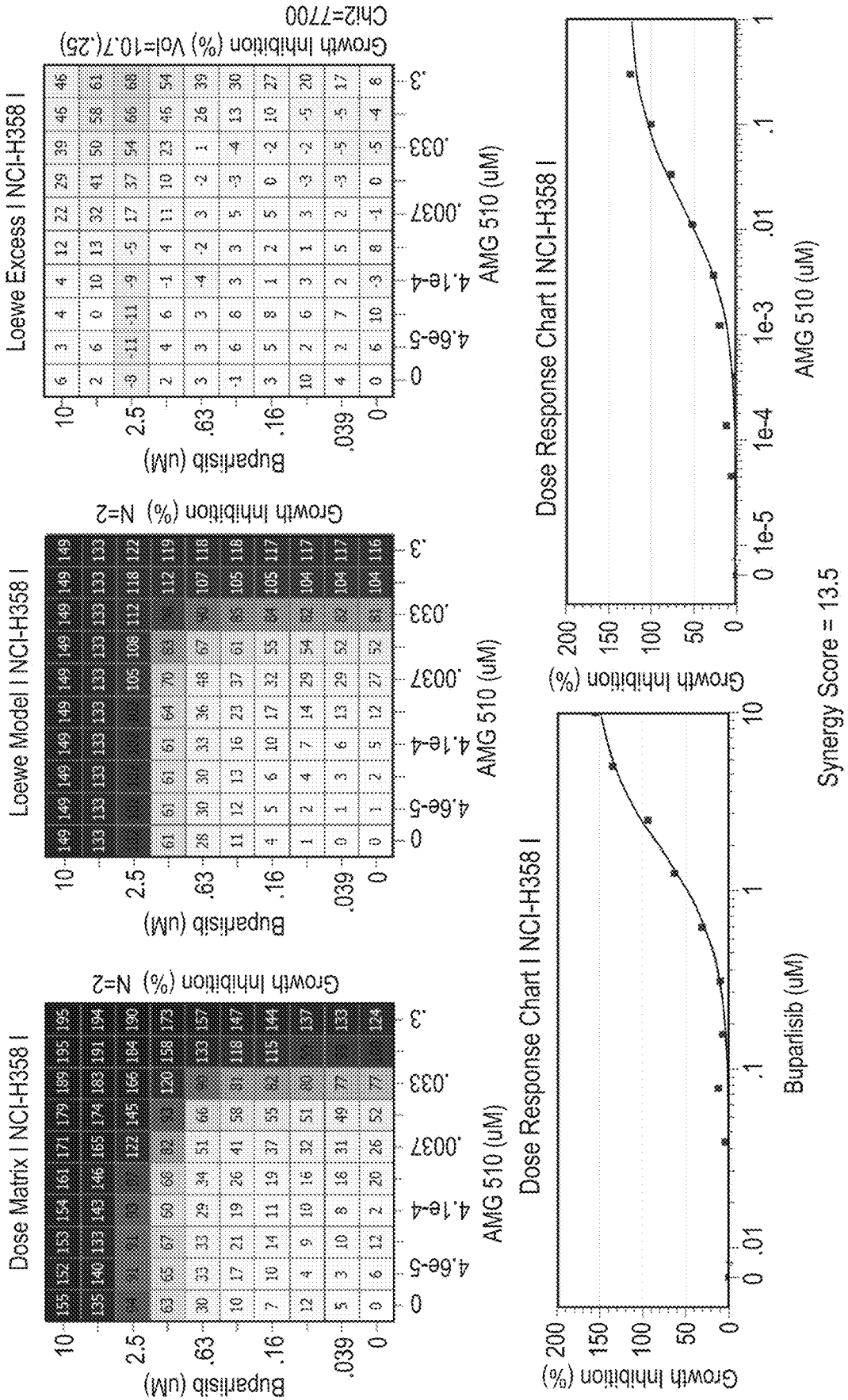

FIG. 35 shows AMG 510 X buparlisib (BKM120) is moderately synergistic in NCI-H358 cell line.

Figure 36:
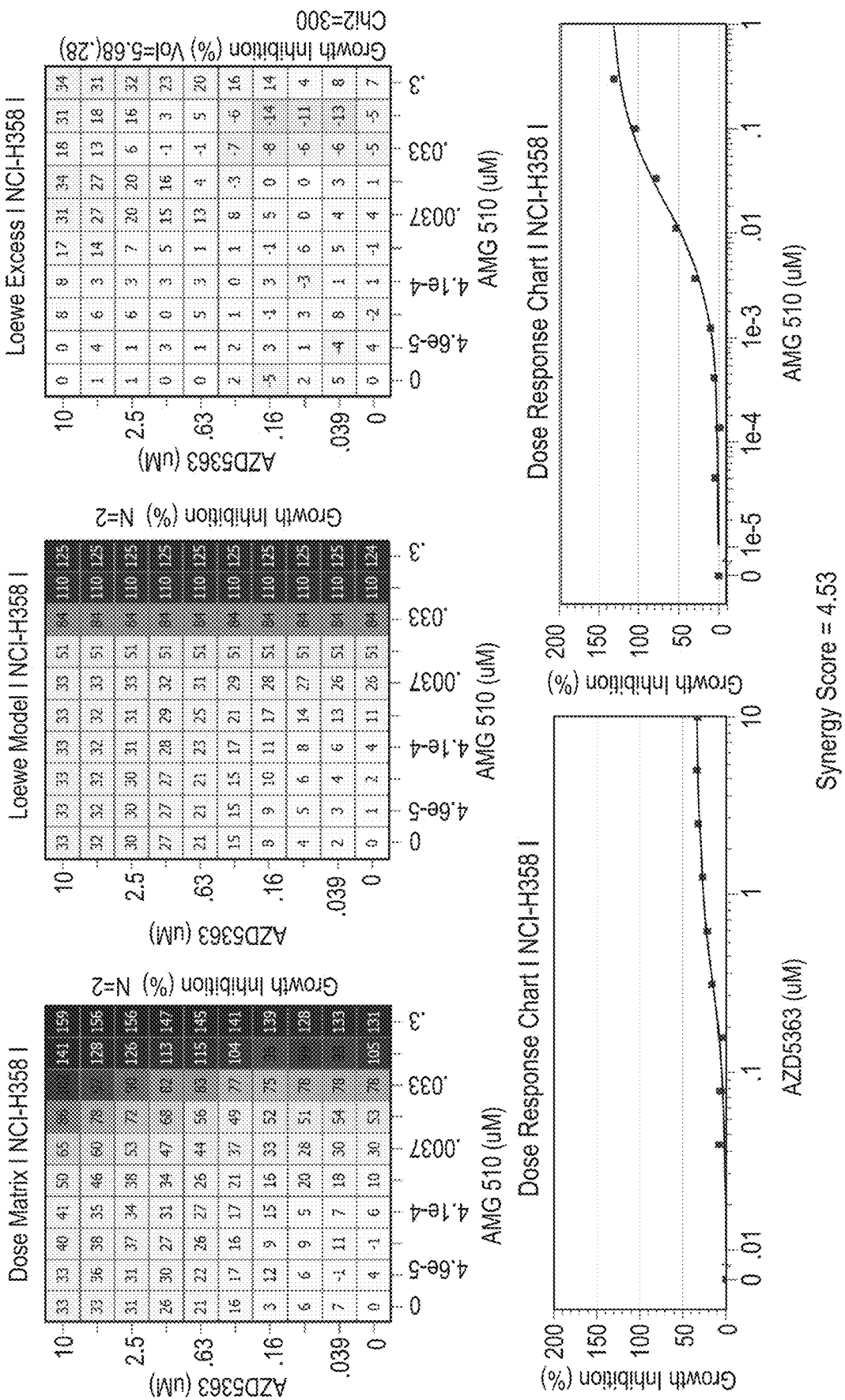

FIG. 36 shows AMG 510 X AZD5363 is weakly synergistic in NCI-H358 cell line.

Figure 37:
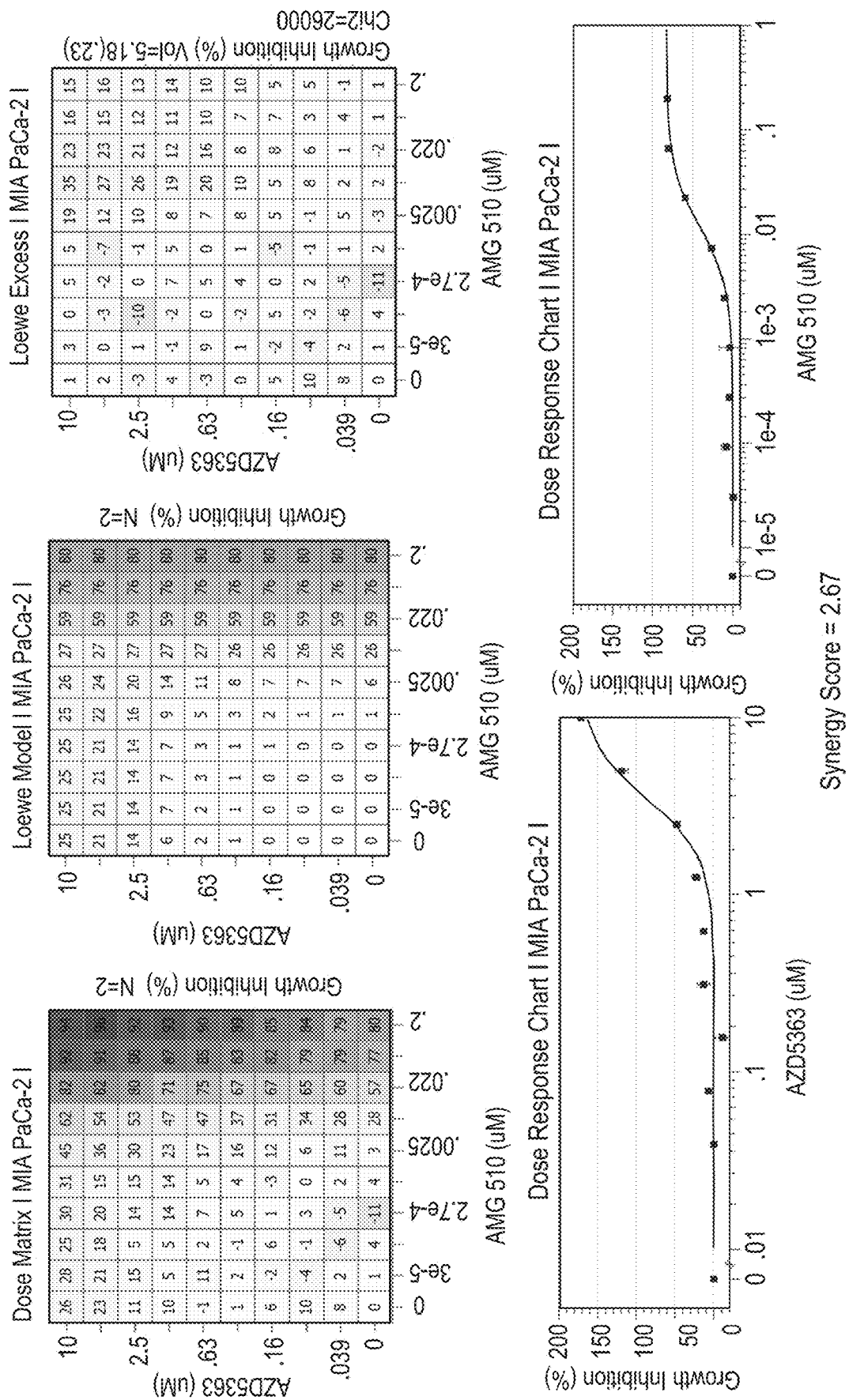

FIG. 37 shows AMG 5120 X AZD5363 is weakly synergistic in MIA PaCa-2.

Figure 38:
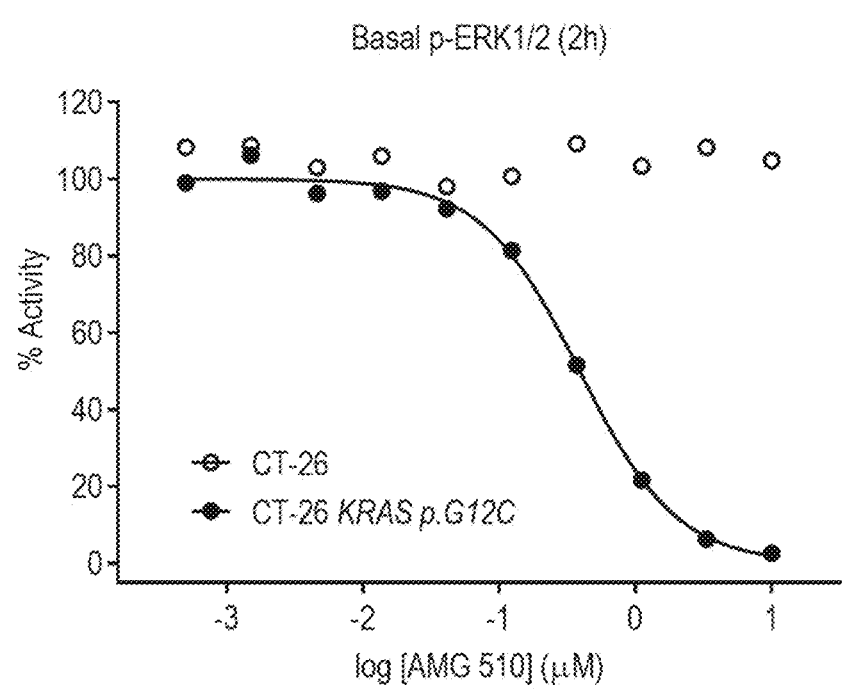

FIG. 38 shows AMG 510 inhibits KRAS signaling in CT-26 KRAS p.G12C in 2D culture.

Figure 39A:
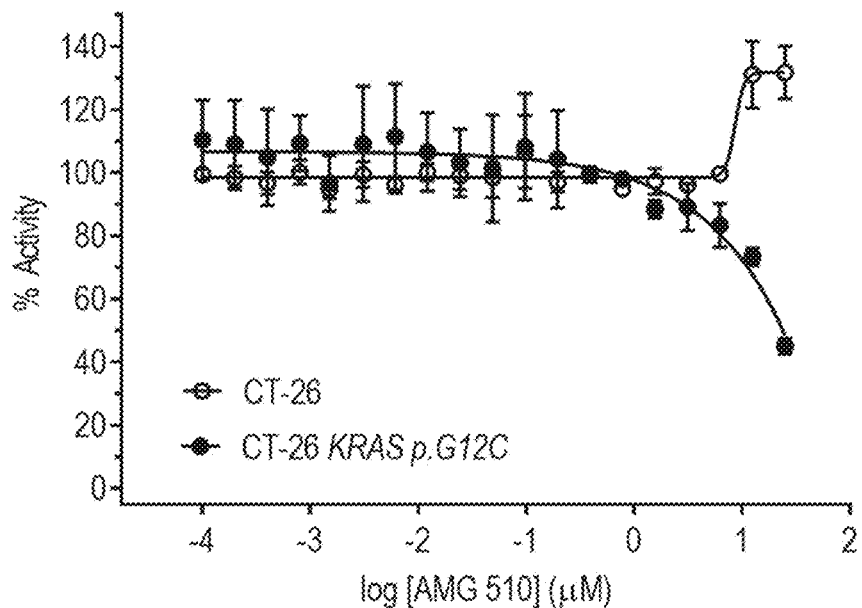
Figure 39B:
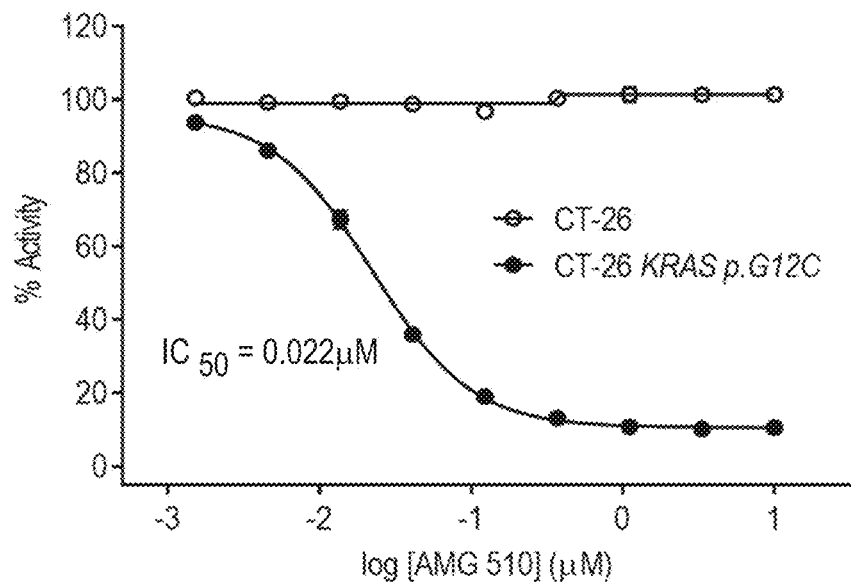

FIGS. 39A and 39B show mouse CT-26 KRAS p.G12C cells are sensitive to AMG 510 in 3D culture.

FIG. 40A shows X-ray co-crystal structure of KRAS$^{G12C/}$ $_{C51S/C80L/C118S}$ bound to GDP and ARS-1620 (PDB ID: 5V9U).

FIG. 40B shows X-ray co-crystal structure of KRAS$^{G12C/}$ $_{C5IS/C80L/C118S}$ bound to GDP and AMG 510 at 1.65 Å resolution (PDB ID: not yet assigned).

FIG. 40C shows biochemical activity of AMG 510 and ARS-1620 as measured in a SOS1-catalyzed nucleotide exchange assay with purified KRAS$^{G12C/C118A}$ or KRAS$^{C118A}$ protein, n=4.

Figure 40D:
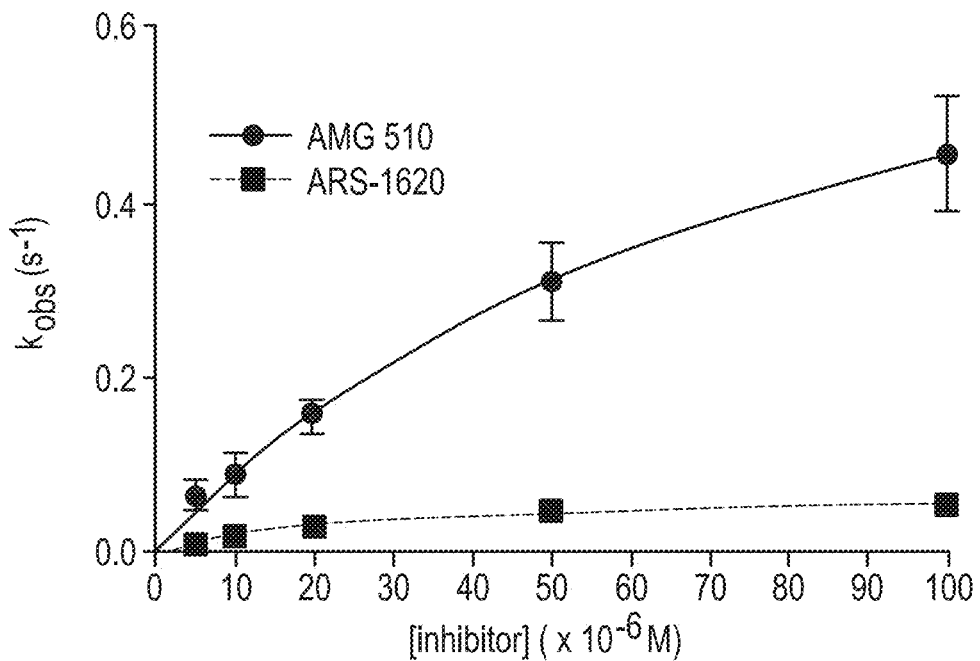

FIG. 40D shows kinetic properties of AMG 510 and ARS-1620 as determined by mass spectrometry (n≥2)

Figure 40E:
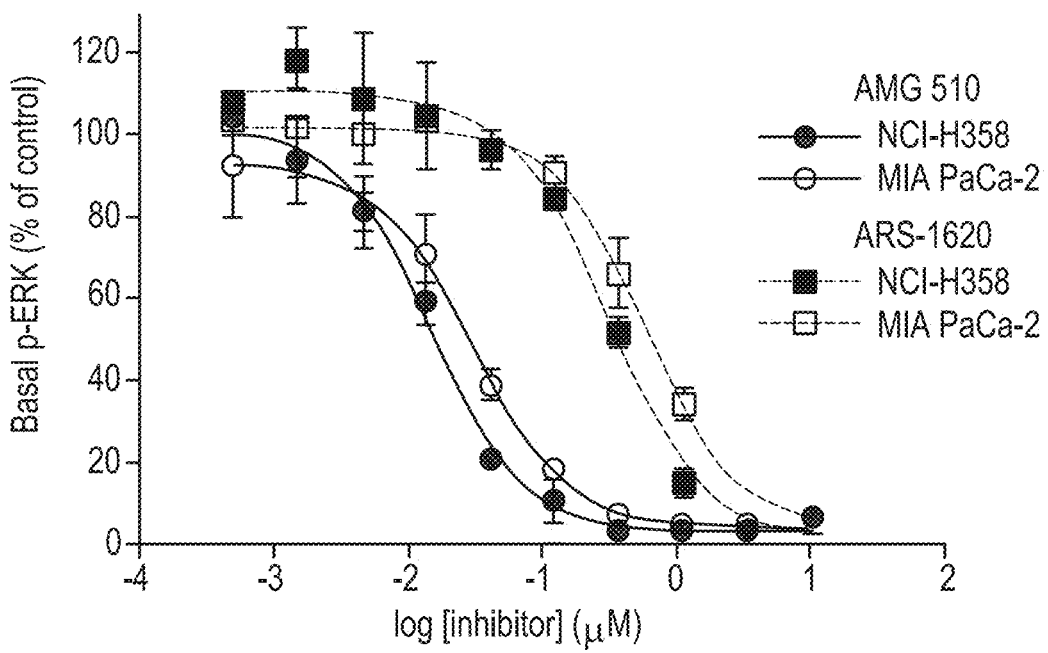

FIG. 40E shows cellular activity of AMG 510 and ARS-1620 in NCI-H358 and MIA PaCa-2 as measured by inhibition of ERK1/2 phosphorylation after 2-hour treatment (n=2).

Figure 40F:
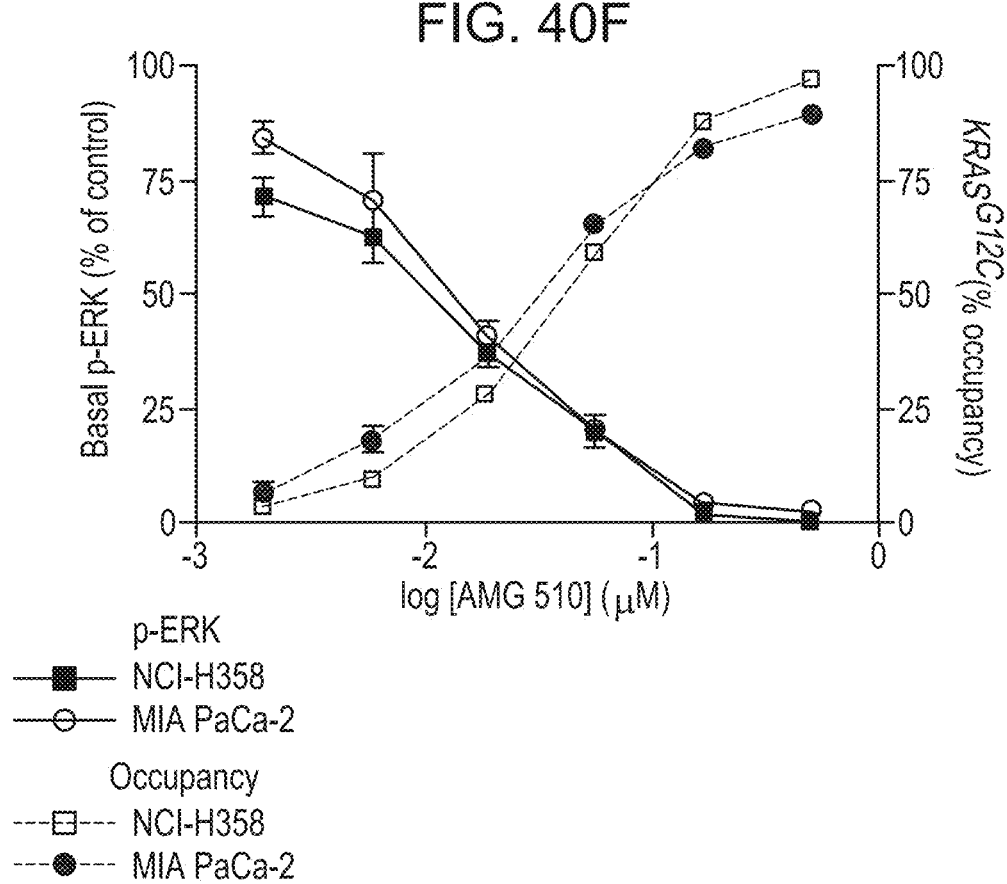

FIG. 40F shows inhibition of ERK phosphorylation and occupancy of KRAS$^{G12C}$ by AMG 510 in NCI-H358 and MIA PaCa-2 cells following 2-hour treatment (n=3).

Figure 40G:
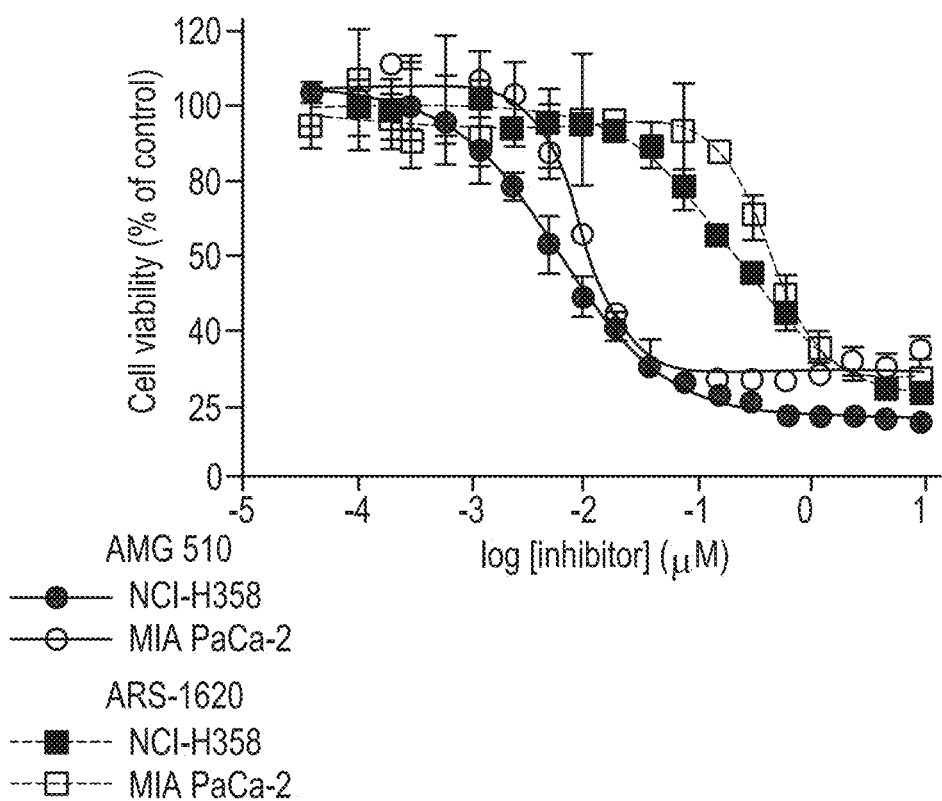

FIG. 40G shows cellular activity of AMG 510 and ARS-1620 in NCI-H358 and MIA PaCa-2 as measured by effects on cell viability after 72-hour treatment (n=3).

Figure 40H:
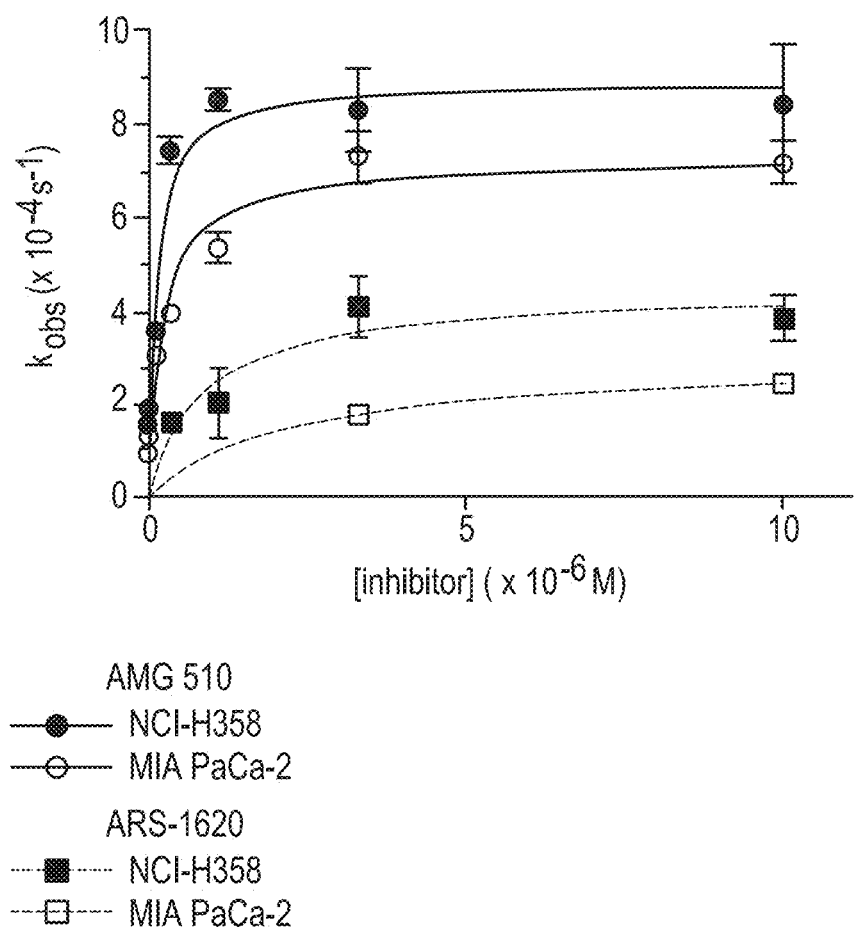

FIG. 40H shows kinetic properties of AMG 510 and ARS-1620 as determined by inhibition of ERK phosphorylation (n≥2).

Figure 41A:
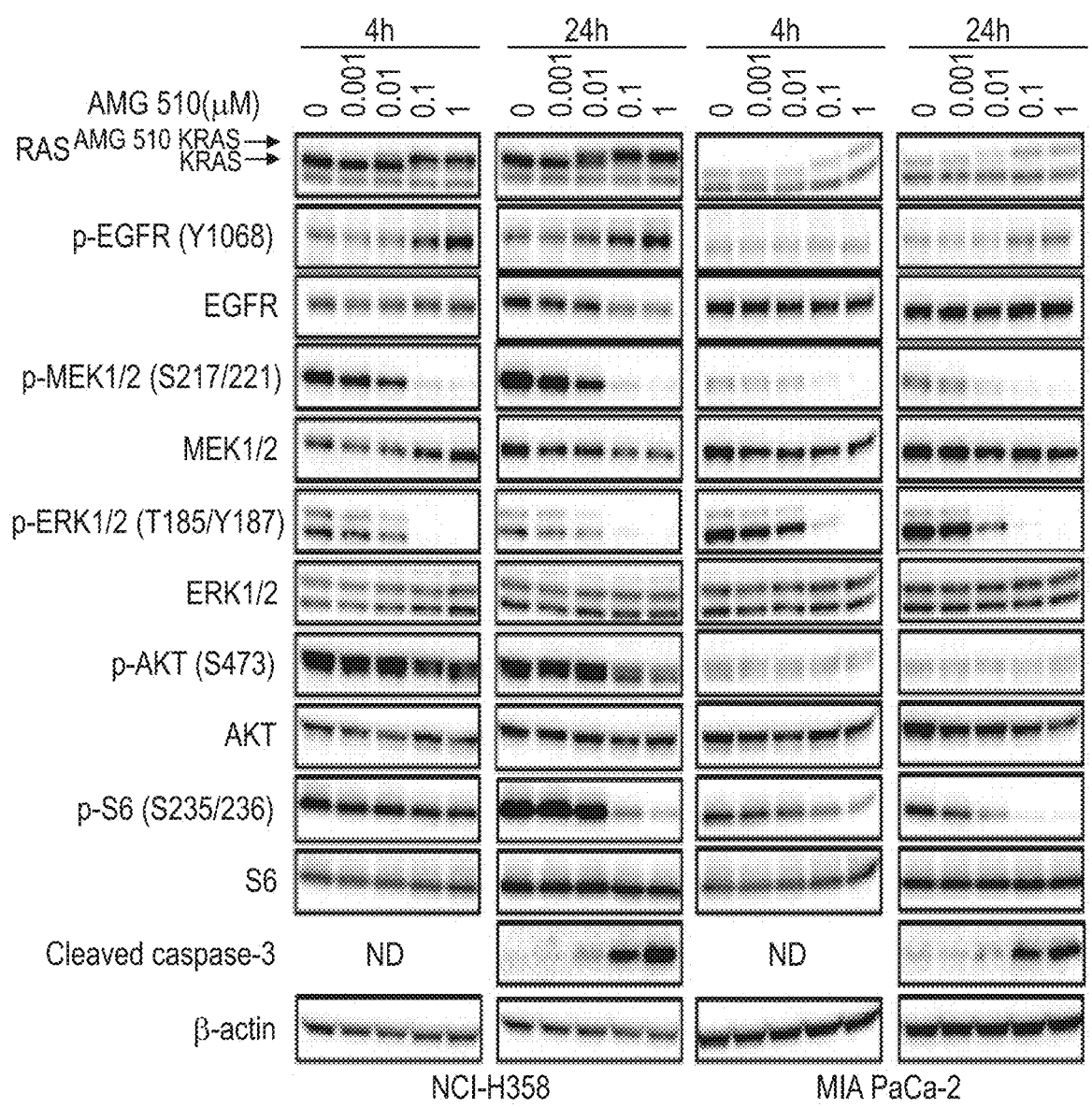

FIG. 41A shows the effect on cellular signaling in NCI-H358 or MIA PaCa-2 after 4- or 24-hour treatment with a dose-response of AMG 510.

Figure 41B:
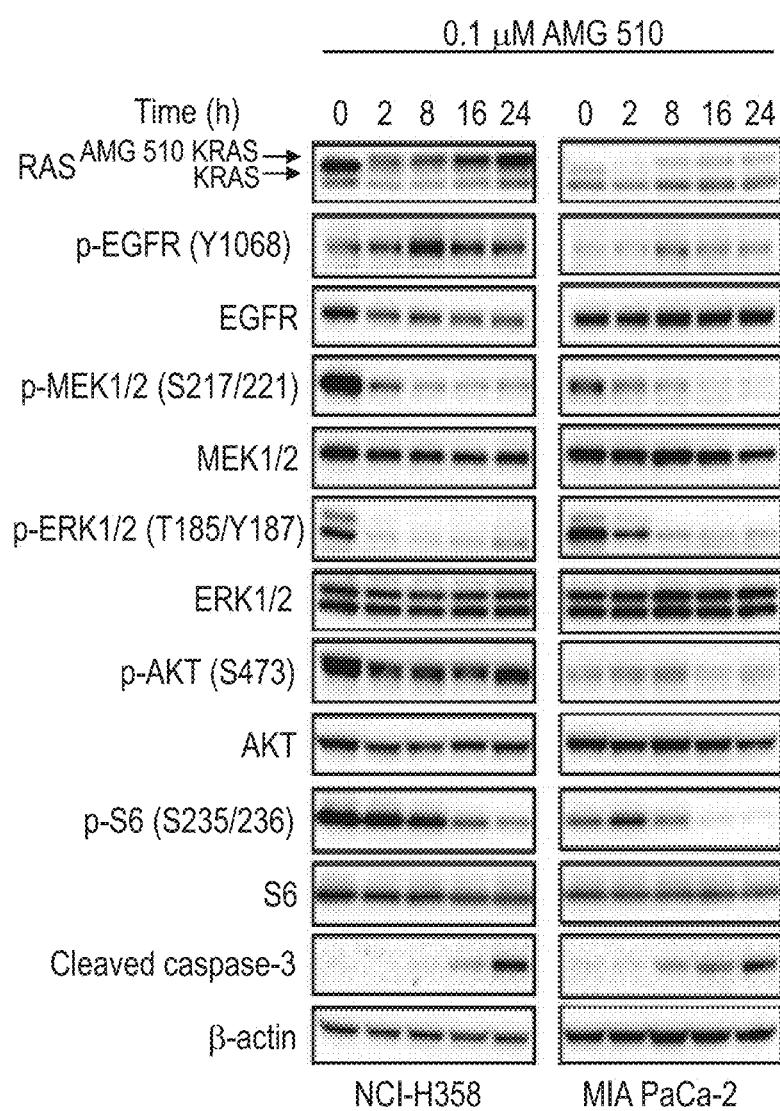

FIG. 41B shows the effect on cellular signaling in NCI-H358 or MIA PaCa-2 after treatment with 0.1 µM AMG 510 at time points up to 24 hours.

Figure 41C:
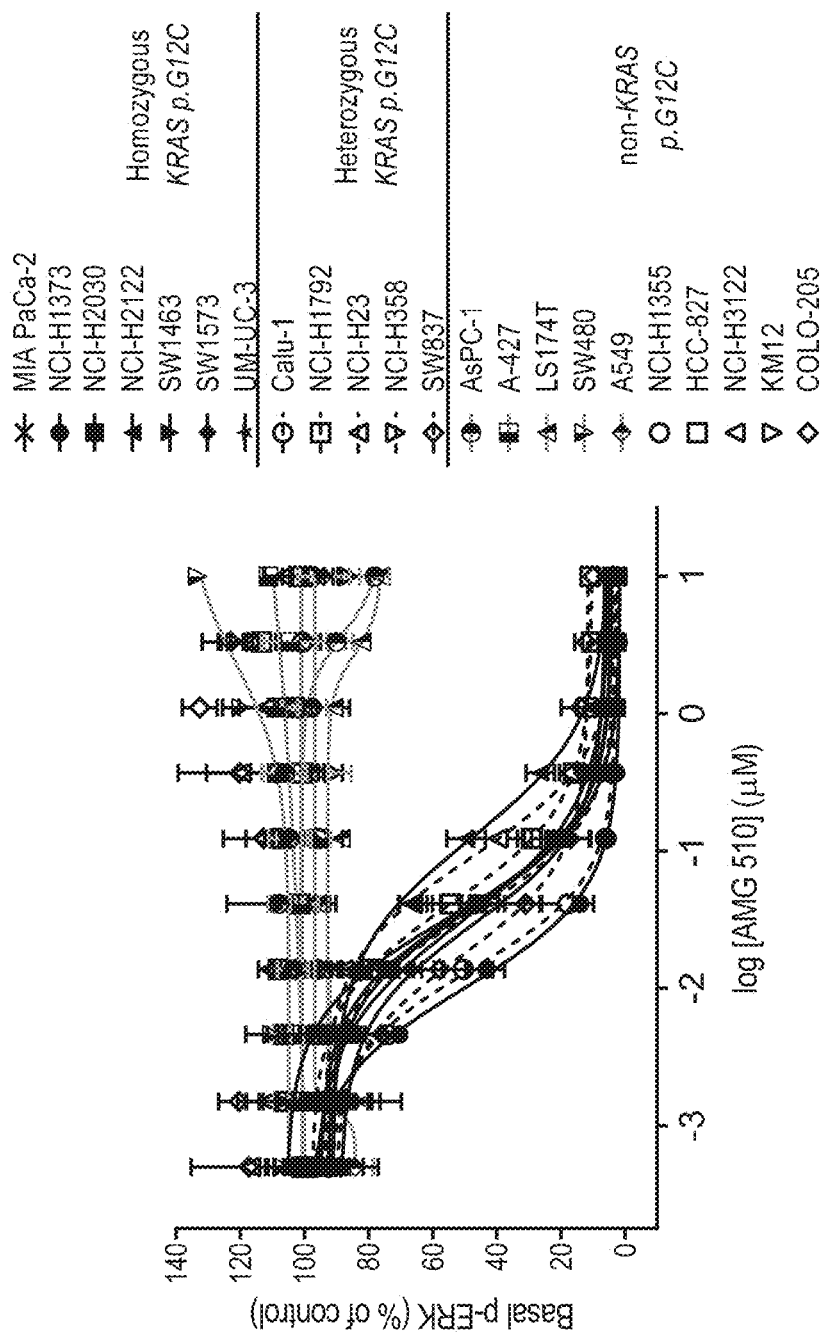

FIG. 41C shows the cellular activity of AMG 510 across a panel of KRAS p.G12C and non-KRAS p.G12C mutant cell lines as measured by inhibition of ERK1/2 phosphorylation after 2-hour treatment (n≥2).

Figure 41D:
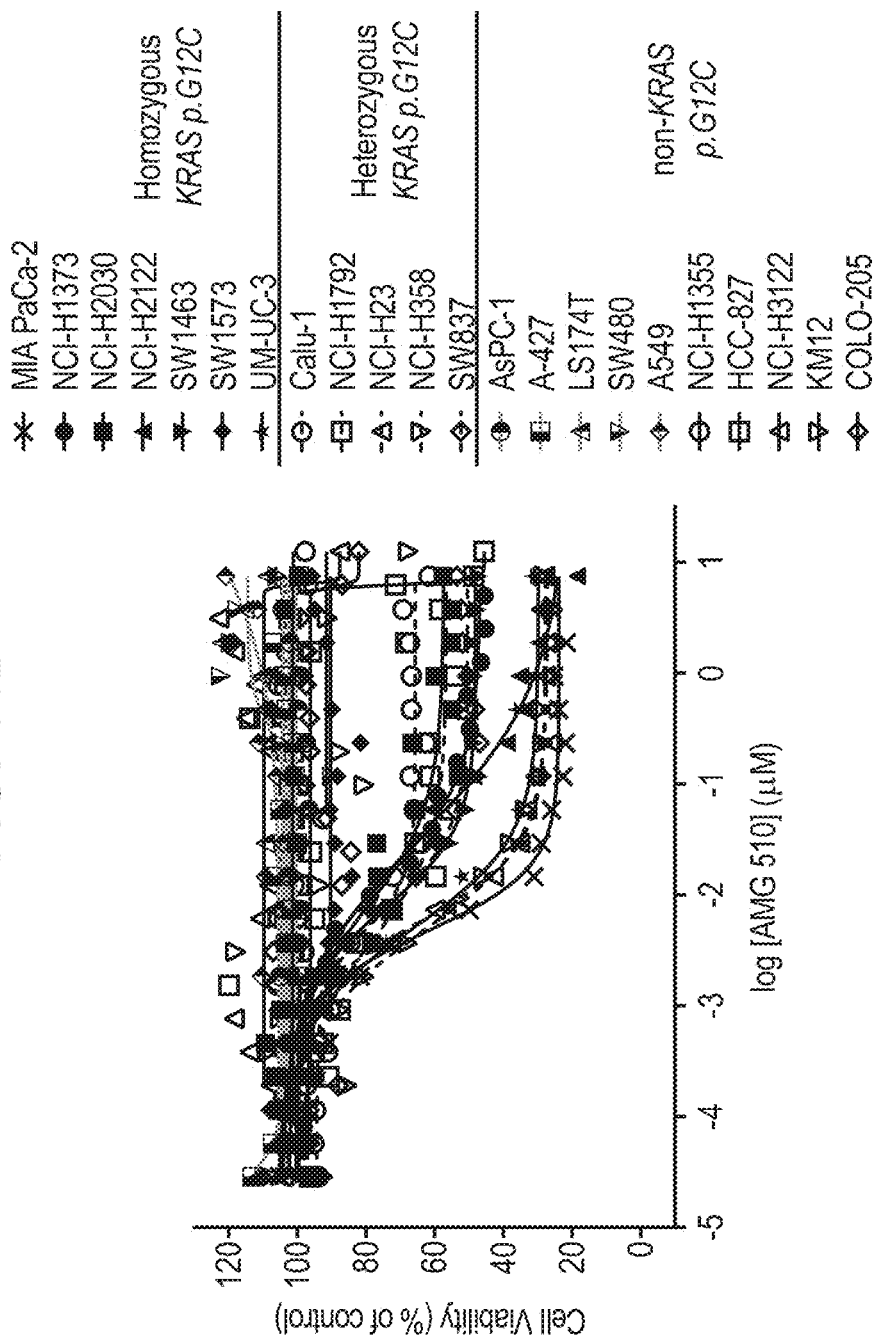

FIG. 41D shows cellular activity of AMG 510 across a panel of KRAS p.G12C and non-KRAS p.G12C mutant cell lines as measured by effects on cell viability after 72-hour treatment.

Figure 41E:
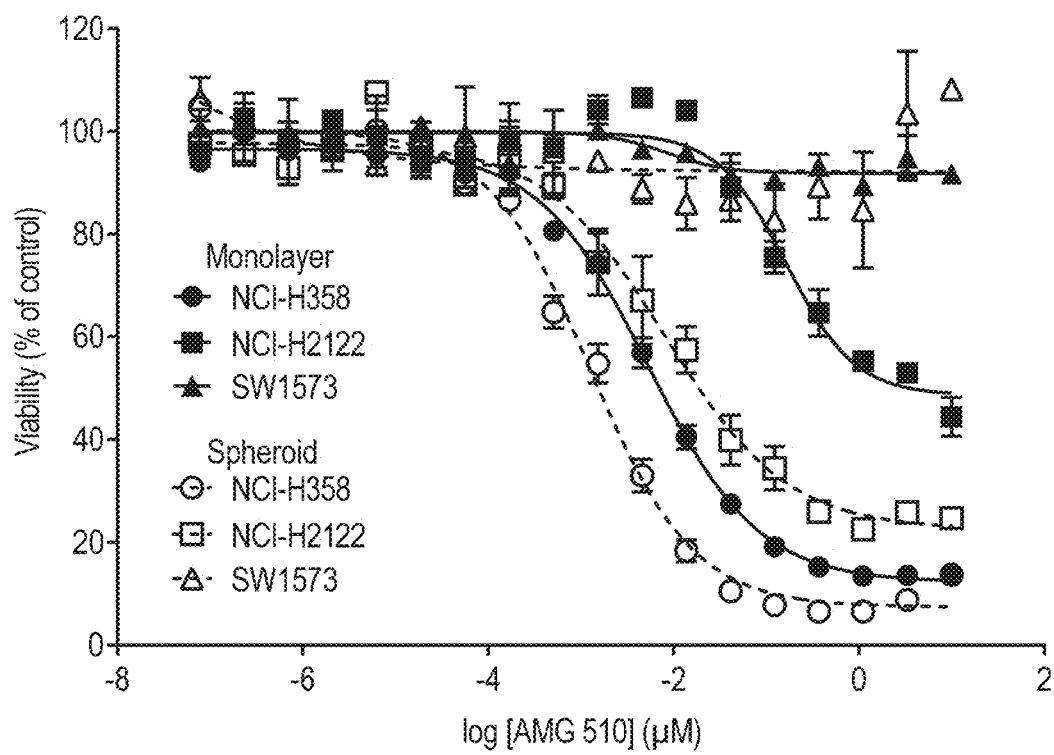

FIG. 41E shows the viability dose response curves are representative examples of at least n=2 experiments. Effect of 72-hour treatment with AMG 510 on cell viability in adherent monolayer or spheroid culture conditions (n=2).

Figure 41F:
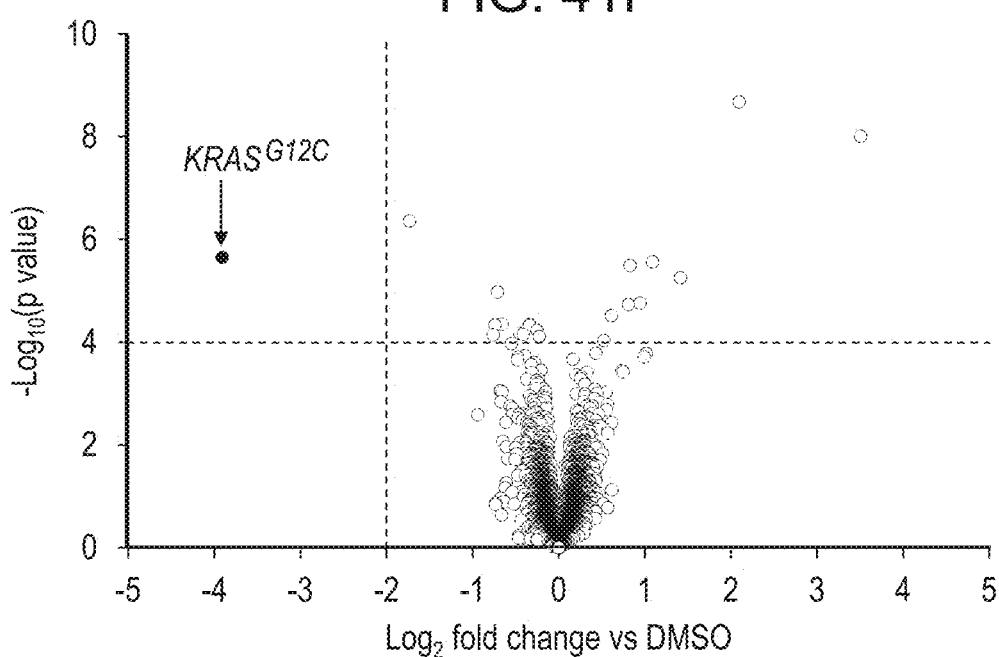

FIG. 41F shows Cysteine proteome analysis of NCI-H358 whole cell lysates after 4-hour treatment with 1 μM AMG 510 (n=5).

FIGS. 42A-D show AMG 510 inhibits ERK ½ phosphorylation in KRAS p.G12C mutant tumors in vivo. Mice bearing MIA PaCa-2 T2 (FIGS. 42A, 42C, 42D) or NCI-H358 (FIG. 42B) tumors were given a single dose with either vehicle orally or AMG 510 orally (all other bars) and harvested 2 hours later (FIGS. 42A, 42B) or over time as indicated (FIGS. 42C, 42D) and assessed for p-ERK levels as measured by MSD immunoassay. Plasma and tumor samples were collected and analyzed for AMG 510 concentrations (red triangles, black open circles, respectively). Data are presented as percent of control versus vehicle. Data represent mean tumor volume±SEM (n=3/group). FIGS. 42A-D, ****P<0.0001: *P<0.05 by Dunnett's.

Figure 42A:
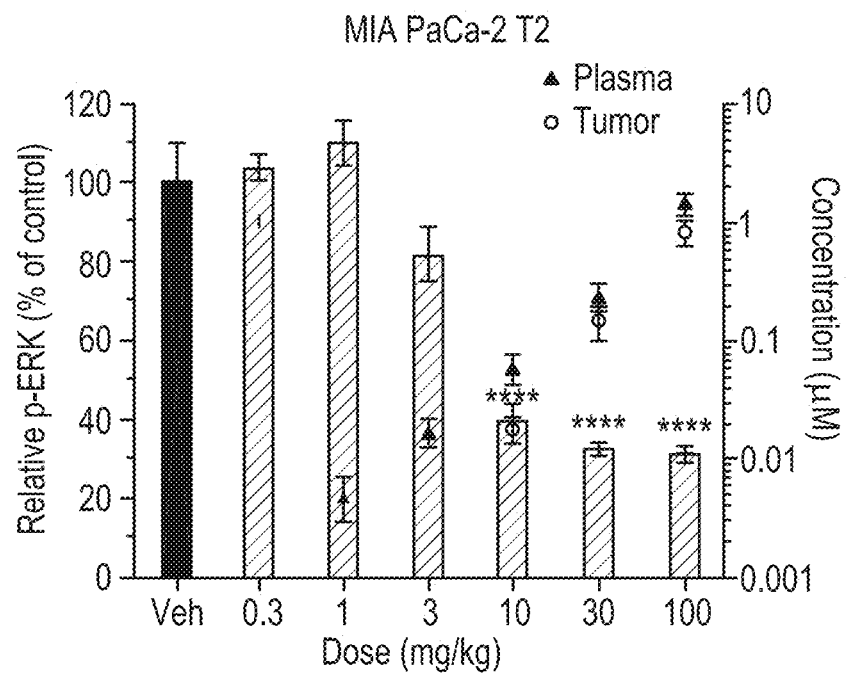
Figure 42B:
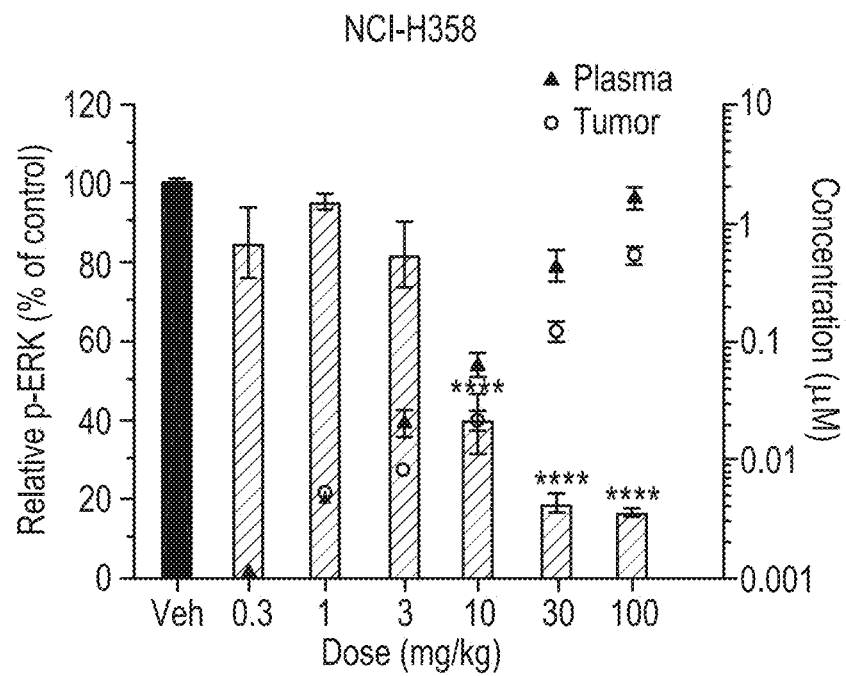
Figure 42C:
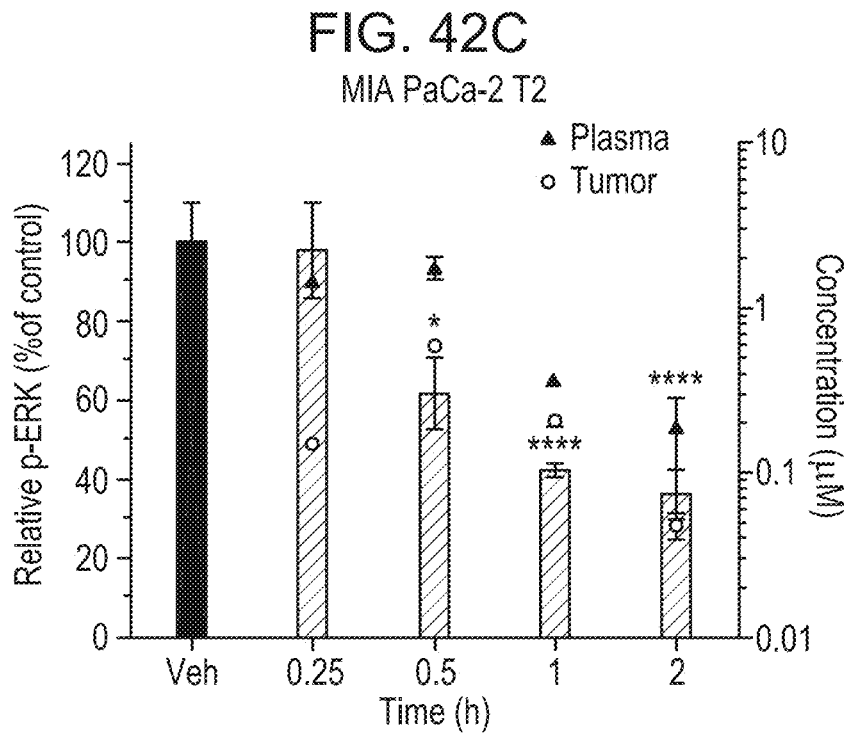
Figure 42D:
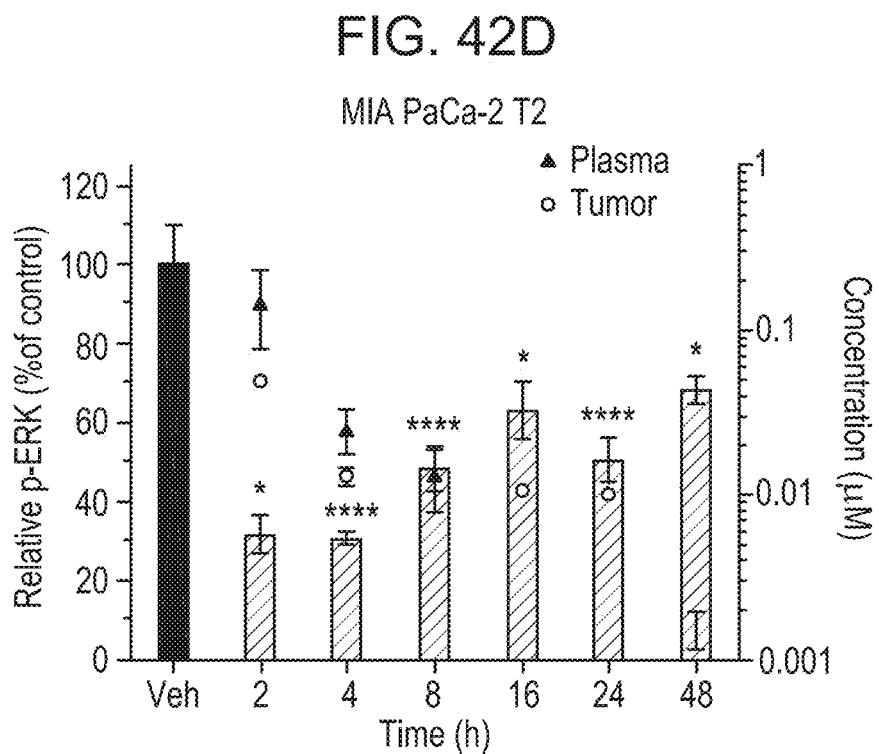
Figure 42E:
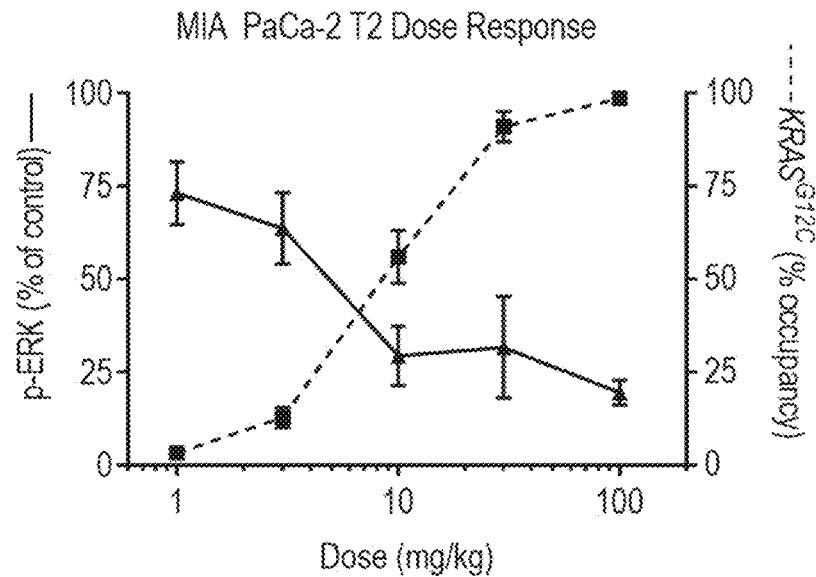

FIG. 42E shows AMG 510 treatment results over a dosing regimen in covalent modification of $KRAS^{G12C}$ using mass spectrometry correlating to p-ERK inhibition in mice bearing MIA PaCa-2 T2.

Figure 42F:
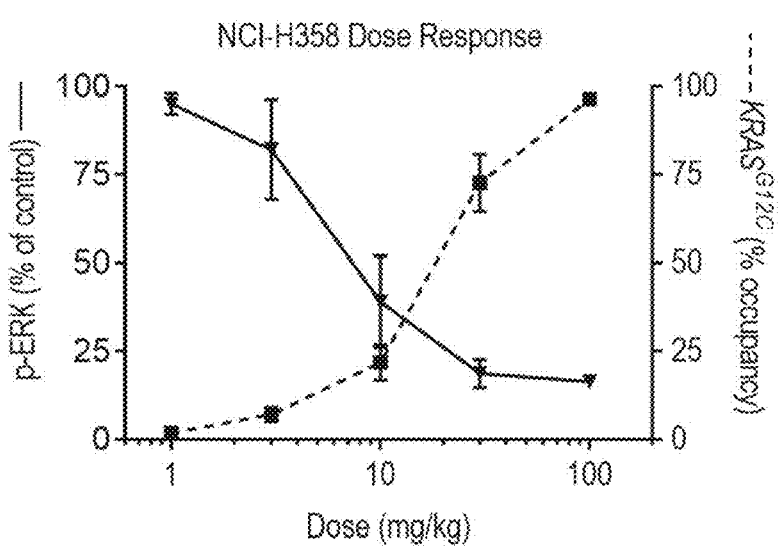

FIG. 42F shows AMG 510 treatment results over a dosing regimen in covalent modification of $KRAS^{G12C}$ using mass spectrometry correlating to p-ERK inhibition in mice bearing NCI-H358.

Figure 42G:
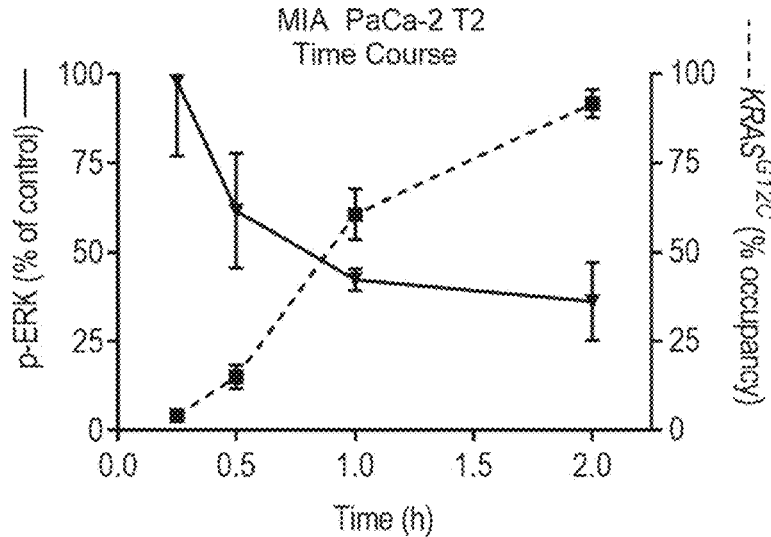

FIG. 42G shows AMG 510 treatment results over time in covalent modification of $KRAS^{G12C}$ using mass spectrometry correlating to p-ERK inhibition in mice bearing MIA PaCa-2 T2.

Figure 43A:
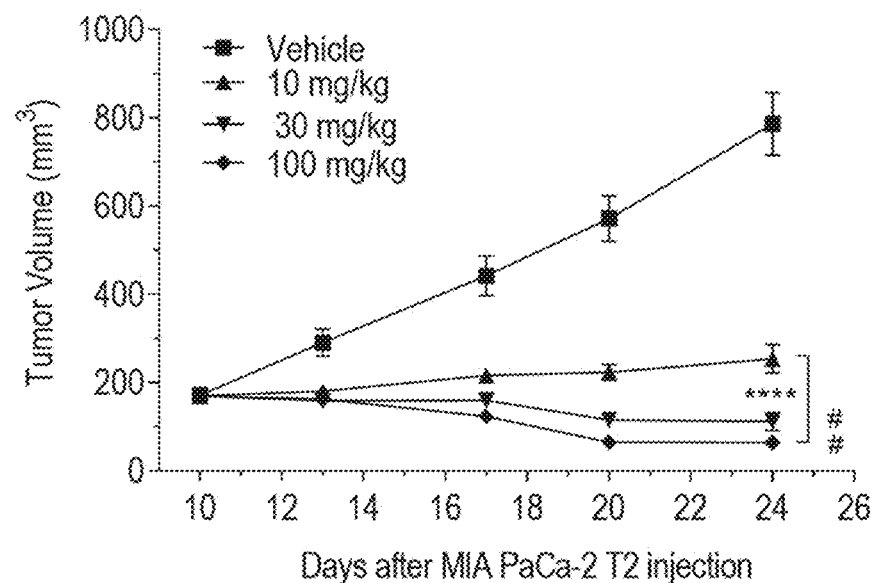

FIG. 43A shows mice with established MIA PaCa-2 T2 KRAS p.G12C tumors were dosed with either vehicle or AMG 510. AMG 510 selectively inhibits in vivo growth of KRAS p.G12C mutant tumors.

Figure 43B:
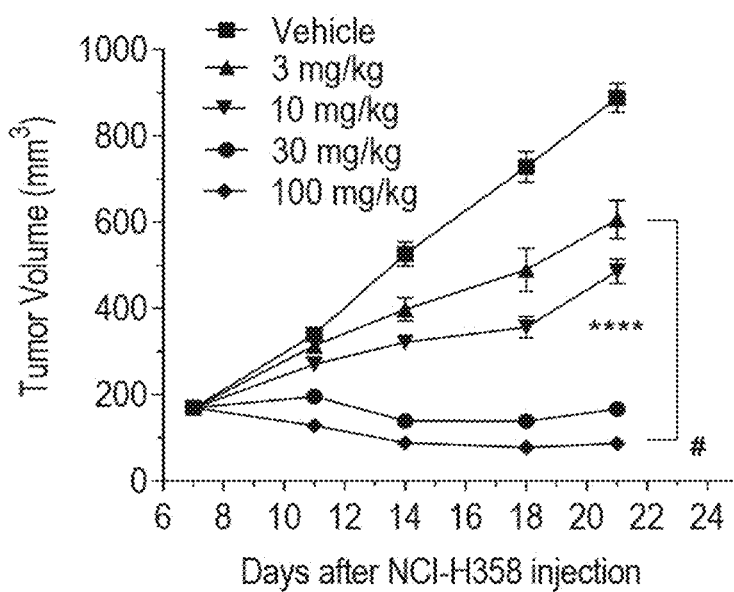

FIG. 43B shows mice with established NCI-H358 KRAS p.G12C tumors were dosed with either vehicle or AMG 510. AMG 510 selectively inhibits in vivo growth of KRAS p.G12C mutant tumors.

Figure 43C:
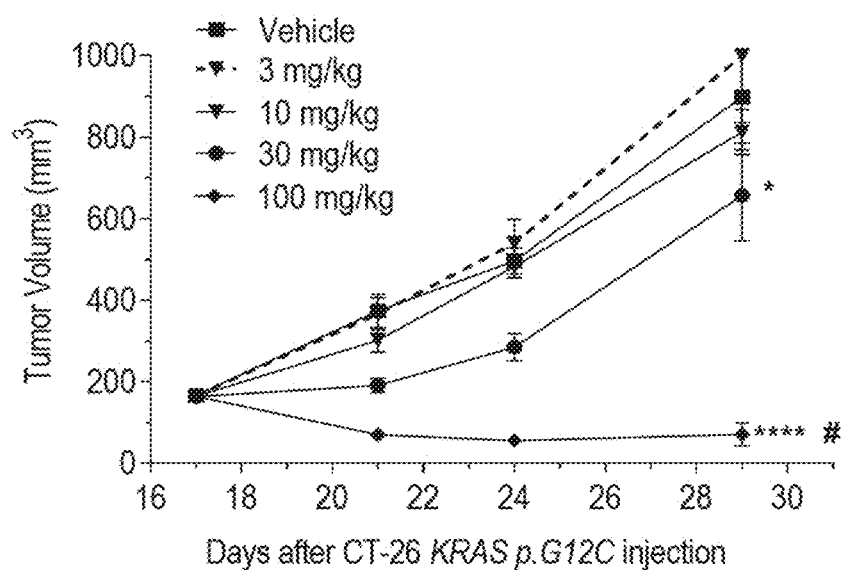

FIG. 43C shows mice with established CT-26 KRAS p.G12C tumors were dosed with either vehicle or AMG 510. AMG 510 selectively inhibits in vivo growth of KRAS p.G12C mutant tumors.

Figure 43D:
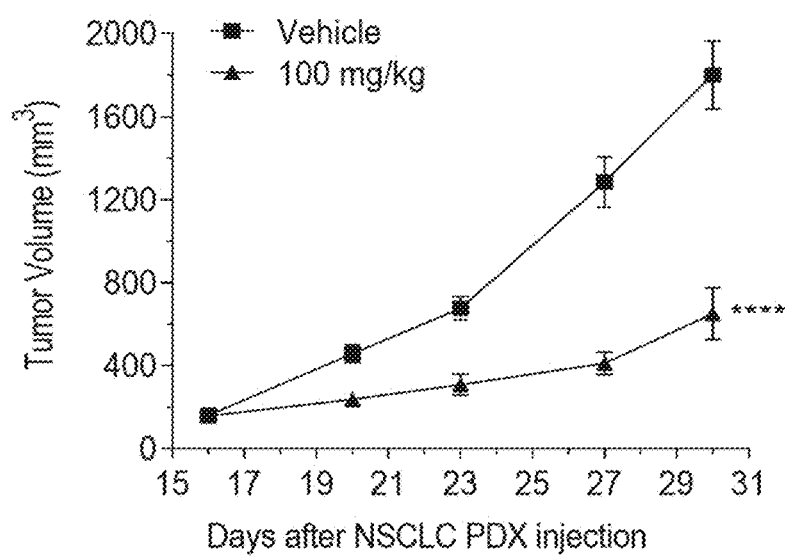

FIG. 43D shows the effects of tumor growth in a $KRAS^{G12C}$ NSCLC PDX model with mice treated with either vehicle or AMG 510. AMG 510 selectively inhibits in vivo growth of KRAS p.G12C mutant tumors.

In FIGS. 43A, 43B, 43C and 43D, the data represent mean tumor volume±SEM (n=10/group). FIGS. 43A, 43B, 43C, ****P<0.0001, *P<0.05 for comparisons of vehicle to treatment group by Dunnett's, #P<0.05 regression Paired t-test, and ****P<0.0001 by RM two-way ANOVA.

Figure 43E:
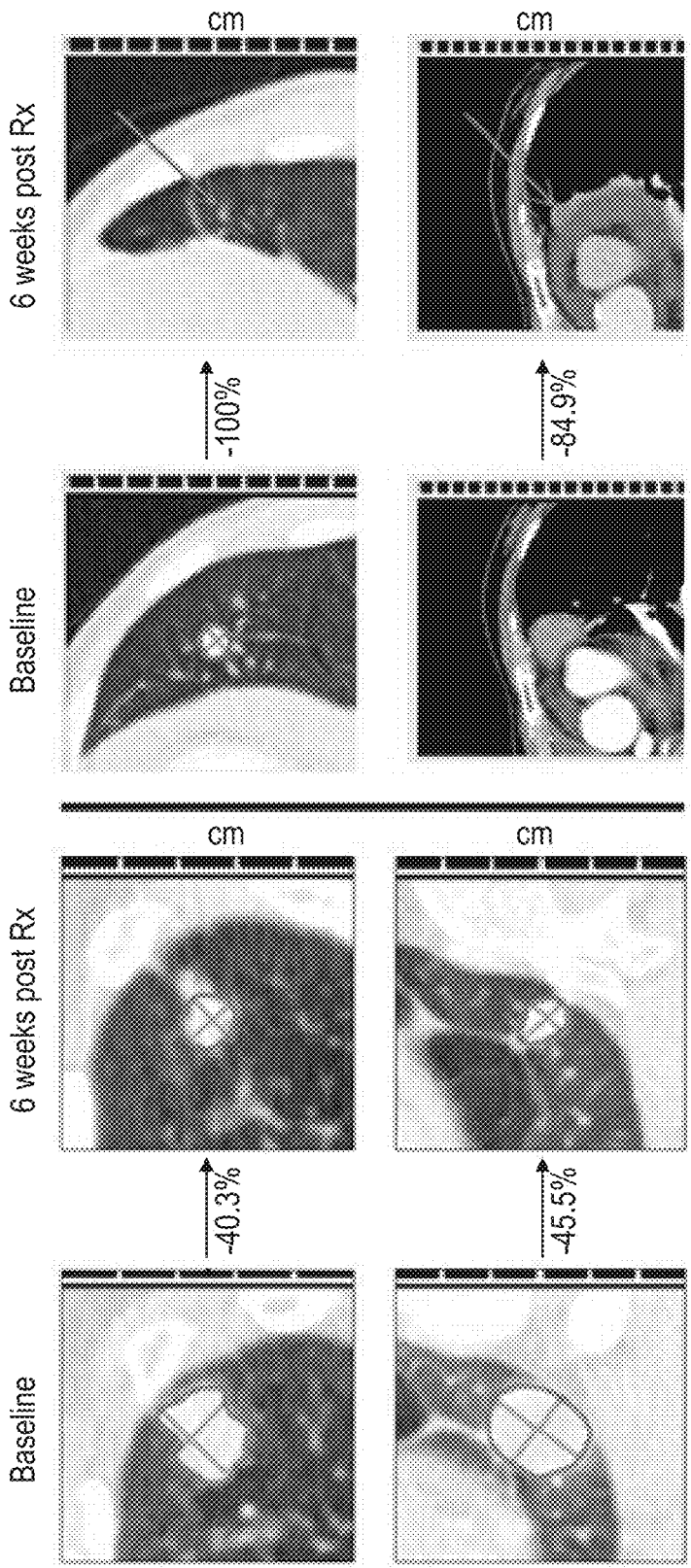

FIG. 43E shows CT scans from two KRAS p.G12C lung carcinoma patients treated with AMG 510. Representative pre-treatment ("baseline") and post-treatment (Rx) scans. Far left: top panels represent the lung upper left lobe, and the bottom panels represent the lung lower right lobe. Far right: top panel represents lung upper left lobe: bottom panel represents pleura. AMG 510 selectively inhibits in vivo growth of KRAS p.G12C mutant tumors.

Figure 43F:
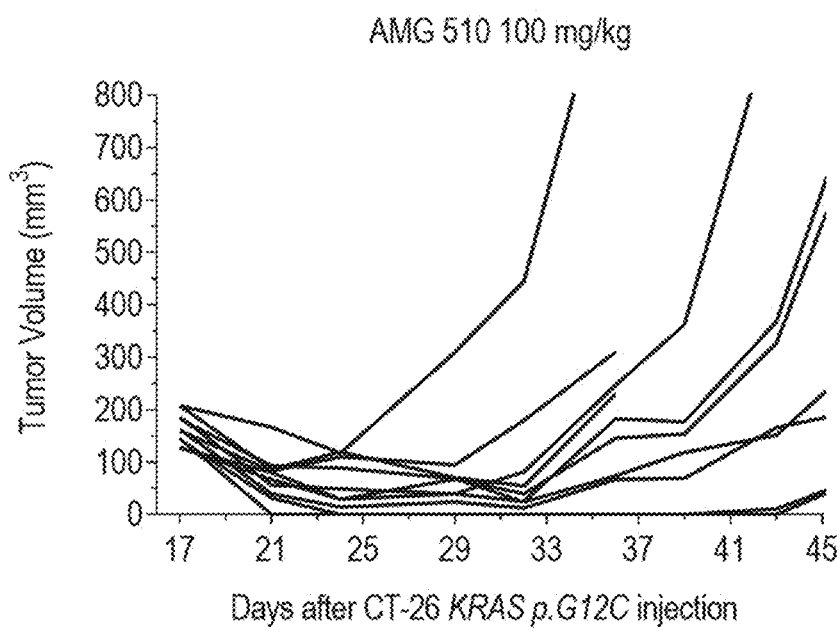

FIG. 43F shows individual CT-26 KRAS p.G12C tumor plots from AMG 510-treated mice (100 mg/kg).

Figure 43G:
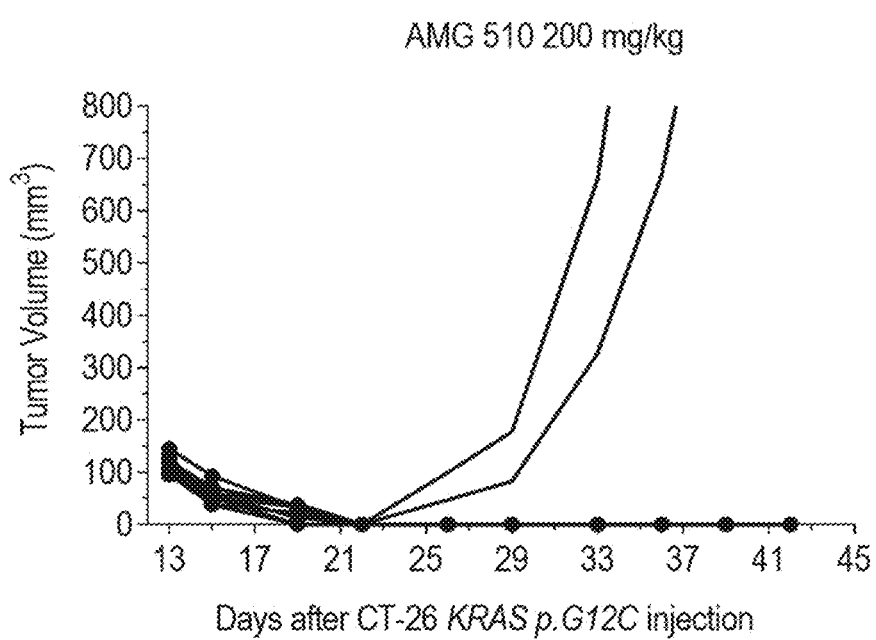

FIG. 43G shows individual CT-26 KRAS p.G12C tumor plots from AMG 510-treated mice (200 mg/kg). Continued treatment of the 100 mg/kg group suggested that regression wasn't durable (FIG. 47F), possibly due to incomplete inhibition of p-ERK (FIG. 47A). Therefore, a 200 mg/kg dose of AMG 510 was evaluated, which resulted in near complete inhibition of p-ERK (FIG. 47A) and led to eight out of ten durable cures (FIG. 43G), with AMG 510 plasma levels just below the cellular IC90 (FIG. 47H).

Figure 44A:
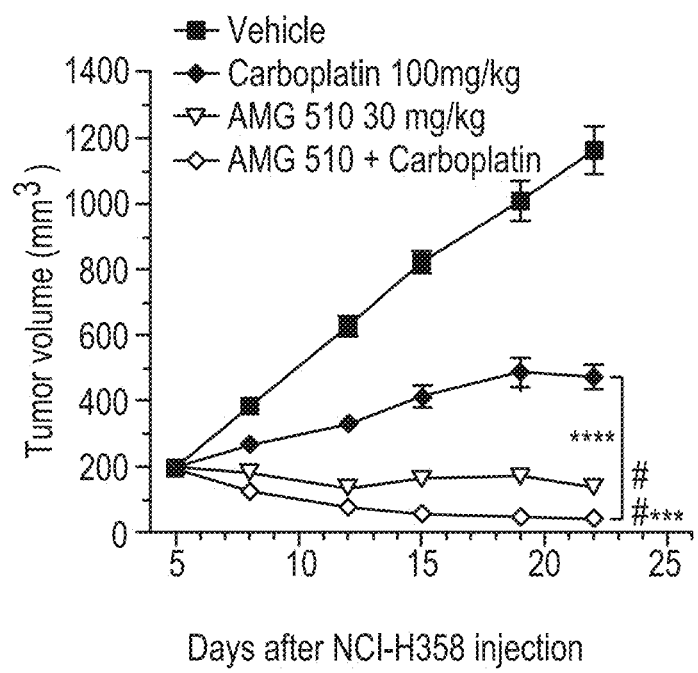

FIG. 44A illustrates AMG 510 in combination with carboplatin on NCI-H358 tumor xenografts.

Figure 44B:
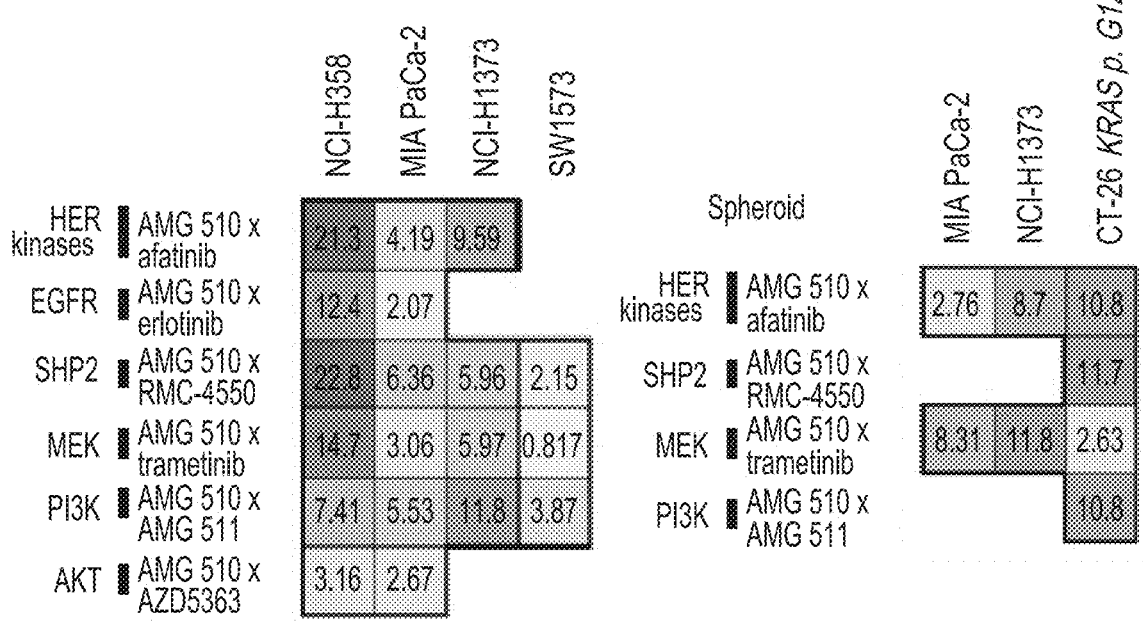

FIG. 44B illustrates the synergy scores for AMG 510 combinations with targeted agents were calculated using a Loewe additivity excess algorithm and represented as a heatmap, with higher scores (darker red) denoting stronger synergistic interactions.

Figure 44C:
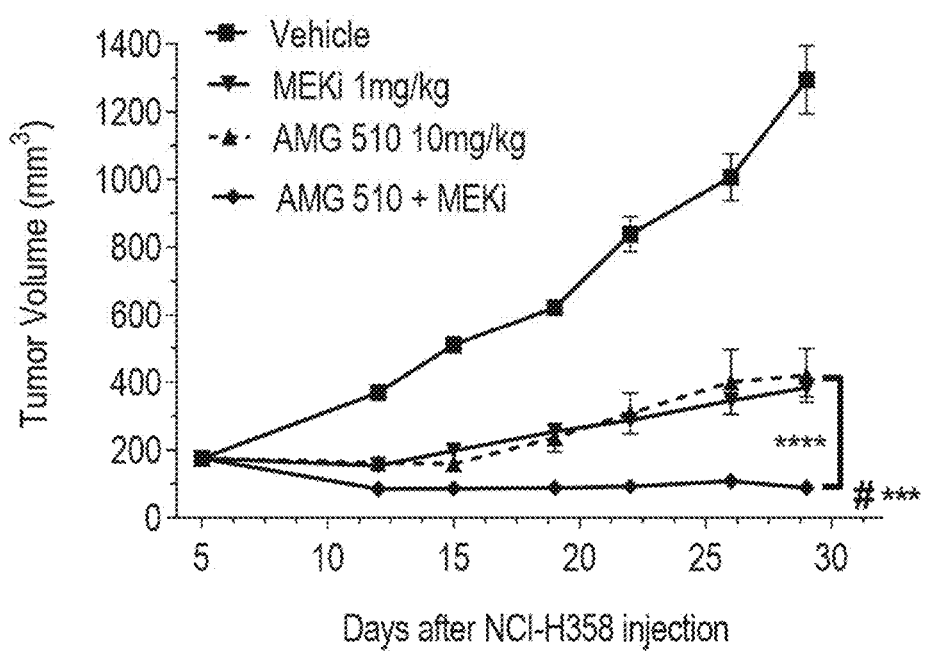

FIG. 44C illustrates AMG 510 in combination with a MEK inhibitor (PD-0325901) on NCI-H358 tumor xenografts.

In FIGS. 44A and 44C, Data represent mean tumor volume±SEM (n=10/group), a P<0.001 for comparison of the combination treatment to each single agent by Dunnett's, #P<0.001 regression by paired t-test, c**P<0.001 combination treatment compared to each single agent by Dunnett's, #P<0.001 regression by paired t-test. Results from all treatment groups were significant compared with vehicle (**P<0.0001 by Dunnett's).

Figure 45A:
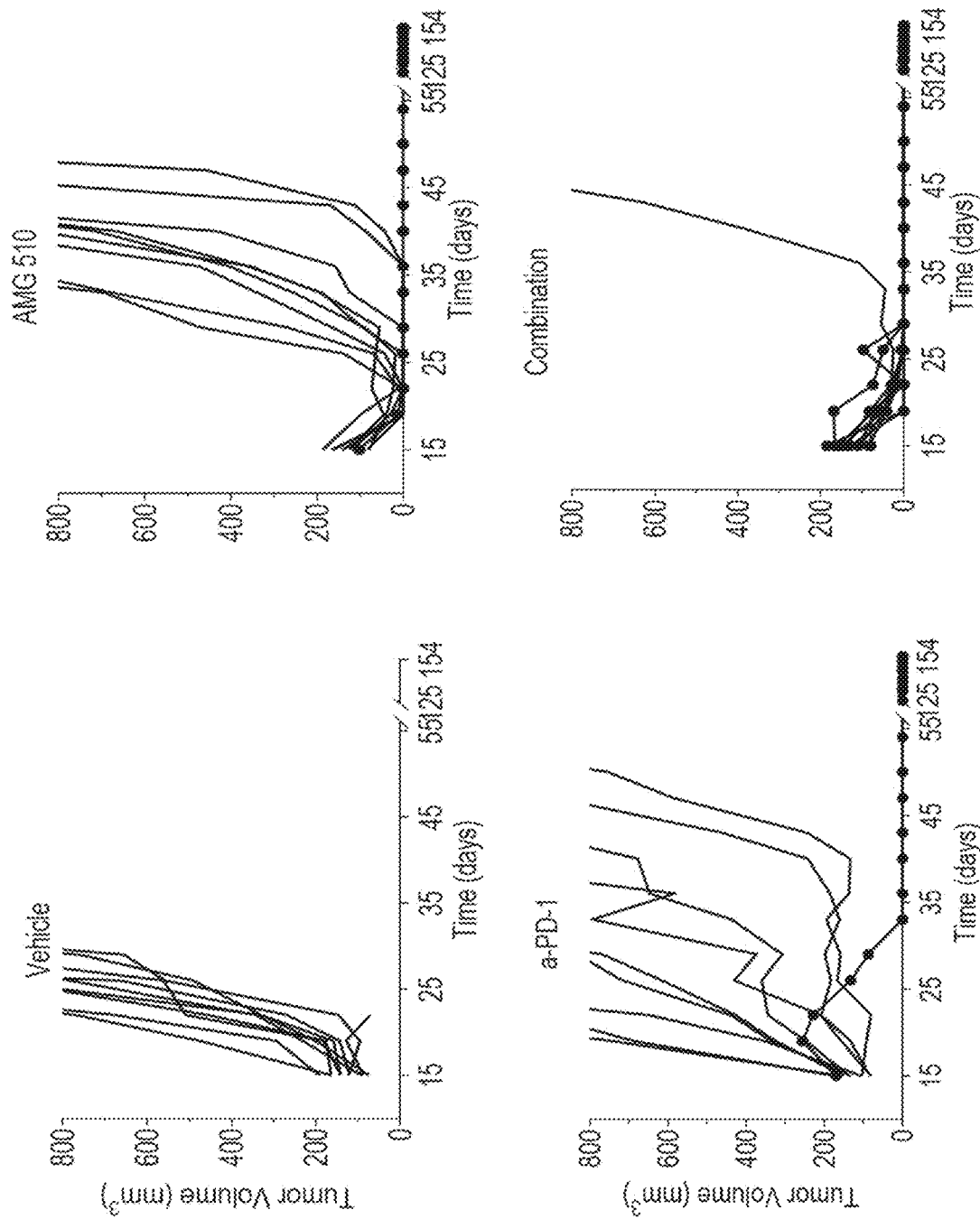

FIG. 45A shows CT-26 KRAS p.G12C tumor growth in individual mice treated with either vehicle, AMG 510, anti-PD-1, or AMG 510 in combination with anti-PD-1 (n=10/group). Lines with circles indicate tumor-free mice.

Figure 45B:
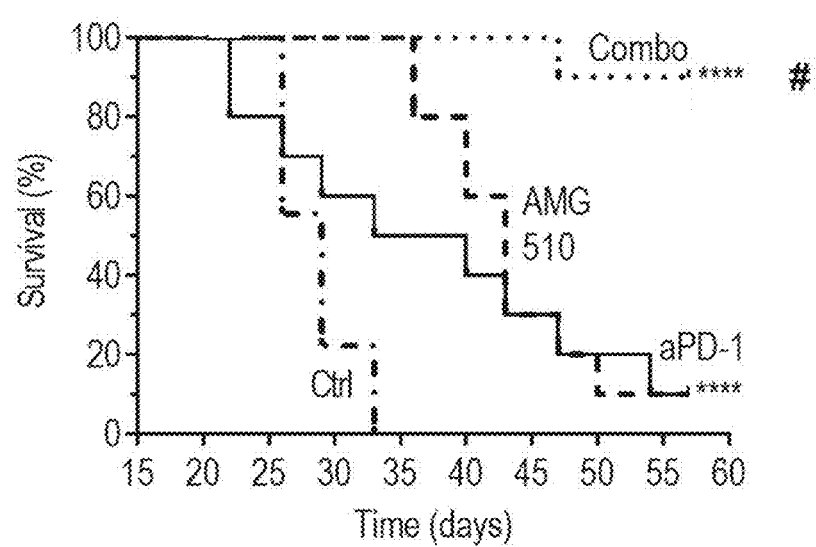

FIG. 45B shows Kaplan Meier analysis of surrogate survival endpoint (tumor size>800 $mm^3$). Mantel-Cox****P<0.001 to vehicle control: #P<0.005 combination versus AMG 510 or anti-PD-1 alone.

Figure 45C:
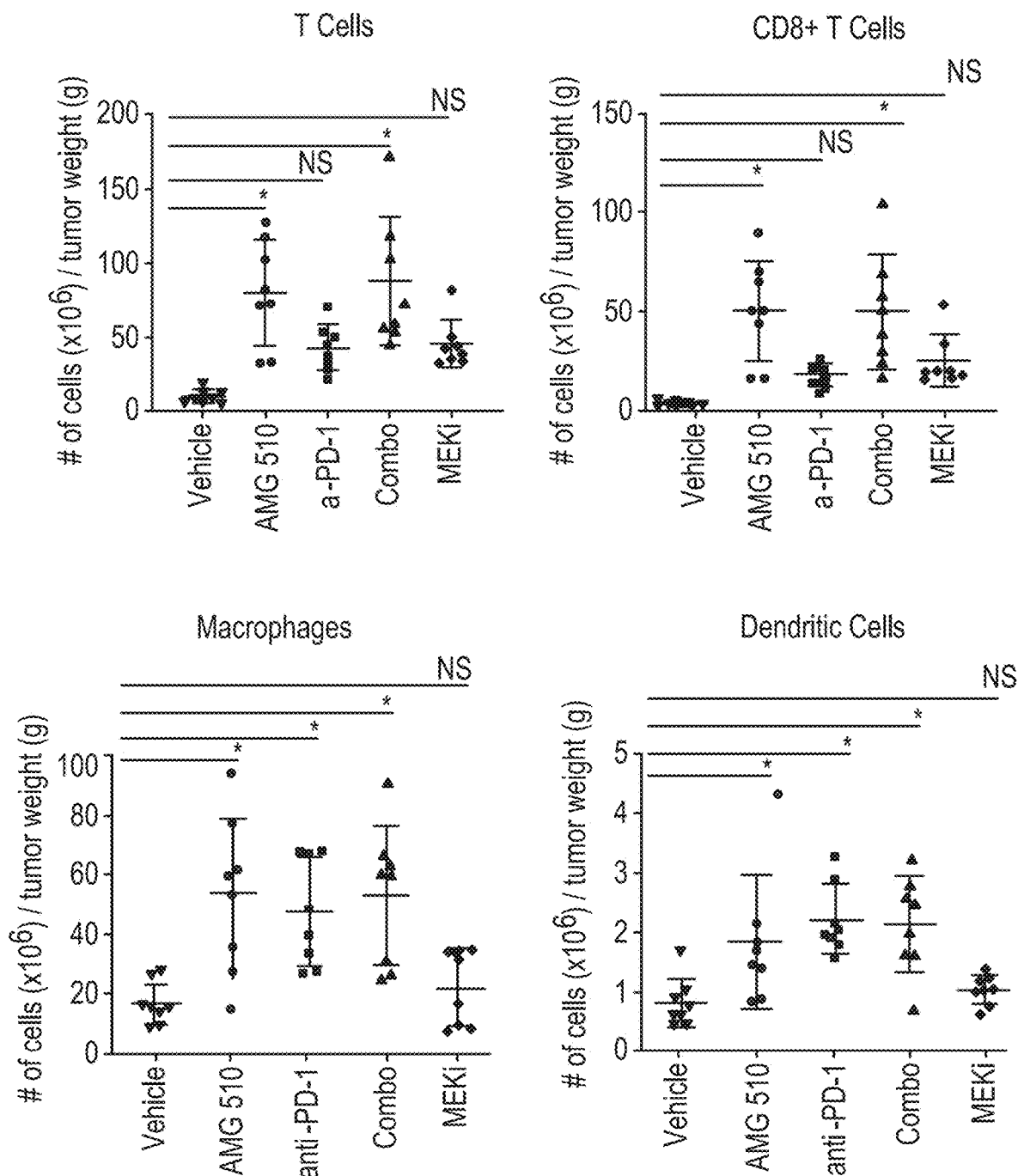

FIG. 45C shows CT-26 KRAS p.G120 tumors from mice treated over four days with either vehicle, AMG 510, anti-PD-1, AMG 510 in combination with anti-PD-1, or MEKi, and immunophenotyped by flow cytometry (n=8/group). **P<0.0001, *P<0.001, **P<0.01, *P<0.05 by Tukey's compared to vehicle control; NS=not significant.

Figure 45D:
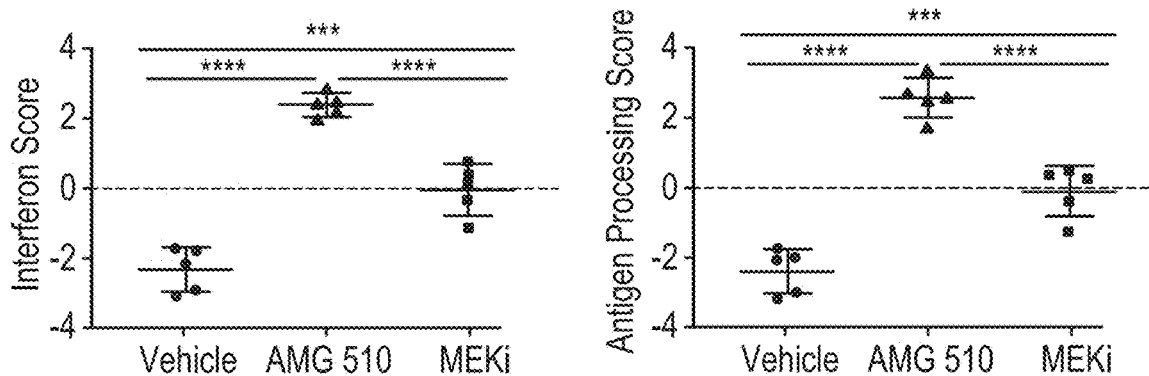

FIG. 45D shows RNA was isolated from CT-26 KRAS p.G12C tumors after two days of treatment (n=5/group). Gene expression and scores were calculated by NanoString technology (see methods). **P<0.0001, *P<0.001 by Tukey's.

Figure 45E:
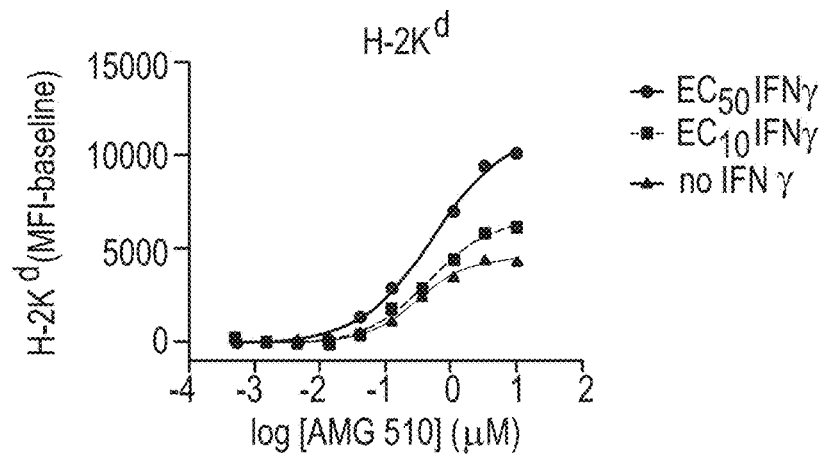

FIG. 45E shows cell surface expression of MHC class I antigen $H-2K^d$ on CT-26 KRAS p.G12C cells following 24-hour treatment with AMG 510 in the presence or absence of Interferon gamma ("IFNγ") as measured by flow cytometry. Levels of secreted IFN-γ were measured by ELISpot assay (n=4-5/group).

Figure 45F:
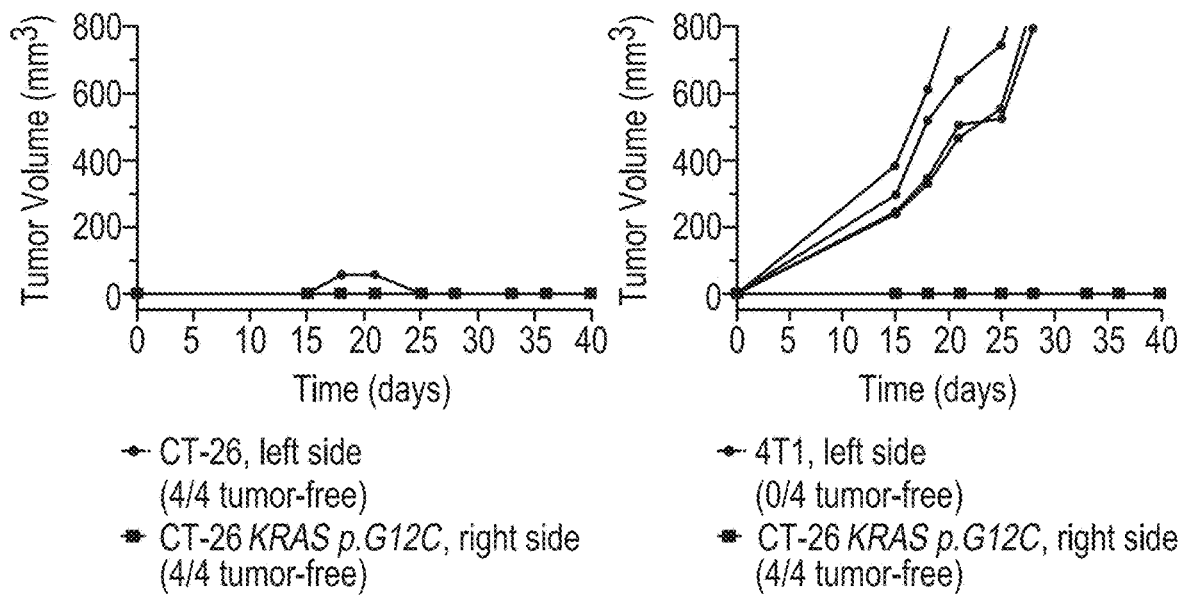

FIG. 45F shows individual tumor growth of mice that were cured with AMG 510 plus anti-PD-1 treatment and re-challenged with CT-26 KRAS p.G12C, CT-26, or 4T1 cells.

Figure 45G:
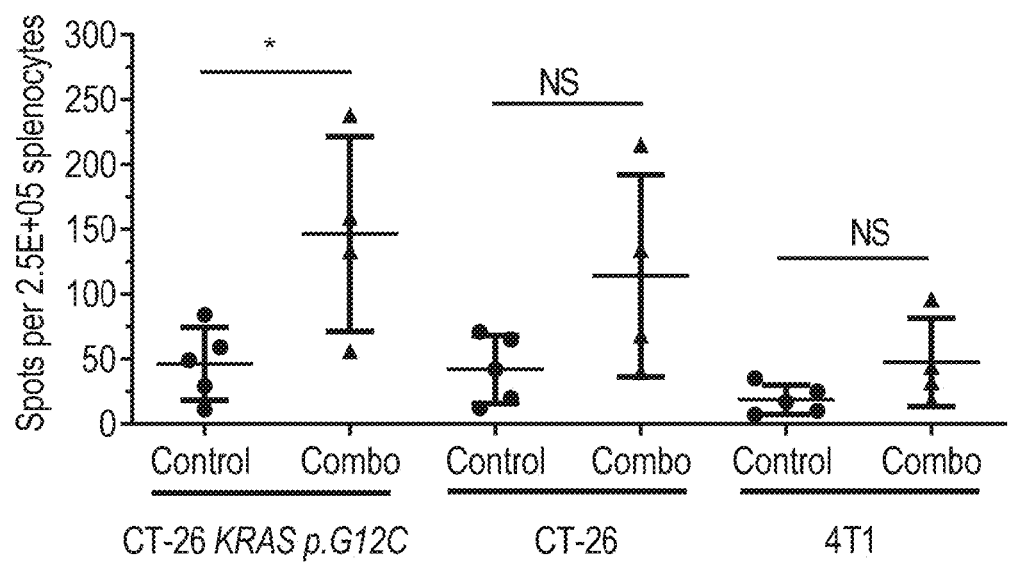

FIG. 45G shows splenocytes were harvested and challenged with the indicated cells, CT-26, CT-26 KRAS p.G12C, or 4T1 cells.*P=0.0269 by unpaired t-test comparison control vs combination.

Figure 45H:
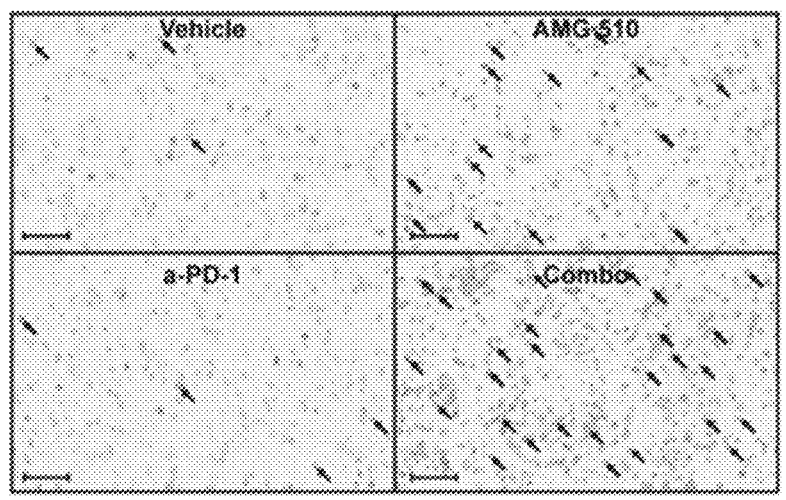

FIG. 45H shows AMG 510 treatment induces a pro-inflammatory tumor microenvironment. CT-26 KRAS p.G12C tumors from mice treated over four days with either vehicle, AMG 510, anti-PD-1, AMG 510 in combination with anti-PD-1, or MEKi, were immunophenotyped by immunohistochemistry (n=5/group), Immunohistochemical staining for CD3/Ki67. Ki67 immunopositive stain is blue and nuclear, and CD3 and CD8 immunopositive stain is brown and cytoplasmic. Arrows in h point to examples of cells with dual immunopositivity for CD3 and Ki67.

Figure 45I:
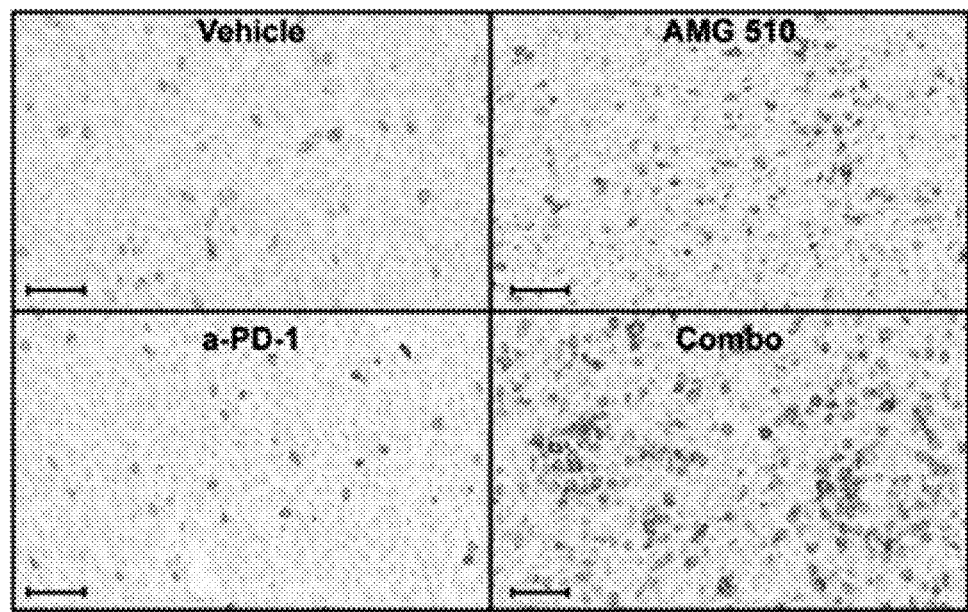

FIG. 45I shows AMG 510 treatment induces a pro-inflammatory tumor microenvironment, CT-26 KRAS p.G12C tumors from mice treated over four days with either vehicle, AMG 510, anti-PD-1, AMG 510 in combination with anti-PD-1, or MEKi, were immunophenotyped by immunohistochemistry (n=5/group), Immunohistochemical staining for CD8. Ki67 immunopositive stain is blue and nuclear, and CD3 and CD8 immunopositive stain is brown and cytoplasmic.

Figure 46D:
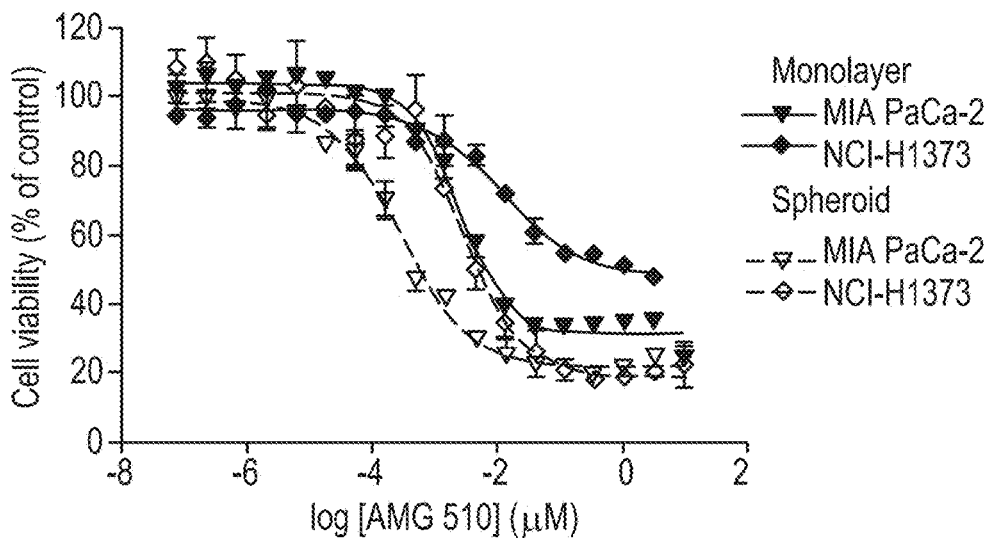

FIG. 46A shows Biochemical activity of AMG 510 and its non-reactive propionamide analog as measured in a SOS1-catalyzed nucleotide exchange assay with purified $KRAS^{G12C/C118A}$ or $KRAS^{C118A}$ protein (n≥2). For all FIGS. 46A-46E, data represent mean±SD for the number of independent replicates indicated.

FIG. 46B shows calculated maximal reaction rates and the concentrations that achieve half-maximal rate of AMG 510 and ARS-1620.

FIG. 46C shows inhibition of ERK phosphorylation with RMC-4550 in NCI-H358 cells with $t_{1/2}$=12.2 min (n=2).

FIG. 46D shows the effect of 72-hour treatment with AMG 510 on cell viability in adherent monolayer or spheroid culture conditions in MIA PaCa-2 and NCI-H1373 (n=2).

Figure 46E:
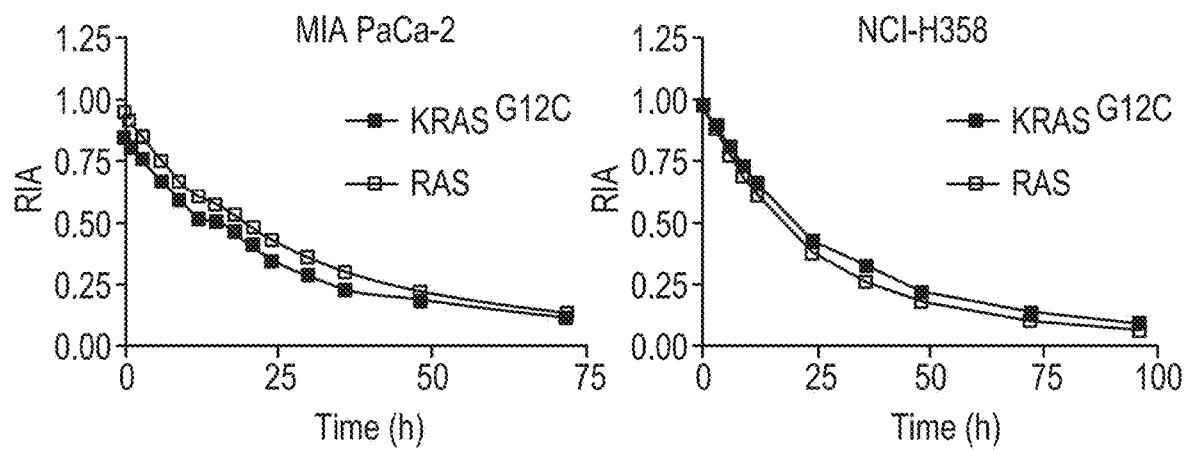

FIG. 46E shows the half-life determination of KRAS in MIA PaCa-2 and NCI-H358 cells by Stable Isotope Labeling by/with Amino acids in Cell culture (SILAC).

FIGS. 47A-47C show CT-26 KRAS p.G120 tumor bearing mice were treated with a single dose of vehicle orally or with the indicated doses of AMG 510 orally and harvested 2 hours later. Levels of p-ERK were measured by MSD immunoassay. Plasma and tumor samples were collected and analyzed for AMG 510 concentrations (red triangles, black open circles, respectively). Data are presented as percent of control (POC) versus vehicle. ****$P<0.0001$, *$P<0.05$ by Dunnett's compared to vehicle.

FIG. 47D shows AMG 510 treatment results in covalent modification of $KRAS^{G12C}$ inversely correlating with p-ERK inhibition.

FIG. 47E shows the effect of AMG 510 on tumor growth in the SW480-1AC xenograft model.

FIG. 47F shows the effect of AMG 510 treatment on tumor growth in a $KRAS^{G12C}$ SCLC PDX model. In FIGS. 47E and 47F, treatment began when tumors reached approximately 200 mm$^3$. ****$P<0.0001$ by RM two-way ANOVA.

FIG. 47G shows plasma levels of AMG 510 from MIA PaCa-2 T2, NCI-H358 xenograft.

FIG. 47H shows plasma levels of AMG 510 from CT-26 KRASp.G12C xenograft.

FIG. 47I shows individual CT-26 KRAS p.G12C tumor plots of AMG 510 treated mice (200 mg/kg) in BALB/c nude mice from day 14 to day 32.

Figure 47J:
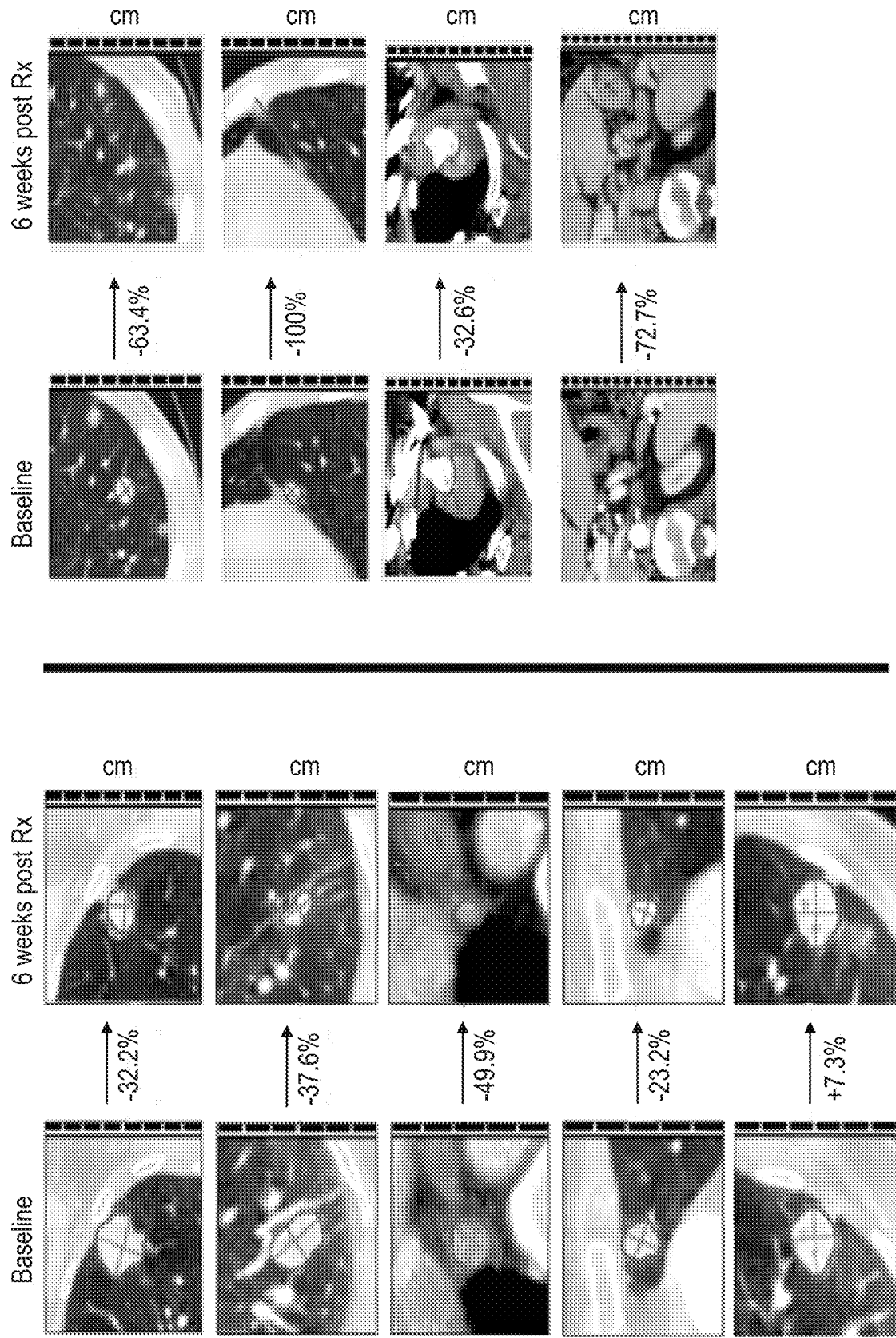

FIG. 47J shows CT scans from two KRAS p.G12C lung carcinoma patients treated with AMG 510. Additional representative pre-treatment ("baseline") and post-treatment (Rx) scans from patients previously described in FIG. 43D (far left from top to bottom) lung upper left lobe, lung lower left lobe, lymph node, lung upper left lobe, lung upper left lobe. Far right top to bottom, lung lower left lobe, lung lower left lobe, pleura, and adrenal gland.

Figure 47K:
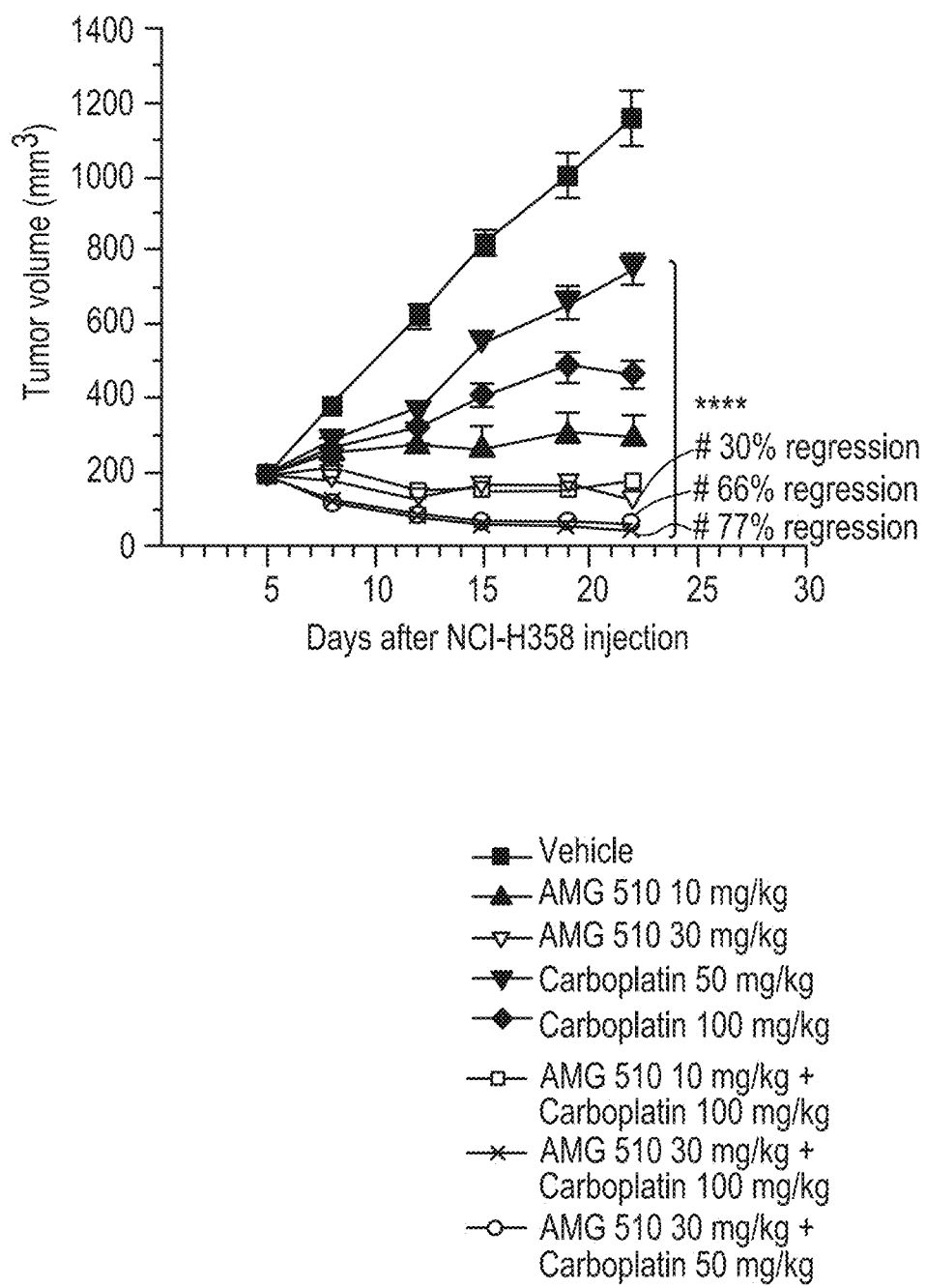
Figure 48C:
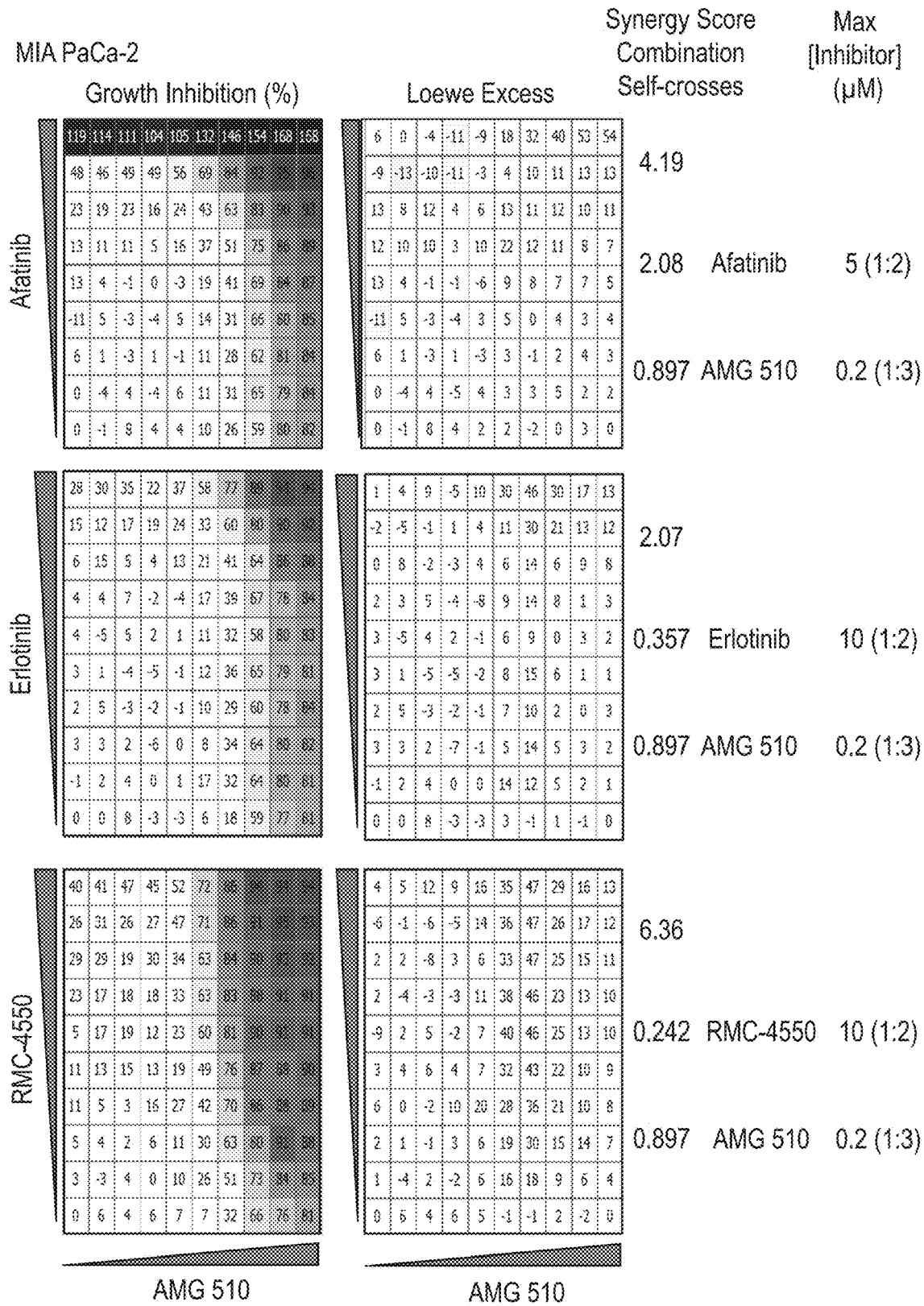
Figure 48D:
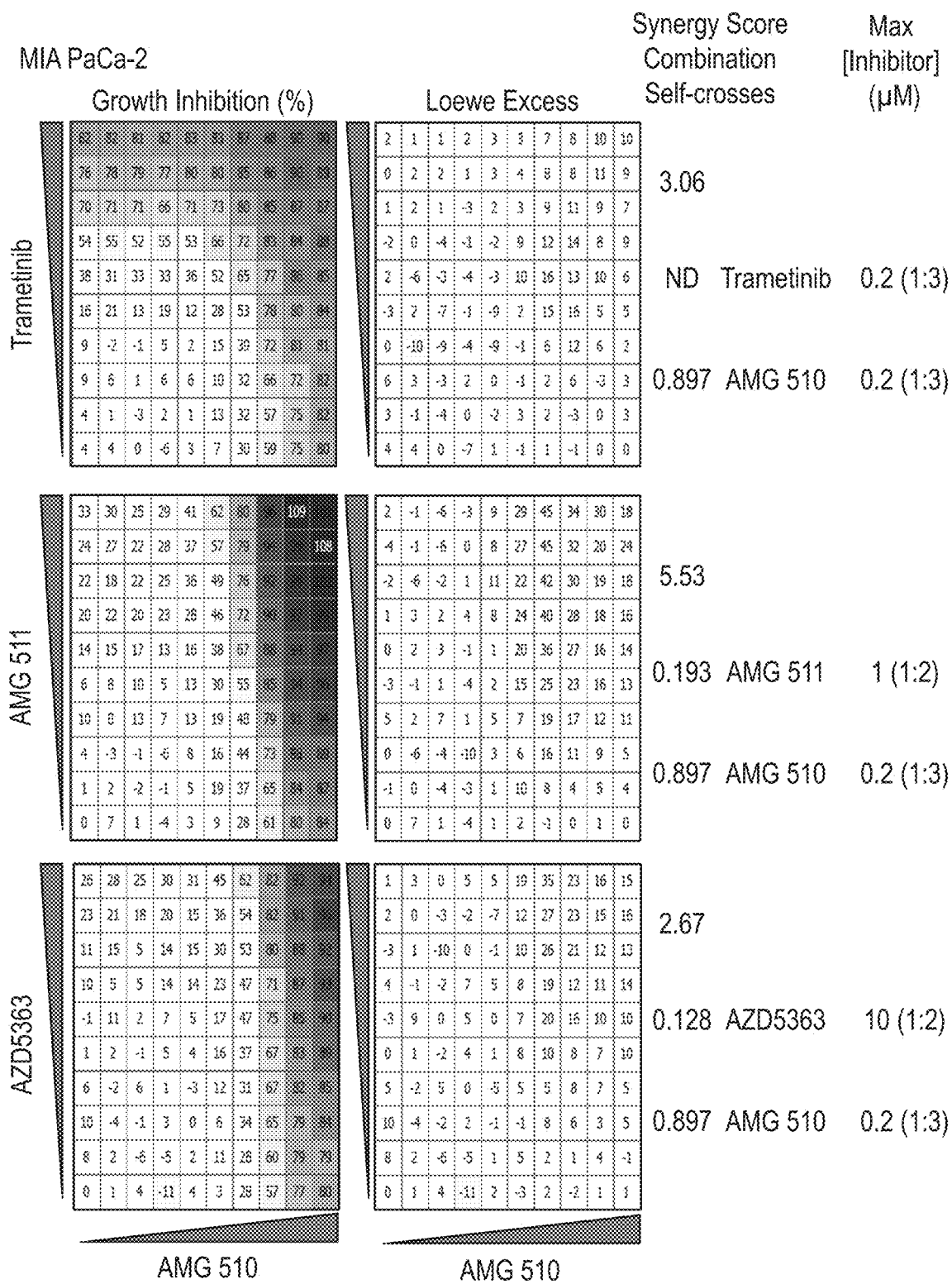
Figure 48E:
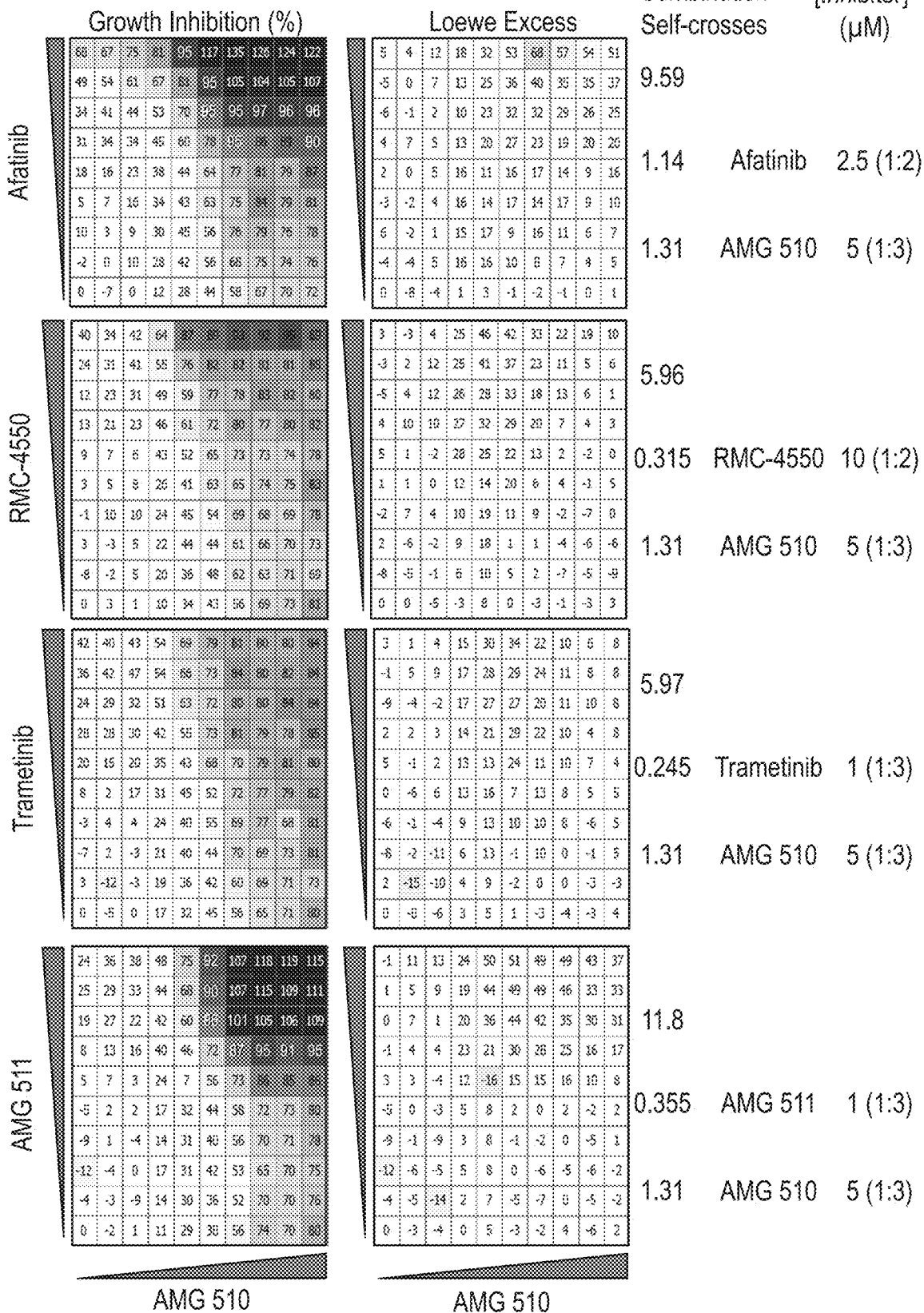
Figure 48G:
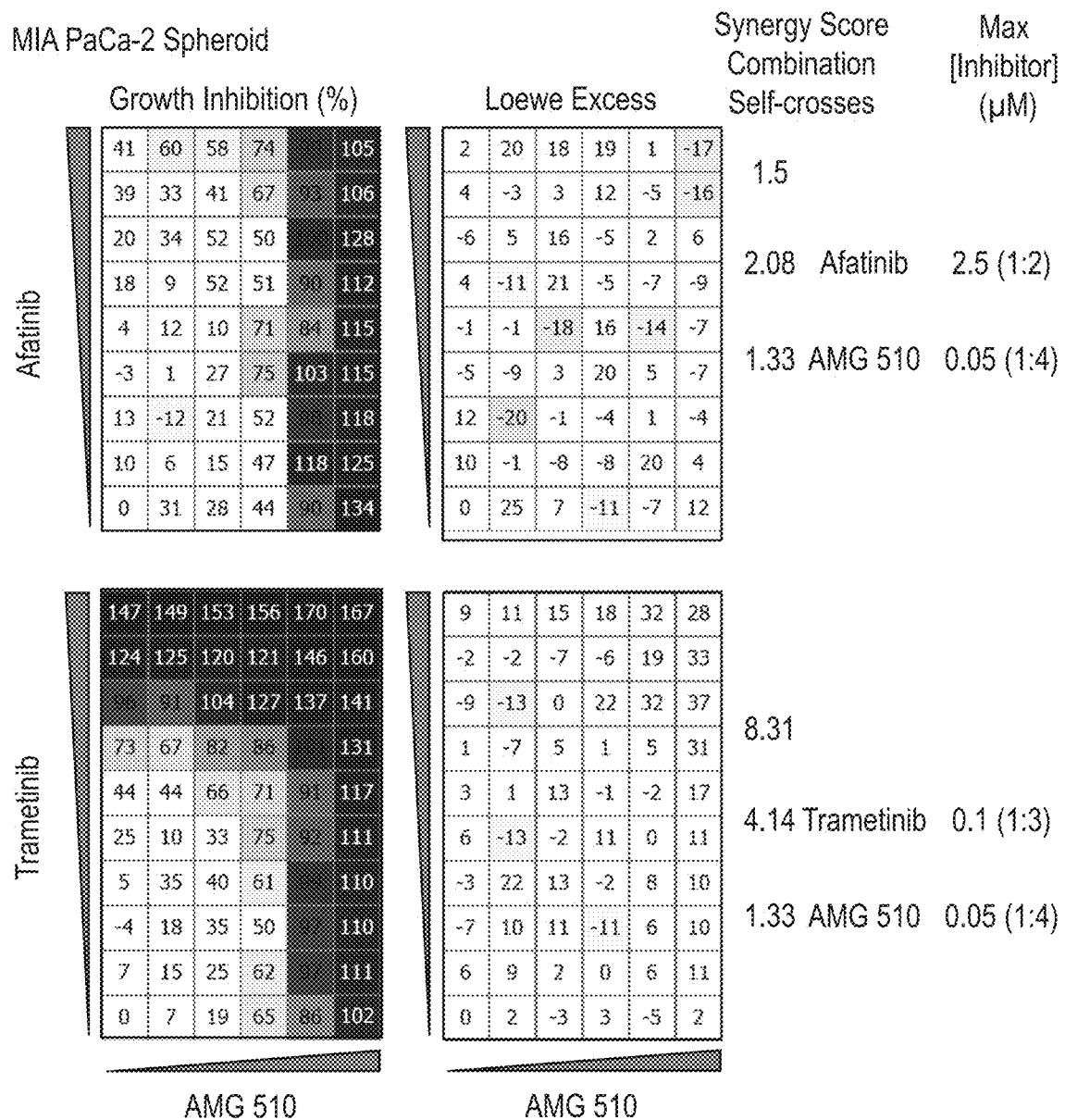

FIG. 47K illustrates AMG 510 as a single agent or in combination with carboplatin on NCI-H358 tumor xenografts. ****$P<0.0001$ by Dunnett's compared to vehicle control, #$P<0.001$ regression by paired t-test.

Figure 48A:
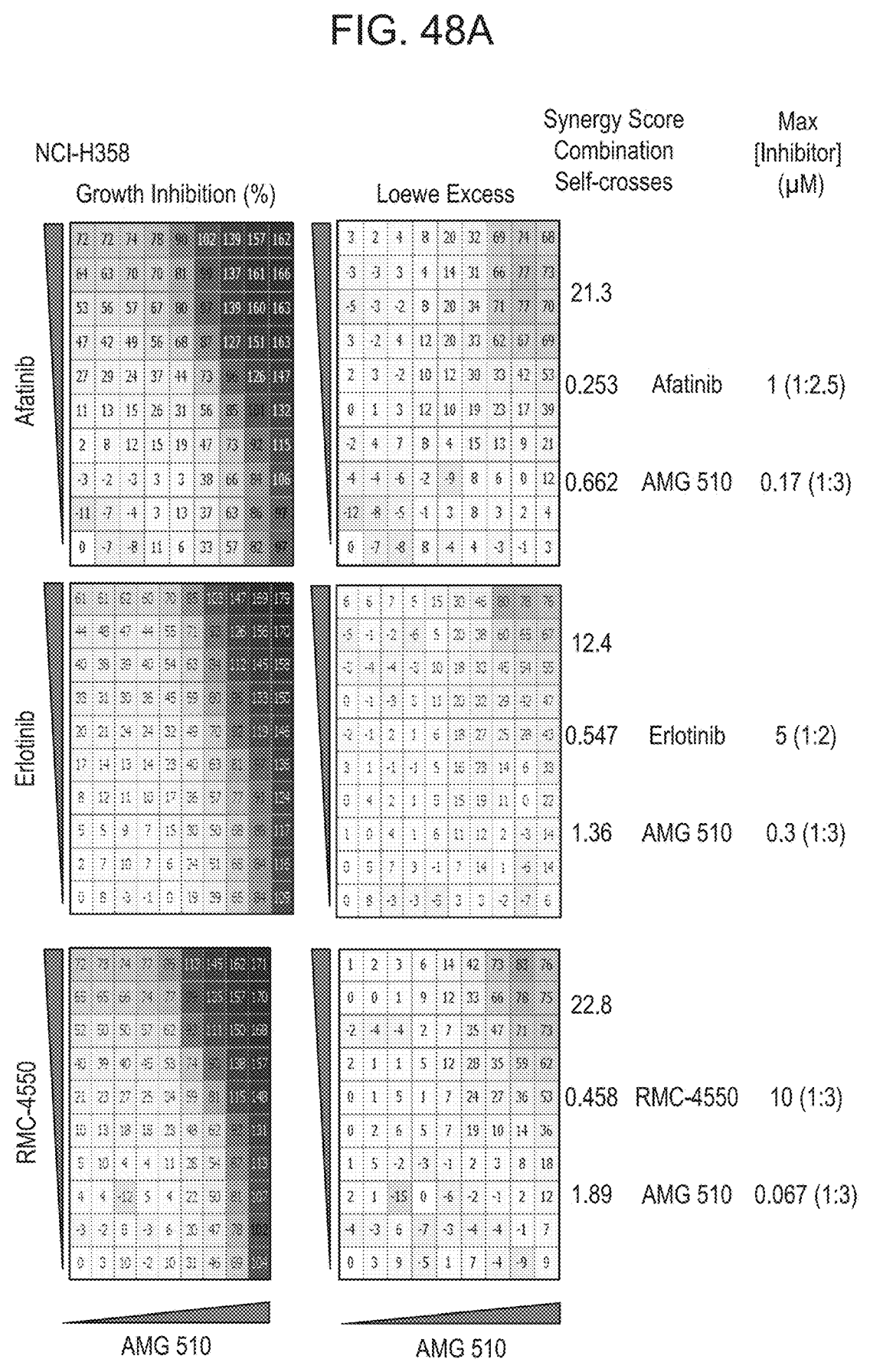
Figure 48B:
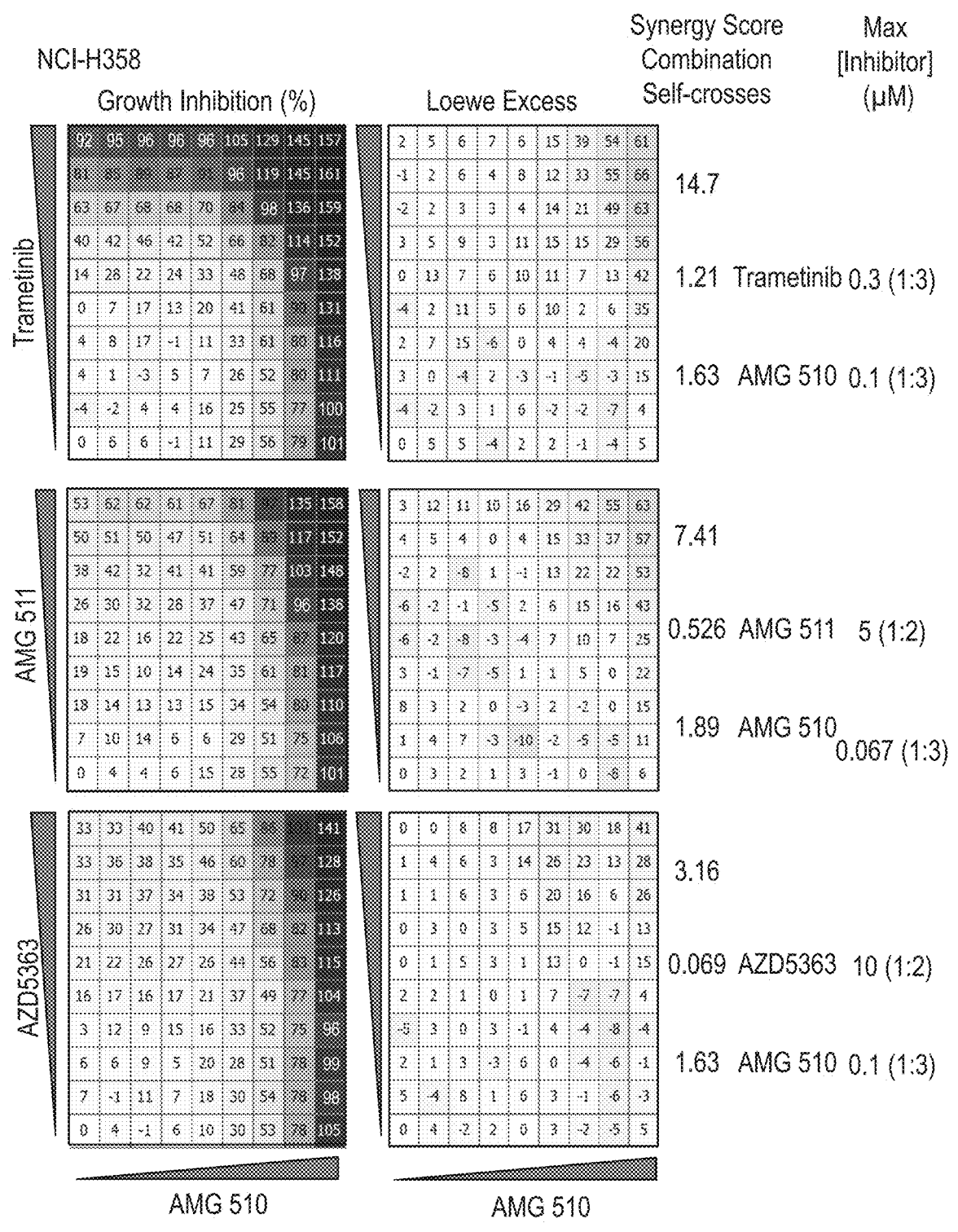
Figure 48H:
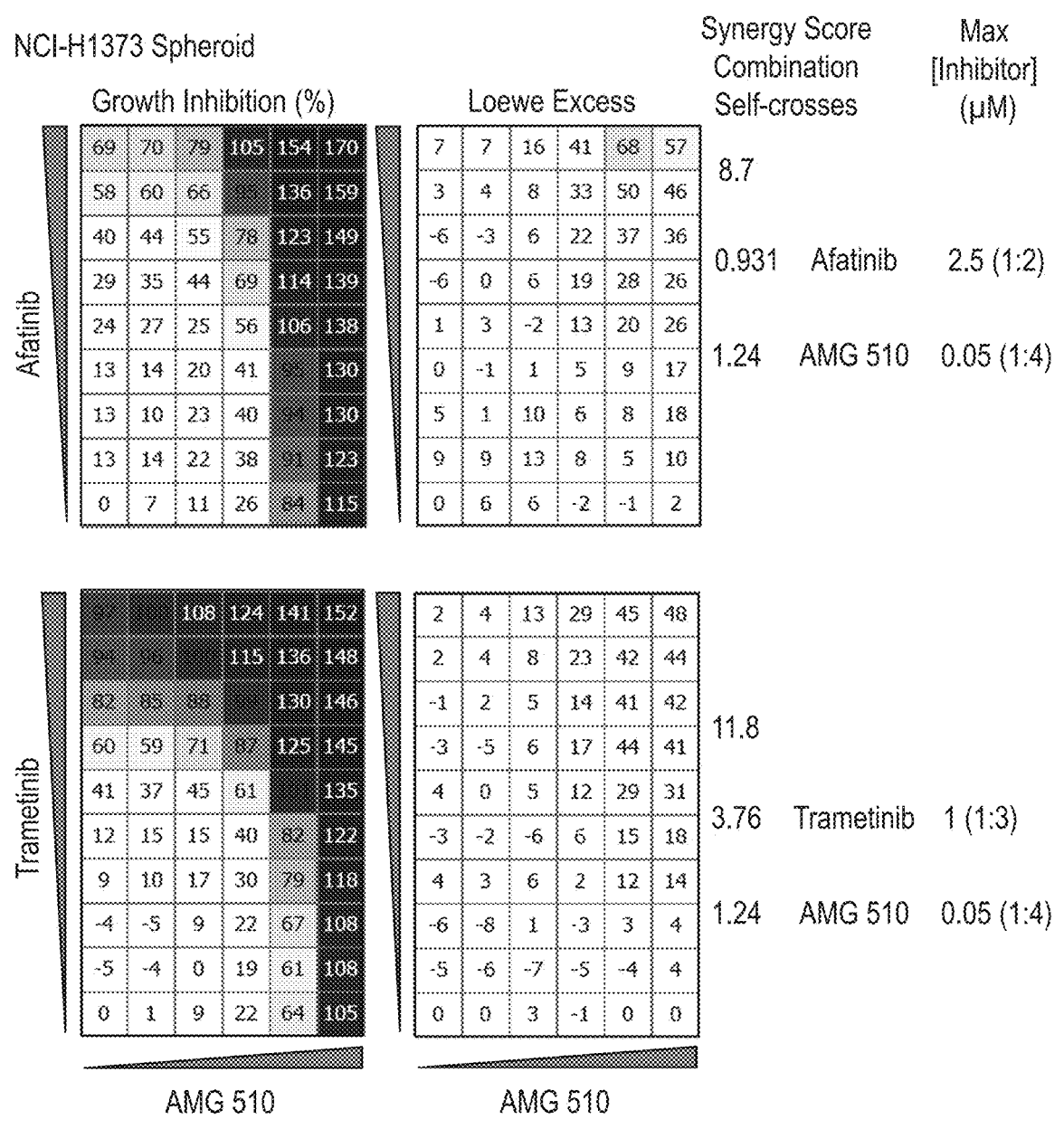

FIGS. 48A, 48B, 48C, 48D, 48E, 48F, 48G, 48H, and 48I show the growth inhibition matrices and Loewe additivity excess of AMG 510 dosed in combination with targeted agents in the indicated cell line, with darker colors denoting greater cell killing (growth inhibition) and stronger synergistic interaction (Loewe excess). The maximum concentration tested of the inhibitors and the dose range covered by the matrices in each combination are listed. Individual heterologous combinations (A×B) were evaluated by comparing their respective synergy scores to that of their component self-crosses (A×A or B×B). Heterologous combinations were considered synergistic only when their synergy score exceeded three times that of either component self-cross synergy score.

Figure 49A:
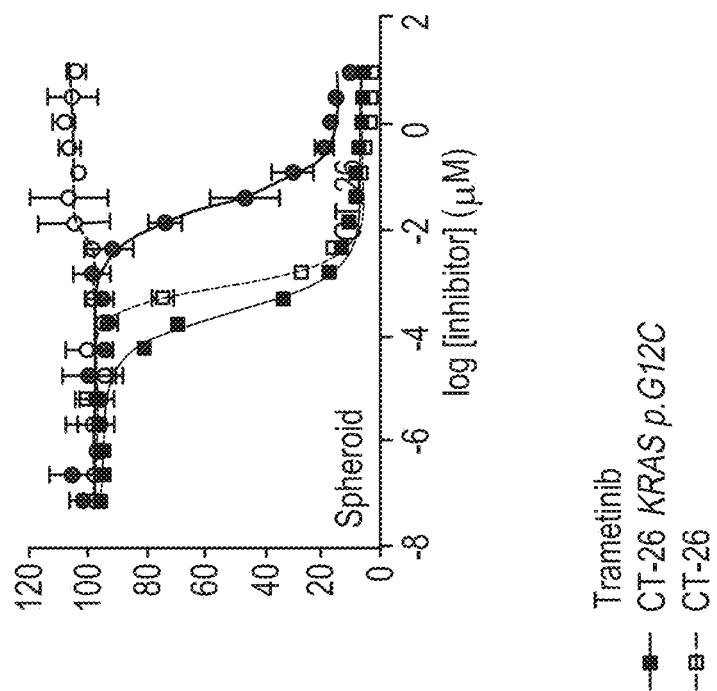

FIG. 49A shows the cellular activity of AMG 510 and the MEK inhibitor trametinib in CT-26 KRAS p.G12C and parental CT-26 cell lines as measured by inhibition of ERK1/2 phosphorylation after 2-hour treatment (n≥2).

Figure 49B:
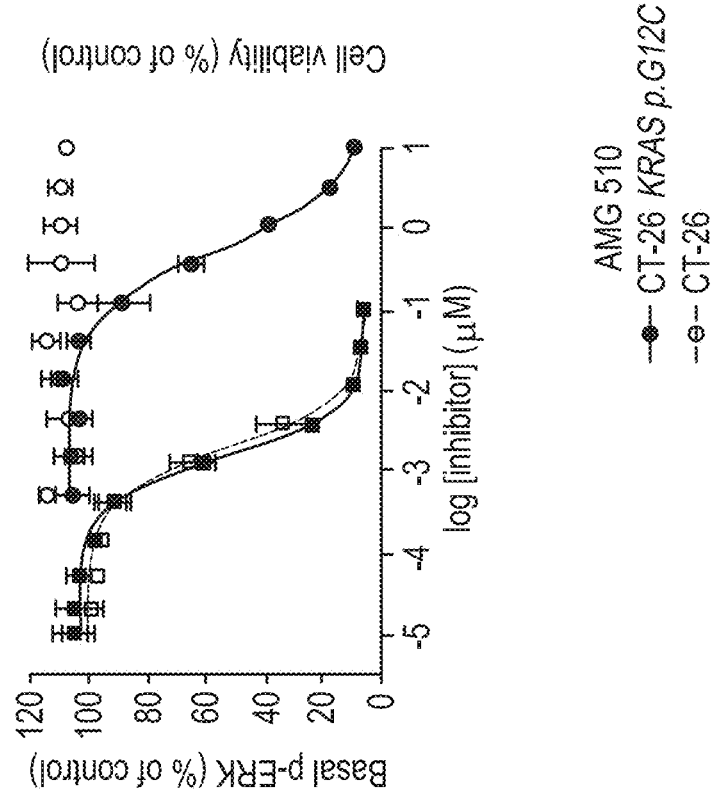

FIG. 49B shows the cellular activity of AMG 510 and the MEK inhibitor trametinib in CT-26 KRAS p.G12C and parental CT-26 cell lines as measured by effects on cell viability after 72-hour treatment in spheroid culture (n=2).

Figure 50A:
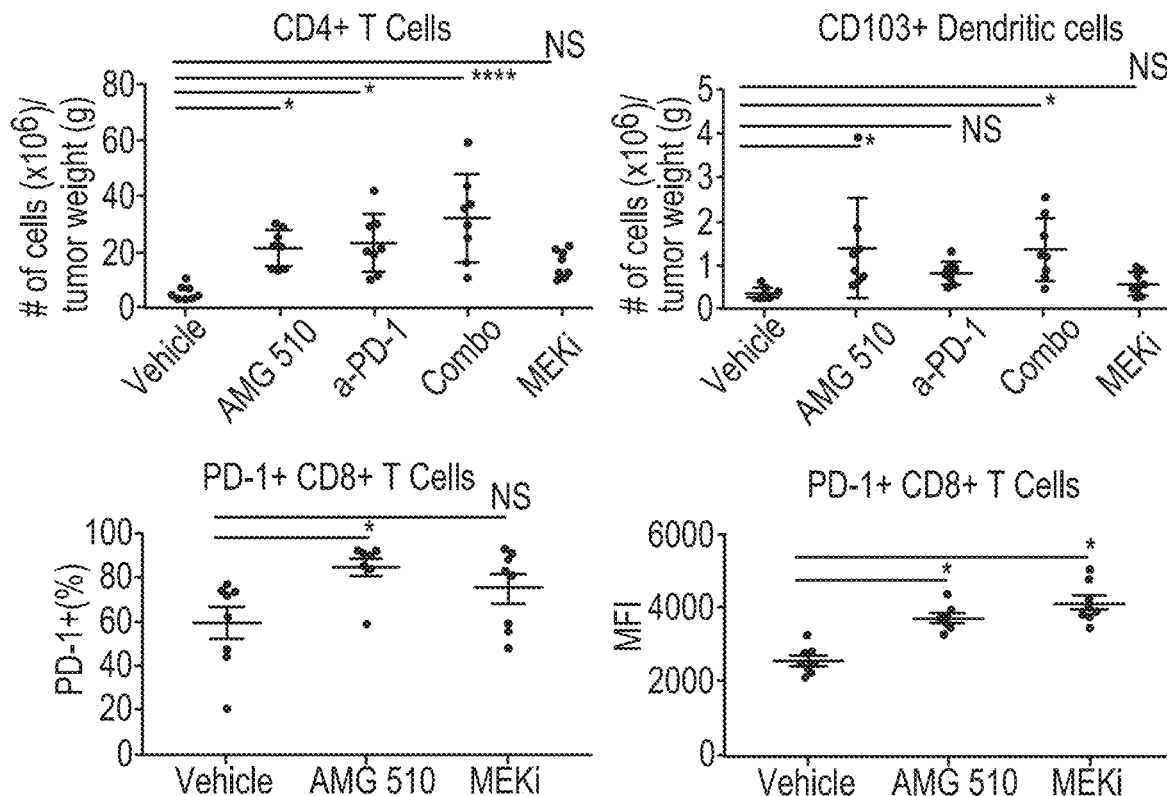

FIG. 50A shows CT-26 KRAS p.G12C tumors from mice treated over four days with either vehicle, AMG 510, anti-PD-1, AMG 510 plus anti-PD-1, or MEKi, and immunophenotyped by flow cytometry (n=8/group).

Figure 50B:
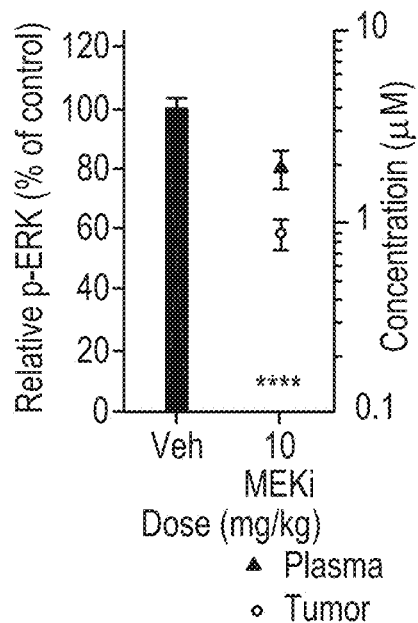

FIG. 50B shows CT-26 KRAS p.G12C tumor bearing mice were treated with a single dose of vehicle orally (black bar) or with the indicated dose of MEKi orally (blue bar) and harvested 2 hours later. Levels of p-ERK were measured by MSD immunoassay. Plasma and tumor samples were collected and analyzed for MEKi concentration (red triangle, black open circle, respectively). Data are presented as percent of control (POC) versus vehicle.

Figure 50C:
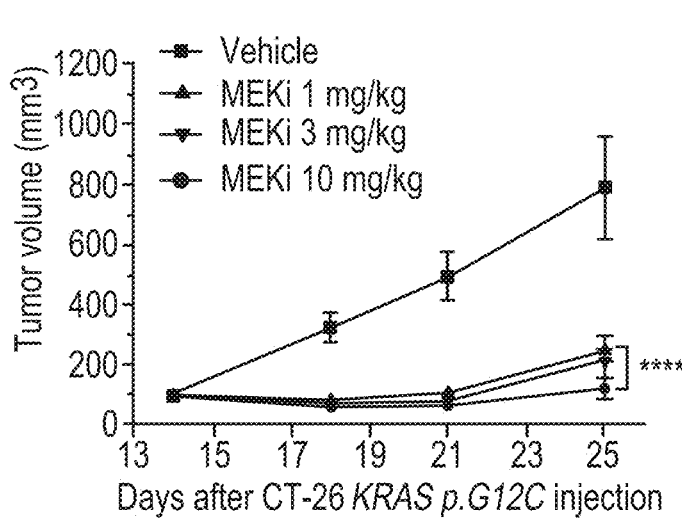

FIG. 50C shows the effect of MEKi treatment on tumor growth over time was measured in CT-26 KRAS p.G12C tumor bearing mice. Data represent mean tumor volume±SEM (n=10/group).

Figure 50D:
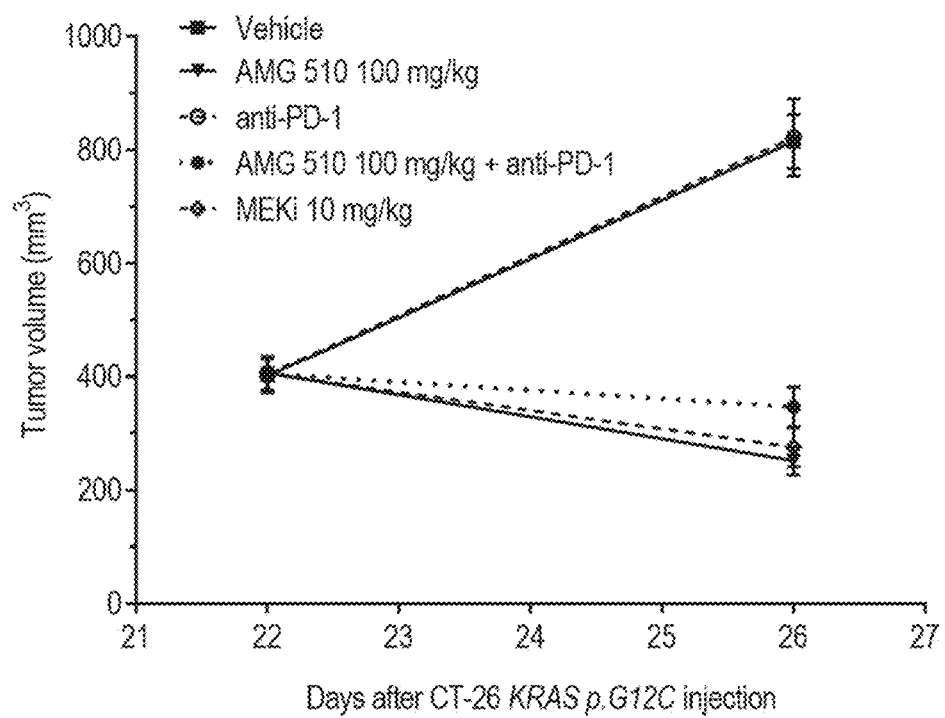

FIG. 50D shows tumor volumes in CT-26 KRAS p.G12C tumor bearing mice treated over four days with either vehicle, AMG 510, anti-PD-1, AMG 510 plus anti-PD-1, or MEKi. Data represent mean tumor volume±SEM (n=8/group).

Figure 50E:
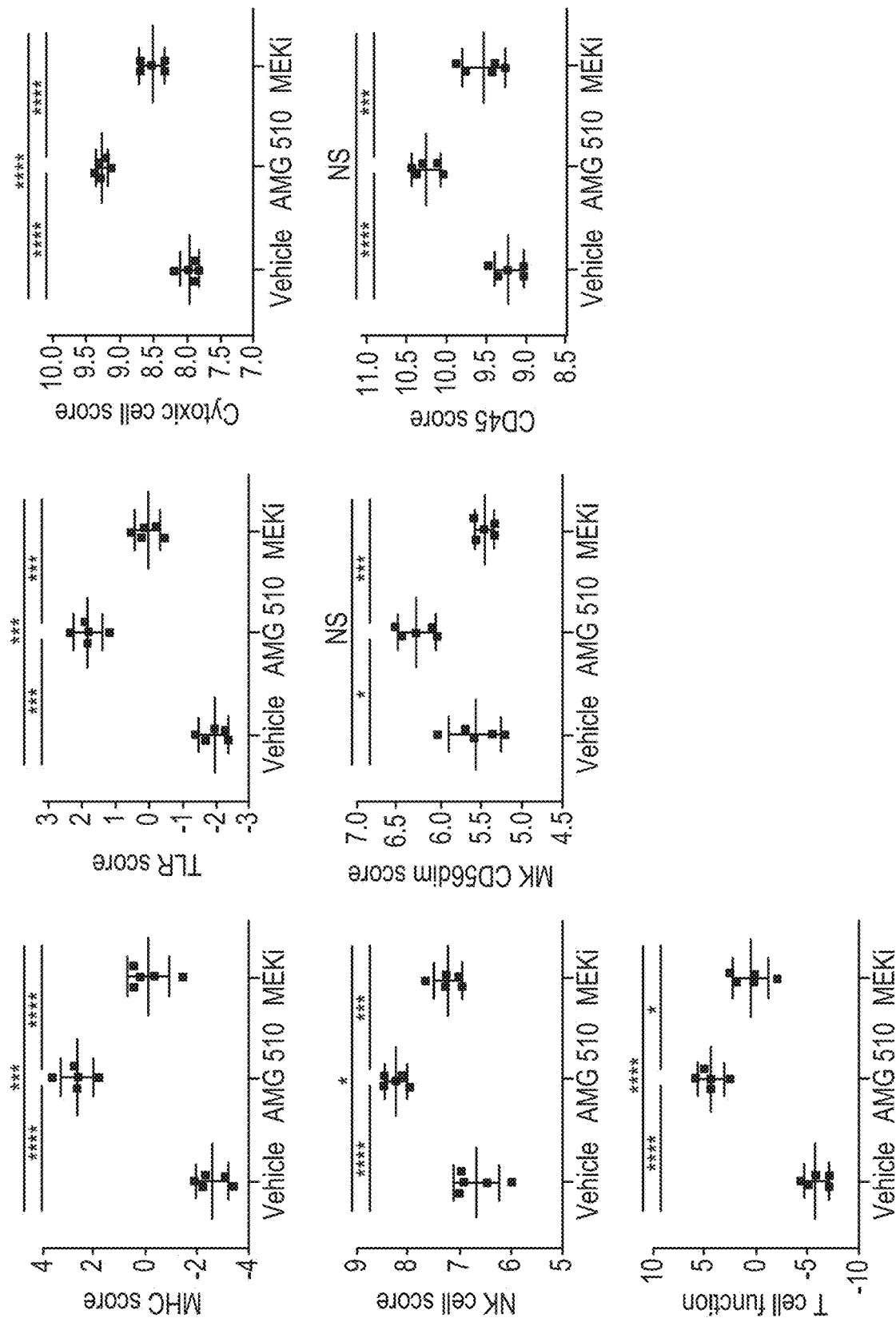

FIG. 50E shows RNA was isolated from CT-26 KRAS p.G12C tumors after two days of treatment. Gene expression and scores were calculated by NanoString technology (n=5/group).

Figure 50F:
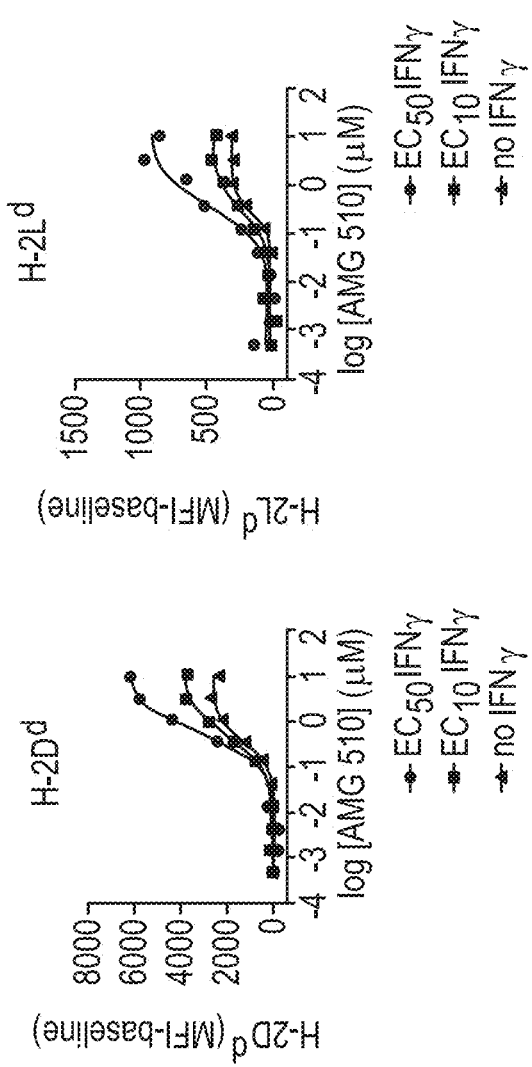

FIG. 50F shows cell surface expression of MHC class I antigens (H-2D$^d$ and H-2L$^d$) on CT-26 KRAS p.G120 cells following 24-hour treatment with AMG 510 in the presence or absence of IFNγ as measured by flow cytometry.

Figure 50G:
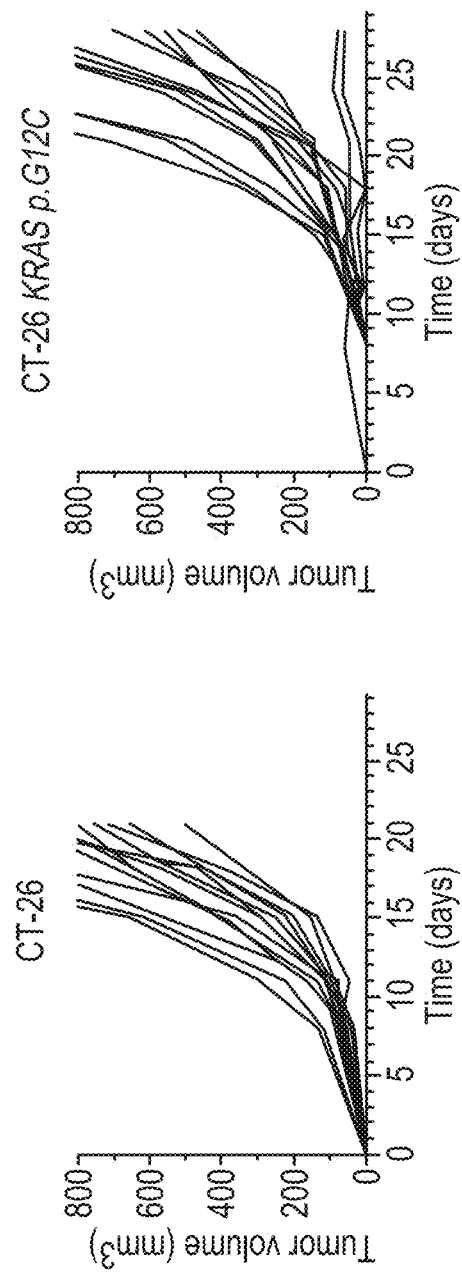

FIG. 50G shows growth curves in Balb/c mice bearing either CT-26 or CT-26 KRAS p.G12C tumors.

Figure 50H:
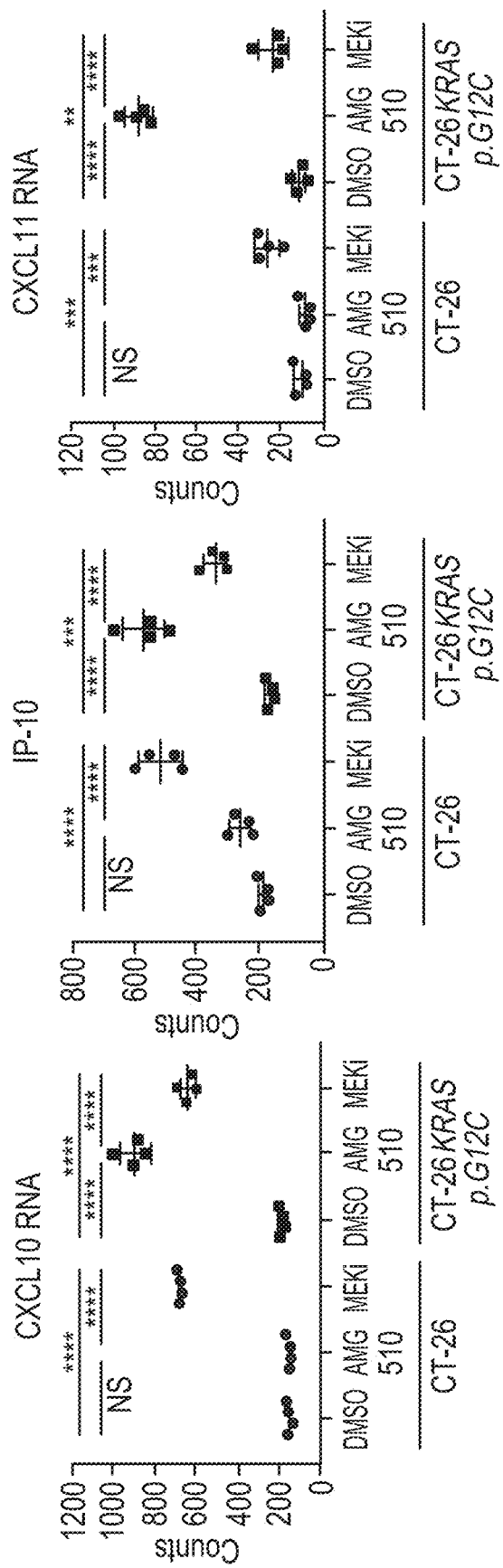

FIG. 50H shows Quantitation of CXCL10 or CXCL11 transcript, as well as secreted IP-10 protein, following 24-hour treatment of parental CT-26 or CT-26 KRAS p.G12C cells with AMG 510 or MEKi.

FIG. 50I shows Cell surface expression of MHC class I antigens (HLA, H-2D$^d$ and H-2K$^d$) on CT-26 KRAS p.G12C cells following 24-hour treatment with SW-1573 after 48 hours of treatment and MIA PaCA-2 after 48 hours of treatment with AMG 510 in the presence or absence of IFNγ as measured by flow cytometry.

In FIGS. 50A, 50B, 50C, and 50E, *$P<0.05$ by Tukey's to vehicle control; NS is not significant: *$P<0.001$ by Dunnett's compared to vehicle; and **$P<0.0001$ by Dunnett's compared to vehicle control.

DETAILED DESCRIPTION OF THE INVENTION

The present invention provides combination therapy that includes an $KRAS^{G12C}$ inhibitor and one or more additional pharmaceutically active agents, particularly for the treatment of cancers. The invention also relates to pharmaceutical compositions that contain an KRAS$^{G12C}$ inhibitor and one or more additional pharmaceutically active agents for the treatment of cancers. The compounds disclosed herein include all pharmaceutically acceptable isotopically-labeled compounds wherein one or more atoms of the compounds disclosed herein are replaced by atoms having the same atomic number, but an atomic mass or mass number different from the atomic mass or mass number usually found in nature. Examples of isotopes that can be incorporated into the disclosed compounds include isotopes of hydrogen, carbon, nitrogen, oxygen, phosphorous, fluorine, chlorine, and iodine, such as 2H, 3H, 11C, 13C, 14C, 13N, 15N, 15O, 17O, 18O, 31P, 32P, 35S, 18F, 36Cl, 123I, and 125I, respectively. These radio-labelled compounds could be useful to help determine or measure the effectiveness of the compounds, by characterizing, for example, the site or mode of action, or binding affinity to pharmacologically important site of action. Certain isotopically-labeled compounds of the disclosure, for example, those incorporating a radioactive isotope, are useful in drug and/or substrate tissue distribution studies. The radioactive isotopes tritium, i.e. 3H, and carbon-14, i.e. 14C, are particularly useful for this purpose in view of their ease of incorporation and ready means of detection.

Substitution with heavier isotopes such as deuterium, i.e. 2H, may afford certain therapeutic advantages resulting from greater metabolic stability, for example, increased in vivo half-life or reduced dosage requirements, and hence are preferred in some circumstances.

Substitution with positron emitting isotopes, such as 11C, 18F, 15O and 13N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Isotopically-labeled compounds as disclosed herein can generally be prepared by conventional techniques known to those skilled in the art or by processes analogous to those described in the accompanying examples and schemes using an appropriate isotopically-labeled reagent in place of the non-labeled reagent previously employed.

Certain of the compounds as disclosed herein may exist as stereoisomers (i.e., isomers that differ only in the spatial arrangement of atoms) including optical isomers and conformational isomers (or conformers). The compounds disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the compounds disclosed herein include all tautomeric forms of the compounds.

Certain of the compounds disclosed herein may exist as atropisomers, which are conformational stereoisomers that occur when rotation about a single bond in the molecule is prevented, or greatly slowed, as a result of steric interactions with other parts of the molecule. The compounds disclosed herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted. The separation and isolation of the isomeric species is duly designated by the well known and accepted symbols "M" or "P".

In another embodiment, these compounds can be used as intermediates in the process of making compounds in the present application.

In another embodiment, these compounds can be in the form of a pharmaceutically acceptable salt and in a pharmaceutical formulation with a pharmaceutically acceptable excipient.

Also provided herein are pharmaceutical compositions that include a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

In another embodiment, these compounds can be used as intermediates in the process of making compounds in the present application.

In another embodiment, these compounds can be in the form of a pharmaceutically acceptable salt and in a pharmaceutical formulation with a pharmaceutically acceptable excipient.

Also provided herein are pharmaceutical compositions that include a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound is described in more detail below:

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pennsylvania, 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil. L-leucine, calcium phosphate tribasic. L-tyrosine. L-proline. L-lysine acetate. DATEM (an emulsifier). L-glutamine. L-valine, potassium phosphate dibasic. L-isoleucine. L-arginine. L-alanine, glycine. L-asparagine monohydrate. L-serine, potassium citrate. L-threonine, sodium citrate, magnesium chloride, L-histidine. L-methionine, ascorbic acid, calcium carbonate. L-glutamic acid. L-cysteine dihydrochloride. L-tryptophan. L-aspartic acid, choline chloride, taurine, m-inositol, ferrous sulfate, ascorbyl palmitate, zinc sulfate. L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein. "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine. N,N'-dibenzylethylenediamine, chloroprocaine, choline, diethanolamine, dicyclohexylamine, ethylenediamine. N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid: with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxy benzoic acid, 2-acetoxy benzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1.2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate. N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KRAS-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KRAS activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most preferred dosage can be tailored to the individual subject, as is understood and determinable by one of skill in the art, without undue experimentation. This typically involves adjustment of a standard dose (e.g., reduction of the dose if the patient has a low body weight).

While individual needs vary, determination of optimal ranges of effective amounts of the compound is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less. 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 1 mg/day to about 1000 mg/day, about 20 mg/day to about 750 mg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or it may be divided into multiple doses.

Methods of Using KRAS$^{G12C}$ Inhibitors

The present disclosure provides a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The disclosure also provides methods of using the compounds or pharmaceutical compositions of the present disclosure to treat disease conditions, including but not limited to conditions implicated by G12C KRAS, HRAS or NRAS mutation (e.g., cancer).

In some embodiments, a method for treatment of cancer is provided, the method comprising administering an effective amount of any of the foregoing pharmaceutical compositions comprising a compound as disclosed herein to a subject in need thereof. In some embodiments, the cancer is mediated by a KRAS, HRAS or NRAS G12C mutation. In various embodiments, the cancer is pancreatic cancer, colorectal cancer or lung cancer. In some embodiments, the cancer is gall bladder cancer, thyroid cancer, and bile duct cancer.

In some embodiments the disclosure provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of at least one compound as disclosed herein or a pharmaceutically acceptable salt thereof.

The disclosed compounds inhibit anchorage-independent cell growth and therefore have the potential to inhibit tumor metastasis. Accordingly, another embodiment the disclosure provides a method for inhibiting tumor metastasis, the method comprising administering an effective amount a compound disclosed herein.

KRAS, HRAS or NRAS G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL). Acute myelogenous leukemia (AML), Chronic lymphocytic leukemia (CLL), small lymphocytic lymphoma (SLL). Chronic myelogenous leukemia (CML). Acute monocytic leukemia (AMOL) and/or other leukemias. In other embodiments, the compounds are useful for treatment of lymphomas such as all subtypes of Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art. (e.g. Accession No. NP203524).

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays. PCR sequencing, mutant allele-specific PCR amplification (MASA) assays, direct sequencing, primer extension reactions, electrophoresis, oligonucleotide ligation assays, hybridization assays. TaqMan assays. SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The disclosure also relates to a method of treating a hyperproliferative disorder in a mammal that comprises administering to said mammal a therapeutically effective amount of a compound as disclosed herein, or a pharmaceutically acceptable salt thereof. In some embodiments, said method relates to the treatment of a subject who suffers from a cancer such as acute myeloid leukemia, cancer in adolescents, adrenocortical carcinoma childhood. AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors. Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors. CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer. Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma. T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some embodiments, the methods for treatment are directed to treating lung cancers, the methods comprise administering an effective amount of any of the above described compounds (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas.

The disclosure further provides methods of modulating a G12C Mutant KRAS, HRAS or NRAS protein activity by contacting the protein with an effective amount of a compound of the disclosure. Modulation can be inhibiting or activating protein activity. In some embodiments, the disclosure provides methods of inhibiting protein activity by contacting the G12C Mutant KRAS, HRAS or NRAS protein with an effective amount of a compound of the disclosure in solution. In some embodiments, the disclosure provides methods of inhibiting the G12C Mutant KRAS, HRAS or NRAS protein activity by contacting a cell, tissue, or organ that expresses the protein of interest. In some embodiments, the disclosure provides methods of inhibiting protein activity in subject including but not limited to rodents and mammal (e.g., human) by administering into the subject an effective amount of a compound of the disclosure. In some embodiments, the percentage modulation exceeds 25%. 30%, 40%, 50%. 60%. 70%. 80%, or 90%. In some embodiments, the percentage of inhibiting exceeds 25%. 30%. 40%. 50%. 60%. 70%, 80%, or 90%.

In some embodiments, the disclosure provides methods of inhibiting KRAS, HRAS or NRAS G12C activity in a cell by contacting said cell with an amount of a compound of the disclosure sufficient to inhibit the activity of KRAS, HRAS or NRAS G12C in said cell. In some embodiments, the disclosure provides methods of inhibiting KRAS, HRAS or NRAS G12C activity in a tissue by contacting said tissue with an amount of a compound of the disclosure sufficient to inhibit the activity of KRAS, HRAS or NRAS G12C in said tissue. In some embodiments, the disclosure provides methods of inhibiting KRAS, HRAS or NRAS G12C activity in an organism by contacting said organism with an amount of a compound of the disclosure sufficient to inhibit the activity of KRAS, HRAS or NRAS G12C in said organism. In some embodiments, the disclosure provides methods of inhibiting KRAS, HRAS or NRAS G12C activity in an animal by contacting said animal with an amount of a compound of the disclosure sufficient to inhibit the activity of KRAS, HRAS or NRAS G12C in said animal. In some embodiments, the disclosure provides methods of inhibiting KRAS, HRAS or NRAS G12C activity in a mammal by contacting said mammal with an amount of a compound of the disclosure sufficient to inhibit the activity of KRAS, HRAS or NRAS G12C in said mammal. In some embodiments, the disclosure provides methods of inhibiting KRAS, HRAS or NRAS G12C activity in a human by contacting said human with an amount of a compound of the disclosure sufficient to inhibit the activity of KRAS, HRAS or NRAS G12C in said human. The present disclosure provides methods of treating a disease mediated by KRAS, HRAS or NRAS G12C activity in a subject in need of such treatment.

Combination Therapy

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, and radiation treatment, to provide a synergistic or additive therapeutic effect.

Many chemotherapeutics are presently known in the art and can be used in combination with the compounds of the disclosure. The compounds or pharmaceutical compositions of the disclosure can be used in combination with at least one or more chemotherapeutic agents. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec®; (Imatinib Mesylate), Kyprolis® (carfilzomib), Velcade®; (bortezomib), Casodex (bicalutamide), Iressa®; (gefitinib), Venclexta™ (venetoclax) and Adriamycin™, (docorubicin) as well as a host of chemotherapeutic agents. Non-limiting examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including al tretamine, triethylenemelamine, triety lenephosphoramide, triethylenethiophosphaoramide and trimethylolomelamine; nitrogen mustards such as chlorambucil, chlornaphazine, chlorocyclophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine. 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g, paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen. (Nolvadex™), raloxifene, aromatase inhibiting 4(5)-imidazoles. 4-hydroxytamoxifen, trioxifene, keoxifene. LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO).

Where desired, the compounds or pharmaceutical composition of the present disclosure can be used in combination with commonly prescribed anti-cancer drugs such as Herceptin®. Avastin®, Erbitux®, Rituxan®, Taxol®, Arimidex®, Taxotere®, ABVD, AVICINE, Abagovomab. Acridine carboxamide. Adecatumumab. 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy." as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source. I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from chemotherapeutic agents, anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors. MMP-9) (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EP0818442, European Patent Publication EP1004578, WO 98/07697, WO 98/03516, WO 98/34918, WO 98/34915, WO 98/33768, WO 98/30566, European Patent Publication 606046, European Patent Publication 931 788, WO 90/05719, WO 99/52910, WO 99/52889, WO 99/29667, WO1999007675, European Patent Publication EP1786785, European Patent Publication No, EP1181017, United States Publication No, US20090012085, U.S. Pat. Nos. 5,863,949, 5,861,510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340. RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole. ANCER, ancestim. ARGLABIN, arsenic trioxide. BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-$_{n3}$, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid: abarelix: AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800

(Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Collectively, antibodies form a family of plasma proteins known as immunoglobulins and comprise of immunoglobulin domains. (Janeway et al., Immunobiology: The Immune System in Health and Disease, 4th ed., Elsevier Science Ltd./Garland Publishing, 1999. As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. The constant region allows the antibody to recruit cells and molecules of the immune system. The variable region is made of the N-terminal regions of each light chain and heavy chain, while the constant region is made of the C-terminal portions of each of the heavy and light chains. (Janeway et al., "Structure of the Antibody Molecule and the Immunoglobulin Genes". Immunobiology: The Immune System in Health and Disease. 4$^{th}$ ed. Elsevier Science Ltd./Garland Publishing. (1999)).

The general structure and properties of CDRs of antibodies have been described in the art. Briefly, in an antibody scaffold, the CDRs are embedded within a framework in the heavy and light chain variable region where they constitute the regions largely responsible for antigen binding and recognition. A variable region typically comprises at least three heavy or light chain CDRs (Kabat et al., 1991. Sequences of Proteins of Immunological Interest. Public Health Service N.I.H., Bethesda. Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk. 1987, supra).

Antibodies can comprise any constant region known in the art. Human light chains are classified as kappa and lambda light chains. Heavy chains are classified as mu, delta, gamma, alpha, or epsilon, and define the antibody's isotype as IgM. IgD. IgG. IgA, and IgE, respectively. IgG has several subclasses, including, but not limited to IgG1, IgG2, IgG3, and IgG4, IgM has subclasses, including, but not limited to, IgM1 and IgM2. Embodiments of the present disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in exemplary embodiments, the antibody is an antibody of isotype IgA, IgD, IgE, IgG, or IgM, including any one of IgG1, IgG2, IgG3 or IgG4.

The antibody can be a monoclonal antibody or a polyclonal antibody. In some embodiments, the antibody comprises a sequence that is substantially similar to a naturally-occurring antibody produced by a mammal, e.g., mouse, rabbit, goat, horse, chicken, hamster, human, and the like. In this regard, the antibody can be considered as a mammalian antibody, e.g., a mouse antibody, rabbit antibody, goat antibody, horse antibody, chicken antibody, hamster antibody, human antibody, and the like. In certain aspects, the antibody is a human antibody. In certain aspects, the antibody is a chimeric antibody or a humanized antibody. The term "chimeric antibody" refers to an antibody containing domains from two or more different antibodies. A chimeric antibody can, for example, contain the constant domains from one species and the variable domains from a second, or more generally, can contain stretches of amino acid sequence from at least two species. A chimeric antibody also can contain domains of two or more different antibodies within the same species. The term "humanized" when used in relation to antibodies refers to antibodies having at least CDR regions from a non-human source which are engineered to have a structure and immunological function more similar to true human antibodies than the original source antibodies. For example, humanizing can involve grafting a CDR from a non-human antibody, such as a mouse antibody, into a human antibody. Humanizing also can involve select amino acid substitutions to make a non-human sequence more similar to a human sequence.

An antibody can be cleaved into fragments by enzymes, such as, e.g., papain and pepsin. Papain cleaves an antibody to produce two Fab fragments and a single Fc fragment.

Pepsin cleaves an antibody to produce a F(ab')2 fragment and a pFc' fragment. As used herein, the term "antigen binding antibody fragment refers to a portion of an antibody molecule that is capable of binding to the antigen of the antibody and is also known as "antigen-binding fragment" or "antigen-binding portion". In exemplary instances, the antigen binding antibody fragment is a Fab fragment or a F(ab')2 fragment.

The architecture of antibodies has been exploited to create a growing range of alternative formats that span a molecular-weight range of at least about 12-150 kDa and has a valency (n) range from monomeric (n=1), to dimeric (n=2), to trimeric (n=3), to tetrameric (n=4), and potentially higher; such alternative formats are referred to herein as "antibody protein products". Antibody protein products include those based on the full antibody structure and those that mimic antibody fragments which retain full antigen-binding capacity, e.g., scFvs, Fabs and VHH/VH (discussed below). The smallest antigen binding antibody fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab fragments can be easily produced in host cells, e.g., prokaryotic host cells. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, BsAb fragments, bispecific fusion proteins and BsAb conjugates. See, e.g., Spiess et al., Molecular Immunology 67(2) Part A: 97-106 (2015).

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 176; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163 L), aurora kinase inhibitors (e.g., MLN8237), cell surface monoclonal antibodies (e.g., anti-CD38 (HUMAX-CD38), anti-CS1 (e.g., elotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torc1/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The KRAS$^{G12C}$ inhibitors of the present invention can be used in combination with Aurora kinase inhibitors, such as those found in published PCT application WO2011/031842. A particular compound is AMG 900 (Example 1 of WO2011/031842, herein incorporated by reference for all purposes).

The KRAS$^{G12C}$ inhibitors of the present invention can be used in combination with MAP kinase pathway inhibitors. Examples of proteins in the MAP kinase pathway that can be inhibited and the inhibitors of such proteins used in combination with an KRAS$^{G12C}$ inhibitors are BRAF inhibitors, Pan-RAF inhibitors, and MEK inhibitors. There are three main RAF isoforms: ARAF, BRAF and CRAF. A pan-RAF inhibitor shows inhibitory activity on more than one RAF isoform. In contrast, a BRAF inhibitor exhibits more inhibitor activity (or selectivity) towards BRAF than the other RAF proteins.

The compounds of the present invention may also be used in combination with an additional pharmaceutically active compound that disrupts or inhibits RAS-RAF-ERK or PI3K-AKT-TOR signaling pathways. In other such combinations, the additional pharmaceutically active compound is a PD-1 and PD-L1 antagonist. The compounds or pharmaceutical compositions of the disclosure can also be used in combination with an amount of one or more substances selected from EGFR inhibitors, MEK inhibitors, PI3K inhibitors, AKT inhibitors, TOR inhibitors, Mcl-1 inhibitors, BCL-2 inhibitors, SHP2 inhibitors, proteasome inhibitors, and immune therapies, including monoclonal antibodies, immunomodulatory imides (IMiDs), anti-PD-1 (or alternatively PD-1 inhibitor), anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. EGFR inhibitors that can be used in the present combinations include, but are not limited to, afatinib (Tradename: Gilotrif®, commercially available from Boehringer Ingelheim), Erlotinib (Tradename: Tarceva®, commercially available from Genetech/Astellas), and Lapatinib Tradename: Tykerb®, commercially available from Novartis). KRAS$^{G12C}$ inhibitors can also be used in combination with EGFR antibodies in the present invention. EGFR antibodies that can be used in the present combinations include, but are not limited to, cetuximab (Tradename: Erbitux® from Lilly). Useful antibody inhibitors of EGFR include panitumumab (Vectibix), zalutumumab, nimotuzumab, and matuzumab.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published January 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12):1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

The KRAS$^{G12C}$ inhibitors of the present invention can be used in combination with MEK inhibitors, such as those found in published PCT application WO2002/006213. A particular compound is N-(((2R)-2,3-dihydroxypropyl)oxy)-3,4-difluoro-2-((2-fluoro-4-iodophenyl)amino)benzamide, also known as AMG 1009089 or 1009089, (Example 39).

The KRAS$^{G12C}$ inhibitors of the present invention can be used in combination with BRAF inhibitors, such as those found in published PCT application WO2008/153,947. A particular compound is AMG 2112819 (also known as 2112819)(Example 56). Another particular BRAF inhibitor that can be used in the combinations of the present invention is dabrafenib. Another BRAF inhibitor that can be used in the combinations of the present invention is vemurafenib.

Pan-RAF inhibitors can also be used along with KRAS$^{G12C}$ inhibitors in the combinations of the present invention. Particular Pan-Raf inhibitor include RAF265 and MLN-2480.

The KRAS$^{G12C}$ inhibitors of the present invention can be used in combination with MEK inhibitors. Particular MEK inhibitors that can be used in the combinations of the present invention include PD-325901, trametinib, pimasertib, MEK162 [also known as binimetinib], TAK-733, GDC-0973 and AZD8330. A particular MEK inhibitor that can be used along with KRAS$^{G12C}$ inhibitor in the combinations of the present invention is trametinib (tradename: Mekinist®, commercially available from Novartis Pharmaceuticals Corp.). Another particular MEK inhibitor is N-(((2R)-2,3-dihydroxypropyl)oxy)-3,4-difluoro-2-((2-fluoro-4-iodophenyl)amino)benzamide, also known as AMG 1009089, 1009089 or PD-325901. Another particular MEK inhibitor that can be used in the combinations of the present invention includes cobimetinib.

MEK inhibitors include, but are not limited to, CI-1040, AZD6244, PD318088, PD98059, PD334581, RDEA119, ARRY-142886, and ARRY-438162.

In another aspect, the present invention relates to the use of the compound of the present invention in combination with one or more pharmaceutical agent that is an inhibitor of a protein in the phosphatidylinositol 3-kinase (PI3K) pathway. Examples of proteins in the PI3K pathway include PI3K, mTOR and PKB (also known as Akt or AKT). The PI3K protein exists in several isoforms including α, β, δ, or γ. It is contemplated that a PI3K inhibitor that can be used in the present invention can be selective for one or more isoform. By selective it is meant that the compounds inhibit one or more isoform more than other isoforms. Selectivity is a concept well known to those is the art and can be measured with well-known in vitro or cell-based activity assays. Preferred selectivity includes greater than 2-fold, preferably 10-fold, or more preferably 100-fold greater selectivity for one or more isoform over the other isoforms. In one aspect, the PI3K inhibitors that can be used in combination with compounds of the present invention are PI3K a selective inhibitors. In another aspect the compound is a PI3K δ selective inhibitor. In still another aspect the compound is a PI3K β selective inhibitor.

Examples of PI3K inhibitors that can be used in combination with one or more compounds of the present invention include those disclosed in the following: PCT published application no. WO2010/151791; PCT published application no. WO2010/151737; PCT published application no. WO2010/151735; PCT published application no. WO2010/151740; PCT published application no. WO2008/118455; PCT published application no. WO2008/118454; PCT published application no. WO2008/118468; U.S. published application no. US20100331293; U.S. published application no. US20100331306; U.S. published application no. US20090023761; U.S. published application no. US20090030002; U.S. published application no. US20090137581; U.S. published application no. US2009/0054405; U.S. published application no. U.S. 2009/0163489; U.S. published application no. US 2010/0273764; U.S. published application no. U.S. 2011/0092504; or PCT published application no. WO2010/108074. PI3K inhibitors include, but are not limited to, wortmannin, 17-hydroxy-wortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

Preferred PI3K inhibitors for use in combination with the compound of the present invention include:

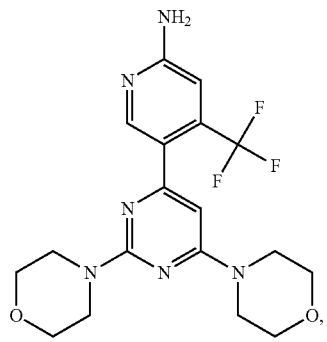 [SMILES: Nc1cc(C(F)(F)F)c(-c2cc(N3CCOCC3)nc(N3CCOCC3)n2)cn1]

also known as buparlisib, an investigational small molecule from Novartis Pharmaceuticals,

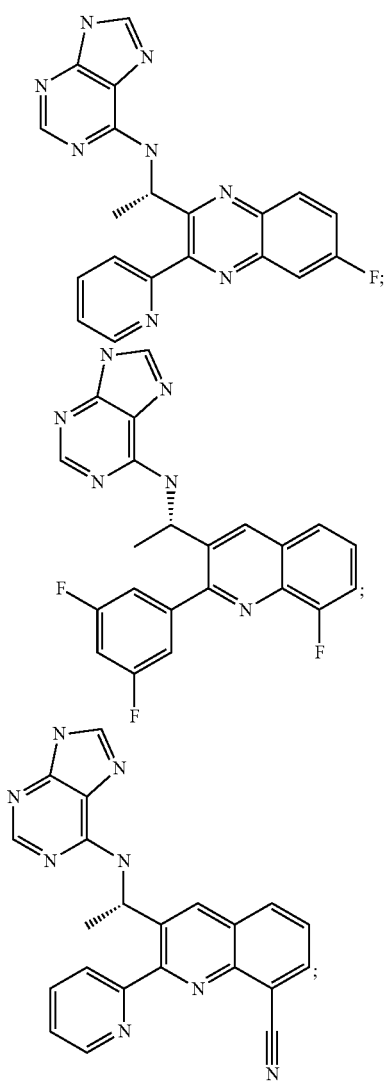

-continued

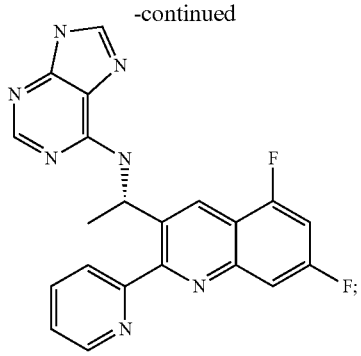

or a pharmaceutically acceptable salt thereof.

Also preferred is a compound of Formula IIa below, or a pharmaceutically acceptable salt thereof,

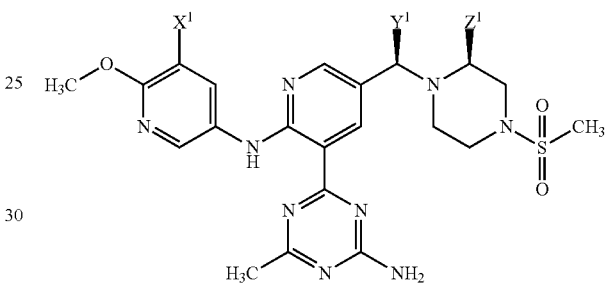

IIa wherein $X^1$ is fluorine or hydrogen; $Y^1$ is hydrogen or methyl; and $Z^1$ is hydrogen or methyl. A particular PI3K inhibitor that can be used in the combinations of the present invention is AMG 511 (also known as AMG 2539965 or 2539965), which is Example 148 of published PCT application WO2010/126895.

Other PI3K inhibitors that can be used in combination with $KRAS^{G12C}$ inhibitors in the combinations of the present invention include Pan-PI3K inhibitors such as BKM120 and GDC-0941; PI3Kα selective inhibitors such as BYL719; and PI3K 3 selective inhibitors such as GSK-2636771.

Compounds that inhibit both PI3K and mTOR (dual inhibitors) are known. In still another aspect, the present invention provides the use of dual PI3K and mTOR inhibitors for use in combination with $KRAS^{G12C}$ inhibitors. An example of a particular dual inhibitor is GDC-0980.

$KRAS^{G12C}$ inhibitors can also be used in combination with SHP2 inhibitors in the present invention. SHP2 inhibitors that can be used in the present combinations include, but are not limited to, SHP099, and RMC-4550 or RMC-4630, from Revolutions Medicines in Redwood City, CA.

mTOR is a protein in the PI3K pathway. It is another aspect of the present invention to use an mTOR inhibitor in combination with $KRAS^{G12C}$ inhibitors. mTOR inhibitors that can be used in combination with the compound of the present invention include those disclosed in the following documents: PCT published application no. WO2010/132598 and PCT published application no. WO2010/096314. mTOR inhibitors that can be used in combination with $KRAS^{G12C}$ inhibitors in the combinations of the present invention include AZD2014 and MLN0128.

TOR inhibitors include, but are not limited to, AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, or AP23841; 40-(2-hydroxyethyl)rapamycin, 40-[3-hydroxy (hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

PKB (AKT) is also a protein in the PI3K pathway. It is another aspect of the present invention to use an AKT inhibitor in combination with an KRAS$^{G12C}$ inhibitor. AKT inhibitors that can be used in combination with the compound of the present invention include those disclosed in the following documents: U.S. Pat. Nos. 7,354,944; 7,700,636; 7,919,514; 7,514,566; U.S. patent application publication no. US 2009/0270445 A1; U.S. Pat. Nos. 7,919,504; 7,897, 619; or PCT published application no. WO 2010/083246 A1. Particular AKT inhibitors that can be used in combination with KRAS$^{G12C}$ inhibitors in the combinations of the present invention include MK-2206, GDC-0068 and AZD5363.

AKT inhibitors include, but are not limited to, Akt-1-1 (inhibits Akt1) (Barnett et al. (2005) *Biochem. J.*, 385 (Pt. 2), 399-408); Akt-1-1,2 (inhibits Ak1 and 2) (Barnett et al. (2005) *Biochem. J.* 385 (Pt. 2), 399-408); API-59CJ-Ome (e.g., Jin et al. (2004) *Br. J Cancer* 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) *J Nutr.* 134(12 Suppl), 3493S-3498S); perifosine (e.g., interferes with Akt membrane localization; Dasmahapatra et al. (2004) *Clin. Cancer Res.* 10(15), 5242-52, 2004); phosphatidylinositol ether lipid analogues (e.g., Gills and Dennis (2004) *Expert. Opin. Investig. Drugs* 13, 787-97); and triciribine (TCN or API-2 or NCI identifier: NSC 154020; Yang et al. (2004) *Cancer Res.* 64, 4394-9).

MCl-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

Proteasome inhibitors include, but are not limited to, Kyprolis® (carfilzomib), Velcade® (bortezomib), and oprozomib.

Immune therapies include, but are not limited to, anti-PD-1 agents, anti-PDL-1 agents, anti-CTLA-4 agents, anti-LAG1 agents, and anti-OX40 agents.

Monoclonal antibodies include, but are not limited to, Darzalex® (daratumumab), Herceptin® (trastuzumab), Avastin® (bevacizumab), Rituxan® (rituximab), Lucentis® (ranibizumab), and Eylea® (aflibercept).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Anti-PD-1 inhibitors, including but not limited to antibodies include, but are not limited to, pembrolizumab (Keytruda®) and nivolumab (Opdivo®). Exemplary anti-PD-1 antibodies and methods for their use are described by Goldberg et al., *Blood* 110(1):186-192 (2007), Thompson et al., *Clin. Cancer Res.* 13(6):1757-1761 (2007), and Korman et al., International Application No. PCT/JP2006/309606 (publication no. WO 2006/121168 A1), each of which are expressly incorporated by reference herein. include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

In a particular embodiment, the compounds of the present invention are used in combination with an anti-PD-1 antibody, such as AMG 404. In a specific embodiment, the anti-PD-1 antibody (or antigen binding antibody fragment thereof) comprises 1, 2, 3, 4, 5, or all 6 the CDR amino acid sequences of SEQ ID NOs: 1-6 (representing HC CDR1, HC CDR2, HC CDR3, LC CDR1, LC CDR2, and LC CDR3, in that order). In specific embodiments, the anti-PD-1 antibody (or antigen binding antibody fragment thereof) comprises all 6 of the CDR amino acid sequences of SEQ ID NOs: 1-6. In other embodiments, the anti-PD-1 antibody (or antigen binding antibody fragment thereof) comprises (a) the heavy chain variable region amino acid sequence in SEQ ID NO: 7, or a variant sequence thereof which differs by only one or two amino acids or which has at least or about 70% sequence identity, or (b) the light chain variable region amino acid sequence in SEQ ID NO: 8 or a variant sequence thereof which differs by only one or two amino acids or which has at least or about 70% sequence identity. In an exemplary embodiment, the anti-PD-1 antibody (or antigen binding antibody fragment thereof) comprises the heavy chain variable region amino acid sequence in SEQ ID NO: 7 and the light chain variable region amino acid sequence in SEQ ID NO: 8. In other embodiments, the anti-PD-1 antibody (or antigen binding antibody fragment thereof) comprises (a) the heavy chain amino acid sequence of SEQ ID NO: 9 or a variant sequence thereof which differs by only one or two amino acids or which has at least or about 70% sequence identity; or (b) the light chain amino acid sequence of SEQ ID NO: 10 or a variant sequence thereof which differs by only one or two amino acids or which has at least or about 70% sequence identity. In an exemplary embodiment, the anti-PD-1 antibody (or antigen binding antibody fragment thereof) comprises the heavy chain amino acid sequence of SEQ ID NO: 9 and the light chain amino acid sequence of SEQ ID NO: 10.

The present disclosure further provides nucleic acid sequences encoding the anti-PD-1 antibody (or an antigen binding portion thereof). In exemplary aspects, the antibody comprises 1, 2, 3, 4, 5, or all 6 CDRs encoded by the nucleic acid(s) of SEQ ID NOs: 11-16 (representing HC CDR1, HC CDR2, HC CDR3, LC CDR1, LC CDR2, and LC CDR3, in that order). In another exemplary aspect, the antibody comprises all 6 CDRs encoded by the nucleic acids of SEQ ID NOs: 11-16. In some embodiments, the anti-PD-1 antibody (or an antigen binding portion thereof) comprises (a) a heavy chain variable region encoded by SEQ ID NO: 17 or a variant sequence thereof which differs by only 1, 2, 3, 4, 5, or 6 nucleic acids or which has at least or about 70%, 85%, 90%, or 95% sequence identity, or (b) a light chain variable region encoded by SEQ ID NO: 18 or a variant sequence thereof which differs by only 1, 2, 3, 4, 5, or 6 nucleic acids or which has at least or about 70%, 85%, 90%, or 95% sequence identity. In an exemplary embodiment, the anti-PD-1 antibody (or an antigen binding portion thereof) comprises a heavy chain variable region encoded by SEQ ID NO: 17 and a light chain variable region encoded by SEQ ID NO: 18. In other embodiments, the anti-PD-1 antibody (or an antigen binding portion thereof) comprises (a) a heavy chain encoded by SEQ ID NO: 19 or a variant sequence thereof which differs by only 1, 2, 3, 4, 5, or 6 nucleic acids or which has at least or about 70%, 85%, 90%, or 95% sequence identity, or (b) a light chain encoded by SEQ ID NO: 20 or a variant sequence thereof which differs by only 1, 2, 3, 4, 5, or 6 nucleic acids or which has at least or about 70%, 85%, 90%, or 95% sequence identity. In an exemplary embodiment, the anti-PD-1 antibody (or an antigen binding portion thereof) comprises a heavy chain encoded by SEQ ID NO: 19 and a light chain encoded by SEQ ID NO: 20. CT-26 KRAS p.G12C cells were generated from the murine T-26 colorectal line (ATCC) using the CRISPR technology to replace both KRAS p.G12D alleles with p.G12C (ThermoFisher Scientific) as encoded by SEQ ID NO: 21.

| SEQ ID NO. | Sequence Type | Sequence |
|---|---|---|
| 1 | PRT | Ser Tyr Asp Met Ser |
| 2 | PRT | Leu Ile Ser Gly Gly Gly Ser Gln Thr Tyr Tyr Ala Glu Ser Val Lys |
| 3 | PRT | Pro Ser Gly His Tyr Phe Tyr Ala Met Asp Val |
| 4 | PRT | Arg Ala Ser Gln Gly Ile Ser Asn Trp Leu Ala |
| 5 | PRT | Ala Ala Ser Ser Leu Gln Ser |
| 6 | PRT | Gln Gln Ala Glu Ser Phe Pro His Thr |
| 7 | PRT | Glu Val Gln Leu Leu Glu Ser Gly Gly Gly Leu Val Gln Pro Gly Gly Ser Leu Arg Leu Ser Cys Ala Ala Ser Gly Phe Thr Phe Ser Ser Tyr Asp Met Ser Trp Val Arg Gln Ala Pro Gly Lys Gly Leu Glu Trp Val Ser Leu Ile Ser Gly Gly Gly Ser Gln Thr Tyr Tyr Ala Glu Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Phe Cys Ala Ser Pro Ser Gly His Tyr Phe Tyr Ala Met Asp Val Trp Gly Gln Gly Thr Thr Val Thr Val Ser Ser |
| 8 | PRT | Asp Ile Gln Met Thr Gln Ser Pro Ser Ser Val Ser Ala Ser Val Gly Asp Arg Val Thr Ile Thr Cys Arg Ala Ser Gln Gly Ile Ser Asn Trp Leu Ala Trp Tyr Gln Gln Lys Pro Gly Lys Ala Pro Lys Leu Leu Ile Phe Ala Ala Ser Ser Leu Gln Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Ala Glu Ser Phe Pro His Thr Phe Gly Gly Gly Thr Lys Val Glu Ile Lys |
| 9 | PRT | Met Asp Met Arg Val Pro Ala Gln Leu Leu Gly Leu Leu Leu Leu Trp Leu Arg Gly Ala Arg Cys Glu Val Gln Leu Leu Glu Ser Gly Gly Gly Leu Val Gln Pro Gly Gly Ser Leu Arg Leu Ser Cys Ala Ala Ser Gly Phe Thr Phe Ser Ser Tyr Asp Met Ser Trp Val Arg Gln Ala Pro Gly Lys Gly Leu Glu Trp Val Ser Leu Ile Ser Gly Gly Gly Ser Gln Thr Tyr Tyr Ala Glu Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Phe Cys Ala Ser Pro Ser Gly His Tyr Phe Tyr Ala Met Asp Val Trp Gly Gln Gly Thr Thr Val Thr Val Ser Ser Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Gly Ser Thr Tyr Arg Cys Val Ser Val Leu Thr Val Leu His Gln Asp Trp Leu Asn Gly Lys |

| SEQ ID NO. | Sequence Type | Sequence |
|---|---|---|
| | | Glu Tyr Lys Cys Lys Val Ser Asn Lys Ala Leu Pro Ala Pro Ile
Glu Lys Thr Ile Ser Lys Ala Lys Gly Gln Pro Arg Glu Pro Gln
Val Tyr Thr Leu Pro Pro Ser Arg Glu Glu Met Thr Lys Asn Gln
Val Ser Leu Thr Cys Leu Val Lys Gly Phe Tyr Pro Ser Asp Ile
Ala Val Glu Trp Glu Ser Asn Gly Gln Pro Glu Asn Asn Tyr Lys
Thr Thr Pro Pro Val Leu Asp Ser Asp Gly Ser Phe Phe Leu Tyr
Ser Lys Leu Thr Val Asp Lys Ser Arg Trp Gln Gln Gly Asn Val
Phe Ser Cys Ser Val Met His Glu Ala Leu His Asn His Tyr Thr
Gln Lys Ser Leu Ser Leu Ser Pro Gly Lys |
| 10 | PRT | Met Asp Met Arg Val Pro Ala Gln Leu Leu Gly Leu Leu Leu
Leu Trp Leu Arg Gly Ala Arg Cys Asp Ile Gln Met Thr Gln Ser
Pro Ser Ser Val Ser Ala Ser Val Gly Asp Arg Val Thr Ile Thr
Cys Arg Ala Ser Gln Gly Ile Ser Asn Trp Leu Ala Trp Tyr Arg
Gln Lys Pro Gly Lys Ala Pro Lys Leu Leu Ile Phe Ala Ala Ser
Ser Leu Gln Ser Gly Val Pro Ser Arg Phe Ser Gly Ser Gly Ser
Gly Thr Asp Phe Thr Leu Thr Ile Ser Ser Leu Gln Pro Glu Asp
Phe Ala Thr Tyr Tyr Cys Gln Gln Ala Glu Ser Phe Pro His Thr
Phe Gly Gly Gly Thr Lys Val Glu Ile Lys Arg Thr Val Ala Ala
Pro Ser Val Phe Ile Phe Pro Pro Ser Asp Glu Gln Leu Lys Ser
Gly Thr Ala Ser Val Val Cys Leu Leu Asn Asn Phe Tyr Pro Arg
Glu Ala Lys Val Gln Trp Lys Val Asp Asn Ala Leu Gln Ser Gly
Asn Ser Gln Glu Ser Val Thr Glu Gln Asp Ser Lys Asp Ser Thr
Tyr Ser Leu Ser Ser Thr Leu Thr Leu Ser Lys Ala Asp Tyr Glu
Lys His Lys Val Tyr Ala Cys Glu Val Thr His Gln Gly Leu Ser
Ser Pro Val Thr Lys Ser Phe Asn Arg Gly Glu Cys |
| 11 | DNA | agctatgaca tgagc |
| 12 | DNA | cttattagtg gtggtggtag tcaaacatac tacgcagaat ccgtgaaggg c |
| 13 | DNA | cccagtggcc actacttcta cgctatggac gtc |
| 14 | DNA | cgggcgagtc agggtattag caactggtta gcc |
| 15 | DNA | gctgcatcca gtttgcaaag t |
| 16 | DNA | caacaggctg aaagtttccc tcacact |
| 17 | DNA | gaggtgcagc tgttggagtc tgggggaggc ttggtacagc ctggggggtc
cctgagactc tcctgtgcag cctctggatt cacctttagc agctatgaca tgagctgggt
ccgccaggct ccagggaagg ggctggaatg ggtctcactt attagtggtg
gtggtagtca aacatactac gcagaatccg tgaagggccg gttcaccatc
tccagagaca attccaagaa cacgctgtat ctgcaaatga acagcctgag
agccgaggac acggccgtat atttctgtgc gtccccagt ggccactact
tctacgctat ggacgtctgg ggccaaggga ccacggtcac cgtctcctca |
| 18 | DNA | gacatccaga tgacccagtc tccatcttcc gtgtctgcat ctgttggaga
cagagtcacc atcacttgtc gggcgagtca gggtattagc aactggttag
cctggtatca gcagaaacca gggaaagccc taagctcct gatctttgct
gcatccagtt tgcaaagtgg ggtcccatca aggttcagcg gcagtggatc
tgggacagat ttcaccctca ccatcagcag cctgcagcct gaagattttg
caacttacta ttgtcaacag gctgaaagtt tccctcacac tttcggcgga
gggaccaagg tggagatcaa a |
| 19 | DNA | atggacatga gggtgcccgc tcagctcctg gggctcctgc tgctgtggct
gagaggtgcg cgctgtgagg tgcagctgtt ggagtctggg ggaggcttgg
tacagcctgg ggggtccctg agactctcct gtgcagcctc tggattcacc
tttagcagct atgacatgag ctgggtccgc caggctccag gaaggggct
ggaatgggtc tcacttatta gtggtggtgg tagtcaaaca tactacgcag
aatccgtgaa gggccggttc accatctcca gagacaattc caagaacacg
ctgtatctgc aaatgaacag cctgagagcc gaggacacgg ccgtatattt
ctgtgcgtcc ccagtggcc actacttcta cgctatggac gtctggggcc
aagggaccac ggtcaccgtc tcctcagcct ccaccaaggg cccatcggtc
ttccccctgg cacctcctc caagagcacc tctgggggca cagcggccct
gggctgcctg gtcaaggact acttccccga accggtgacg gtgtcgtgga
actcaggcgc cctgaccagc ggcgtgcaca ccttcccggc tgtcctacag
tcctcaggac tctactccct cagcagcgtg gtgaccgtgc cctccagcag
cttgggcacc cagacctaca tctgcaacgt gaatcacaag cccagcaaca
ccaaggtgga caagaaagtt gagcccaaat cttgtgacaa aactcacaca
tgcccaccgt gcccagcacc tgaactcctg ggggaccgt cagtcttcct
cttccccca aaacccaagg acaccctcat gatctcccgg acccctgagg
tcacatgcgt ggtggtggac gtgagccacg aagaccctga ggtcaagttc
aactggtacg tggacggcgt ggaggtgcat aatgccaaga caaagccgtg
cgaggagcag tacggcagca cgtaccgttg cgtcagcgtc ctcaccgtcc |

| SEQ ID NO. | Sequence Type | Sequence |
|---|---|---|
| | | tgcaccagga ctggctgaat ggcaaggagt acaagtgcaa ggtgtccaac |
| | | aaagccctcc cagcccccat cgagaaaacc atctccaaag ccaaagggca |
| | | gccccgagaa ccacaggtgt acaccctgcc cccatcccgg gaggagatga |
| | | ccaagaacca ggtcagcctg acctgcctgg tcaaaggctt ctatcccagc |
| | | gacatcgccg tggagtggga gagcaatggg cagccggaga acaactacaa |
| | | gaccacgcct cccgtgctgg actccgacgg ctccttcttc ctctatagca |
| | | agctcaccgt ggacaagagc aggtggcagc aggggaacgt cttctcatgc |
| | | tccgtgatgc atgaggctct gcacaaccac tacacgcaga agagcctctc |
| | | cctgtctccg ggtaaa |
| 20 | DNA | atggacatga gggtgcccgc tcagctcctg gggctcctgc tgctgtggct |
| | | gagaggtgcg cgctgtgaca tccagatgac ccagtctcca tcttccgtgt |
| | | ctgcatctgt tggagacaga gtcaccatca cttgtcgggc gagtcagggt |
| | | attagcaact ggttagcctg gtatcagcag aaaccaggga aagccctaa |
| | | gctcctgatc tttgctgcat ccagtttgca aagtggggtc ccatcaaggt |
| | | tcagcggcag tggatctggg acagatttca ccctcaccat cagcagcctg |
| | | cagcctgaag attttgcaac ttactattgt caacaggcta aaagtttccc tcacactttc |
| | | ggcggaggga ccaaggtgga gatcaaacga acggtggctg caccatctgt |
| | | cttcatcttc ccgccatctg atgagcagtt gaaatctgga actgcctctg ttgtgtgcct |
| | | gctgaataac ttctatccca gagaggccaa agtacagtgg aaggtggata |
| | | acgccctcca atcgggtaac tcccaggaga gtgtcacaga gcaggacagc |
| | | aaggacagca cctacagcct cagcagcacc ctgacgctga gcaaagcaga |
| | | ctacgagaaa cacaaagtct acgcctgcga agtcacccat cagggcctga |
| | | gctcgcccgt cacaaagagc ttcaacaggg gagagtgt |
| 21 | PRT | Cys Thr Thr Gly Thr Gly Ala Thr Gly Gly Thr Thr Gly Gly Ala Gly Cys Thr Gly Ala |

GITR agonists include, but are not limited to, GITR fusion proteins and anti-GITR antibodies (e.g., bivalent anti-GITR antibodies), such as, a GITR fusion protein described in U.S. Pat. No. 6,111,090 box.c, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

KRAS$^{G12C}$ inhibitors can also be used in combination with CDK4 and/or 6 inhibitors in the present invention. CDK 4 and/or 6 inhibitors that can be used in the present combinations include, but are not limited to, those disclosed in the following documents: PCT published application no. WO 2009/085185 or U.S. patent application publication no. US2011/0097305.

Other compounds that can be used in combination with KRAS$^{G12C}$ inhibitors in the combinations of the present invention include compounds that inhibit proteins that are part of the intrinsic apoptosis pathway. Examples of such compounds include, but are not limited to, Bcl2/BclxL inhibitors such as navitoclax and Bcl2 inhibitors as such as ABT-199.

Other compounds that can be used in combination with KRAS$^{G12C}$ inhibitors in the combinations of the present invention include BCR-ABL inhibitors such as, but are not limited to, dasatinib and HDAC inhibitors such as panobinostat.

Other compounds that can be used in combination with KRAS$^{G12C}$ inhibitors in the combinations of the present invention include platinums, such as Cisplatin, Carboplatin and Oxaliplatin; Topoisomerase II inhibitors, typically of the anthracycline class, such as doxorubicin, daunorubicin, idarubicin, epirubicin, pegylated liposomal doxorubicin hydrochloride, myocet and etoposide; Topoisomerase I inhibitors such as irinotecan (CPT-11); DNA alkylation agents such as temozolomide; and nucleoside analogs such as cytarabine and decitabine.

Other compounds that can be used in combination with KRAS$^{G12C}$ inhibitors in the combinations of the present invention include receptor and non-receptor kinase inhibitors including tyrosine kinase inhibitors. Example of such compounds include imatinib, dasatinib, ponatinib, bosutinib, nilotininb, quizartinib, midostaurin, erlotinib and lapatinib.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

Synthesis of AMG 510

The $KRAS^{G12C}$ inhibitors of the present invention include those disclosed in published PCT application WO 2018/119183. A synthesis of AMG 510, having the structure

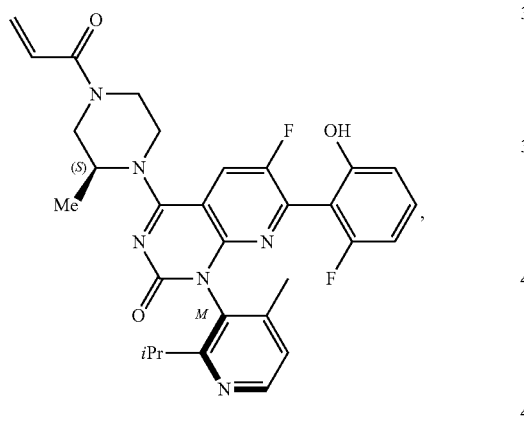

is set forth in U.S. Ser. No. 15/984,855, filed May 21, 2018, which claims the priority and benefit of Provisional Application No. 62/509,629, filed on May 22, 2017, as described below.

6-Fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one was prepared using the following process, in which the final product was resolved to isolate the M-atropisomer.

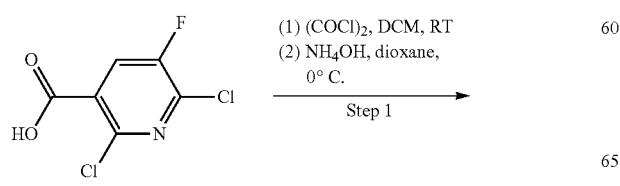

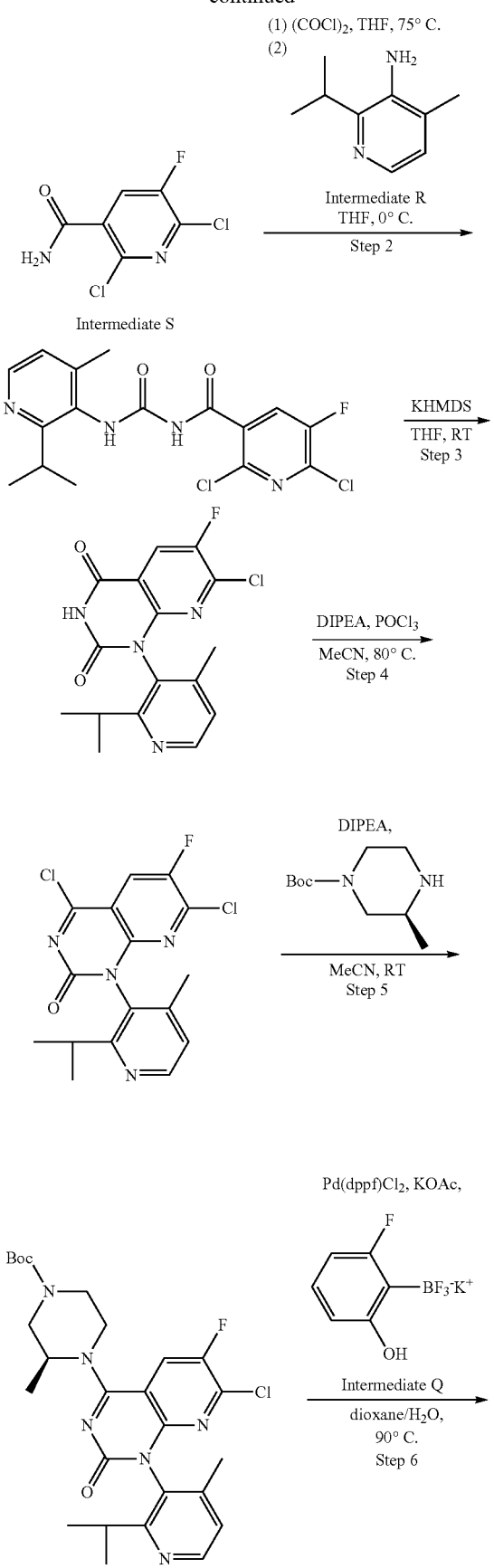

-continued

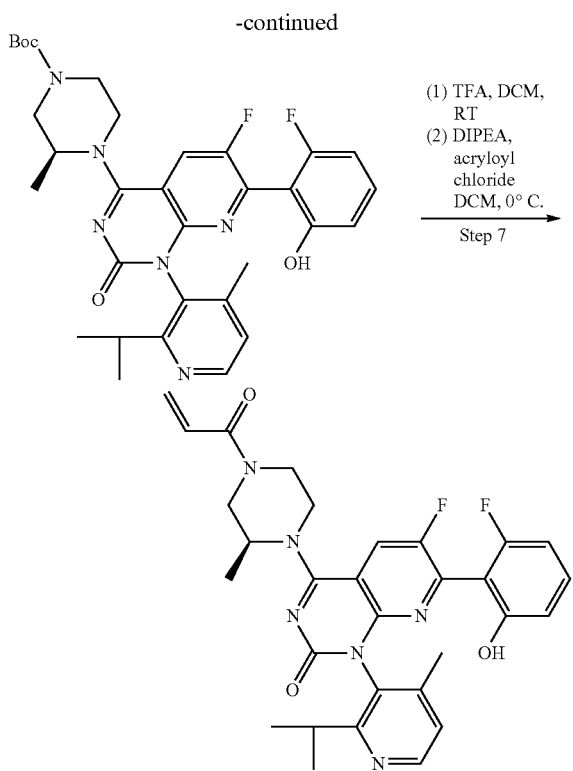

(1) TFA, DCM, RT
(2) DIPEA, acryloyl chloride DCM, 0° C.
Step 7

Step 1: 2,6-Dichloro-5-fluoronicotinamide (Intermediate S). To a mixture of 2,6-dichloro-5-fluoro-nicotinic acid (4.0 g, 19.1 mmol, AstaTech Inc., Bristol, PA) in dichloromethane (48 mL) was added oxalyl chloride (2M solution in DCM, 11.9 mL, 23.8 mmol), followed by a catalytic amount of DMF (0.05 mL). The reaction was stirred at room temperature overnight and then was concentrated. The residue was dissolved in 1,4-dioxane (48 mL) and cooled to 0° C. Ammonium hydroxide solution (28.0-30% NH3 basis, 3.6 mL, 28.6 mmol) was added slowly via syringe. The resulting mixture was stirred at 0° C. for 30 min and then was concentrated. The residue was diluted with a 1:1 mixture of EtOAc/Heptane and agitated for 5 min, then was filtered. The filtered solids were discarded, and the remaining mother liquor was partially concentrated to half volume and filtered. The filtered solids were washed with heptane and dried in a reduced-pressure oven (45° C.) overnight to provide 2,6-dichloro-5-fluoronicotinamide. $^1$H NMR (400 MHz, DMSO-$d_6$) δ ppm 8.23 (d, J=7.9 Hz, 1H) 8.09 (br s, 1H) 7.93 (br s, 1H). m/z (ESI, +ve ion): 210.9 (M+H)$^+$.

Step 2: 2,6-Dichloro-5-fluoro-N-((2-isopropyl-4-methylpyridin-3-yl)carbamoyl)nicotinamide. To an ice-cooled slurry of 2,6-dichloro-5-fluoronicotinamide (Intermediate S, 5.0 g, 23.9 mmol) in THF (20 mL) was added oxalyl chloride (2 M solution in DCM, 14.4 mL, 28.8 mmol) slowly via syringe. The resulting mixture was heated at 75° C. for 1 h, then heating was stopped, and the reaction was concentrated to half volume. After cooling to 0° C., THF (20 mL) was added, followed by a solution of 2-isopropyl-4-methylpyridin-3-amine (Intermediate R, 3.59 g, 23.92 mmol) in THF (10 mL), dropwise via cannula. The resulting mixture was stirred at 0° C. for 1 h and then was quenched with a 1:1 mixture of brine and saturated aqueous ammonium chloride. The mixture was extracted with EtOAc (3×) and the combined organic layers were dried over anhydrous sodium sulfate and concentrated to provide 2,6-dichloro-5-fluoro-N-((2-isopropyl-4-methylpyridin-3-yl)carbamoyl)nicotinamide. This material was used without further purification in the following step. m/z (ESI, +ve ion): 385.1 (M+H)$^+$.

Step 3: 7-Chloro-6-fluoro-1-(2-isopropyl-4-methylpyridin-3-yl)pyrido[2,3-d]pyrimidine-2,4(1H,3H)-dione. To an ice-cooled solution of 2,6-dichloro-5-fluoro-N-((2-isopropyl-4-methylpyridin-3-yl)carbamoyl)nicotinamide (9.2 g, 24.0 mmol) in THF (40 mL) was added KHMDS (1 M solution in THF, 50.2 mL, 50.2 mmol) slowly via syringe. The ice bath was removed and the resulting mixture was stirred for 40 min at room temperature. The reaction was quenched with saturated aqueous ammonium chloride and extracted with EtOAc (3×). The combined organic layers were dried over anhydrous sodium sulfate and concentrated. The residue was purified by silica gel chromatography (eluent: 0-50% 3:1 EtOAc-EtOH/heptane) to provide 7-chloro-6-fluoro-1-(2-isopropyl-4-methylpyridin-3-yl)pyrido[2,3-d]pyrimidine-2,4(1H,3H)-dione. $^1$H NMR (400 MHz, DMSO-$d_6$) δ ppm 12.27 (br s, 1H), 8.48-8.55 (m, 2H), 7.29 (d, J=4.8 Hz, 1H), 2.87 (quin, J=6.6 Hz, 1H), 1.99-2.06 (m, 3H), 1.09 (d, J=6.6 Hz, 3H), 1.01 (d, J=6.6 Hz, 3H). $^{19}$F NMR (376 MHz, DMSO-$d_6$) δ: −126.90 (s, 1F). m/z (ESI, +ve ion): 349.1 (M+H)$^+$.

Step 4: 4,7-Dichloro-6-fluoro-1-(2-isopropyl-4-methylpyridin-3-yl)pyrido[2,3-d]pyrimidin-2(1H)-one. To a solution of 7-chloro-6-fluoro-1-(2-isopropyl-4-methylpyridin-3-yl)pyrido[2,3-d]pyrimidine-2,4(1H,3H)-dione (4.7 g, 13.5 mmol) and DIPEA (3.5 mL, 20.2 mmol) in acetonitrile (20 mL) was added phosphorus oxychloride (1.63 mL, 17.5 mmol), dropwise via syringe. The resulting mixture was heated at 80° C. for 1 h, and then was cooled to room temperature and concentrated to provide 4,7-dichloro-6-fluoro-1-(2-isopropyl-4-methylpyridin-3-yl)pyrido[2,3-d]pyrimidin-2(1H)-one. This material was used without further purification in the following step. m/z (ESI, +ve ion): 367.1 (M+H)$^+$.

Step 5: (S)-tert-Butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate. To an ice-cooled solution of 4,7-dichloro-6-fluoro-1-(2-isopropyl-4-methylpyridin-3-yl)pyrido[2,3-d]pyrimidin-2(1H)-one (13.5 mmol) in acetonitrile (20 mL) was added DIPEA (7.1 mL, 40.3 mmol), followed by (S)-4-N-Boc-2-methyl piperazine (3.23 g, 16.1 mmol, Combi-Blocks, Inc., San Diego, CA, USA). The resulting mixture was warmed to room temperature and stirred for 1 h, then was diluted with cold saturated aqueous sodium bicarbonate solution (200 mL) and EtOAc (300 mL). The mixture was stirred for an additional 5 min, the layers were separated, and the aqueous layer was extracted with more EtOAc (1×). The combined organic layers were dried over anhydrous sodium sulfate and concentrated. The residue was purified by silica gel chromatography (eluent: 0-50% EtOAc/heptane) to provide (S)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate. m/z (ESI, +ve ion): 531.2 (M+H)$^+$.

Step 6: (3S)-tert-Butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate. A mixture of (S)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (4.3 g, 8.1 mmol), potassium trifluoro(2-fluoro-6-hydroxyphenyl)borate (Intermediate Q, 2.9 g, 10.5 mmol), potassium acetate (3.2 g, 32.4 mmol) and [1,1′-bis(diphenylphosphino)ferrocene]dichloropalladium(II), complex with dichloromethane (661 mg, 0.81 mmol) in 1,4-dioxane (80 mL) was degassed with nitrogen for 1 min. De-oxygenated water (14 mL) was added, and the resulting mixture was heated at 90° C. for 1 h. The reaction was allowed to cool to room temperature, quenched with half-saturated aqueous sodium bicarbonate, and extracted with EtOAc (2×) and DCM (1×). The combined organic layers were dried over anhydrous sodium sulfate and concentrated. The residue was purified by silica gel chromatography (eluent: 0-60% 3:1 EtOAc-EtOH/heptane) to provide (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate. $^1$H NMR (400 MHz, DMSO-$d_6$) δ ppm 10.19 (br s, 1H), 8.38 (d, J=5.0 Hz, 1H), 8.26 (dd, J=12.5, 9.2 Hz, 1H), 7.23-7.28 (m, 1H), 7.18 (d, J=5.0 Hz, 1H), 6.72 (d, J=8.0 Hz, 1H), 6.68 (t, J=8.9 Hz, 1H), 4.77-4.98 (m, 1H), 4.24 (br t, J=14.2 Hz, 1H), 3.93-4.08 (m, 1H), 3.84 (br d, J=12.9 Hz, 1H), 3.52-3.75 (m, 1H), 3.07-3.28 (m, 1H), 2.62-2.74 (m, 1H), 1.86-1.93 (m, 3H), 1.43-1.48 (m, 9H), 1.35 (dd, J=10.8, 6.8 Hz, 3H), 1.26-1.32 (m, 1H), 1.07 (dd, J=6.6, 1.7 Hz, 3H), 0.93 (dd, J=6.6, 2.1 Hz, 3H). $^{19}$F NMR (376 MHz, DMSO-$d_6$) δ: −115.65 (s, 1F), −128.62 (s, 1F). m/z (ESI, +ve ion): 607.3 (M+H)$^+$.

Step 7: 6-Fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one. Trifluoroacetic acid (25 mL, 324 mmol) was added to a solution of (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate (6.3 g, 10.4 mmol) in DCM (30 mL). The resulting mixture was stirred at room temperature for 1 h and then was concentrated. The residue was dissolved in DCM (30 mL), cooled to 0° C., and sequentially treated with DIPEA (7.3 mL, 41.7 mmol) and a solution of acryloyl chloride (0.849 mL, 10.4 mmol) in DCM (3 mL; added dropwise via syringe). The reaction was stirred at 0° C. for 10 min, then was quenched with half-saturated aqueous sodium bicarbonate and extracted with DCM (2×). The combined organic layers were dried over anhydrous sodium sulfate and concentrated. Chromatographic purification of the residue (silica gel; eluent: 0-100% EtOAc-EtOH (3:1)/heptane) followed by chiral resolution using supercritical fluid chromatography (Chiralpak IC, 30×250 mm, 5 μm, 55% MeOH/CO$_2$, 120 mL/min, 102 bar; first-eluting peak collected) provided AMG 510 (2.25 g, 43% yield). 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one. $^1$H NMR (400 MHz, DMSO-$d_6$) δ ppm 10.20 (s, 1H), 8.39 (d, J=4.8 Hz, 1H), 8.24-8.34 (m, 1H), 7.23-7.32 (m, 1H), 7.19 (d, J=5.0 Hz, 1H), 6.87 (td, J=16.3, 11.0 Hz, 1H), 6.74 (d, J=8.6 Hz, 1H), 6.69 (t, J=8.6 Hz, 1H), 6.21 (br d, J=16.2 Hz, 1H), 5.74-5.80 (m, 1H), 4.91 (br s, 1H), 4.23-4.45 (m, 2H), 3.97-4.21 (m, 1H), 3.44-3.79 (m, 2H), 3.11-3.31 (m, 2H), 2.67-2.77 (m, 1H), 1.91 (s, 3H), 1.35 (d, J=6.8 Hz, 3H), 1.08 (d, J=6.6 Hz, 3H), 0.94 (d, J=6.8 Hz, 3H). $^{19}$F NMR (376 MHz, DMSO-$d_6$) δ ppm−115.64 (s, 1F), −128.63 (s, 1F). m/z (ESI, +ve ion): 561.2 (M+H)$^+$.

AMG 510, as referred to herein, is the M atropisomer of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, having the formula:

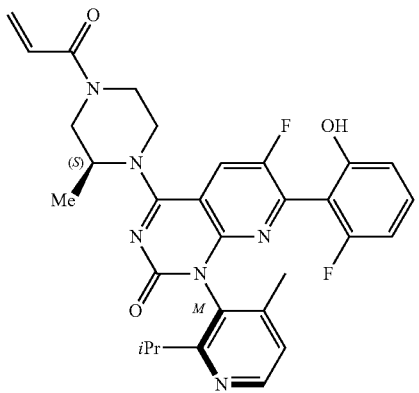

or a pharmaceutically acceptable salt thereof.

Synthesis of Intermediates

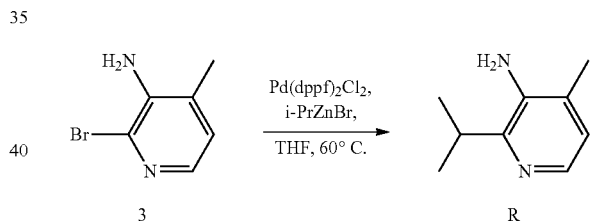

2-Isopropyl-4-methylpyridin-3-amine (R): [1,1'-bis(diphenylphosphino)ferrocene]dichloropalladium(II), complex with dichloromethane (79 mg, 0.10 mmol) was added to a slurry of 3-amino-2-bromo-4-picoline (3; 360 mg, 1.9 mmol, Combi-Blocks, San Diego, CA) in THF (4 mL), and the resulting mixture was sparged with argon for 2 min. 2-Propylzinc bromide (0.5 M solution in THF, 5.40 mL, 2.7 mmol) was added, and the resulting solution was heated at 60° C. for 17 h, then allowed to cool to room temperature. Water (10 mL) and 1 N aqueous NaOH (20 mL) were added, and the resulting mixture was extracted with EtOAc (2×). The combined organic layers were dried over anhydrous sodium sulfate and concentrated in vacuo. Chromatographic purification of the residue (silica gel, eluent: 0-15% MeOH/DCM) furnished R (284 mg, 98% yield). $^1$H-NMR (400 MHz, DMSO-$d_6$): δ 7.66 p.p.m. (d, J=4.6 Hz, 1H), 6.78 (d, J=4.8 Hz, 1H), 4.72 (br s, 2H), 3.14-3.25 (m, 1H), 2.08 (s, 3H), 1.14 (d, J=6.8 Hz, 6H); m/z (ESI, +ve ion): 151.1 (M+H)$^+$.

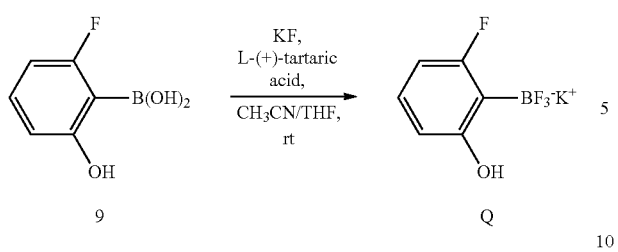

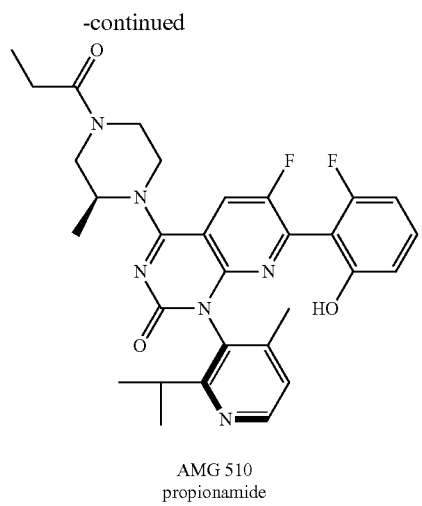

AMG 510
propionamide (2-Fluoro-6-hydroxyphenyl)potassium trifluoroborate (Q): A solution of potassium fluoride (44.7 g, 770 mmol) in water (75 mL) was added to a suspension of (2-fluoro-6-hydroxyphenyl)boronic acid (9; 30 g, 192 mmol, Combi-Blocks, San Diego, CA) in acetonitrile (750 mL). After 2 min of stirring, a solution of L-(+)-tartaric acid (72.2 g, 481 mmol) in THF (375 mL) was added over 10 min. The resulting mixture was mechanically stirred for 1 h. Suspended solids were removed by filtration and washed with a small amount of THF. The combined filtrate was then partially concentrated in vacuo until solids began to precipitate. The filtrate was cooled to −20° C. and stirred for 16 h, then slowly warmed to ambient temperature. 2-Propanol (20 mL) was added, and the precipitated solids were collected by filtration and washed with 2-propanol to provide 27.5 g of solid. The filtrate was again partially concentrated (until precipitation observed), cooled to −20° C., and stirred for 20 min. Additional 2-propanol was added, and the precipitated solid was collected by filtration and washed with 2-propanol. The two batches of solid were combined to provide Q (34.6 g, 82% yield). $^1$H-NMR (400 MHz, DMSO-d$_6$): δ 8.07 p.p.m. (q, J=14.7 Hz, 1H), 6.93 (q, J=7.5 Hz, 1H), 6.30-6.38 (m, 2H).

Synthesis of AMG 510 Propionamide

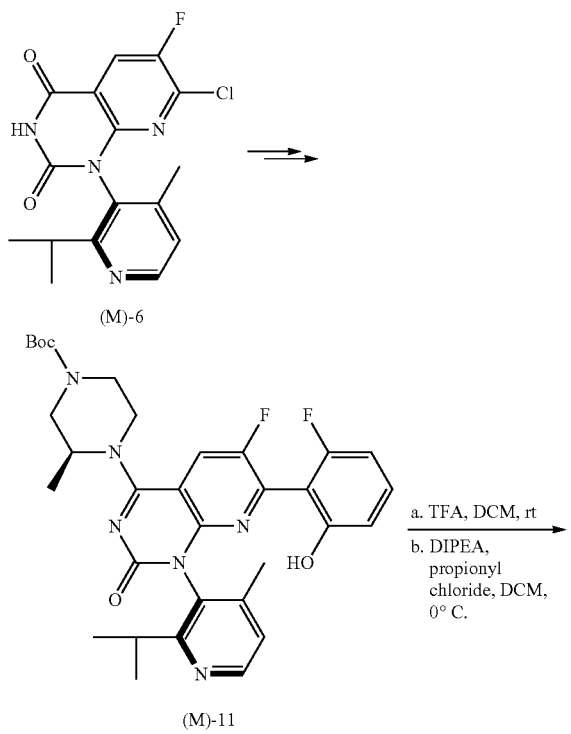

(M)-6 & (M)-11: Racemic 6 was resolved by supercritical fluid chromatography (Chiralpak AD, 21×250 mm, 5 μm, 40% MeOH/CO$_2$, 80 mL/min, 110 bar; second-eluting peak collected) to provide (M)-6, which was converted to (M)-11 using the procedures reported for racemic substrates.

(M)-6-Fluoro-7-(2-fluoro-6-hydroxyphenyl)-1-(4-methyl-2-(2-propanyl)-3-pyridinyl)-4-((2S)-2-methyl-4-propanoyl-1-piperazinyl)pyrido[2,3-d]pyrimidin-2(1H)-one (AMG 510 propionamide): Trifluoroacetic acid (4.0 ml, 51.9 mmol) was added to a solution of (M)-11 (0.196 g, 0.323 mmol) in DCM (5 mL), and the resulting mixture was stirred at room temperature for 20 min. The mixture was then concentrated in vacuo, and the residue was taken up in DCM (10 mL), cooled to 0° C., and sequentially treated with DIPEA (0.169 mL, 0.969 mmol) and propionyl chloride (0.016 mL, 0.194 mmol). The resulting mixture was stirred at 0° C. for 10 min, then diluted with saturated aqueous sodium bicarbonate and extracted with DCM (2×). The combined extracts were dried over anhydrous sodium sulfate and concentrated in vacuo. Chromatographic purification of the residue (silica gel; eluent: 0-70% EtOAc-EtOH (3:1)/heptane) provided AMG 510 propionamide (0.180 g, 99% yield). $^1$H-NMR (400 MHz, DMSO-d$_6$): δ 10.20 p.p.m (s, 1H), 8.40 (d, J=5.0 Hz, 1H), 8.27 (br dd, J=15.1, 9.3 Hz, 1H), 7.27 (m, 1H), 7.21 (br d, J=4.8 Hz, 1H), 6.73 (d, J=8.3 Hz, 1H), 6.69 (t, J=8.9 Hz, 1H), 4.87 (br s, 1H), 4.31 (m, 1.5H), 4.21 (br d, J=13.5 Hz, 0.5H), 3.94 (br d, J=12.2 Hz, 0.5H), 3.82 (br d, J=13.3 Hz, 0.5H), 3.62-3.76 (m, 1H), 3.52-3.62 (m, 0.5H), 3.43-3.51 (m, 0.5H), 3.18 (br dd, J=13.3, 3.3 Hz, 0.5H), 3.06 (br t, J=10.7 Hz, 0.5H), 2.73 (br dd, J=10.5, 6.1 Hz, 1H), 2.33-2.48 (m, 2H), 1.91 (s, 3H), 1.29-1.42 (m, 3H), 0.98-1.12 (m, 6H), 0.94 (d, J=6.6 Hz, 3H); m/z (ESI, +ve ion): 563.2 (M+H)$^+$.

In an alternative process, AMG 510 was synthesized and the relevant intermediates were described in U.S. provisional patent application No. 62/768,802, filed Nov. 16, 2018. The alternative process comprises the following steps wherein the resolution of the rac-Dione in Steps 4 and 5 promotes the successful separation of the atropisomers:

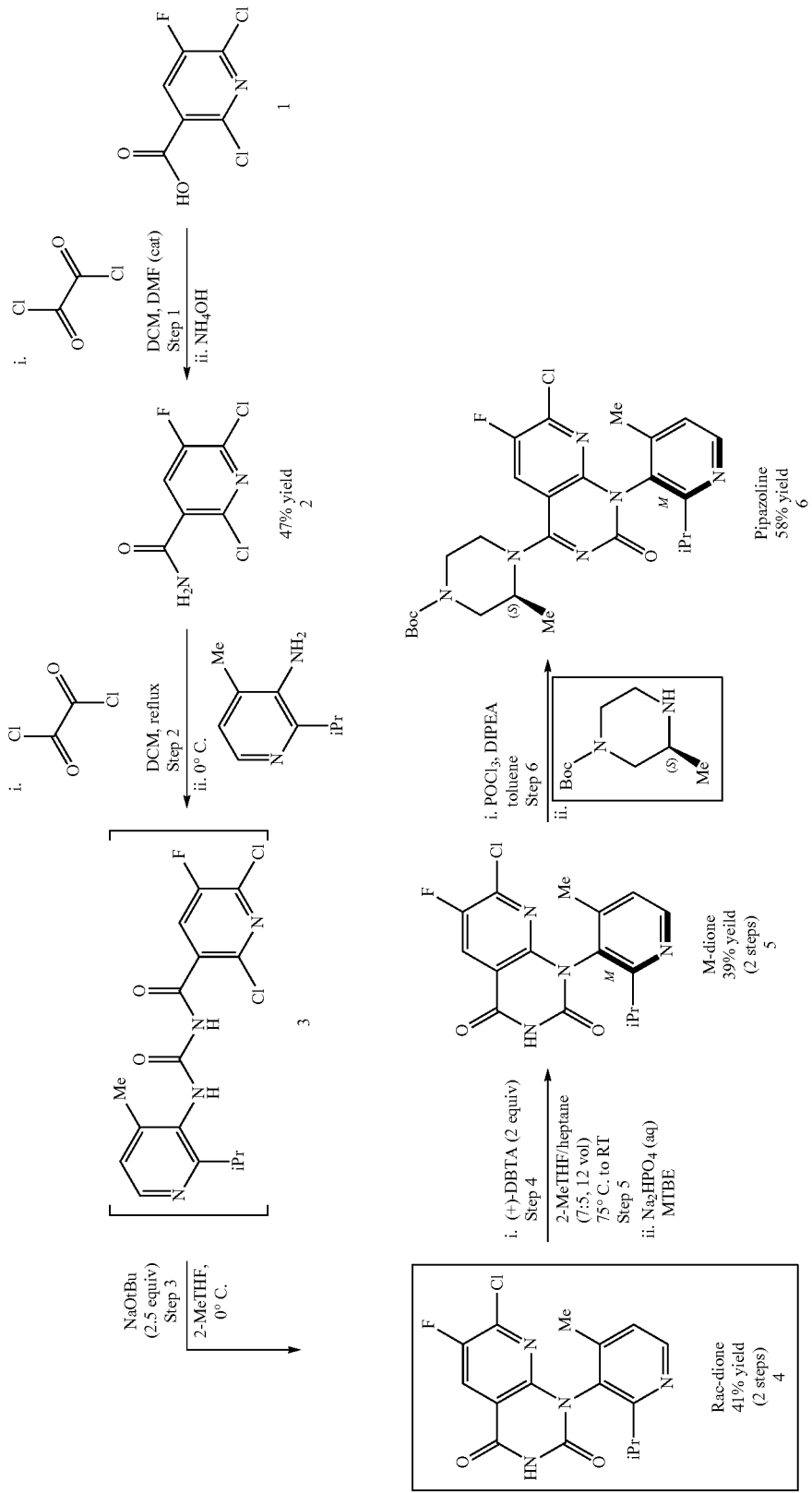

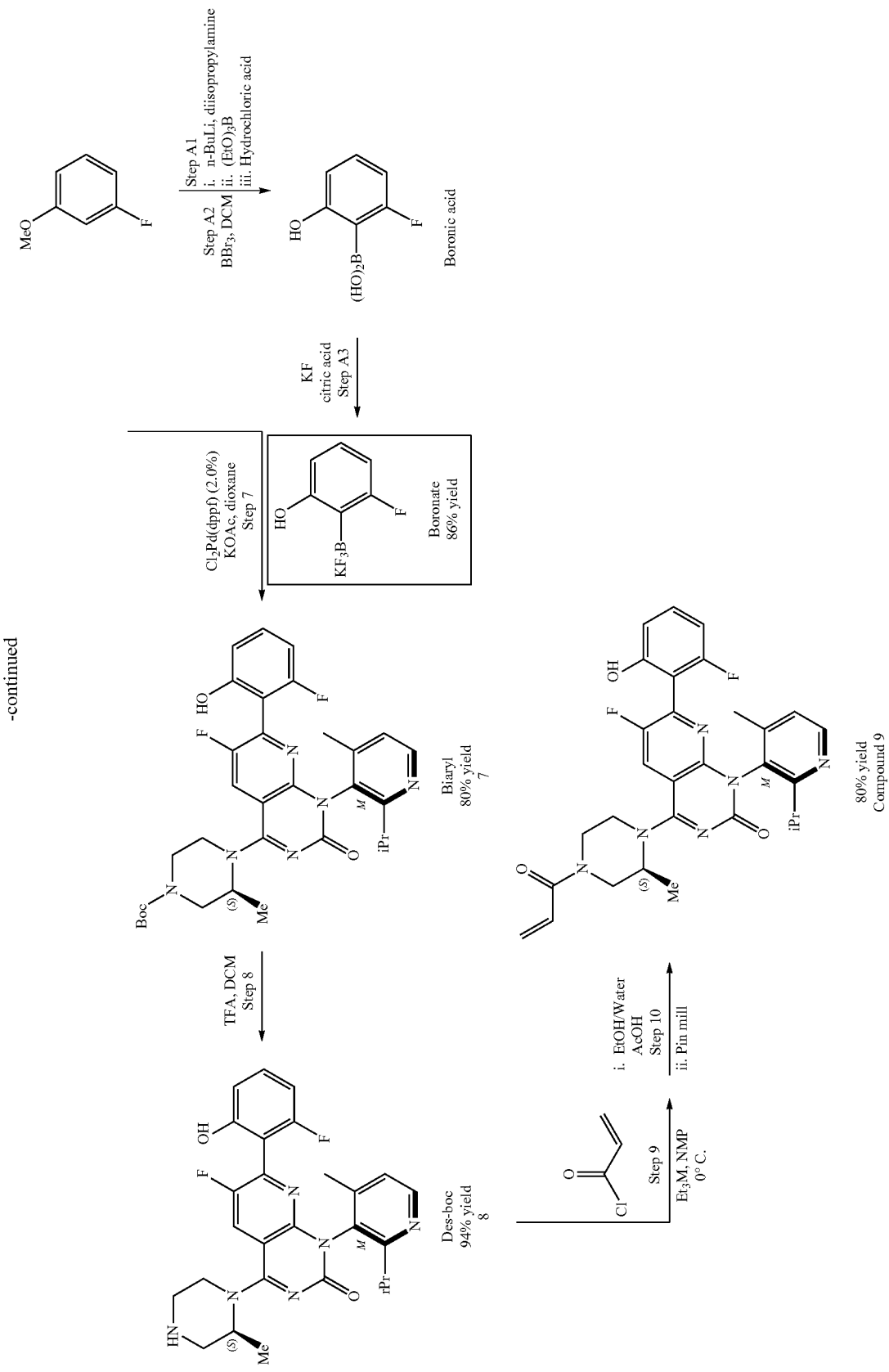

Process Description
Step 1

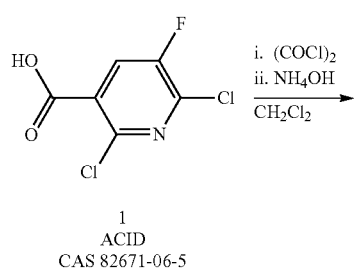

1
ACID
CAS 82671-06-5

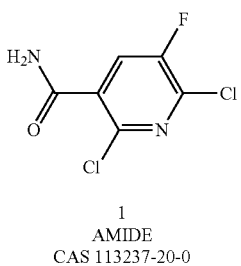

1
AMIDE
CAS 113237-20-0

| Material | CAS# | MW (g/mol) | Equivalents/ Volumes | Moles | Theoretical | |
|---|---|---|---|---|---|---|
| 2,6-dichloro-5-fluoro-3-pyridinecarboxylic acid | 82671-06-5 | 209.99 | 1.0 equiv. | 119.1 | 25 | kg |
| DCM | 74-09-2 | 84.93 | 16.51 equiv. | 2354.9 | 200 | kg |
| DMF | 68-12-2 | 73.09 | 0.068 equiv. | 8.1 | 592 | g |
|  |  |  |  |  | (627 | mL) |
| Oxalyl Chloride | 79-37-8 | 126.93 | 1.25 equiv. | 148.9 | 18.9 | kg |
| Ammonium Hydroxide | 1336-21-6 | 35.05 | 5 equiv. | 595.5 | 40.2 | L |
| Water | 7732-18-5 | 18.02 | N/A | N/A | 261 | L |

To a solution of 2,6-dichloro-5-fluoro-3-pyridinecarboxylic acid (Compound 1) (25 kg; 119.1 mol) in dichloromethane (167 kg) and DMF (592 g) was added Oxalyl chloride (18.9 kg; 148.9 mol) while maintaining an internal temp between 15-20° C. Additional dichloromethane (33 kg) was added as a rinse and the reaction mixture stirred for 2h. The reaction mixture is cooled then quenched with ammonium hydroxide (40.2 L; 595.5 mol) while maintaining internal temperature 0±10° C. The resulting slurry was stirred for 90 min then the product collected by filtration. The filtered solids were washed with DI water (3×87 L) and dried to provide 2,6-dichloro-5-fluoronicotinamide (Compound 2).

Step 2

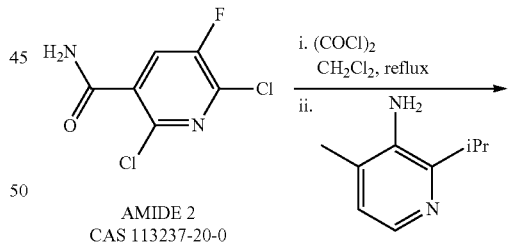

AMIDE 2
CAS 113237-20-0

ANILINE
CAS 1698293-93-4

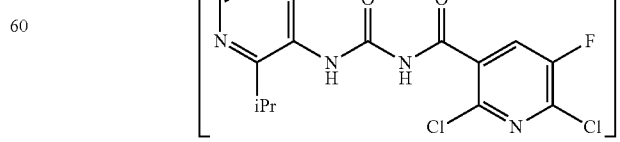

UREA 3

| Material | CAS# | MW (g/mol) | Equivalents/ Volumes | Moles | Theoretical |
|---|---|---|---|---|---|
| Amide (2,6-dichloro-5-fluoronicotinamide) | 113237-20-0 | 209.99 | 1.0 equiv. | 77.8 | 16.27 kg |
| Oxalyl Chloride | 79-37-8 | 126.93 | 1.2 equiv. | 93.8 | 11.9 kg (7.9 L) |
| Dichloromethane | 75-09-2 | 84.93 | N/A | N/A | 730.7 kg (551.5 L) |
| Aniline DCM Solution 2-isopropyl-4-methylpyridin-3-amine | 1698293-93-4 | 150.22 | 1.1 equiv. | 85.9 | 12.9 kg (Aniline contained wt) |

In reactor A, a solution of 2,6-dichloro-5-fluoronicotinamide (Compound 2) (16.27 kg; 77.8 mol) in dichloromethane (359.5 kg) was added oxalyl chloride (11.9 kg; 93.8 mol) while maintaining temp ≤25° C. for 75 min. The resulting solution was then headed to 40° C.±3° C. and aged for 3h. Using vacuum, the solution was distilled to remove dichloromethane until the solution was below the agitator. Dichloromethane (300 kg) was then added and the mixture cooled to 0±5° C. To a clean, dry reactor (reactor B) was added, 2-isopropyl-4-methylpyridin-3-amine (ANILINE) (12.9 kg; 85.9 mol) followed by dichloromethane (102.6 kg). The ANILINE solution was azeodried via vacuum distillation while maintaining a internal temperature between 20-25°), replacing with additional dichloromethane until the solution was dry by KF analysis (limit≤0.05%). The solution volume was adjusted to approx. 23 L volume with dichloromethane. The dried ANILINE solution was then added to reactor A while maintaining an internal temperature of 0±5° C. throughout the addition. The mixture was then heated to 23° C. and aged for 1 h. the solution was polish filtered into a clean reactor to afford 2,6-dichloro-5-fluoro-N-((2-isopropyl-4-methylpyridin-3-yl)carbamoyl)nicotinamide (Compound 3) as a solution in DCM and used directly in the next step.

Step 3

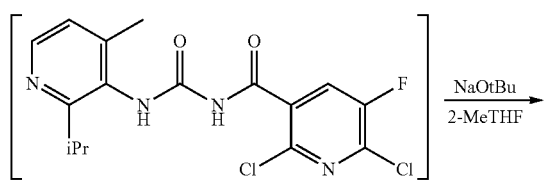

UREA 3

NaOtBu
2-MeTHF

-continued

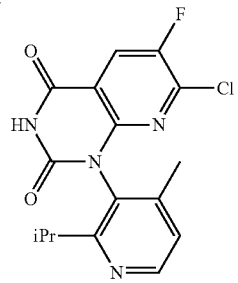

rac-DIONE 4

| Material | CAS # | MW (g/mol) | Equivalents/ Volumes | Moles | Theoretical |
|---|---|---|---|---|---|
| Urea, solution in DCM 2,6-dichloro-5-fluoro-N-{[4-methyl-2-(propan-2-yl)pyridin-3-yl]carbamoyl}pyridine-3-carboxamide | N/A | 385.22 | 1.0 equiv. | 38.9 | 208.3 kg (15 kg contained weight) |
| 2-methyltetrahydrofuran | 96-47-9 | 86.13 | N/A | N/A | 308 kg (358 L) |
| Sodium tert-butoxide | 865-48-5 | 96.11 | 2.0 equiv | 97.8 | 9.4 kg |
| Ammonium Chloride | 12125-02-9 | 53.49 | N/A | 430 | 23.0 kg |
| Hydrochloric Acid | 7467-01-0 | 36.46 | N/A | 41 | 1.6 kg |
| Magnesium Sulfate | 7487-88-9 | 120.37 | N/A | 195 | 23.5 kg |
| Sodium Chloride | 7647-14-5 | 58.44 | N/A | 282 | 16.5 kg |
| Heptane | 142-82-5 | 100.21 | N/A | N/A | 94 L |
| 10% citric acid | | | | | 75 kg |

A dichloromethane solution of 2,6-dichloro-5-fluoro-N-{[4-methyl-2-(propan-2-yl)pyridin-3-yl]carbamoyl}pyridine-3-carboxamide (UREA(Compound 3)) (15 kg contained; 38.9 mol) was solvent exchanged into 2-MeTHF using vacuum distillation while maintaining internal temperature of 20-25° C. The reactor volume was adjusted to 40 L and then additional 2-MeTHF was charged (105.4 kg). Sodium t-butoxide was added (9.4 kg; 97.8 mol) while maintaining 5-10° C. The contents where warmed to 23° C. and stirred for 3h. The contents where then cooled to 0-5C and ammonium chloride added (23.0 kg; 430 mol) as a solution in 60 L of DI water. The mixture was warmed to 20 C and DI water added (15 L) and further aged for 30 min. Agitation was stopped and the layers separated. The aqueous layer was removed and to the organic layer was added DI water (81.7 L). A mixture of conc HCl (1.5 kg) and water (9 L) was prepared then added to the reactor slowly until pH measured between 4-5. The layers were separated, and the aqueous layer back extracted using 2-MeTHF (42.2 kg). The two organic layers combined and washed with a 10% citric acid solution (75 kg) followed by a mixture of water (81.7 L) and saturated NaCl (19.8 kg). The organic layer was then washed with saturated sodium bicarbonate (75 kg) repeating if necessary to achieve a target pH of ≥7.0 of the aqueous. The organic layer was washed again with brine (54.7 kg) and then dried over magnesium sulfate (5 kg). The mixture was filtered to remove magnesium sulfate rinsing the filtered bed with 2-MeTHF (49.2 kg). The combined filtrate and washes where distilled using vacuum to 40 L volume. The concentrated solution was heated to 55° C. and heptane (10-12 kg) slowly added until cloud point. The solution was cooled to 23° C. over 2h then heptane (27.3 kg) was added over 2h. The product slurry was aged for 3h at 20-25° C. then filtered and washed with a mixture of 2-MeTHF (2.8 kg) and heptane (9 kg). The product was dried using nitrogen and vacuum to afford solid 7-chloro-6-fluoro-1-(2-isopropyl-4-methylpyridin-3-yl)pyrido[2,3-d]pyrimidine-2,4(1H,3H)-dione (rac-DIONE (Compound 4)).

Step 4

| Material | CAS # | MW (g/mol) | Equivalents/ Volumes | Moles | Theoretical |
|---|---|---|---|---|---|
| Rac-dione | N/A | 348.76 | 1.0 | — | — |
| (+)-2,3-dibenzoyl-D-tartaric acid | 17026-42-5 | 358.30 | 2.0 | — | — |
| 2-methyltetrahydrofuran | 96-47-9 | 86.13 | 7.0 | — | — |
| heptane | 142-82-5 | 100.21 | 2.0 | — | — |
| heptane | 142-82-5 | 100.21 | 3.0 | — | — |
| 2-methyltetrahydrofuran | 96-47-9 | 86.13 | 4.0 | — | — |
| heptane | 142-82-5 | 100.21 | 2.0 | — | — |

To a vessel, an agitated suspension of Compound 4, (1.0 eq.) in 2-methylterahydrofuran (7.0 L/kg) was added (+)-2,3-dibenzoyl-D-tartaric acid (2.0 eq.) under an atmosphere of

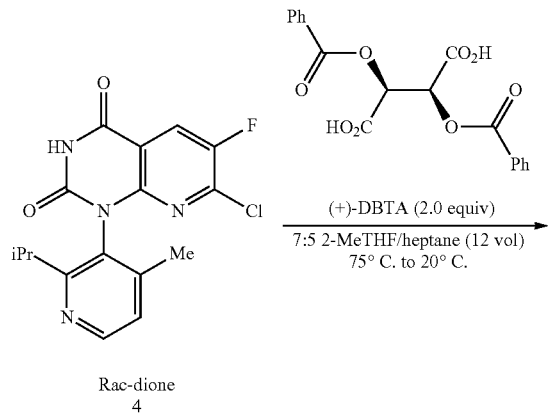

Rac-dione
4

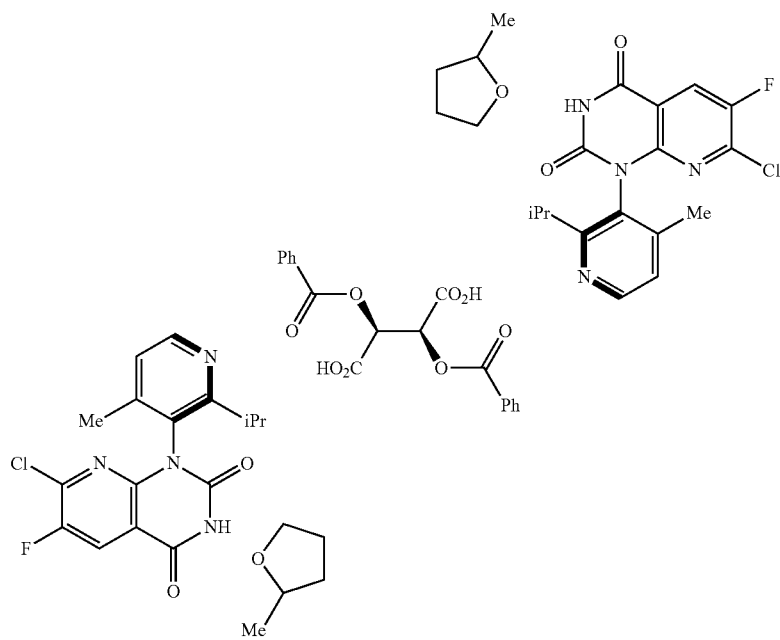

4a
M-dione DBTA co-crystal nitrogen. 2-MeTHF is chiral, but it is used as a racemic mixture. The different enantiomers of 2-MeTHF are incorporated randomly into the co-crystal. The resulting suspension was warmed to 75° C. and aged at 75° C. until full dissolution was observed (≤30 mins.). The resulting solution was polish filtered at 75° C. into a secondary vessel. To the polish filtered solution was charged n-Heptane (2.0 L/kg) at a rate that maintained the internal temperature above 65° C. The solution was then cooled to 60° C., seeded with crystals (0.01 kg/kg) and allowed to age for 30 minutes. The resulting suspension was cooled to 20° C. over 4 hours and then sampled for chiral purity analysis by HPLC. To the suspension, n-Heptane (3.0 L/kg) was charged and then aged for 4 hours at 20° C. under an atmosphere of nitrogen. The suspension was filtered, and the isolated solids were washed two times with (2:1) n-Heptane:2-methyltetrahydrofuran (3.0 L/kg). The material was dried with nitrogen and vacuum to afford M-Dione:DBTA: Me-THF complex (Compound 4a).

Step 5

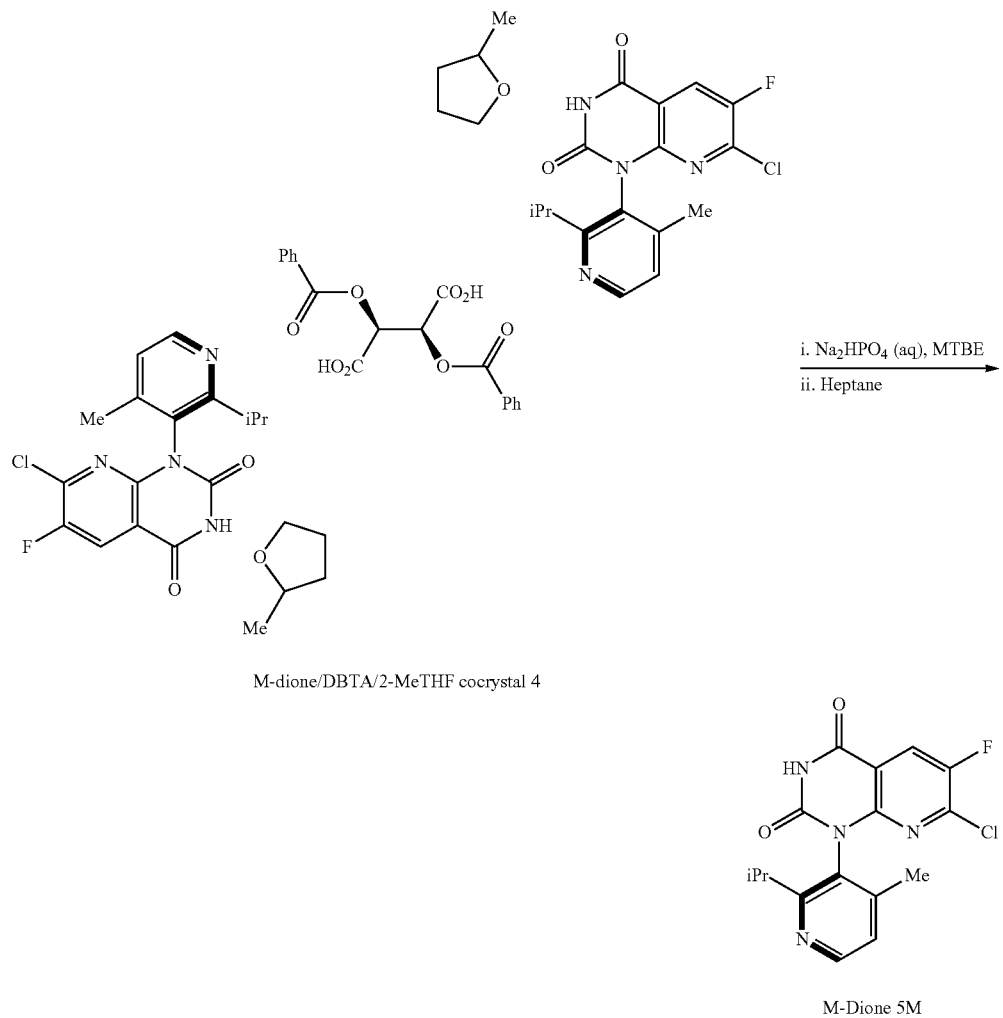

| Material | CAS # | MW (g/mol) | Equivalents/ Volumes | Moles | Theoretical |
|---|---|---|---|---|---|
| M-Dione/DBTA/Me-THF cocrystal | N/A | 1228.08 | 1.0 | 74.2 | 46.9 kg (25.9 kg corrected for M-dione) |
| Methyl tert-butyl ether | 1634-04-4 | 88.15 | 45.0 | 17593 | 2100 L |
| Disodium hydrogen phosphate | 7558-79-4 | 141.96 | 2.0 | 148.4 | 21.1 kg |
| USP purified water | | | | | As needed |
| Magnesium sulfate | 7487-88-9 | 120.37 | N/A | N/A | 25 kg |
| Heptane | 142-82-5 | 100.20 | 60.0 | 19322 | 2835 L |

To vessel A, a suspension of disodium hydrogen phosphate (21.1 kg, 2.0 equiv) in DI water (296.8 L, 6.3 L/kg) was agitated until dissolution was observed (≥30 min.). To vessel B, a suspension of the M-Dione:DBTA: Me-THF complex (Composition 4a)[46.9 kg (25.9 kg corrected for M-dione, 1.0 equiv.)] in methyl tert-butyl ether (517.8 L, 11.0 L/kg) was agitated for 15 to 30 minutes. The resulting solution from vessel A was added to vessel B, and then the mixture was agitated for more than 3 hours. The agitation was stopped, and the biphasic mixture was left to separate for more than 30 minutes. The lower aqueous phase was removed and then back extracted with methyl tert-butyl ether (77.7 L, 1.7 L/kg). The organic phases were combined in vessel B and dried with magnesium sulfate (24.8 kg, 0.529 kg/kg). The resulting suspension from vessel B was agitated for more than three hours and then filtered into vessel C. To vessel B, a methyl tert-butyl ether (46.9 L, 1.0 L/kg) rinse was charged and then filtered into vessel C. The contents of vessel C were cooled to 10° C. and then distilled under vacuum while slowly being warmed to 35° C. Distillation was continued until 320-350 kg (6.8-7.5 kg/kg) of methyl tert-butyl ether was collected. After cooling the contents of vessel C to 20° C., n-Heptane (278.7 L, 5.9 L/kg) was charged over one hour and then distilled under vacuum while slowly being warmed to 35° C. Distillation was continued until a 190-200 kg (4.1-4.3 kg/kg) mixture of methyl tert-butyl ether and n-Heptane was collected. After cooling the contents of vessel C to 20° C., n-Heptane (278.7 L, 5.9 L/kg) was charged a second time over one hour and then distilled under vacuum while slowly being warmed to 35° C. Distillation was continued until a 190-200 kg (4.1-4.3 kg/kg) mixture of methyl tert-butyl ether and n-Heptane was collected. After cooling the contents of vessel C to 20° C., n-Heptane (195.9 L, 4.2 L/kg) was charged a third time over one hour and then sampled for solvent composition by GC analysis. The vessel C suspension continued to agitate for more than one hour. The suspension was filtered, and then washed with a n-Heptane (68.6 L, 1.5 L/kg) rinse from vessel C. The isolated solids were dried at 50° C., and a sample was submitted for stock suitability. Afforded 7-chloro-6-fluoro-(1M)-1-[4-methyl-2-(propan-2-yl)pyridin-3-yl]pyrido[2,3-d]pyrimidine-2,4(1H,3H)-dione (M-DIONE) Compound 5M.

The first-generation process highlighted above has been successfully scaled on 200+kg of rac-dione starting material (Compound 5). In this process, seeding the crystallization with the thermodynamically-stable rac-dione crystal form (which exhibits low solubility) would cause a batch failure. Based on our subsequent studies, we found that increasing the DBTA equivalents and lowering the seed temperature by adjusting heptane charge schedule improves robustness of the process. The improved process is resistant to the presence of the thermodynamically-stable rac-dione crystal form and promotes successful separation of atropisomers. Subsequent batches will incorporate the improved process for large scale manufacture.

Step 6

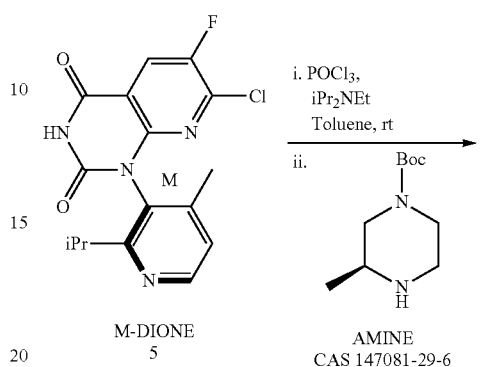

M-DIONE
5

AMINE
CAS 147081-29-6

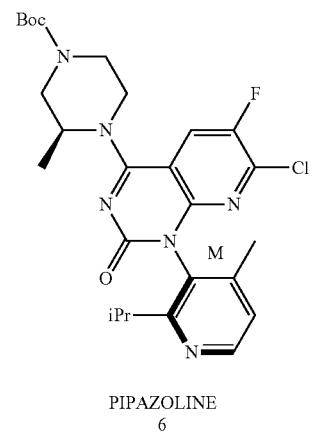

PIPAZOLINE
6

| Material | CAS # | MW (g/mol) | Equivalents/ Volumes | Moles | Theoretical |
|---|---|---|---|---|---|
| M-DIONE | N/A | 348.76 | 1 equiv. | 9.8 | 3.7 kg |
| Toluene | 108-88-3 | 92.14 | N/A | 375 | 34.6 kg (40 L) |
| Phosphoryl chloride | 10025-87-3 | 153.33 | 1.2 equiv. | 11.7 | 1.8 kg (1.1 L) |
| N,N-Diisopropylethylamine | 7087-68-5 | 129.24 | 3.0 equiv. | 29.4 | 3.8 kg (5.1 L) |
| (s)-1-Boc-3-methylpiperazine | 147081-29-6 | 200.28 | 1.1 equiv. | 10.8 | 2.214 kg |
| Sodium bicarbonate | 144-55-8 | 84.01 | N/A | N/A | 973 g |
| Dichloromethane | 75-09-2 | 84.93 | N/A | 871 | 74 kg (55.6 L) |
| Sodium Chloride | 7647-14-5 | 58.44 | N/A | 103 | 6.0 kg |
| Ethyl acetate | 141-78-6 | 88.11 | N/A | 288 | 25.4 kg (28.2 L) |

7-chloro-6-fluoro-(1M)-1-[4-methyl-2-(propan-2-yl)pyridin-3-yl]pyrido[2,3-d]pyrimidine-2,4(1H,3H)-dione (M-DIONE) (3.7 kg; 9.8 mol) was combined in reactor (A) with 10.5 kg of toluene and distilled down to an oil to remove water while maintaining a set point of 45° C. Toluene (21 kg) was added to the residue and the mixture stirred for 30 min at 40-45° C. The contents where cooled to 22° C. then phosphoryl chloride (1.8 kg; 11.7 mol) added. The mixture was cooled to 0-5° C. before adding N,N-Diisopropylethylamine (2.5 kg; 19.34 mol) while maintaining a temperature <5° C. The solution was aged for 3h at 22° C. In a separate reactor (B), (s)-1-boc-3-methylpiperazine (2.21 kg; 10.8 mol) and N,N-diisopropylethylamine (1.26 kg; 9.75 mol)) where combined in toluene (6 kg) and then charged to reactor (A) while maintaining <25° C. The reaction mixture was aged for 15 min at 22C then quenched with sodium bicarbonate (973 g) in water (12.9 L) while maintaining a temperature <25 C. The mixture was stirred for 30 min then DCM (36.8 kg) added while continuing to stir for 1h. The layers were allowed to separate, and the lower organic layer drained to reactor (C). The aqueous layer in reactor (A) was back extracted using DCM (18.4 kg) and the combined organic layers washed with brine solution (6.0 kg NaCl; 16.5 kg DI water). The organic layer was distilled under atmospheric pressure maintaining an internal temperature between 45-55 C. DCM is replaced during the distillation to azeotropically dry the solution. Following the distillation, the solution volume was adjusted to 19 L using DCM. The solution was cooled to 30 C and polish filtered. The filtrate was combined with ethyl acetate (8.5 kg) and then distilled at atmospheric pressure until 11-13 kg is collected in the receiver. The solution was seeded with 30 g of authentic product and aged for 1 h at 25-30° C. then further distilled under atmospheric pressure at 45-55 C internal temperature until 8.2 kg of distillate had been collected. The slurry was cooled to 22° C. and aged overnight then further cooled to 0-5° C. The product was collected by filtration and washed twice using ethyl acetate (4.2 kg each). The cake was dried with nitrogen and vacuum to afford tert-butyl (3S)-4-{7-chloro-6-fluoro-(1M)-1-[4-methyl-2-(propan-2-yl)pyridin-3-yl]-2-oxo-1,2-dihydropyrido[2,3-d]pyrimidin-4-yl}-3-methylpiperazine-1-carboxylate (Compound 6, PIPAZOLINE).

Step 7

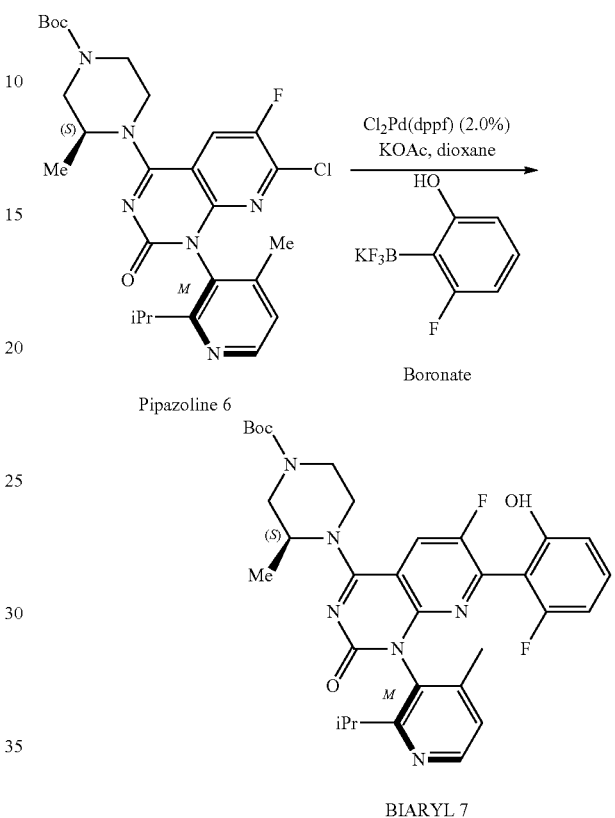

| Material | CAS # | MW (g/mol) | Equivalents/ Volumes | Moles | Theoretical |
|---|---|---|---|---|---|
| [1,1'-Bis(diphenylphosphino)ferrocene] dichloropalladium(II) | 72287-26-4 | 731.714 | 0.020 | 1.01 | 0.74 kg |
| Dichloromethane | 75-09-2 | 84.93 | — | N/A | 400 kg |
| 1,4-Dioxane | 123-91-1 | 88.1052 | 5.0 | N/A | 168 kg |
| Ethylenediaminetetraacetic acid disodium salt dihydrate | 6381-92-6 | 336.207 | 1.0 | 45.2 | 15.2 kg |
| Heptane | 142-82-5 | 100.21 | — | — | 200 kg |
| Nitrogen | — | — | — | — | As needed |
| Pipazoline | N/A | 531.0 | 1.0 | 45.2 | 24.0 kg |
| Potassium acetate | 127-08-2 | 98.1417 | 5.0 | 225.99 | 22.2 kg |
| Potassium trifluoro(2-fluoro-6-hydroxyphenyl)borate | N/A | 233.03 | 1.20 | 54.24 | 12.6 kg |
| 2-Propanol | 67-63-0 | 66.10 | — | N/A | 850 kg |
| Si-Thiol | N/A | N/A | — | N/A | 13.2 kg |
| Sodium hydroxide | 1310-73-2 | 40.00 | — | — | 6.5 kg |
| USP purified water | — | — | — | — | As needed |

To a reactor was added degassed dioxane (74.2 kg), tert-butyl (3S)-4-{7-chloro-6-fluoro-(1M)-1-[4-methyl-2-(propan-2-yl)pyridin-3-yl]-2-oxo-1,2-dihydropyrido[2,3-d]pyrimidin-4-yl}-3-methylpiperazine-1-carboxylate (Compound 6, Pipazoline) (24.0 kg, 45.2 mol), potassium acetate (22.2 kg, 45.2 mol), and (dppf)PdCl$_2$ (0.74 kg, 1.01 mol). The reactor was inerted with nitrogen gas. The solution was sparged with nitrogen gas until the oxygen content was <500 mg/L. The reaction was heated to 87.5° C. A solution of potassium trifluoro(2-fluoro-6-hydroxyphenyl)borate (12.6 kg, 54.3 mol) in degassed dioxane (49.4 kg) and degassed water (14.4 kg) with oxygen content <500 mg/L was transferred to the reaction, maintaining an internal temperature of 82.5° C.±7.5° C. The reaction was adjusted to 87.5° C.±1.5° C. and stirred for 75 min±15 min. A 1.0 M EDTA solution (47.3 kg) followed by water (40.1 kg) was charged to the reactor while maintaining an internal temperature of 85° C.±5° C. The reaction was cooled to 20° C.±3° C. over >2 h and then stirred for >16 h. The reaction was filtered and the crude solids were rinsed with water (3×120 kg). The solids were rinsed with a mixture of heptane (28.8 kg) and 2-propanol (33.1 kg) and then dried at <50° C. for >10 h. A clean reactor was loaded with crude solids and dichloromethane (240 kg). The contents were stirred at 20° C.±5° C. for >30 min. To the reactor was added Si-Thiol (144 kg) and dichloromethane (14.9 kg). The reaction was stirred at 20° C.±5° C. for 18 h. The reaction was filtered and rinsed with dichloromethane (84 kg). The solution was distilled and solvent swapped to 2-propanol. The reaction was heated to 60° C.±3° C. and heptane (108 kg) was charged while maintaining a reaction temperature of 60° C.±3° C. The reaction was stirred for 45 min and then cooled and stirred at 20° C.±5° C. for 2.5 h. The reaction was filtered and rinsed with 50% v/v heptane/2-propanol (61.9 kg). The isolated solids were dried at <50° C. for >12 h to afford tert-butyl (3S)-4-{6-fluoro-7-(2-fluoro-6-hydroxyphenyl)-(1M)-1-[4-methyl-2-(propan-2-yl)pyridin-3-yl]-2-oxo-1,2-dihydropyrido[2,3-d]pyrimidin-4-yl}-3-methylpiperazine-1-carboxylate (Compound 7, BIARYL).

Step 8

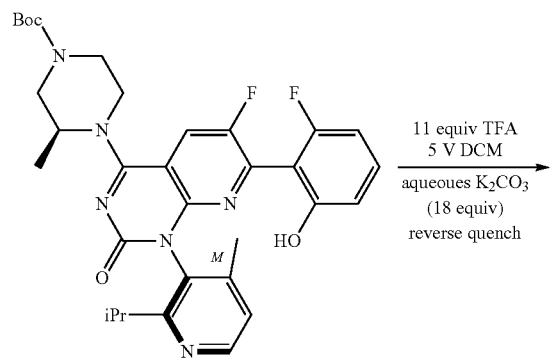

BIARYL 7

11 equiv TFA
5 V DCM
→
aqueoues K$_2$CO$_3$
(18 equiv)
reverse quench

Des-BOC 8

General Note: All Equivalents and Volumes are Reported in Reference to BIARYL 7

| Material | CAS # | MW (g/mol) | Equivalents/Volumes | Moles | Theoretical |
|---|---|---|---|---|---|
| BIARYL 7 | NA | 606.67 | 1.0 equiv. | 5.27 | 2.75 kg |
| TFA | 76-05-1 | 114.02 | 11 equiv. | 49.7 | 5.67 kg |
| DCM | 74-09-2 | 84.93 | 5 vol | NA | 13.71 L |
| Methanol | 67-56-1 | 32.04 | 5 vol | NA | 13.71 L |
| Water | 7732-18-5 | 18.02 | 20 vol | NA | 54.8 L |
| Potassium Carbonate | 584-08-7 | 138.20 | 18 equiv. | 94.91 | 11.24 kg |
| DCM | 74-09-2 | 84.93 | 1 vol | NA | 2.75 L |
| Water | 7732-18-5 | 18.02 | 10 vol | NA | 27.5 L |
| Water | 7732-18-5 | 18.02 | 10 vol | NA | 27.5 L |

To a reactor was added tert-butyl (3S)-4-{6-fluoro-7-(2-fluoro-6-hydroxyphenyl)-(1M)-1-[4-methyl-2-(propan-2-yl)pyridin-3-yl]-2-oxo-1,2-dihydropyrido[2,3-d]pyrimidin-4-yl}-3-methylpiperazine-1-carboxylate (Compound 7, BIARYL) (2.75 kg, 5.27 mol), DCM (13.7 L), and TFA (5.67 kg, 49.7 mol). The reaction was stirred for 8-16 h at 20±5° C. To a second reactor was added potassium carbonate (11.24 kg), water (54.8 L), and methanol (13.7 L) to form a homogenous solution. The reaction mixture was added to the potassium carbonate solution over 2 h. The mixture was stirred at 20±5° C. for an additional 12 h. The resulting slurry was filtered and rinsed with water (2×27.5 L). The wet cake was dried for 24 h to give 6-fluoro-7-(2-fluoro-6-hydroxyphenyl)-4-[(2S)-2-methylpiperazin-1-yl]-(1M)-1-[4-methyl-2-(propan-2-yl)pyridin-3-yl]pyrido[2,3-d]pyrimidin-2(1H)-one (Compound 8, DESBOC).

Step 9

Des-BOC 8 i.

1.3 equiv
NMP 4 V, 2 h
ii. aq. Na$_2$HPO$_4$ quench
→
iii. Heat cycle
iv. Filter, water wash

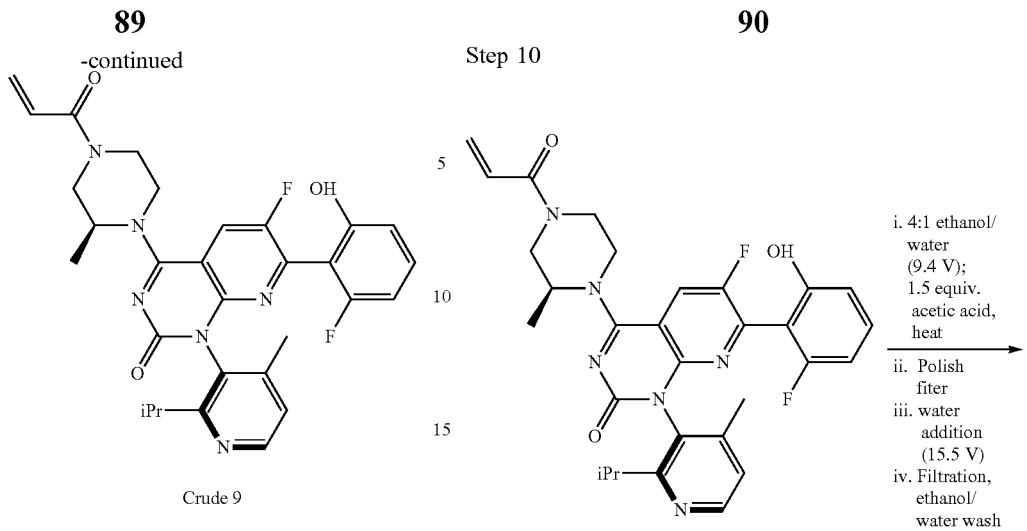

Crude 9

Step 10

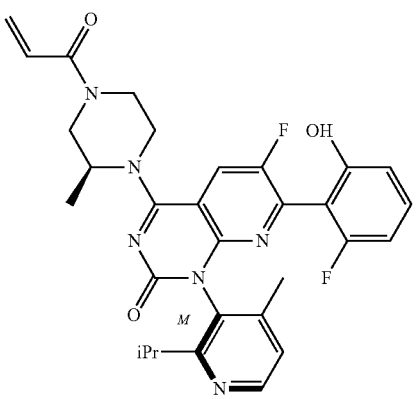

Crude Compound 9 i. 4:1 ethanol/water (9.4 V); 1.5 equiv. acetic acid, heat
ii. Polish filter
iii. water addition (15.5 V)
iv. Filtration, ethanol/water wash General Note: All Equivalents and Volumes are Reported in Reference to Des-BOC

| Material | CAS# | MW (g/mol) | Equivalents/Volumes | mmol | mass | volume |
|---|---|---|---|---|---|---|
| Des-BOS | NA | 506.56 | 1.0 equiv. | 308.4 | 156.25 g | — |
| Acryloyl chloride[1] | 814-68-6 | 90.51 | 1.3 equiv. | 401.0 | 36.29 g | — |
| NMP N-methyl pyrrolidinone[2] | 872-50-4 | 99.13 | 4 vol | NA | | 625 mL |
| Water | 7732-18-5 | 18.02 | 20 vol | NA | 3125 g | 3125 mL |
| $Na_2HPO_4$[3] | 7558-79-4 | 141.96 | 4 equiv. | 1233.6 | 175.12 g | — |
| Water | 7732-18-5 | 18.02 | 20 vol | NA | 3125 g | 3,125 mL |

[1]acryloyl chloride was added over 7 mins on this scale. Avoid over cooling reaction. Colder reaction temperatures led to slower reaction time leading to higher levels of m/z 1066 impurity as the starting material reacts with the product. Ideal temp range is 22-25 C.
[2]NMP content of dried cake typically 1-2 wt %.
[3]Disodium phosphate in table is as anhydrous basis. Hydrate may be used, adjust mass accordingly to obtain desired mmol.

[4]Results for this lead lot: 154.06 g isolated mass, 93% wt, 82.9% corrected yield, 18,000 ppm NMP 6-fluoro-7-(2-fluoro-6-hydroxyphenyl)-4-[(2S)-2-methylpiperazin-1-yl]-(1M)-1-[4-methyl-2-(propan-2-yl)pyridin-3-yl]pyrido[2,3-d]pyrimidin-2(1H)-one (Compound 8, DESBOC) (156.25 g) was combined with N-methyl pyrrolidinone (625 mL) and stirred at ambient temperature. To the resulting solution was added acryloyl chloride (36.29 g; 401.0 mmol) while maintaining <30° C. internal temperature. The contents where stirred for 2h at 25° C. In a separate reactor a solution of disodium phosphate (175.1 g; 1234 mmol) in DI water (3.1 L) was prepared. The crude product solution was then transferred to the reactor containing the disodium phosphate solution over >2h at 25° C. The slurry was heated to 45° C. midway through the addition and after complete addition, aged for 2h at the same temperature. The mixture was cooled to 25° C. and aged for 4h before collecting the solids by vacuum filtration. The solids where washed twice with water (1.5 L each) and the product dried under nitrogen and vacuum to afford the product 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl)piperazin-1-yl]pyrido[2,3-d]pyrimidin-2(1H)-one (crude Compound 9).[4]

-continued

Compound 9

General Note: All Equivalents and Volumes are Reported in Reference to Crude Drug Substance

| Material | CAS# | MW (g/mol) | Equivalents/Volumes | mmol | mass | volume |
|---|---|---|---|---|---|---|
| Crude Compound 9 | NA | 560.60 | 1.0 equiv. | 253.9 | 142.33 g | — |
| Ethanol (200 proof) | 64-17-5 | — | 7.5 V | — | — | 1067 mL |
| USP Water | — | 18.02 | 1.9 V | — | — | 270 mL |
| Acetic acid | 64-19-7 | 60.05 | 1.5 equiv. | 380.8 | 22.87 g | 21.82 mL |
| WFI Water | — | 18.02 | 15.5 vol | — | — | 2200 mL |
| Ethanol (for wash) | 64-17-5 | — | 2.5 V | — | — | 356 mL |
| WFI Water (for wash) | — | — | 5.0 V | — | — | 712 mL |
| Compound 9 seed[5] | — | 560.60 | 0 | — | 0.3-0.7 g | — |

[5] Seed performs best when reduced in particle size via milling or with other type of mechanical grinding if mill is not available (mortar/pestle). Actual seed utilized will be based on seed availability. 0.25%- 0.5% is seed is target amount.

6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl)piperazin-1-yl]pyrido[2,3-d]pyrimidin-2(1H)-one (crude Compound 9) (142.33 g; 253.9 mmol) was combined with ethanol (996 mL) and water (270 mL). Acetic acid (21.8 ml; 380.8 mmol) was added and the mixture heated to 75° C. to form a solution which was polish filtered into a clean reactor. The solution was cool to 45° C. and then water (1067 mL) was added while maintaining an internal temperature >40° C. The solution was seeded with authentic Compound 9 and the resulting mixture aged for 30 min. Water (1138 mL) was then added over 2h. The mixture was cooled to 25° C. and aged for 8h after which the solid was collected by vacuum filtration and washed using a mixture of ethanol (355.8 mL) and water (711.6 mL). The solid was dried using vacuum and nitrogen to obtain 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl)piperazin-1-yl]pyrido[2,3-d]pyrimidin-2(1H)-one (Compound 9).

Step A1 Reaction Scheme and Charge Table

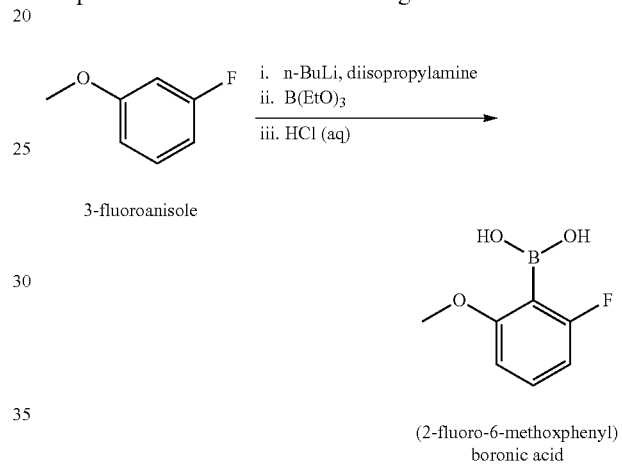

(2-fluoro-6-methoxphenyl) boronic acid

| Material | CAS# | MW (g/mol) | Equivalents/Volumes | mol | Mass (g) | Volume (L) |
|---|---|---|---|---|---|---|
| 3-Fluoroanisole | 456-49-5 | 126.13 | 1.0 | 1.19 | 150 | 0.136 |
| n-butyllithium (2.5M in hexane) | 109-72-8 | 64.06 | 1.5 | 1.78 | N/A | 0.712 |
| diisopropylamine | 108-18-9 | 101.19 | 1.4 | 1.66 | 168 | 0.233 |
| Triethylborate | 150-46-9 | 145.99 | 2.0 | 2.38 | 347.5 | 0.405 |
| Tetrahydrofuran | 109-99-9 | 72.11 | 12 vol | N/A | N/A | 1.8 |
| Hydrochloric acid (2N) | 7647-01-0 | 36.46 | 10 vol | N/A | N/A | 1.5 |
| Methyl tert-butyl ether | 1634-04-4 | 88.15 | 12 Vol | N/A | N/A | 1.8 |
| Heptane | 142-82-5 | 100.20 | 10.5 Vol | N/A | N/A | 1.575 |

Reactor A was charged with THF (6 vol) and Diisopropylamine (1.4 equiv). The resulting solution was cooled to −70° C. and n-BuLi (2.5 M in hexane, 1.5 equiv) was slowly added. After addition is complete, a solution of 3-fluoroanisole (1.0 equiv) in THF (6 vol) was added slowly and kept at −70° C. for 5 min. B(EtO)₃ (2.0 equiv) was added slowly and kept at −70° C. for 10 min. The reaction mixture was quenched with 2N HCl. The quenched reaction mixture was extracted with MTBE (3×4 vol). The combined organic phases were concentrated to 1.5-3 total volumes. Heptane (7-9 vol) was added drop-wise and the mixture was cooled to 0-10° C. and stirred for 3 h. The mixture was filtrated and rinsed with heptane (1.5 vol). The solid was dried under nitrogen at <30° C. to afford (2-fluoro-6-methoxyphenyl) boronic acid.

Step A2 Reaction Scheme and Charge Table

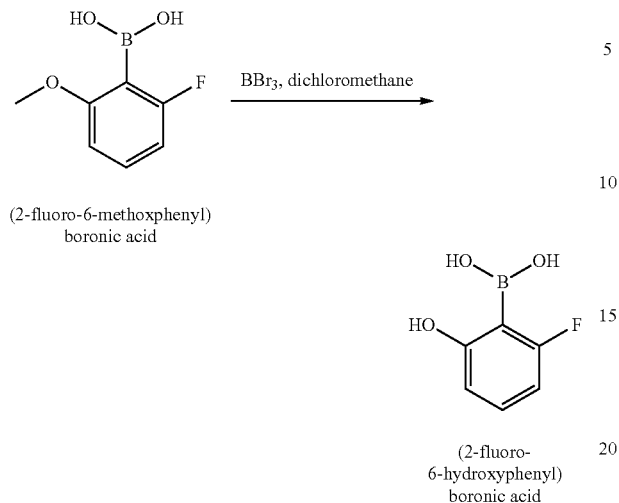

(2-fluoro-6-methoxphenyl) boronic acid (2-fluoro-6-hydroxyphenyl) boronic acid

| Material | CAS# | MW (g/mol) | Equivalents/Volumes | mol | Mass (g) | Volume (L) |
|---|---|---|---|---|---|---|
| (2-fluoro-6-methoxyphenyl) boronic acid. | 78495-63-3 | 169.95 | 1.0 | 0.118 | 20 | N/A |
| Boron tribromide | 10294-33-4 | 250.52 | 1.5 | 0.177 | 44.2 | 0.017 |
| Dichloromethane | 75-09-2 | 84.93 | 4 vol | N/A | N/A | 0.080 |
| Water | 7732-18-5 | 18.02 | 13 vol | N/A | N/A | 0.26 |
| Methyl tert-butyl ether | 1634-04-4 | 88.15 | 13 Vol | N/A | N/A | 0.26 |
| Heptane | 142-82-5 | 100.20 | 10 Vol | N/A | N/A | 0.20 |

Reactor A was charged with dichloromethane (4 vol) and 2-fluoro-6-methoxy-4-methylphenylboronic acid (1 equiv). The reaction mixture was cooled to −30° C. and 1.5 BBr$_3$ (1.5 equiv) was added dropwise. When the addition completed, the mixture was warmed to 25° C. and stirred 2 h. The reaction mixture was quenched into ice cold (0-5° C.) water (10 vol). MTBE (10 vol) was added and the mixture warmed to 25° C. and stirred for 1-2 h or until all solids dissolved. The aqueous phase was separated and extracted with MTBE (3 vol). The combined organic extracts were washed with water (3 vol) and then concentrated to 1 total volumes. Heptane (10 vol) was added to the mixture and stirred for 2 h. The resulting product was isolated by filtration and dried at <30° C. to afford (2-fluoro-6-hydroxyphenyl)boronic acid.

Step A3 Reaction Scheme and Charge Table

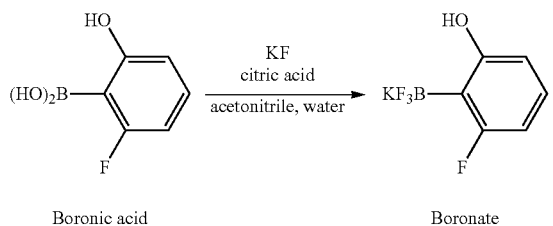

Boronic acid → Boronate

| Material | CAS # | MW (g/mol) | Equivalents/ Volumes | mol | Mass (kg) | Volume (L) |
|---|---|---|---|---|---|---|
| (2-fluoro-6-hydroxyphenyl)boronic acid | 1256345-60-4 | 155.92 | 1.0 | 89.79 | 14.00 | N/A |
| Citric acid monohydrate | 5949-29-1 | 210.14 | 1.64 | 147.26 | 30.94 | N/A |
| Acetonitrile | 75-05-8 | 41.05 | 21 Vol | N/A | 220.1 | 294 |
| Potassium fluoride | 7789-23-3 | 58.10 | 4.00 | 359.16 | 20.87 | N/A |
| USP Water | 7732-18-5 | 18.02 | 2.0 Vol | N/A | 28.00 | 28.00 |
| Celite | N/A | N/A | N/A | N/A | 7.00 | N/A |
| 2-Propanol | 67-63-0 | 60.10 | 25 Vol | N/A | 275 | 350 |

Step A3

Potassium Fluoride (21.0 kg; 20.87 mol) was combined with water (28 L) in a reactor (reactor A) and the contents stirred for 30 min. In a separate reactor (reactor B), (2-fluoro-6-hydroxyphenyl)boronic acid (14.00 kg, 89.79 mol) was charged followed by acetonitrile (206.1 kg) and citric acid (30.94 kg; 147.26 mol) at 25° C. The contents of reactor A was added to reactor B at 25C and stirred at that temperature for 10h. The reaction mixture was filtered through a bed of celite (7.0 kg) and rinsed with acetonitrile (42 kg). The filtrate was combined with isopropanol (56 kg) and then distilled under vacuum at a temperature <35° C. replacing the distilled volume to the reactor with isopropanol and repeated as needed to complete the solvent swap from acetonitrile to isopropanol. The slurry was cooled to 15C and aged for 1h before filtered and washing with 28 kg of isopropanol. The cake was dried using vacuum and nitrogen and packaged to afford Compound A3.

Resolution of the M-Dione Compound 5

Chromatographic Resolution of M-Dione Intermediate

Numerous chiral chromatographic techniques and methods were used to isolate the M-dione from Compound 4. The techniques and stationary phases are well known in the art and are outlined in Table 1.

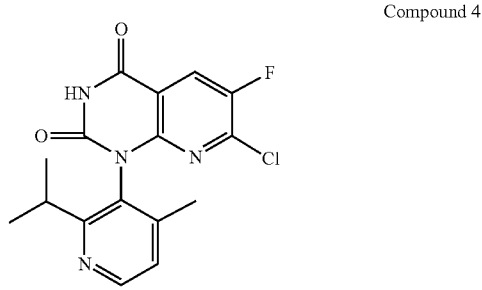 [SMILES: Cc1ccnc(C(C)C)c1-n1c(=O)[nH]c(=O)c2cc(F)c(Cl)nc21]

Compound 4

TABLE 1

| Technique | Stationary Phase | Mobile Phase | Yield^ |
|---|---|---|---|
| SFC | Chiralpak ® AD | 40% methanol/60% CO2 * | ~95% |
| HPLC | Chiralpak ® AD | 90/10/0.1 ethanol/ methanol/ triethylamine | ~94% |
| HPLC | Chiralpak ® IG | 60/40/0.1 ethanol/ methanol/ Triethylamine | ~92% |
| Simulated Moving Bed (SMB) | Chiralpak ® IC | Acetonitrile | ~96% |

^Yield is defined as % of available M-Dione that was recovered at the required purity of > 98% ee.
* This separation was performed multiple times. For each lot of material, the mobile phase may have been slightly modified to accommodate for variations in the lots. Additional mobile phases used for purification included:
1) 25/75 methanol/$CO_2$,
2) 30/70 methanol/$CO_2$, and
3) 50/50 methanol/$CO_2$.

The SFC, HPLC, and SMB techniques are well known in the art and the Chiralpak® stationary phases are commercially available from commercial sources, such as Fisher Scientific and Daicel Corporation.

However, it is desired to develop a more efficient process to isolate the M-Dione (Compound 5).

Classical Resolution

The present invention is directed to the development of a viable classical resolution process for M/P-Dione racemate (Compound 4).

A total of 100 cocrystal screening experiments were performed and three potential cocrystals of Dione were identified. Based on the highest area ratio of M/P-Dione in the residual solid and lowest area ratio in the supernatant, (+)-2, 3-dibenzoyl-D-tartaric acid (DBTA) was selected as the chiral reagent for resolution.

According to the results from 100 cocrystal screening experiments and 20 more solvent screening, 2-MeTHF/n-heptane was found to provide a better resolution result than other solvent systems. Based on the solubility results of M-Dione cocrystal and P-Dione cocrystal in different ratios of 2-MeTHF and n-heptane, 2-MeTHF/n-heptane (1.4:1, v/v) was selected as the optimal solvent composition for resolution.

In order to find out any possible form conversion to Dione racemate or M/P-Dione during crystallization process of chiral resolution, the solubility of M-Dione cocrystal, P-Dione cocrystal, M+P-Dione cocrystal mixture (1:1, w/w), Dione racemate and DBTA were determined at different temperatures in 2-MeTHF/n-heptane (1.4:1, v/v). No form change was observed for M-Dione cocrystal and P-Dione cocrystal at different temperatures for 7 days. However, Dione racemate Type C was obtained after stirring of a mixture of M+P-Dione cocrystal mixture (1:1, w/w) at different temperatures for 7 days. Dione racemate Type D (20 and 30° C.) or Dione racemate Type C (40, 50, 60 and 65° C.) were observed after stirring of Dione racemate at corresponding temperatures for 7 days. A solubility of ~100 mg/mL was observed under all the temperatures for DBTA.

To further optimize the resolution process, the ternary phase diagram of M/P-Dione cocrystal was drawn based on the equilibrium solubility results and no eutectic point was obtained likely because racemate Type C could crystallize out when both M-Dione cocrystal and P-Dione cocrystal were present. Another ternary phase diagram of M/P-Dione was drawn based on the equilibrium solubility results and no eutectic point was obtained likely because Dione racemate Type C or Type D could crystallize out when both M-Dione and P-Dione were present.

In summary, a chiral reagent (DBTA) and a solvent system ((2-MeTHF/n-heptane (1.4:1, v/v)) were identified for resolution of Dione racemate. Small scale crystallization process using the resolving reagent and solvent system could achieve a yield of 39% and ee purity of 99% for M-Dione. In addition, polymorphism of Dione racemate was observed and investigated during screening experiments.

The compound of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compound of the present invention may also be used in combination with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: the compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compound can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of the compound of the present invention include ointments, powders, sprays and inhalants. The active compound or compounds are admixed under sterile condition with a physiologically acceptable carrier, and any preservatives, buffers, or propellants that may be required. Ophthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. A particular dosage of a compound of the present invention is the FDA approved dosage, if the compound has been approved.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compound of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compound of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compound of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, because the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy) ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-3)alkyl.

The compounds of the present invention may contain asymmetric or chiral centers, and therefore, exist in different stereoisomeric forms. It is contemplated that all stereoisomeric forms of the compound as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that the compounds of the present invention may exist in different tautomeric forms. All tautomers of the compound of the present invention are contemplated. For example, all of the tautomeric forms of the tetrazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{18}O$, $^{31}P$, $^{32}P$, $^{35}S$, $^{18}F$, and $^{36}Cl$. In one aspect, the present invention relates to compounds wherein one or more hydrogen atom is replaced with deuterium ($^2H$) atoms.

The compounds of the present invention that contains the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing the compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents, patent applications and other documents recited herein are hereby incorporated by reference in their entirety.

The examples presented below illustrate specific embodiments of the present invention. These examples are meant to be representative and are not intended to limit the scope of the claims in any manner.

Examples

AMG 510 has been developed as an orally bioavailable, covalent inhibitor of $KRAS^{G12C}$ with potent biochemical and cellular activity, and robust in vivo efficacy. Cysteine proteome analysis of NCI-H358 cells treated with AMG 510 revealed that only the G12C-containing peptide of KRAS was covalently modified. AMG 510 inhibited SOS-catalyzed nucleotide exchange of recombinant mutant $KRAS^{G12C/C118A}$ but had minimal effect on $KRAS^{C118A}$ which is wild-type at position 12. In cellular assays, AMG 510 covalently modified $KRAS^{G12C}$ and inhibited $KRAS^{G12C}$ signaling as measured by phosphorylation of ERK1/2 in all KRAS p.G12C-mutant cell lines tested but did not inhibit ERK1/2 phosphorylation in cell lines with various other KRAS mutations. AMG 510 also selectively impaired viability of KRASp.G12C mutant cell lines but did not affect cell lines with other KRAS mutations. In vivo pharmacodynamic assays demonstrated dose- and time-dependent inhibition of $KRAS^{G12C}$ signaling as measured by phosphorylation of ERK1/2 (p-ERK) in human pancreatic (MIA PaCa-2 T2) and NSCLC (NCI-H358) tumor xenografts. Covalent modification of $KRAS^{G12C}$ by AMG 510 was measured by mass spectrometry and correlated with p-ERK inhibition in tumors. Time course studies in tumor-bearing mice demonstrated that the plasma exposure of AMG 510 peaked at 0.5 hours post dose, followed closely by inhibition of p-ERK in tumors. AMG 510 significantly inhibited the growth of MIA PaCa-2 T2 and NCI-H358 xenografts and resulted in tumor regression at higher doses. Treatment of KRAS p.G12C lines with covalent $KRAS^{G12C}$ inhibitors increased the expression of HLA. Combination treatment of AMG 510 with inhibitors of other cellular signaling pathways exhibited evidence for synergistic effects on cell viability. Combination treatment of AMG 510 with the standard-of-care carboplatin demonstrated enhanced NCI-H358 tumor growth inhibition compared to either single agent. Similarly, AMG 510 combined with a MEK inhibitor resulted in enhanced anti-tumor efficacy compared to either single agent.

To test the impact of $KRAS^{G12C}$ inhibition on immune surveillance in vivo, a novel syngeneic tumor cell line was generated that is suitable for testing AMG 510 in combination with checkpoint inhibitor therapies and thus characterized in vitro. In the newly developed model of KRAS-G12C mutant cancer, AMG 510 treatment significantly inhibited tumor growth and caused regression. Strikingly, the combination of AMG 510 with an immune checkpoint inhibitor resulted in markedly improved overall survival and led to durable cures. Immunophenotyping of murine KRASp.G12C tumors revealed a significant increase in T-cell infiltration post treatment suggesting that AMG 510 may induce a tumor microenvironment more sensitive to immune checkpoint inhibition.

A Novel Syngeneic CT-26 KRAS p.G12C Tumor Model

Murine CT26 (Colon Tumor #26) cells were developed in 1975 by exposing BALB/c mice to N-nitroso-N-methylurethane (NMU), resulting in a rapid-growing grade IV carcinoma that is easily implanted and readily metastasizes. Used in over 500 published studies, the CT26 colon carcinoma is one of the most commonly used cell lines in drug development. Numerous cytotoxic agents as well as therapeutics targeting specific signaling pathways have been studied with these cells. Moreover, as the CT26 model in BALB/c mice provides a syngeneic in vivo test system, it is frequently used for developing and testing immunotherapeutic concepts, *BMC Genomics*. 2014 Mar. 13; 15:190. doi: 10.1186/ 1471-2164-15-190. *Immunomic, genomic and transcriptomic characterization of CT26 colorectal carcinoma*.

A syngeneic CT-26 KRAS p.G12C tumor model was developed to enable the combination studies with the cell lines and immunotherapy as outlined in Table A and FIGS. 3, 4A-B, 5A-C, 6A-B, 18, 24, 31, 34, 38 and 39A-B. The CT-26 syngeneic tumor cell line was chosen based on it having a KRAS-G12D mutation present in the parental line. The presence of the KRAS-G12D mutation suggested that the cell line growth and survival may be driven by constitutive KRAS signaling (G12D), and would potentially be sensitive to KRAS inhibition. CT-26 KRASp.G12C cells were generated from a CT-26 murine colorectal tumor cell line. CRISPR technology, as described in prior art by Liang et al. (Journal of Biotechnology 241 (2017) 136-146), was utilized to replace both KRASp.G12D alleles with KRAS p.G12C, utilizing the sequence CTTGTGATGGTTGGAGCTGA (SEQ ID NO: 21). Clone 10 was determined to be homozygous for the KRASp.G12C allele by next-generation sequencing (NGS) and is identified as CT-26 KRAS G12C-H10. This new isolated syngeneic tumor cell line, CT-26 KRAS p.G12C, which allows inhibition of KRAS signaling by AMG 510 was used for all CT-26 G12C in vivo studies (See FIGS. 3, 4A-B, 5A-C, 6A-B) and in vitro studies (See FIGS. 18, 24, 31, 34, 38 and 39A-B).

The present invention encompasses a novel isolated cell line comprising the two $KRAS^{G12C}$ alleles and a method of generating a cell line comprising two $KRAS^{G12C}$ alleles, the method comprising:
 a) incubating a cell line comprising two $KRAS^{G}12D$ alleles with a CRISPR construct that induces the replacement of a nucleotide on both the two KRAS alleles such that two $KRAS^{G}12C$ alleles are formed; and
 b) isolating the cell line comprising the two $KRAS^{G}12C$ alleles.

Next-generation sequencing (NGS), also known as high-throughput sequencing, is the catch-all term used to describe a number of different modern sequencing technologies including:
 Illumina (Solexa) sequencing
 Roche 454 sequencing
 Ion torrent: Proton/PGM sequencing
 SOLiD™ sequencing
 Ion Torrent™ Personal Genome Machine™ platform, commercially available from Thermo-Fisher Scientific, was used in the present invention. These recent technologies allow scientists to sequence DNA and RNA much more quickly and cheaply than the previously used Sanger sequencing.

In Vitro Cell-Based Combination Studies

Cell lines were purchased from American Type Culture Collection (ATCC), German Collection of Microorganisms and Cell Cultures (DSMZ), and Japanese Collection of Research Bioresources (JCRB). Each line was cultured in its recommended growth medium.

For two-way compound combinations, cells were seeded either into 96-well or 384-well cell culture plates at initial densities ranging from 500 to 2500 cells per well.

Sixteen to 24 hours later, compounds were added to the culture plates in a matrixed format, with one agent titrated along the x-axis and the second agent along the y-axis. For all combinations tested in any given cell line, the starting high concentration and dilution factor of each compound were chosen to well-define the curve maximum, curve minimum, and slope over the range of doses selected for the combination screening format. CellTiter-Glo® Luminescent Cell Viability (Promega) assay kits were used to determine the numbers of viable cells.

Luminescence was measured with an EnVision® Multilabel Reader (Perkin Elmer) for each cell line at time zero (V0) before the addition of compounds, as well as after 72 hours of compound treatment. Growth inhibition (GI) was calculated on a 200-point scale according to the following equations, where V72 was luminescence of DMSO control at 72 hours and T72 was luminescence of the compound-treated sample: if T72>V0, then GI=100×(1−((T72−V0)/(V72−V0))); if T72<V0, then GI=100×(1−((T72−V0)/V0)). GI values of 0, 100, and 200 represented uninhibited cell growth (i.e. DMSO control), cell stasis, and complete cell killing, respectively. Sigmoidal dose response curves were plotted using a 4-parameter logistic model. Data were analyzed for synergistic interactions using the Chalice™ Analyzer software (Zalicus) which generated synergy scores based on the Loewe Additivity model.

Growth inhibition for each well of the matrix was calculated as previously described, and the data were analyzed for synergistic interactions using Chalice™ Analyzer software (Zalicus; Cambridge, MA) which generated synergy scores based on the Loewe Additivity model (Lehàr, J., et al. (2009). "Synergistic drug combinations tend to improve therapeutically relevant selectivity." *Nat Biotech* 27(7): 659-666) and Rickles, et al (2012) "Adenosine A2A and Beta-2 Adrenergic Receptor Agonists: Novel Selective and Synergistic Multiple Myeloma Targets Discovered through Systematic Combination Screening" Mol Cancer Therapeutics 11 (7): 1432.

The Loewe ADD (additivity) model (as shown in FIGS. 7-37) quantifies combination effects. Combinations were ranked initially by Additivity Excess Volume, which is defined as ADD Volume=$\Sigma C_X, C_Y (I_{data}-I_{Loewe})$, where $I_{Loewe}(C_X,C_Y)$ is the inhibition that satisfies $(C_X/EC_X)+(C_Y/EC_Y)=1$, and $EC_{X,Y}$ are the effective concentrations at $I_{Loewe}$ for the single agent curves. A "Synergy Score" was also used, where the Synergy Score S=$\log f_X \log f_Y \Sigma I_{data}(I_{data}-I_{Loewe})$, summed over all non-single-agent concentration pairs, and where $\log f_{X,Y}$ is the natural logarithm of the dilution factors used for each single agent. This effectively calculates a volume between the measured and Loewe additive response surfaces, weighted towards high inhibition and corrected for varying dilution factors. An uncertainty $\sigma_s$ was calculated for each synergy score, based on the measured errors for the $I_{data}$ values and standard error propagation.

In the examples shown, the Growth Inhibition (%) matrices contain the consensus growth inhibition values calculated from the luminescence data using the formulas described above; the ADD Model Growth Inhibition (%) matrices contain the predicted growth inhibition values based on the Loewe additivity model, which was derived from the modeled single agent growth inhibition curves; and the ADD Excess Growth Inhibition (%) matrices contain the values of growth inhibition in excess of the additivity model. The additivity model serves as a "null-hypothesis" and assumes no synergistic interaction between the two agents. Any activity observed after subtraction of the ADD model from the Growth Inhibition dose response matrix (=ADD Excess Growth Inhibition) is indicative of synergy.

Table A below illustrates specific in vitro combinations of a KRAS$^{G12C}$ inhibitor with one or more additional pharmaceutically active agents for particular cancers types. The data obtained and summarized in the FIGS. 7-39 indicate that the combinations set forth in Table A show enhanced anti-cancer activity over what is expected when the individual members of the combination therapy are used alone. It is noted that the magnitude of the therapeutic synergy that is seen can vary depending on the type of cancer treated and agent used.

in the FIGS. indicates that the combinations set forth in the FIGS. show enhanced anti-cancer activity over what is expected when the individual members of the combination therapy are used alone. It is noted that the magnitude of the therapeutic synergy that is seen can vary depending on the type of cancer treated and agent used.

Figure 1A:
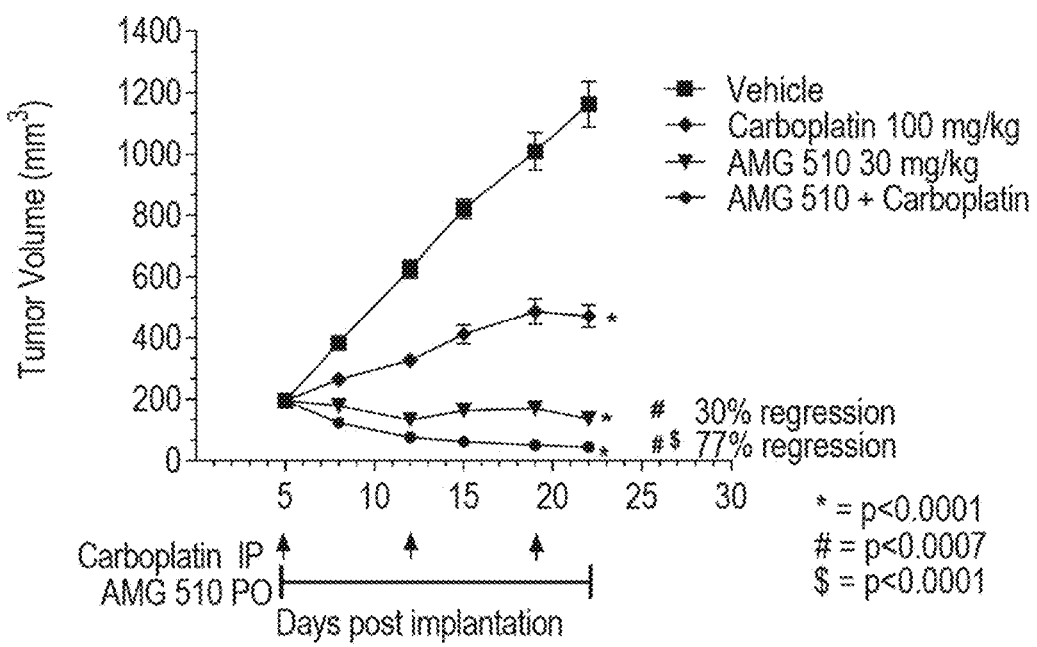
Figure 1B:
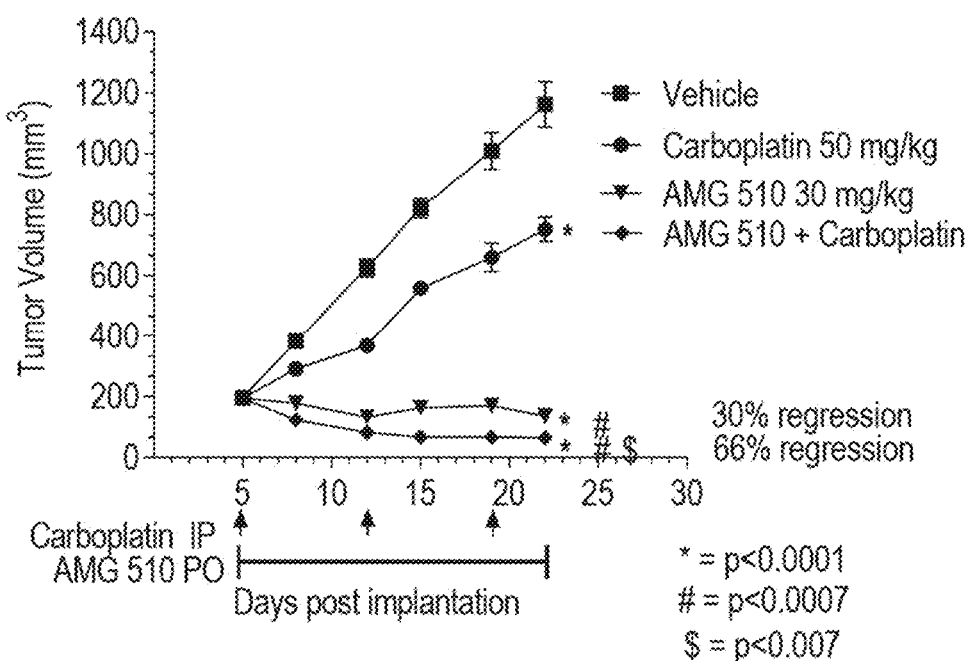
Figure 2A:
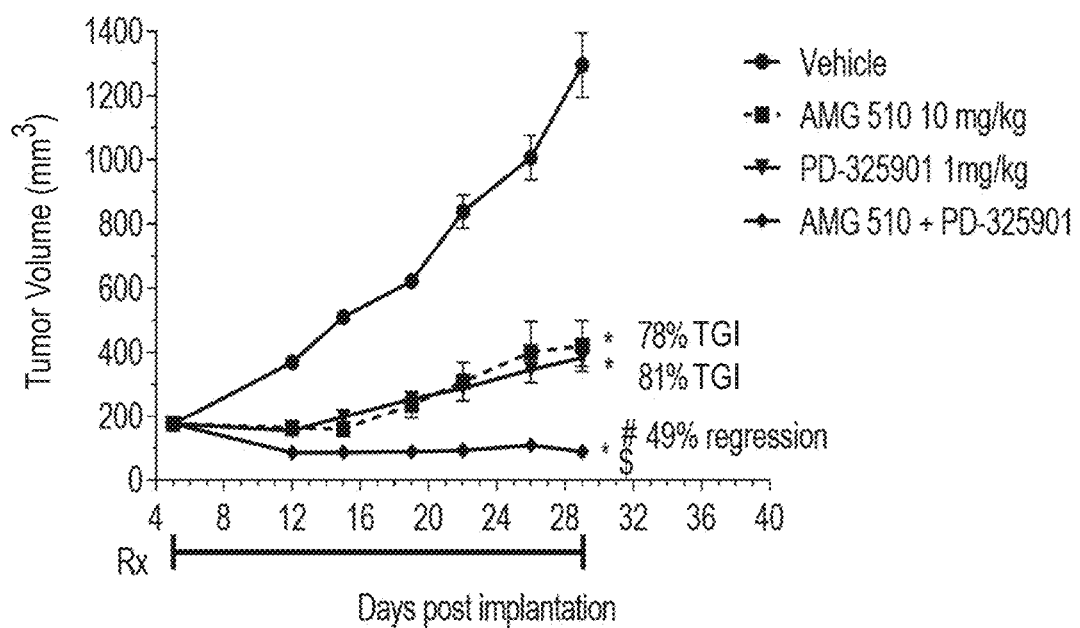
FIGS. 2A and 2B show AMG 510 combined with the MEK inhibitor PD-325901 results in enhanced efficacy in the NSCLC NCI-H358 xenograft model.
Figure 2B:
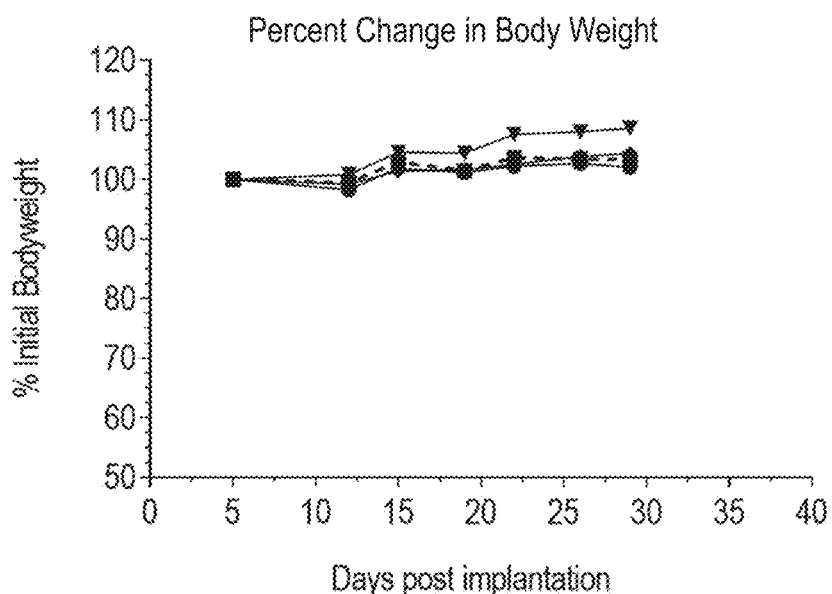
Figure 3:
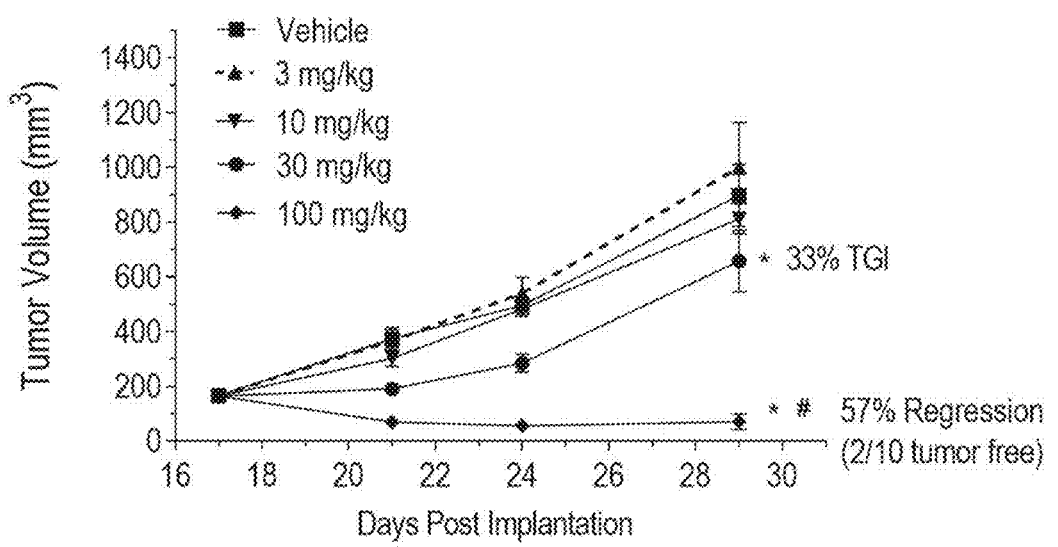
FIG. 3 shows AMG 510 inhibits the in vivo growth of CT-26 KRAS p.G12C tumors.
Figure 4B:
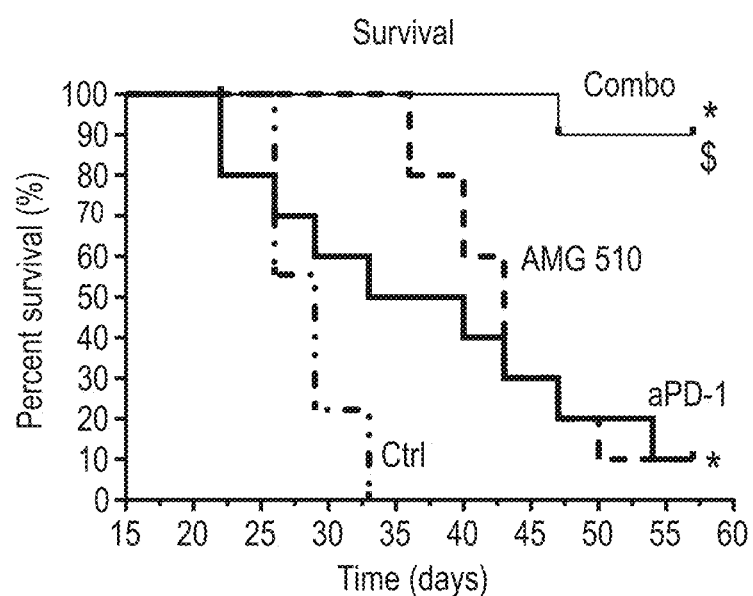
Figure 5A:
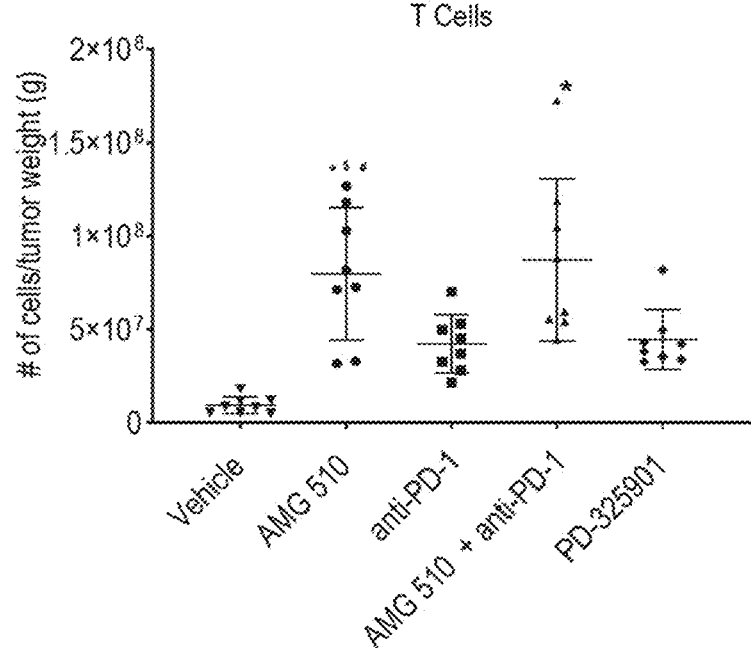
Figure 5B:
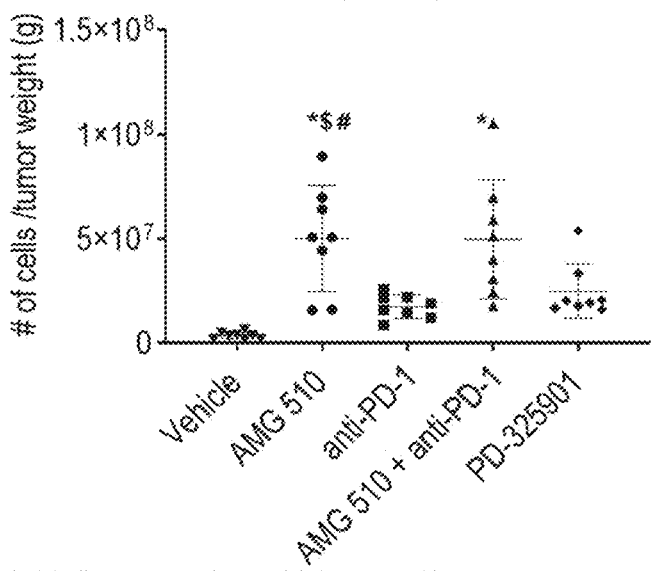
Figure 6A:
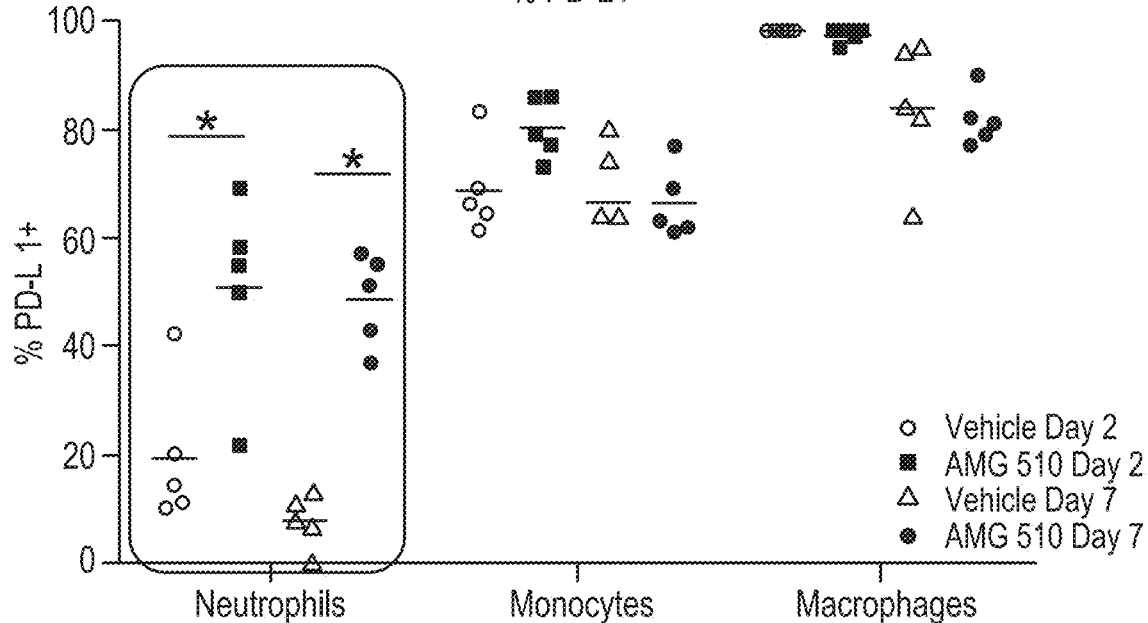
FIGS. 6A and 6B show AMG 510 treatment leads to increase in PD-L1 positive neutrophils in CT-26 G12C-H10 tumors.
Figure 6B:
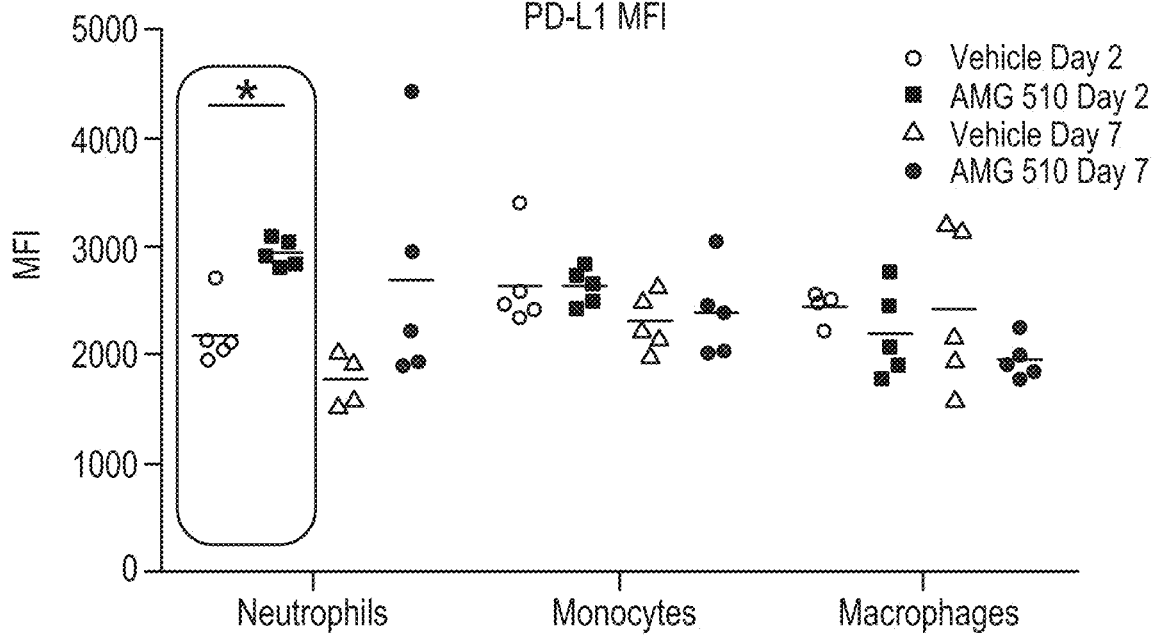

In FIGS. 4A-B, the combined treatment of AMG 510 and an anti-PD1 antibody (clone 29F.1A12) in the CT26-KRASG12C syngeneic tumor model resulted in signifi-

TABLE A

|  | EGFRi | | | SHP2i | MEKi | PI3Ki | | AKTi | EGFR Ab |
|---|---|---|---|---|---|---|---|---|---|
|  | AMG 510 Afatinib | AMG 510 Erlotinib | AMG 510 Lapatinib | AMG 510 RMC-4550 | AMG 510 Trametinib | AMG 510 AMG 511 | AMG 510 Buparlisib | AMG 510 AZD5363 | AMG 510 Cetuximib |
| NCI-H358 (lung) | 22.3 | 12.4 | 19.7 | 25 | 17 | 10.5 | 13.5 | 4.53 | — |
| MIA PaCa-2 (pancreas) | 4.7 | 2.07 | — | 6.36 | 3.06 | 5.53 | — | 2.67 | — |
| MIA PaCa-2 3D | 2.76 | — | — | — | 7.46 | — | — | — | — |
| NCI-H1373 3D (lung) | 8.7* | — | — | — | 11.8 | — | — | — | — |
| CT-26 KRAS p.G12C 3D (Mouse Colon) | 10.8* | — | — | 11.7* | 2.63 | 10.8 | — | — | — |
| SW837 (colon) | — | — | — | — | — | — | — | — | 2.96 |

*Off-target effects at higher concentrations possibly contributing to elevated synergy scores In Vivo Tumor Xenograft Combination Studies In vivo tumor xenograft studies were conducted following these general procedures:

Tumor cells were cultured, harvested and implanted subcutaneously into the right flank of female athymic nude mice. When tumors reached about 200 mm$^3$, mice were randomized into treatment groups (n=10/group) and treatment was initiated (on days indicated on graphs). Tumor sizes and body weights were measured 2 to 3 times per week. Tumor volume was measured by digital calipers, calculated as L×W×H and expressed in mm$^3$. Statistical significance of observed differences between growth curves was evaluated by repeated measures analysis of covariance (RMANOVA) of the log transformed tumor volume data with Dunnett adjusted multiple comparisons comparing the control group to the treatment groups. For combination studies, RMANOVA was run with the combination group compared one to one with each single agent treatment group.

BD Matrigel™ Basement Membrane Matrix is a solubilized basement membrane preparation extracted from the Engelbreth-Holm-Swarm (EHS) mouse sarcoma (BD Biosciences, San Jose, CA).

All studies were measured in a blinded manner.

In FIGS. 3, 4A-B, 5A-C and 6A-B, the anti-mouse PD-1(clone 29F.1A12) antibody is commercially available from Bio X Cell, West Lebanon, New Hampshire.

FIGS. 1A-C, 2A-B, 3, 4A-B, 5A-C, and 6A-B illustrate specific in vivo combinations of a KRAS$^{G12C}$ inhibitor with one or more additional pharmaceutically active agents for particular cancer types. The data obtained and summarized cantly improved survival and led to durable cures compared to either single agent treatment. AMG 510 monotherapy, or anti-PD1 monotherapy, resulted in delayed tumor growth compared to the control group. Each monotherapy treatment resulted in 1/10 complete responder. The combination treatment of AMG 510+anti-PD1 resulted in 9/10 complete responders. These were considered durable cures and those 9 mice remained tumor free after treatment was stopped (day 43), out to day 57 when the study was terminated.

Enhanced Binding and Potency of AMG 510

Although ARS-1620 validated the approach of direct inhibition of KRAS$^G$12C, the identification of improved inhibitors suitable for clinical testing has proven difficult. We believe a significant challenge is sub-optimal potency due to the small volume of the allosteric pocket occupied by ARS-1620, which offers limited avenues for additional protein-ligand interactions. This was illustrated by the X-ray crystal structure of the KRAS$^{G12C}$/ARS-1620 covalent complex (FIG. 40A), in which hydrogen bonding between ARS-1620 and histidine 95 (H95) featured prominently (dashed line). Our breakthrough was the discovery that a surface groove, created by an alternative orientation of H95, could be occupied by substituted aromatic rings, which enhanced interactions with KRAS$^{G12C}$. AMG 510 emerged as the top candidate from an optimization campaign of H95 groove-binding molecules, as it represented the convergence of improved potency and favorable development properties. The X-ray co-crystal structure of the covalent AMG 510-KRAS$^{G12C}$ complex (FIG. 40B) highlights the binding of AMG 510 in the P2 pocket of KRAS. The isopropylmethylpyridine substituent occupies the groove between Y96, H95, and Q99, and engages in a continuous network of 25 ligand-protein van der Waals contacts extending from the backbone of helix 2 (H95, Y96) to the backbone of the flexible Switch II loop (E62, E63).

To assess the impact that enhanced interactions had on the potency of AMG 510, we used two assays that employed recombinant GDP-bound $KRAS^{C118A}$ or $KRAS^{G12C/C118A}$ with an additional cysteine-to-alanine substitution at residue 118 to avoid reactivity with non-C12 cysteines. An enzymatic nucleotide-exchange assay utilized SOS1-catalyzed GDP/GTP exchange to promote the binding of the RAS-binding domain (RBD) of c-RAF to both versions of KRAS. In a 40-minute reaction, AMG 510 demonstrated ~10-fold greater potency (mean $IC_{50}$=0.09 µM) than ARS-1620 (FIG. 40C). AMG 510 did not appreciably inhibit $KRAS^{C118A}$ (FIG. 40C), and a non-reactive analog of AMG 510 had minimal activity in these assays (FIG. 46A). The kinetics of the reaction between AMG 510 and GDP-$KRAS^{G12C/C118A}$ under pseudo-first order conditions were measured by mass spectrometry (MS). A nonlinear fit of the concentration-rate data (FIG. 40D) established the maximal rate of reaction $k_{inact}$=0.85±0.08 $s^{-1}$ and the AMG 510 concentration at the half-maximal rate $K_I$=8.6E-05±1.4E-05 M, resulting in a $k_{inact}/K_I$ ratio of 9.8E+03±1.8E+03 $M^{-1}$ $s^{-1}$. The kinetics of the reaction between AMG 510 and $KRAS^{G12C/C118A}$ were significantly improved relative to ARS-1620. Relative to cysteine-targeted kinase inhibitors in the clinic, AMG 510 was characterized by a significantly larger $k_{inact}$, consistent with the KRAS-induced catalysis mechanism that has been previously described for ARS-1620. The non-specific reactivity of AMG 510 with 5 mM glutathione was relatively slow (AMG 510 t/2=196 min) and within the range of clinical covalent acrylamides.

Inhibition of Tumor Cell Signaling and Growth

The cellular activity of AMG 510 was assessed by measuring basal phosphorylation of ERK1/2 (p-ERK) and by MS to detect the covalent conjugation (i.e. occupancy) of $KRAS^{G12C}$ by AMG 510. In two KRASp.G12C cell lines, AMG 510 potently inhibited p-ERK ($IC_{50}$~0.02 and 0.03 µM, respectively) to near undetectable levels after 2-hour treatment and was 20-fold more potent than ARS-1620 (FIG. 40E). This inhibition closely tracked the occupancy of $KRAS^{G12C}$ by AMG 510, with near maximal levels achieved in both assays at ~0.2 µM (FIG. 40F). AMG 510 also potently impaired cellular viability in both lines ($IC_{50}$~0.006 µM and 0.009 µM, ~40-fold more potent than ARS-1620) (FIG. 40G).

The cellular kinetics of AMG 510 in two KRAS p.G12C cell lines were determined using the time- and concentration-dependence of the inhibition of p-ERK, which mirrors the occupancy of $KRAS^{G12C}$ by AMG 510. The rate of p-ERK inhibition increased with the concentration of AMG 510, with saturation occurring at concentrations above 3 µM. The concentration-rate curve-fits for AMG 510 and ARS-1620 (FIG. 40H and FIG. 46B), indicated that the cellular kinetic efficiency for inhibition of $KRAS^{G}12C$ by AMG 510 was approximately 23-fold greater than ARS-1620. The maximal inhibition rate of ERK phosphorylation by AMG 510 (8.9E-04 $s^{-1}$) is approximately 2-fold greater than the rate-limiting GTP-$KRAS^{G12C}$ hydrolysis rate proposed in a recent kinetic model (estimated rate from EGFR-inhibition=4.2E-04 $s^{-1}$; $t_{1/2}$=27.4 min). To provide an alternative estimate of the rate of GTP-hydrolysis by $KRAS^{G12C}$, a SHP2 inhibitor was employed to eliminate all upstream signaling to KRAS. This experiment yielded a cellular GTP hydrolysis rate of 9.4E-04 $s^{-1}$, ($t_{1/2}$=12.2 min; FIG. 46C), congruent with the rate observed for AMG 510.

For broader evaluation of the signaling impact of $KRAS^{G12C}$ inhibition, two cell lines were treated with multiple doses of AMG 510 for 4 and 24 hours, and western blots were performed to evaluate multiple signaling nodes (FIG. 41A). Covalent adduct formation of AMG 510 with $KRAS^{G12C}$ was detected by a shift in the mobility of the slower-migrating KRAS band (top arrow). This shifted species accumulated with increasing time and dose and was consistent with downstream inhibition of the MAPK pathway (i.e. p-MEK1/2 and p-ERK1/2) in both cell lines (FIGS. 41A and 41B). KRAS inhibition by AMG 510 also led to an accumulation of active EGFR (p-EGFR Y1068). Inhibition of AKT phosphorylation (p-AKT) was apparent in one line, but a decrease in the phosphorylation of ribosomal protein S6 (p-S6) was observed at 24 hours in both lines. Cleavage of caspase-3 was also observed at 24 hours, suggesting induction of apoptosis. In a more extensive time course, AMG 510 treatment at 0.1 µM (FIG. 41B), elicited rapid (<2 h) and sustained (>24 h) effects on MAPK and EGFR whereas p-S6 and caspase-cleavage emerged 8-16 hours after treatment in both lines.

To assess activity and selectivity, AMG 510 was profiled in 22 cell lines harboring either heterozygous or homozygous KRASp.G12C or KRAS mutations other than p.G12C, as well as wild-type (WT) KRAS lines. Two-hour treatment with AMG 510 inhibited basal p-ERK in all KRASp.G12C cell lines, with $IC_{50}$ values ranging from 0.010 µM to 0.123 µM (FIG. 41C and Supplementary Table 1). AMG 510 did not inhibit p-ERK in any non-KRASp.G12C lines ($IC_{50}$>10 µM; FIG. 41C and Supplementary Table 1).

In cell viability assays, AMG 510 impaired the growth of all homozygous and heterozygous KRASp.G12C cell lines, except SW1573, with $IC_{50}$ values ranging from 0.004 M to 0.032 µM (FIG. 41D and Supplementary Table 1). Although all KRASp.G12C lines displayed similar maximum inhibition of p-ERK, the maximum effect on cell viability varied. Cell lines with KRAS mutations other than p.G12C or with mutations in genes other than KRAS were insensitive to AMG 510 ($IC_{50}$>7.5 µM; FIG. 41D and Supplementary Table 1). A subset of KRAS p.G12C cell lines was selected to assess viability in low-adherence conditions to induce spheroid formation. As reported for other $KRAS^{G12C}$ inhibitors, these conditions enhanced the sensitivity of all tested lines to AMG 510 and yielded up to a 20-fold increase in potency and 2.5-fold increase in maximum inhibition (FIG. 41E, FIG. 46D, and Supplementary Table 1). SW1573 remained minimally sensitive, possibly due to a co-occurring driver mutation, PIK3CA p.K111E.

To further determine the selectivity of the covalent interaction of AMG 510 with $KRAS^{G12C}$ and to identify other potential 'off-target' cysteine-containing proteins in cells, cysteine-proteome profiling by MS was performed as described. After treating cells with DMSO or 1 µM AMG 510 (>30-fold p-ERK $IC_{50}$) for 4 hours, the cysteine proteome was enriched, and peptides identified. Among 6451 unique cysteine-containing peptides, the Cys12 peptide from $KRAS^{G12C}$ was the only peptide identified that met criteria for covalent target engagement (FIG. 41F).

AMG 510 Inhibits KRAS Signaling In Vivo

The effect of AMG 510 oral treatment on $KRAS^{G12C}$ signaling was evaluated in pharmacodynamic (PD) assays measuring p-ERK. In human tumors harboring KRASp.G12C, AMG 510 inhibited p-ERK in a dose-dependent manner 2 hours post-treatment (FIGS. 42A, 42B). Inhibition of p-ERK after AMG 510 treatment (100 mg/kg)

ranged from 69% (MIA PaCa-2 T2) to 83% (NCI-H358) reduction compared to control. Similar effects of AMG 510 on p-ERK levels were observed in a mouse tumor model (FIG. 47A) using a syngeneic CT-26 KRAS.G12C line which was generated using CRISPR technology. Time course PD assays demonstrated peak plasma and tumor exposure of AMG 510 at 0.5 hours following a single dose (10 mg/kg), leading to maximal inhibition of p-ERK 2-4 hours post-treatment and sustained, significant inhibition for 48 hours (FIGS. 42C, 42D). This is consistent with the relatively long 20- to 24-hour half-life of the $KRAS^{G12C}$ protein (FIG. 46E).

Additionally, in parallel experiments, occupancy of $KRAS^{G12C}$ by AMG 510 was measured by MS and approached 100% at the highest dose (100 mg/kg), correlating with maximal suppression of p-ERK (FIGS. 42E and 42F). Time course studies indicated that partial occupancy by AMG 510 was detectable after 0.5 hours, and ~100% occupancy was observed after 2 hours (FIG. 42G).

Mutant-Selective Tumor Inhibition In Vivo

AMG 510 was evaluated for its ability to inhibit the growth of human KRASp.G12C and KRASp.G12V (SW480-1AC) tumor xenografts in mice. AMG 510 significantly inhibited the growth of MIA PaCa-2 T2 and NCI-H358 tumors at all dose levels, with tumor regression observed at higher doses (FIGS. 43A, 43B). In contrast, AMG 510 treatment had no effect on KRASp.G12V tumor growth (FIG. 47B). Plasma levels of AMG 510 were consistent across all models (data not shown). In a murine CT-26 KRASp.G12C tumor model grown in immunocompetent mice, AMG 510 resulted in tumor growth inhibition and regression at the highest dose (FIG. 43C). Two out of 10 mice (100 mg/kg group) had no detectable tumors when the study was terminated on day 29. AMG 510 also significantly inhibited the growth of human KRASp.G12C mutant patient-derived xenografts (PDX) in mice (FIG. 43D and FIG. 47C).

Evidence of Clinical Activity

The enhanced potency, robust efficacy, and favorable pharmaceutical profile of AMG 510 prompted its selection as the first $KRAS^{G12C}$ inhibitor to enter clinical trials (Clinical trials.gov NCT03600883). Notably, in the first two cohorts of patients, AMG 510 treatment resulted in objective partial responses (per RECIST 1.1) in two patients with KRASp.G12C NSCLC (FIGS. 43E and 47D). Both patients had progressed on multiple prior systemic treatments including carboplatin, pemetrexed, and nivolumab with documented disease progression. The first patient showed 34% tumor shrinkage after 6 weeks of AMG 510 treatment. The second responder showed 67% tumor reduction after just 2 weeks of AMG 510 treatment. These patients remain on AMG 510 treatment after 6 months and 2 months, respectively (at time of current U.S. provisional patent filing date). No adverse events were reported. These patient have become the first ever to respond to a mutant-specific KRAS inhibitor, representing a milestone for cancer patients with KRASp.G12C mutant tumors.

Enhanced Efficacy in Combination

Given the high prevalence of KRASp.G12C in lung adenocarcinoma, a combination treatment of AMG 510 with carboplatin, a standard of care chemotherapeutic for lung cancer, was investigated in the NCI-H358 model. Treatment with either single agent (AMG 510 or carboplatin) resulted in significant tumor growth inhibition (FIG. 44A). However, combination treatment at various doses resulted in significantly improved anti-tumor efficacy (FIGS. 44A and 47E). To our knowledge this is the first demonstration of enhanced efficacy from combining a mutant-selective KRAS inhibitor with a chemotherapeutic agent and provides a rationale for this approach in the clinic.

The clinically validated strategy of combining BRAF and MEK inhibitors suggests that combinations with AMG 510 and other inhibitors in the MAPK (and AKT) signaling pathways might enhance tumor cell killing and overcome resistance[26]. Therefore in vitro combination experiments were conducted in several KRASp.G12C cell lines with matrices of AMG 510 and inhibitors of HER kinases, EGFR, SHP2, PI3K, AKT, and MEK (FIG. 48). As suggested by the induction p-EGFR by AMG 510 (FIG. 41A), the combination of AMG 510 with multiple agents resulted in synergistic tumor cell killing in NCI-H358 (FIGS. 44B and 48). Synergy was more limited in other lines, but the combination with a MEKi was synergistic in multiple settings and was enhanced in spheroid growth conditions (FIG. 44B). Significantly enhanced anti-tumor activity was also observed in vivo with a minimally efficacious dose of AMG 510 in combination with a MEKi, when compared to either single agent alone (FIG. 44C). Together these data suggest an intriguing clinical approach to combine AMG 510 with agents targeting other nodes in the MAPK pathway to extinguish residual or bypass signaling that could limit efficacy or induce resistance.

A Pro-Inflammatory Tumor Microenvironment

Blockade of the immune checkpoint programmed cell death 1/programmed death ligand 1 (PD-1/PD-L1) axis is clinically validated and approved for certain cancer patients. The activity of AMG 510 in combination with anti-PD-1 therapy was assessed in an immunocompetent setting in a CT-26 KRASp.G12C model. This line is dependent on the KRAS p.G12C allele (FIGS. 49A, 49B) and was sensitive to AMG 510 (FIGS. 43C and 47A). As shown previously (FIG. 43C), AMG 510 led to tumor regression as a single agent (FIG. 45A). However, overtime, only 1 out of 10 tumors remained completely regressed (FIG. 45A). Anti-PD-1 monotherapy led to delayed tumor growth with only 1 of 10 tumors showing complete regression. Strikingly, combination treatment led to 9 out of 10 complete responders (FIG. 45A). Treatment was stopped after day 43, and mice continued to be monitored for an additional 112 days. All complete responders from the combination treatment continued to have no detectable tumors, indicating that the combination of AMG 510 with anti-PD-1 antibody led to durable cures. Using a surrogate survival endpoint (tumor volume>800 mm$^3$), combination treatment led to a marked increase in survival compared to monotherapies (FIG. 45B).

To understand the effects of treatment on immune cell composition in tumors, CT-26 KRAS p.G12C tumors were immunophenotyped post-treatment. After 4 days of treatment, AMG 510 resulted in markedly increased T cell infiltration, primarily CD8+ T cells (FIGS. 45C and 50A). Increased CD8+ T cell infiltration was also observed in the combination group, primarily driven by AMG 510, as this did not occur after anti-PD-1 monotherapy. As an additional comparator, an inhibitor of MEK (MEKi) that blocked MAPK signaling downstream of RAS (FIG. 50B) and resulted in similar CT-26 KRAS p.G12C tumor growth inhibition as AMG 510, (FIGS. 50C, 50D) did not affect numbers of infiltrating CD8+ T cells (FIG. 45C). AMG 510 treatment also led to an increased infiltration of macrophages and dendritic cells, which was not observed with the MEKi (FIG. 45C). PD-1 expression on CD8+ T cells was moderately increased by both AMG 510 and the MEKi (FIG. 44A). Whole-tumor RNA was purified post-treatment, and transcriptional profiles of a panel of immune genes were assessed. After only 2 days of treatment, inhibition of KRAS$^{G12C}$ by AMG 510 induced a pro-inflammatory microenvironment characterized by increased interferon signaling, antigen processing, cytotoxic and NK cell activity, as well as markers of innate immune stimulation that was significantly higher compared to the effects induced by MEK inhibition (FIGS. 45D and 44E). AMG 510 also induced expression of MHC-I proteins on CT-26 KRASp.G12C tumor cells (FIGS. 45E and 50F). These data suggested that the treatment effects of AMG 510 on tumor cells may lead to increased T cell priming and antigen recognition. To test this, cured mice from the combination treatment (FIG. 45A) were re-challenged with bilateral tumors of CT-26 KRAS p.G12C and parental CT-26 (KRAS p.G12D), or CT-26 KRAS p.G12C and an unrelated mouse breast tumor model, 4T1. All 4T1 tumors (4/4) grew, but none (0/8) of the CT-26 KRASp.G12C tumors became established (FIG. 45F). Notably, all mice that received CT-26 parental tumors were tumor-free after 40 days (FIG. 45F). In a separate control group of naïve mice, 15 out of 15 (100% take rate) parental CT-26 and CT-26 KRASp.G12C tumors grew (FIG. 50G). Splenocytes harvested from the cured mice were stimulated with either CT-26, CT-26 KRASp.G12C, or 4T1 tumor cells, and levels of secreted IFN-γ were measured as a marker of tumor-specific T cell priming and activity. CT-26 KRASp.G12C cells and parental CT-26 cells caused a ~3-fold increase in IFN-γ which was not induced by 4T1 cells (FIG. 45G).

Discussion

The discovery of a novel interaction with the H95 groove of KRAS$^{G12C}$ enabled markedly increased potency and the identification of AMG 510, a first-in-class oral KRAS$^{G12C}$ inhibitor with evidence of clinical activity in patients. AMG 510 selectively targets KRAS p.G12C tumors and combines with cytotoxic and targeted agents to synergistically kill tumor cells. AMG 510-induced tumor cell death led to an inflamed tumor microenvironment that was exquisitely responsive to immune-checkpoint inhibition. Combination treatment of anti-PD-1 and MEKi has shown compelling preclinical efficacy in several reports, and this was associated with increased T cell infiltration. In the present study, immune cell infiltration after selective KRAS$^{G12C}$ inhibition was significantly more robust than that induced by MEKi. In contrast to the reported effects of non-tumor-selective MEKi which block T cell expansion and priming, selective inhibition of KRAS$^{G12C}$ by AMG 510 resulted in increased T cell priming. These data support a model of enhanced antigen recognition and T cell memory whereby AMG 510-induced tumor cell death, combined with anti-PD-1 treatment, results in an adaptive immune response such that non-p.G12C tumors are recognized and eradicated. There is ample evidence that intra-tumoral KRAS mutation status can be heterogeneous, both within the same tumor as well as between primary and metastatic sites. Taken together, our data suggests that AMG 510 might be an effective anti-tumor agent even in settings where KRAS$^{G12C}$ expression is heterogenous.

Methods

Recombinant Proteins

Recombinant His-tagged human KRAS$^{G12C/C118A}$ (1-169), GST-human c-RAF (1-149), and His-tagged human KRAS$^{C118A}$ (1-169) were expressed in *Escherichia coli* and purified using affinity chromatography and size-exclusion chromatography. Recombinant His-tagged human SOS1 (564-1049, insect codon optimized) was expressed in *Trichoplusia ni* and purified using affinity chromatography; after removal of the His-tag, it was further purified by size-exclusion chromatography. A cysteine-light mutant construct was used for co-crystallization studies based on the work of Ostrem et al[15]. Recombinant His-tagged human KRAS$^{G12C/C51S/C80L/C118S}$ (1-169) was expressed in *E. coli* and purified using affinity chromatography, ion-exchange chromatography, and size-exclusion chromatography, with the His-tag removed for crystallization.

Compounds and Antibodies

ARS-1620, PD-0325901, trametinib, afatinib, erlotinib, RMC-4550, and AZD5363 were obtained from commercial sources. AMG 511 was synthesized in-house. Synthesis of AMG 510 and its nonreactive propionamide are described herein Stocks of AMG 510 and all other inhibitors used for in vitro experiments were prepared as 10 mM solutions in 100% dimethyl sulfoxide (DMSO). For in vivo studies, AMG 510 and the MEKi (PD-0325901) were formulated in 2% HPMC, 1% Tween 80 and administered via oral gavage daily at 10 mL/kg. Carboplatin stock solution at 10 mg/mL was further diluted to 5 mg/mL or 3 mg/mL in 1% PBS and administered by intraperitoneal injection (IP) once per week. The rat anti-mouse PD1 clone 29F.1A12 was chimerized to contain a mouse IgG1 backbone. In addition, the Fc receptor silencing mutation N297G was introduced into the IgG heavy chain region to reduce effector function. Anti-PD-1 antibody, 29F.1A12, was diluted in 1×PBS to a concentration of 500 μg/mL and administered once every 3 days for a total of 3 injections by I.P. All antibodies used in western blotting were purchased from Cell Signaling, except for anti-RAS (Abcam), anti-phospho-ERK1/2 (ThermoFisher Scientific), and anti-beta-actin-HRP (Sigma).

Cell Lines

All cell lines were purchased from American Type Culture Collection (ATCC), except for KM12 and NCI-H3122, which were obtained from the National Cancer Institute. Cell lines were authenticated by short tandem repeat (STR) profiling. To improve in vivo growth kinetics, MIA PaCa-2 T2 and SW480-1AC cells were generated by passaging MIA PaCa-2 and SW480 cells, respectively, in mice. CT-26 KRASp.G12C cells were generated from the murine CT-26 colorectal line using CRISPR technology to replace both KRASp.G12D alleles with p.G12C (ThermoFisher Scientific). Clone H10 was determined to be homozygous for the KRASp.G12C allele, was identified as CT-26 KRASp.G12C-H10, and is referred to as CT-26 KRASp.G12C. All cell lines were cultured in RPMI 1640 medium supplemented with 10% fetal bovine serum and 1×penicillin/streptomycin/L-glutamine at 37° C., 5% $CO_2$ in a humidified incubator.

X-Ray Crystallography

Purified un-tagged KRAS$^{G12C/C51S/C80L/C118S}$ ("KRAS") in 20 mM HEPES pH 7.5, 150 mM NaCl was concentrated to 40 mg/mL and added to a two-fold molar excess of solid AMG 510 compound dissolved in DMSO. The protein-complex sample was placed on an orbital shaker at RT for 16 hours, and subsequently spin-filtered. Co-crystallization was performed using sitting drop vapor diffusion method. "KRAS"-AMG 510 protein-complex sample and crystallization buffer (1 mM $MgCl_2$, 0.1 M MES pH 6.5, 30% w/v polyethylene glycol 4000) were mixed. Flattened rod-shaped crystals appeared in one day at 20° C.

A crystal was equilibrated in the crystallization buffer as a cryoprotectant, prior to freezing in liquid nitrogen. The data set was collected on a Pilatus 6M silicon pixel detector at the Advanced Light Source Beamline 5.0.1 at wavelength 0.97741 Å and temperature 100K. The data were integrated and scaled using HKL2000. The crystal belongs to the orthorhombic space group P212121 with unit cell dimensions of a=40.9 Å, b=58.4 Å, c=65.9 Å, α=90°, β=90°, γ=90° (See Supplementary Table 2). The structure was solved by molecular replacement using MolRep, with an apo KRAS structure as a search model. There is one protein molecule in the asymmetric unit. The structure was refined using Refmac5, and model building was performed using the graphics program Coot. The ligand was generated using PRODRG. The structure of $KRAS^{G12C/C51S/C80L/C118S}$ bound to GDP and AMG 510 was refined to 1.65A with an R-factor of 18.1% and $R_{free}$ of 21.5%. Ramachandran statistics were 98.2% favored, 1.8% allowed, with no outliers. Amino acid residues 105-107 were unresolved in the crystal structure. The atomic coordinates and structure factors will be deposited in the Protein Data Bank (PDB ID code: not yet assigned).

Coupled Nucleotide Exchange Assays

The inhibition of the SOS1-catalyzed nucleotide exchange activity of $KRAS^{G12C/C118A}$ or $KRAS^{C118A}$ was measured using Alpha (Amplified Luminescent Proximity Homogeneous Assay) technology. 20 nM GDP-bound human $KRAS^{G12C/C118A}$ or $KRAS^{C118A}$ protein was incubated with two-fold serially-diluted AMG 510 or DMSO for 5 minutes at room temperature (RT) in reaction buffer (25 mM HEPES, pH 7.4; 10 mM $MgCl_2$; 0.01% Triton X-100). For all subsequent steps, DTT was added to the reaction buffer at a final concentration of 1 mM. Next, GTP and SOS-1 were added in DTT-reaction buffer at final concentrations of 1.25 mM or 500 nM, respectively, and incubated at RT for 30 minutes. Finally, c-RAF RBD (50 nM final), Alpha glutathione donor beads (PerkinElmer; 20 µg/mL final), and AlphaLISA® nickel chelate acceptor beads (PerkinElmer; 20 µg/mL final), all diluted in DTT-reaction buffer, were added. The reaction mixture was incubated at RT for 5 min, and then the plates were read on an EnVision® Multilabel Reader using the AlphaScreen protocol. Luminescence signal was measured at 570 nm following a 180 ms excitation at 680 nm. Signal intensity corresponded with the association of c-RAF RBD with GTP-bound $KRAS^{G12C/C118A}$ or $KRAS^{C118A}$ and was normalized to DMSO control.

ERK1/2 Phosphorylation Assays

For cellular assays, 2.5E+04 cells were seeded per well in 96-well plates and incubated at 37° C., 5% $CO_2$, o/n. The following day, 3-fold serially-diluted compound or DMSO was added to the cells, and the plates were incubated at 37° C., 5% $CO_2$ for 2 hours. Following treatment, the cells were washed with ice-cold PBS and lysed in RIPA lysis buffer (50 mM Tris-HCl, pH 7.5; 1% Igepal; 0.5% sodium deoxycholate; 150 mM NaCl; 0.10% sodium dodecyl sulfate) containing protease and phosphatase inhibitors. Basal ERK1/2 phosphorylation levels were measured in treated cell lysates using phospho-ERK1/2 whole cell lysate kits (Meso Scale Discovery) according to the manufacturer's protocol. Signal intensity corresponded with phospho-ERK1/2 levels and was normalized DMSO control.

For tumor cell lysates from in vivo pharmacodynamic assays, 50 µg of total protein per sample was analyzed using phospho-ERK1/2 and total ERK1/2 whole cell lysate kits (Meso Scale Discovery) according to the manufacturer's protocol. Phospho-ERK1/2 signal was normalized to total ERK1/2 signal for a given sample, and % inhibition of ERK phosphorylation was calculated relative to the vehicle group.

Cell Viability Assays

For adherent viability assays, 0.5-1.0E+03 cells were seeded per well in 384-well plates (or 2.5-4.0E+04 cells per well in 96-well plates) and incubated at 37° C., 5% $CO_2$, o/n. The following day, serially-diluted compound or DMSO was added to the cells, and the plates were incubated at 37° C., 5% $CO_2$ for 72 hours. Cell viability was measured using a CellTiter-Glo® Luminescent Cell Viability Assay kit (Promega) according to the manufacturer's protocol. The luminescence signal of treated samples was normalized to DMSO control.

For spheroid viability assays, 2.5-4.0E+04 cells were seeded per well in 96-well spheroid microplates (Corning) and incubated at 37° C., 5% $CO_2$ for 24 hours. The same procedure was followed as described above, except viability was measured using a CellTiter-Glo® 3D Cell Viability Assay kit (Promega) according to the manufacturer's protocol.

Synergistic Combination Studies

Combination experiments to assess synergistic interactions of AMG 510 with other inhibitors in vitro were carried out as previously described (Saiki, A. Y. et al. MDM2 antagonists synergize broadly and robustly with compounds targeting fundamental oncogenic signaling pathways. *Oncotarget* 5, 2030-2043, doi:10.18632/oncotarget.1918 (2014)).

Kinetic Analyses

Formation of covalent inhibitor-$KRAS^{G12C}$ adducts was measured using MS as previously described[44]. Relative % bound values for various inhibitor concentrations at various incubation times were fit to an exponential equation to generate $k_{obs}$ values for each concentration tested using Prism (GraphPad Software). The resulting $k_{obs}$ values were then replotted versus inhibitor concentration to generate $k_{inact}$ and $K_i$ values.

To determine the kinetic values of covalent inhibitor-$KRAS^{G12C}$ adduct formation in cells, basal ERK1/2 phosphorylation levels were measured following treatment with various inhibitor concentrations at various incubation times exactly as described above, and % activity values were used for the kinetic calculations.

Cysteine Proteomic Analysis

Human non-small cell lung cancer NCI-H358 cells were seeded at 2.0E+06 cells/10 cm plate and incubated at 37° C., 5% $CO_2$, o/n. The following day, the cells were treated with 1 µM AMG 510 or DMSO (n=5) and incubated at 37° C., 5% $CO_2$ for 4 hours. Following treatment, the cells were washed with ice-cold PBS containing protease inhibitors and then removed from the plates. Snap-frozen cell pellets were processed at IQ Proteomics, LLC by mass spectrometry (MS) according to their protocol as that described by Patricelli et al. Briefly, cell pellets were lysed and treated with 100 µM desthiobiotin iodoacetamide to label remaining unreacted solvent exposed cysteines. Following trypsin digestion, the peptide mixture generated from each sample was labeled with TMT-10 plex (Tandem Mass Tag) isobaric label reagents (ThermoFisher Scientific). After labeling, the samples were mixed prior to enrichment of the desthiobiotinylated peptides using high-capacity streptavidin agarose. The enriched peptides were analyzed by nano-LC-MS using a three-hour gradient and synchronous precursor selection (SPS)-based MS3 method on an Orbitrap Lumos mass spectrometer (ThermoFisher Scientific). Identification of desthiobiotinylated peptides was obtained by database searching via a custom informatics pipeline developed in the Gygi Lab at Harvard Medical School that utilizes SEQUEST. All spectra were searched against a Human Uniprot (2018) protein sequence database that was appended with the mutant KRAS$^{G12C}$ protein sequence and common contaminants. Peptides and proteins were filtered to a 1% false discovery rate (FDR), and only those peptides that met the criterion of minimum signal-to-noise ratio of 200 and isolation purity greater than 50% were used for quantitative analysis. All data processing for statistical analysis was performed in Microsoft Excel using normalized peak abundances of the cysteine-containing peptides. Log$_2$-fold changes were calculated between DMSO control and AMG 510-treated sample groups. A two-tailed t test for each peptide was performed to assess the statistical significance of difference between treated and DMSO control sample groups assuming equal variance. A volcano plot showing negative log$_{10}$ p-values was plotted against the log 2-fold changes for each desthiobiotinylated cysteine-containing peptide. Peptides which displayed a log 2-fold decrease in abundance greater than 2 and a p-value less than 0.0001 were designated as covalent targets of AMG 510 (n=5 biological replicates).

Animal Studies

All animal experimental procedures were conducted in accordance with the guidelines of the Amgen Animal Care and Use Committee and the Association for Assessment and Accreditation of Laboratory Animal Care standards. All studies utilized 4- to 7-week-old female athymic nude or female Balb/c mice (Charles River Laboratories). The athymic nude mice were housed five per filter-capped cage in sterile housing, and the Balb/c mice were housed five per filter-capped cage, non-sterile housing in an environmentally controlled room (temperature 23±2° C., relative humidity 50±20%) on a 12-hour light/dark cycle. The mice were fed commercial rodent chow.

Gene Expression Analysis

Total RNA was purified by RNeasy Mini kits (QIAGEN) from CT-26 KRASp.G12C tumors that were treated with vehicle orally, AMG 510 orally (100 mg/kg QD) or MEKi orally (PD-0325901, 10 mg/kg QD) for two days (n=5/group). RNA was quantified by DropSense 96 (PerkinElmer Inc). 300 ng RNA was run on a nCounter™ (NanoString Technologies) with a mouse pan-cancer immune profiling panel containing 750 target genes, 20 housekeeping genes, 8 internal negative controls, and 6 internal positive controls. Raw data were quality controlled, normalized, and analyzed by nSolver software (NanoString Technologies). Raw data were log 2 transformed, and statistical analyses were performed. Pathway scores (Interferon score, Antigen Processing Score, MHC score, TLR score and T Cell Function Score) and cell profiling scores (NK Cell Score, Cytotoxic Cell score and CD45 Score) were generated by nSolver Advanced Analysis (NanoString Technologies).

See Supplementary Table 3A, Table 3B, Table 3C, Table 3D and Table 3E for detailed list of genes included in each score, and p values used to calculate pathway and cell profiling scores.

Tumor Pharmacodynamic Assay

The effect of AMG 510 on ERK1/2 phosphorylation was evaluated in MIA PaCa-2 T2, NCI-H358, and CT-26 KRAS p.G12C tumor bearing mice. MIA PaCa-2 T2 or NCI-H358 tumor cells (5.0E+06 cells) were injected subcutaneously into the flank of female athymic nude mice in a 2:1 ratio of cells to Matrigel (BD Bioscience, San Jose, CA). Mice received a single oral dose of either vehicle or AMG 510 (0.3, 1, 3, 10, 30 and 100 mg/kg) when the average tumor size reached ~300-600 mm$^3$ (n=3/group) and harvested 2 hours later. A single oral dose of AMG 510 (10 mg/kg) was used for the time course studies. Female Balb/c mice were injected subcutaneously with CT-26 KRASp.G12C tumor cells (3.0E+05 cells). Mice were randomized into groups (n=3/group) when tumor volumes averaged 486 mm$^3$ and received a single oral dose of either vehicle or AMG 510 (3, 10, 30, or 100 mg/kg), or MEKi (PD-0325901, 10 mg/kg) and harvested 2 hours later. For all studies, plasma and tumor were analyzed to determine test article concentrations. Tumor samples were also collected at the indicated times, snap frozen in liquid nitrogen and processed for bioanalysis or pulverized using a cryoPREP® Dry Impactor (Covaris). Pulverized samples were resuspended in RIPA lysis buffer containing protease and phosphatase inhibitors and homogenized. Cleared lysates were then assayed for ERK1/2 phosphorylation levels as described above and for covalent modification of KRAS$^{G12C}$ by MS.

Xenograft and Syngeneic Studies

MIA PaCa-2 T2, NCI-H358, or SW480-1AC cells (5.0E+06 cells with Matrigel at a ratio of 2:1) were injected subcutaneously in the flank of female athymic nude mice (n=10/group). Treatment began when tumors were established and approximately 170 mm$^3$ for the MIA PaCa-2 T2 and NCI-H358 studies, or approximately 200 mm$^3$ for the SW480-1AC model. In the dose response studies; mice received either vehicle orally (QD) or AMG 510 orally (3, 10, 30 and 100 mg/kg QD). In the NCI-H358 combination study with AMG 510 and carboplatin, mice were randomized into 8 groups (n=10/group) and received either vehicle orally (QD)+PBS intraperitoneally (1×/week); AMG 510 orally (10 or 30 mg/kg QD)+PBS intraperitoneally (1×/week); vehicle orally (QD)+carboplatin (50 or 100 mg/kg) intraperitoneally (1×/week); AMG 510 orally (10 or 30 mg/kg QD)+carboplatin (50 or 100 mg/kg) intraperitoneally (1×/week). For the combination study with AMG 510 and MEKi, mice were randomized into 4 groups n=10/group and received either vehicle orally (QD); AMG 510 orally (10 mg/kg QD); MEKi orally (1 mg/kg QD); AMG 510 orally (10 mg/kg QD)+MEKi orally (1 mg/kg QD). For the syngeneic studies, CT-26 KRASp.G12C cells (3.0E+05 cells) were injected subcutaneously in the flank of female Balb/c mice. Treatment began when tumors were established and approximately 170 mm$^3$ for the dose response studies and approximately 130 mm$^3$ for the combination study, n=10/group; except for the MEKi dose response study where n=8/group. In the dose response studies, mice received either vehicle orally (QD), AMG 510 orally (3, 10, 30 and 100 mg/kg QD) or MEKi (PD-0325901) orally (1, 3 or 10 mg/kg QD). In the combination study, mice were randomized into 4 groups of n=10/group and received either vehicle orally (QD)+PBS intraperitoneally (Q3Dx3); AMG 510 orally (100 mg/kg QD)+PBS intraperitoneally (Q3Dx3); vehicle orally (QD)+anti-PD-1 antibody (29F.1A12; 100 µg/dose, Q3Dx3) intraperitoneally; AMG 510 orally (100 mg/kg QD)+anti-PD-1 antibody (29F.1A12; 100 µg/dose, Q3Dx3) intraperitoneally from Day 15 through Day 43. Combination treatment studies were performed in a blinded manner. Tumor dimensions were assessed twice weekly with Pro-Max electronic digital caliper (Japan Micrometer Mfg. Co. LTD), and tumor volume was calculated using the formula: length×width×height and expressed as mm$^3$. In the KRASp.G12C lung PDX models, mice were implanted subcutaneously with tumor chunks ~70 mg in size. Mice were randomized when tumor volumes were approximately 160-200 mm$^3$ and received either vehicle orally (QD) or AMG 510 orally (100 mg/kg QD) the day after randomization. Tumor dimensions were collected twice weekly using the formula: width$^2$×length×0.52 and expressed as mm$^3$. Data are expressed as mean±SEM.

AMG 510-KRAS$^{G}$12C Conjugate Detection

Anti-human RAS (anti-RAS) antibody was purchased from Abcam and biotinylated with EZ-Link NHS-PEG4-Biotin (ThermoFisher Scientific) using the protocol described by the vendor. Residual biotin was removed, and the resulting biotin-anti-RAS was loaded onto Dynabeads® MyOne™ Streptavidin C1 beads (ThermoFisher Scientific) at a 1:1 ratio for an hour at RT with shaking. Lysates from in vitro-treated cells or in vivo-treated tumor cells described previously were incubated with biotinylated anti-RAS beads for 3 hours at RT with shaking. Using a magnet, beads were washed with PBST (3×), followed by PBS (1×), and then water (1×). Samples were eluted from the beads using 2% aqueous formic acid/10% aqueous acetonitrile, followed by incubation at RT with shaking for 10 minutes. The supernatant was transferred to a 96-well plate and dried. Samples were resuspended in a denaturation buffer (10 mM TCEP, 8 M urea) and incubated at 65° C. with shaking for 15 minutes. Iodoacetamide (40 mM) was added and incubated at 37° C. for 30 minutes, protected from light. 50 mM $NH_4HCO_3$ and trypsin (0.01 µg/µL) were added, and samples were digested overnight at 37° C. for ~16-20 hours, then finally quenched with formic acid to give a final concentration of 1% (v:v). Samples were analyzed by liquid chromatography-tandem mass spectrometry (LC-MS/MS) by multiple reaction monitoring (MRM) in positive ion electrospray mode using a 6500 QTRAP (AB SCIEX) coupled to an Acquity UPLC (Waters). Samples were injected onto an Acquity UPLC BEH C8 1.7 µm, 2.1×100 mm column (Waters). The mobile phases consisted of mobile phase A (water+0.1% formic acid) and mobile phase B (acetonitrile+0.1% formic acid). The LC gradient was 5-50% B in 5 minutes, 50-95% B in 0.5 minutes and 95% B in 1 minute. The following peptides KRAS$^{G12C}$ LVVVGAC(CAM)GVGK (529.8→846.3) and AMG 510 modified-KRAS$^{G12C}$ AMG 510-LVVVGAC(CAM)GVGK (521.4→675.2) were monitored. The occupancy was calculated as a percentage of AMG 510 modified-KRAS$^{G12C}$ peptide normalized to the sum of unmodified and modified KRAS$^{G12C}$ peptide.

Flow Cytometry

For in vitro analysis of the effect of AMG 510 on MHC Class I antigen expression, CT-26 KRASp.G12C cells (5.0E+04 cells/well) were seeded in a 96-well plate and treated with a three-fold serial dilution of AMG 510 in the absence or presence of IFNγ at a final concentration of 25 or 250 µg/mL. Plates were incubated at 37° C., 5% $CO_2$ for 24 hours. Cells were non-enzymatically detached from the wells, washed with staining buffer (PBS/0.5% BSA), and then incubated with PE-conjugated H-2D$^d$, H-2K$^d$, or H-2L$^d$ antibodies (BioLegend) for 30 minutes on ice. After washing, cells were resuspended in staining buffer containing SYTOX Blue Dead Cell Stain (Life Technologies), and then analyzed by flow cytometry. Acquisition and analysis were performed on a BD LSRFortessa flow cytometer using BD FACSDiva software.

For in vivo studies, CT-26 KRASp.G12C cells were implanted into Balb/c female mice at approximately 6 weeks of age. On day 22 following implantation, mice were randomized into a four-day dosing cohort consisting of 5 groups of n=8/group receiving either vehicle orally (QD)+ PBS intraperitoneally (Q3Dx2); AMG 510 orally (100 mg/kg QD)+PBS intraperitoneally (Q3Dx2); vehicle orally (QD)+anti-PD-1 antibody (29F.1A12; 100 µg/dose, Q3Dx2) intraperitoneally; AMG 510 orally (100 mg/kg QD)+anti-PD-1 antibody (29F.1A12; 100 µg/dose, Q3Dx2) intraperitoneally; or with the MEKi orally (10 mg/kg, QD)+PBS intraperitoneally (Q3Dx2) for 4 days. After four days of dosing, tumors were harvested and dissected from the surrounding fascia, weighed, mechanically minced, and placed in Liberase TL (0.2 mg/ml, Roche) and DNase I (20 µg/ml, Ambion). Tumor solutions were then mechanically homogenized using a gentle MACS Dissociator (Miltenyi Biotech) and incubated at 37° C. for 15 minutes on a MACSmix Tube Rotator (Miltenyi Biotech). Cells were then treated with 0.02% EDTA (Sigma) and heat-inactivated FBS (ThermoFisher Scientific) and passed through a 70 µm filter to remove clumps. Cells were then centrifuged, the supernatant was discarded, and the cell pellets were then resuspended in LIVE/DEAD Fixable Blue Dead Cell Stain (ThermoFisher Scientific) for 30 minutes. Cell surface staining was then performed with the indicated antibodies (Supplementary Table 4) before fixation and permeabilization of the cells (Intracellular Fixation & Permeabilization Buffer Set, eBiosciences) for intracellular staining. CountBright™ Absolute Counting Beads (ThermoFisher Scientific) were added to each sample well to allow cell counting before analysis on an LSR II flow cytometer (BD Biosciences). All analyses were done with FlowJo software v10 (FlowJo). Absolute cell counts were determined by normalizing cell numbers to beads recorded, divided by the volume of tumor aliquot analyzed and the mass of the tumor.

Enzyme-Linked ImmunoSpot (ELISpot) Assays

The antigen-specific T cell response was assessed using an IFN-γ ELISpot assay (Cellular Technology Ltd.). Splenocytes were harvested (n=4-5/group) and used in a whole-cell ELISpot assay. Briefly, 2.5E+05 splenocytes were mixed with 2.5E+04 CT-26, CT-26 KRASp.G12C or 4T1 tumor cells and incubated at 37° C. for 20 hours. A CTLS6 Fluorospot analyzer (Cellular Technology Ltd.) was used to enumerate spots.

Statistical Analysis

Pharmacodynamic experiments were analyzed by One-way ANOVA followed by Dunnett's post-hoc. For efficacy studies, repeated measures analysis of variance (RMANOVA) was conducted followed by Dunnett's post-hoc test using GraphPad Prism 7.04. Regression analysis was conducted by paired t-test. Statistical analysis for survival was determined by Kaplan-Meier estimator with Mantel-Cox log-rank to compare curves using GraphPad Prism 7.04. Flow cytometry data were analyzed by two-way ANOVA multiple comparisons followed by Tukey's post-hoc test. NanoString data were analyzed by one-way ANOVA multiple comparisons followed by Tukey's post-hoc test. ELISpot data comparisons were performed by unpaired t-test using GraphPad Prism.

LC-MS/MS Bioanalytical Methods for AMG 510

Tumor tissue homogenates were prepared by adding water to tissue (4:1 mL:g) using tungsten carbide beads in a TissueLyzer (Qiagen). To 20 µL of sample (plasma or tumor tissue homogenate), 100 µL acetonitrile containing IS (200 ng/mL tolbutamide) was added, the sample was vortexed for 10 min, centrifuged at 3500 g for 10 min, and 90 µL of supernatant was collected. To the collected supernatant 100 µL of water (containing 0.1% formic acid) was added, and 5 µL of the resulting solution was injected onto the LC-MS/MS system. Chromatographic separations were achieved using a Phenomenex Kinetex C18 50×2.1 mm, 2.7 µm, maintained at 50° C., using 0.1% formic acid in $H_2O$ (mobile phase A) and 0.1% formic acid in acetonitrile (mobile phase B). The chromatography gradient was run as follows: isocratic from 0 min to 0.1 min with 10% mobile phase B, linear increase from 0.1 to 0.85 min to 95% mobile phase B, isocratic hold from 0.85 to 1.10 min with 95% mobile phase B, linear decrease from 1.10 to 1.11 min to 10% mobile phase B, isocratic hold from 1.11 to 1.40 min with 10% mobile phase B. An API 4000 mass spectrometer was typically used for analysis and run in positive mode ESI following the MS/MS transition of 561.179>134.100 (AMG 510) and 271.100>134.100 (tolbutamide). Peak areas were integrated using Analyst® (Sciex). Following peak area integration, the data were exported to Watson LIMS™ (ThermoFisher Scientific) and concentrations were determined by a weighted ($1/x^2$) linear regression of peak area ratios (peak area of AMG 510/peak area of IS) versus the nominal concentrations of the plasma calibration standards. The calibration range for AMG 510 in plasma was 1.0 to 10,000 ng/mL (LLOQ 1.0 ng/mL). The calibration range for AMG 510 in tumor tissue homogenate was 5.0 to 50,000 ng/mL (LLOQ 5.0 ng/mL).

Stable Isotope Labeling by Amino Acids in Cell Culture (SILAC)

Light Medium (LM) was prepared by adding the following components to final volume of 1 L: 100 mL dialyzed FBS, 10.4 g powdered RPMI-1640 medium, 2 g sodium bicarbonate, 200 mg L-arginine, 48 mg L-lysine, 100 mg L-leucine, and 1×Pen-Strep, which was filtered with 0.22 μm filter system. Heavy Medium (HM) was prepared identically to LM, but 100 mg [$^{13}C_6$]-L-leucine (Cambridge Isotope Laboratories) was substituted for the non-isotopically enriched L-leucine. MIA PaCa-2 and NCI-H358 cells were seeded (3E+05 cells) into T75 flasks with LM; LM was changed daily. After 48 hours, the cells were washed with 1×PBS, and the media was switched to HM; HM was changed daily for 4 days. On Day 6, the cells were washed with 1×PBS and the media was switched to LM; LM was changed daily. Starting on Day 6, the MIA PaCa-2 samples were collected at 0, 1, 3, 6, 9, 12, 15, 18, 21, 24, 30, 36, 48, and 72 h. Starting on Day 6, the NCI-H358 samples were collected at 0, 3, 6, 9, 12, 24, 36, 48, 72, and 96 h. Separate T75 flasks, prepared in triplicate were collected at each timepoint and processed to lysates.

SILAC Sample Collection and Preparation of Lysate Protein

T75 flasks were washed with 1×PBS, treated with trypsin and incubated for 2 min followed by the addition of ice-cold PBS containing 10% dialyzed FBS. Cells were mixed well and collected, followed by cell counting using a Vi-CELL XR. The remaining cells were centrifuged and washed with ice-cold PBS (no $Mg^{+2}$, no $Ca^{+2}$). Cells were centrifuged again, PBS was removed, and the cells were lysed in a small volume of ice-cold RIPA containing phosphatase (PhosS-TOP, Roche) and protease (cOmplete EDTA-free, Roche) inhibitors. Resulting lysates were vortexed, put on ice for 10 minutes, centrifuged to remove insoluble debris, and then stored at −80° C. until further processing.

SILAC $KRAS^{G12C}$ Target Half-Life Determination

Anti-human RAS (anti-RAS) antibody was purchased from Abcam and biotinylated with EZ-Link NHS-PEG4-Biotin (ThermoFisher Scientific) using the protocol described by the vendor. Residual biotin was removed, and the resulting biotin-anti-RAS was loaded onto Dynabeads® MyOne™ Streptavidin C1 beads (ThermoFisher Scientific) for 1.5 h at RT with shaking. Cell lysate (described above) were incubated with biotinylated anti-RAS beads for 2 hours at RT with shaking. Using a magnet, beads were washed with PBST (3×), followed by PBS (1×). Samples were eluted from the beads using 3% aqueous formic acid/30% aqueous ACN, followed by incubation at RT with shaking for 10 min. The supernatants were transferred to a 96-well plate and dried. Samples were resuspended in a denaturation buffer (10 mM TCEP, 8 M urea) and incubated at 37° C. for 1 h using a water bath. Iodoacetamide (40 mM) was added and incubated at 25° C. for 1 h, protected from light. 50 mM $NH_4HCO_3$ and trypsin (0.1 μg/μL) were added, and samples were digested at 37° C. for 24 hours, then quenched with formic acid to give a final concentration of 1% (v:v). The samples were concentrated to approximately 80 μL before analysis by mass spectrometry. Samples were analyzed by liquid chromatography-tandem mass spectrometry (LC-MS/MS) by multiple reaction monitoring (MRM) in positive ion electrospray mode using a 6500 QTRAP (AB SCIEX) coupled to an Acquity UPLC (Waters). Samples were injected to an Acquity UPLC BEH C8 1.7 μm, 2.1×100 mm column (Waters). The mobile phases consisted of mobile phase A (water+0.1% formic acid) and mobile phase B (acetonitrile+0.1% formic acid). The LC gradient was 5-50% B in 5 minutes, 50-95% B in 0.5 minutes and 95% B in 1 minute. The following peptides for $KRAS^{G12C}$ (LVVVGAC(CAM)GVGK (529.8→846.3) & 13C-LVVVGAC(CAM)GVGK (532.8→846.3)) and RAS WT (LVVVGAGGVGK (478.3→743.2) & 13C-LVVVGAGGVGK (481.3→743.2)) were used to monitor the transition from heavy to light labeling. The Relative Isotope Abundance (RIA) was determined using the following formula:

$$RIA = \frac{A_{heavy}}{A_{light} + A_{heavy}}$$

SILAC Determination of $KRAS^{G12C}$ Half-Life

To account for the impact of cell growth on the determination of protein half-life, cell numbers and RIA data associated with each timepoint were simultaneously fit to a series of equations to determine the half-life of $KRAS^{G12C}$ in MIA PaCa-2 and NCI-H358 cells. The following equations were used:

First Order Equation for Heavy Peptide:

$$\frac{d\,Hv}{dt} = -k_{dec}Hv$$

First Order Equation for Light Peptide:

$$\frac{d\,lt}{dt} = k_{dec}(Hv_0 + lt_0) - k_{dec}lt + \frac{\text{cell}_{new}}{\text{cell}_{(0)}}(Hv_0 + lt_0)k_{dec} - k_{dec}\frac{\text{cell}_{new}}{\text{cell}_{(0)}}lt$$

First Order Equation for Cell Growth:

$$\frac{d\,\text{cell}_{new}}{dt} = -k_{dil}(\text{cell}_{(0)} + \text{cell}_{new})$$

Additional Equations:

$$k_{syn} = k_{dec}(Hv_0 + lt_0)$$

$$\text{Half life} = \frac{0.693}{k_{dec}}$$

Time 0 is defined as time when HM was changed to LM, Hv is the concentration of heavy peptide, lt is the concentration of light peptide, $cell_{new}$ is the number of new cells, $k_{dec}$ is the first-order rate constant for degradation, $k_{syn}$ is the zero-order rate constant for synthesis, $k_{dil}$ is the first-order cell growth constant, $cell_{(0)}$ is the number of cells at time 0, $Hv_{(0)}$ is the concentration of heavy peptide at time 0, $lt_{(0)}$ is the concentration of light peptide at time 0. A step-wise approach was used for modeling wherein in the first step $k_{dil}$ is estimated from the cell number and in the second step $k_{dec}$ is estimated using above equations.

$k_{dil}$ was estimated by quantifying the cell numbers after the change to LM and applying the following equation: $A = A_0 e^{-k_{dil} t}$ where A and $A_0$ represent the cell number at time t and 0, respectively.

Supplementary Table 1. Cellular assay data

| Mutation | Cell Line | Tissue of Origin | Basal p-ERK1/2 IC$_{50}$ (µM) | Cell Viability IC$_{50}$ (µM) | Spheroid Cell Viability IC$_{50}$ (µM) |
|---|---|---|---|---|---|
| KRAS p.G12C homozygous | MIA PaCa-2 | Pancreas | 0.036 ± 0.002 | 0.005 ± 0.001 | 0.001 ± 0.001 |
| | NCI-H1373 | Lung | 0.010 ± 0.0001 | 0.020 ± 0.006 | 0.005 ± 0.002 |
| | NCI-H2030 | Lung | 0.040 ± 0.020 | 0.006 ± 0.003 | ND |
| | NCI-H2122 | Lung | 0.123 ± 0.006 | 0.032 ± 0.005 | 0.009 ± 0.002 |
| | SW1463 | Colon | 0.033 ± 0.004 | 0.015 ± 0.007 | ND |
| | SW1573 | Lung | 0.027 ± 0.001 | >7.5 | >10 |
| | UM-UC-3 | Bladder | 0.029 ± 0.016 | 0.005 ± 0.001 | ND |
| KRAS p.G12C heterozygous | Calu-1 | Lung | 0.013 ± 0.004 | 0.004 ± 0.001 | ND |
| | NCI-H1792 | Lung | 0.045 ± 0.023 | 0.011 ± 0.008 | ND |
| | NCI-H23 | Lung | 0.090 ± 0.017 | 0.006 ± 0.001 | ND |
| | NCI-H358 | Lung | 0.035 ± 0.003 | 0.004 ± 0.001 | 0.003 ± 0.002 |
| | SW837 | Colon | 0.018 ± 0.002 | 0.009 ± 0.006 | ND |
| KRAS p.G12D homozygous | AsPC-1 | Pancreas | >10 | >7.5 | ND |
| KRAS p.G12D heterozygous | A-427 | Lung | >10 | >7.5 | ND |
| | LS 174T | Colon | >10 | >7.5 | ND |
| KRAS p.G12V homozygous | SW480 | Colon | >10 | >7.5 | ND |
| KRAS p.G12S homozygous | A549 | Lung | >10 | >7.5 | ND |
| KRAS p.G13C heterozygous | NCI-H1355 | Lung | >10 | >7.5 | ND |
| KRAS WT EGFR p.E746_A750del | HCC-827 | Lung | >10 | >7.5 | ND |
| KRAS WT EML4-ALK fusion | NCI-H1322 | Lung | >10 | >7.5 | ND |
| KRAS WT TPM3-NTRK fusion | KM12 | Colon | >10 | >7.5 | ND |
| KRAS WT BRAF p.V600E | COLO-205 | Colon | >10 | >7.5 | ND |

Mutation annotations were obtained from the Catalogue of Somatic Mutations in Cancer (COSMIC)[1] or Misale et al. 2019[2].
Mean IC$_{50}$ values for basal ERK1/2 phosphorylation and cell viability assays were obtained from at least n = 2 experiments.
ND = not determined Supplementary Table 2. Data collection and refinement statistics (molecular replacement)

| | KRAS$^{G12C/C51S/C80L/C118S}$ AMG 510 |
|---|---|
| Data collection | |
| Space group | P 21 21 21 |
| Cell dimensions | |
| a, b, c (Å) | 40.87, 58.42, 65.89 |
| α, β, γ (0) | 90. 90. 90 |
| Resolution (Å) | 30.0-1.65 (1.71-1.65) |
| R$_{sym}$ | 0.162 (0.521) |
| I/σI | 6.9 (2.5) |
| Completeness (%) | 97.0 (96.3) |
| Redundancy | 4.4 (4.2) |
| Refinement | |
| Resolution (Å) | 30.00-1.65 |
| No. reflections | 18077 |
| R$_{work}$/R$_{free}$ | 0.1809/0.2152 |
| No. atoms | 1613 |
| Protein | 1336 |
| Ligand/ion | 70 |
| Water | 207 |
| B-factors | 24.8 |
| Protein | 24.3 |

Supplementary Table 2. Data collection and refinement statistics (molecular replacement)

|  | KRAS$^{G12C/C51S/C80L/C118S}$ AMG 510 |
|---|---|
| Ligand/ion | 24.1 |
| Water | 34.1 |
| R.m.s. deviations |  |
| Bond lengths (Å) | 0.005 |
| Bond angles (°) | 1.08 |

One crystal data set was collected for this structure
*Values in parentheses are for highest-resolution shell.

Supplementary Table 3. Gene expression pathway score analysis Supplementary Table 3A

| Genes Involved in the T Cell Function Pathway Score Calculation | P-value | Genes Involved in the T Cell Function Pathway Score Calculation | P-value |
|---|---|---|---|
| STAT1 | 1.72E−09 | LCP1 | 1.20E−04 |
| H2-T23 | 2.70E−09 | IKZF2 | 1.46E−04 |
| ADA | 5.22E−09 | SOCS1 | 1.63E−04 |
| EGR1 | 7.09E−09 | TCF7 | 2.02E−04 |
| TGFB3 | 1.22E−08 | CEBPB | 2.26E−04 |
| TLR6 | 1.24E−08 | IL1R1 | 5.42E−04 |
| ITGA1 | 1.40E−08 | JAK3 | 6.60E−04 |
| THY1 | 1.65E−08 | PVRL2 | 6.90E−04 |
| NFATC2 | 2.31E−08 | CD1D1 | 8.57E−04 |
| H2-AB1 | 3.62E−08 | CD274 | 8.63E−04 |
| H2-AA | 4.93E−08 | ICOS | 9.52E−04 |
| CTSH | 5.80E−08 | TNFSF13B | 9.63E−04 |
| CD48 | 6.78E−08 | IL4RA | 1.02E−03 |
| ITGAL | 6.82E−08 | STAT4 | 1.07E−03 |
| CD74 | 7.35E−08 | FAS | 1.09E−03 |
| ITGAM | 8.78E−08 | LGALS3 | 1.18E−03 |
| IL2RG | 8.97E−08 | IL13RA1 | 1.28E−03 |
| H2-DMA | 1.33E−07 | IFNG | 1.29E−03 |
| CD83 | 1.41E−07 | FASL | 1.39E−03 |
| TNFRSF14 | 1.48E−07 | IRF4 | 1.47E−03 |
| MAF | 1.60E−07 | TRAF6 | 1.63E−03 |
| CD247 | 1.66E−07 | CD2 | 1.65E−03 |
| PTPRC | 1.70E−07 | TIGIT | 1.65E−03 |
| TAP1 | 2.32E−07 | TLR4 | 1.69E−03 |
| CD3G | 2.80E−07 | CD47 | 2.26E−03 |
| MILL2 | 3.39E−07 | VEGFA | 2.31E−03 |
| CD27 | 3.64E−07 | PDCD1LG2 | 2.47E−03 |
| LCK | 4.04E−07 | BCL6 | 2.48E−03 |
| CD3E | 4.62E−07 | IL12RB1 | 3.49E−03 |
| SPP1 | 5.19E−07 | RORA | 3.60E−03 |
| IKZF1 | 5.24E−07 | NFKB1 | 3.96E−03 |
| CCR2 | 7.34E−07 | CXCL12 | 4.63E−03 |
| ZAP70 | 7.73E−07 | RIPK2 | 4.83E−03 |
| NFATC1 | 8.07E−07 | GFI1 | 4.88E−03 |
| LAG3 | 8.54E−07 | IL15 | 5.01E−03 |
| IRF1 | 8.95E−07 | IL12B | 5.09E−03 |
| SYK | 9.31E−07 | IL2RA | 5.56E−03 |
| IRF8 | 1.17E−06 | CD276 | 6.24E−03 |
| PSMB10 | 1.17E−06 | BTLA | 6.27E−03 |
| XCL1 | 1.36E−06 | FOXP3 | 6.70E−03 |
| PVR | 1.54E−06 | ANXA1 | 7.25E−03 |
| CXCR3 | 1.54E−06 | SOCS3 | 7.29E−03 |
| CD3D | 1.56E−06 | CD40 | 7.52E−03 |
| IL18R1 | 1.93E−06 | CD80 | 1.21E−02 |
| EOMES | 1.95E−06 | MAPK1 | 1.22E−02 |
| PSEN2 | 2.40E−06 | MAP3K7 | 1.43E−02 |
| CCL5 | 3.67E−06 | TRP53 | 1.46E−02 |
| IFNAR1 | 3.85E−06 | TRAF2 | 1.59E−02 |
| JAK1 | 4.90E−06 | IL12RB2 | 1.78E−02 |
| CXCR4 | 4.94E−06 | NOS2 | 1.79E−02 |
| CARD11 | 6.83E−06 | TGFB1 | 2.02E−02 |
| ICAM1 | 6.84E−06 | JAK2 | 2.46E−02 |
| FCGR4 | 6.94E−06 | SPN | 2.48E−02 |
| IL1B | 7.10E−06 | YY1 | 2.53E−02 |
| CCL2 | 7.33E−06 | STAT6 | 2.90E−02 |
| CMA1 | 7.69E−06 | CCL3 | 2.97E−02 |
| H2-K1 | 9.48E−06 | MAPK8 | 3.73E−02 |
| VCAM1 | 1.03E−05 | IL7R | 5.28E−02 |
| IL6ST | 1.16E−05 | TNFSF11 | 5.45E−02 |
| BCL2 | 1.21E−05 | CCND3 | 6.50E−02 |
| ICOSL | 1.35E−05 | TNF | 1.23E−01 |
| TYK2 | 1.57E−05 | CSF2 | 1.54E−01 |
| ITGB2 | 1.62E−05 | RELB | 1.55E−01 |
| CD86 | 1.68E−05 | CCL11 | 1.73E−01 |
| IL18RAP | 1.72E−05 | SELL | 1.91E−01 |
| CCR5 | 1.74E−05 | ITGAX | 2.11E−01 |
| ITK | 1.84E−05 | CCR7 | 2.17E−01 |
| ITCH | 1.94E−05 | TNFRSF4 | 2.31E−01 |
| IL18 | 2.01E−05 | RPS6 | 2.43E−01 |
| CD8A | 2.41E−05 | HAVCR2 | 3.03E−01 |
| REL | 2.69E−05 | TNFSF18 | 3.43E−01 |
| CD8B1 | 3.06E−05 | FLT3 | 3.64E−01 |
| CD5 | 3.39E−05 | GZMB | 3.89E−01 |
| H2-D1 | 3.80E−05 | FUT7 | 4.36E−01 |
| STAT5B | 3.93E−05 | IDO1 | 4.69E−01 |
| PDCD1 | 5.10E−05 | CASP3 | 4.78E−01 |
| CCL7 | 5.31E−05 | CCR6 | 5.02E−01 |
| CREBBP | 5.39E−05 | TMED1 | 5.07E−01 |
| H2-M3 | 5.67E−05 | BCL10 | 5.21E−01 |
| CD4 | 5.83E−05 | CXCL13 | 6.89E−01 |
| TBX21 | 7.14E−05 | CD28 | 7.48E−01 |
| PSEN1 | 7.20E−05 | TNFSF14 | 7.51E−01 |
| GATA3 | 7.48E−05 | CTLA4 | 7.97E−01 |
| POU2F2 | 7.52E−05 | CD40LG | 8.17E−01 |
| TXK | 8.94E−05 | IL7 | 8.86E−01 |
| DPP4 | 9.70E−05 | RORC | 1.00E+00 |

Supplementary Table 3B

| Genes Involved in the Interferon Pathway Score Calculation | P-value | Genes Involved in the Interferon Pathway Score Calculation | P-value |
|---|---|---|---|
| GBP5 | 7.49E−09 | DDX58 | 1.73E−05 |
| IFIT3 | 2.66E−08 | IFIT2 | 5.17E−05 |
| H2-AB1 | 3.62E−08 | TBK1 | 5.83E−05 |
| H2-AA | 4.93E−08 | IFI35 | 7.52E−05 |
| IFI44L | 8.05E−08 | SH2D1B1 | 4.08E−04 |
| IFNAR2 | E13E−07 | IFITM2 | 5.30E−04 |
| IRGM2 | E18E−07 | IFI27 | 6.90E−04 |
| CIITA | E68E−07 | ULBP1 | 9.81E−04 |
| CD3E | 4.62E−07 | TMEM173 | 1.10E−03 |
| IFNGR1 | 5.77E−07 | H60A | 2.91E−03 |
| IFIH1 | 7.59E−07 | IFIT1 | 3.52E−03 |
| IRF8 | 1.17E−06 | IL12RB2 | 1.78E−02 |
| IRF7 | 1.19E−06 | NOS2 | 1.79E−02 |
| NLRC5 | 1.46E−06 | RUNX3 | 9.02E−02 |
| EOMES | 1.95E−06 | CCR7 | 2.17E−01 |
| IFNAR1 | 3.85E−06 | FADD | 2.37E−01 |
| CXCL16 | 6.82E−06 | IFITM1 | 6.10E−01 |
| IFI44 | 8.06E−06 | MAVS | 8.59E−01 |

Supplementary Table 3C

Genes Involved in the MHC Pathway Score Calculation

| Gene | P-value |
|---|---|
| H2-T23 | 2.70E−09 |
| KLRK1 | 3.47E−08 |
| H2-AB1 | 3.62E−08 |
| H2-EB1 | 4.45E−08 |
| H2-AA | 4.93E−08 |
| CTSH | 5.80E−08 |
| CD74 | 7.35E−08 |
| MR1 | 9.98E−08 |
| H2-DMA | 1.33E−07 |
| CIITA | 1.68E−07 |
| TAP1 | 2.32E−07 |
| FCER1G | 2.41E−07 |
| LAG3 | 8.54E−07 |
| CD160 | 1.02E−06 |
| FCGR3 | 1.13E−06 |
| NLRC5 | 1.46E−06 |
| FCGR1 | 1.50E−06 |
| TAPBP | 1.53E−06 |
| H2-K1 | 9.48E−06 |
| H2-D1 | 3.80E−05 |
| TAP2 | 4.89E−05 |
| PML | 5.37E−05 |
| H2-M3 | 5.67E−05 |
| FCGR2B | 6.05E−05 |
| H2-DMB1 | 1.80E−04 |
| CD1D1 | 8.57E−04 |
| H2-DMB2 | 1.17E−02 |
| H2-Q2 | 4.41E−02 |
| H2-OB | 1.92E−01 |
| CD40LG | 8.17E−01 |

Supplementary Table 3D

Genes Involved in the Antigen Processing Pathway Score Calculation

| Gene | P-value |
|---|---|
| H2-T23 | 2.70E−09 |
| H2-AB1 | 3.62E−08 |
| H2-EB1 | 4.45E−08 |
| H2-AA | 4.93E−08 |
| H2-EA-P | 4.94E−08 |
| NOD1 | 4.97E−08 |
| CD74 | 7.35E−08 |
| MR1 | 9.98E−08 |
| H2-DMA | 1.33E−07 |
| PSMB8 | 2.03E−07 |
| TAP1 | 2.32E−07 |
| FCER1G | 2.41E−07 |
| FCGR3 | 1.13E−06 |
| FCGR1 | 1.50E−06 |
| TAPBP | 1.53E−06 |
| PSMB9 | 2.02E−06 |
| SLC11A1 | 2.53E−06 |
| ICAM1 | 6.84E−06 |
| H2-K1 | 9.48E−06 |
| H2-D1 | 3.80E−05 |
| TAP2 | 4.89E−05 |
| H2-M3 | 5.67E−05 |
| FCGR2B | 6.05E−05 |
| H2-DMB1 | 1.80E−04 |
| CD1D1 | 8.57E−04 |
| H2-DMB2 | 1.17E−02 |
| H2-Q2 | 4.41E−02 |
| RELB | 1.55E−01 |
| H2-OB | 1.92E−01 |
| CCR7 | 2.17E−01 |
| NOD2 | 2.69E−01 |

Supplementary Table 3E

Genes Involved in the TLR Pathway Score Calculation

| Gene | P-value |
|---|---|
| TLR6 | 1.24E−08 |
| TICAM2 | 1.88E−08 |
| TLR7 | 4.46E−08 |
| TLR8 | 9.04E−08 |
| TLR9 | 1.23E−07 |
| TLR1 | 2.11E−07 |
| TLR2 | 3.63E−06 |
| CD86 | 1.68E−05 |
| TLR3 | 2.63E−05 |
| TBK1 | 5.83E−05 |
| IRAK2 | 1.44E−04 |
| PRKCE | 3.72E−04 |
| TICAM1 | 8.09E−04 |
| IRF4 | 1.47E−03 |
| TRAF6 | 1.63E−03 |
| TLR4 | 1.69E−03 |
| TLR5 | 1.90E−03 |
| MYD88 | 4.49E−03 |
| GFI1 | 4.88E−03 |
| MAP3K7 | 1.43E−02 |
| IRF3 | 3.71E−02 |
| MAPKAPK2 | 1.16E−01 |
| IRAK1 | 1.39E−01 |
| NFKBIA | 1.62E−01 |
| TRAF3 | 6.07E−01 |
| TIRAP | 9.18E−01 |

Supplementary Table 4. Flow cytometry antibodies

| Antibody | Clone | Catalog # | Supplier |
|---|---|---|---|
| BUV737 Rat Anti-Mouse CD4 | RM4-5 | 564933 | BD Biosciences |
| BV421 Rat Anti-Mouse CD8a | 53-6.7 | 563898 | BD Biosciences |
| BV510 Rat Anti-CD11b | M1/70 | 562950 | BD Biosciences |
| BUV737 Rat Anti-CD11b | M1/70 | 564443 | BD Biosciences |
| BV421 Hamster Anti-Mouse CD11c | HL3 | 562782 | BD Biosciences |
| BB700 Rat Anti-Mouse CD19 | 1D3 | 566411 | BD Biosciences |
| FITC Rat Anti-Mouse CD24 | M1/69 | 11-0242-81 | ThermoFisher Scientific |
| BV650 Rat Anti-Mouse CD25 | PC61 | 564021 | BD Biosciences |
| BV786 Mouse Anti-Mouse CD45.2 | 104 | 563686 | BD Biosciences |
| APC/Cy7 Rat Anti-Mouse CD90.2 | 30-H12 | 105328 | BioLegend |
| APC Hamster Anti-Mouse CD103 | 2E7 | 17-1031-80 | ThermoFisher Scientific |

| Supplementary Table 4. Flow cytometry antibodies | | | |
|---|---|---|---|
| Antibody | Clone | Catalog # | Supplier |
| PE Rat Anti-Mouse CD274 | MIH5 | 558091 | BD Biosciences |
| PE Hamster Anti-Mouse CD279 (PD-1) | J43 | 12-9985-82 | ThermoFisher Scientific |
| FITC Rat Anti-Mouse CD335 (NKp46) | 29A1.4 | 560756 | BD Biosciences |
| BV650 Rat Anti-Mouse F4/80 | BM8 | 123149 | BioLegend |
| APC Rat Anti-Mouse FOXP3 | FJK-16s | 17-5773 | ThermoFisher Scientific |
| BV711 Rat Anti-Mouse Ly-6C | HK1.4 | 128037 | BioLegend |
| APC-H7 Rat Anti-Mouse Ly-6G | 1A8 | 565369 | BD Biosciences |
| BV510 Rat Anti-Mouse I-A/I-E (MHCII) | M5/114.15.2 | 107635 | BioLegend |
| BV711 Hamster Anti-Mouse TCR β Chain | H57-597 | 563135 | BD Biosciences |

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed is:

1. A method of treating cancer mediated by a KRAS G12C mutation in a human subject in need thereof, the method comprising administering to the human subject a therapeutically effective amount of 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enolyl)piperazin-1-yl]pyrido[2,3-d]pyrimidin-2(1H-one, or a pharmaceutically acceptable salt thereof, and a therapeutically effective amount of an EGFR inhibitor, wherein the cancer is non-small cell lung cancer, small intestine cancer, appendix cancer, colorectal cancer, endometrial cancer, pancreatic cancer, skin cancer, gastric cancer, nasal cavity cancer, or bile duct cancer.

2. The method of claim 1, wherein the EGFR inhibitor is afatinib, erlotinib, lapatinib, cetuximab, or panitumumab.

3. The method of claim 1, wherein the EGFR inhibitor is panitumumab.

4. The method of claim 1, wherein the cancer is colorectal cancer.

5. The method of claim 1, wherein the cancer is non-small cell lung cancer.

6. The method of claim 1, wherein the cancer is pancreatic cancer.

7. The method of claim 3, wherein the cancer is colorectal cancer.

8. The method of claim 3, wherein the cancer is non-small cell lung cancer.

9. The method of claim 3, wherein the cancer is pancreatic cancer.

10. The method of claim 1, wherein the 6-fluoro-7-(2-fluoro-6-hydroxyphenyl)-(1M)-1-[4-methyl-2-(propan-2-yl)

11. The method of claim 1, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, and the EGFR inhibitor are administered separately.

12. The method of claim 4, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, and the EGFR inhibitor are administered simultaneously.

13. The method of claim 4, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, and the EGFR inhibitor are administered separately.

14. The method of claim 5, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, and the EGFR inhibitor are administered simultaneously.

15. The method of claim 5, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, and the EGFR inhibitor are administered separately.

16. The method of claim 3, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, and the panitumumab are administered simultaneously.

17. The method of claim 3, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, and the panitumumab are administered separately.

18. The method of claim 7, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, and the panitumumab are administered simultaneously.

19. The method of claim 7, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, and the panitumumab are administered separately.

20. The method of claim 8, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, and the panitumumab are administered simultaneously.

21. The method of claim 8, wherein 6-fluoro-7-(2-fluoro-6-hydroxyphenyl)-(1M)-1-[4-methyl-2-(propan-2-yl) pyridin-3-yl]-4-[(2S)-2-methyl-4-(prop-2-enoyl) piperazin-1-yl] pyrido [2,3-d]pyrimidin-2(1H)-one, or the pharmaceutically acceptable salt thereof, and the panitumumab are administered separately.

22. The method of claim 1, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, is administered to an adult.

23. The method of claim 1, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, is administered as a solid dosage form.

24. The method of claim 23, wherein the solid dosage form is a tablet.

25. The method of claim 24, wherein the tablet is administered orally.

26. The method of claim 3, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, is administered to an adult.

27. The method of claim 3, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one, or the pharmaceutically acceptable salt thereof, is administered as a solid dosage form.

28. The method of claim 27, wherein the solid dosage form is a tablet.

29. The method of claim 28, wherein the tablet is administered orally.

30. A method of treating cancer mediated by a KRAS G12C mutation in a human subject in need thereof, the method comprising administering to the human subject a therapeutically effective amount of 6-fluoro-7-(2-fluoro-6-hydroxyphenyl)-(1M)-1-[4-methyl-2-(propan-2-yl) pyridin-3-yl]-4-[(2S)-2-methyl-4-(prop-2-enoyl) piperazin-1-yl] pyrido [2,3-d]pyrimidin-2(1H) -one and a therapeutically effective amount of panitumumab, wherein the cancer is colorectal cancer, non-small cell lung cancer, or pancreatic cancer.

31. The method of claim 30, wherein the cancer is colorectal cancer.

32. The method of claim 31, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one and the panitumumab are administered separately.

33. The method of claim 31, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one and the panitumumab are administered simultaneously.

34. The method of claim 31, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2 (1H)-one is administered to an adult.

35. The method of claim 31, wherein the 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl) piperazin-1-yl]pyrido [2,3-d]pyrimidin-2(1H)-one is administered as a solid dosage form.

36. The method of claim 35, wherein the solid dosage form is a tablet.

37. The method of claim 36, wherein the tablet is administered orally.

\* \* \* \* \*